(12) United States Patent
Nishino et al.

(10) Patent No.: US 9,527,828 B2
(45) Date of Patent: *Dec. 27, 2016

(54) METHOD FOR EXPANDING HEMATOPOIETIC STEM CELLS USING HETEROCYCLIC COMPOUND

(75) Inventors: Taito Nishino, Tokyo (JP); Norihisa Ishiwata, Minamisaitama-gun (JP); Katsuaki Miyaji, Funabashi (JP); Shunsuke Iwamoto, Funabashi (JP); Yasuyuki Asai, Tokyo (JP); Makiko Yui, Tokyo (JP)

(73) Assignees: Nissan Chemical Industries, Ltd., Tokyo (JP); ReproCELL Incorporated, Yokohama (JP)

( * ) Notice: Subject to any disclaimer, the term of this patent is extended or adjusted under 35 U.S.C. 154(b) by 643 days.

This patent is subject to a terminal disclaimer.

(21) Appl. No.: 12/746,666

(22) PCT Filed: Dec. 6, 2008

(86) PCT No.: PCT/JP2008/072207
§ 371 (c)(1),
(2), (4) Date: Jun. 7, 2010

(87) PCT Pub. No.: WO2009/072635
PCT Pub. Date: Jun. 11, 2009

(65) Prior Publication Data
US 2010/0266556 A1    Oct. 21, 2010

(30) Foreign Application Priority Data
Dec. 6, 2007  (JP) ................. 2007-316276

(51) Int. Cl.
| | |
|---|---|
| C12N 5/00 | (2006.01) |
| C07D 333/38 | (2006.01) |
| C07D 409/14 | (2006.01) |
| C07D 413/14 | (2006.01) |
| C07D 417/14 | (2006.01) |
| C12N 5/0789 | (2010.01) |
| A61K 35/00 | (2006.01) |

(52) U.S. Cl.
CPC .......... *C07D 333/38* (2013.01); *C07D 409/14* (2013.01); *C07D 413/14* (2013.01); *C07D 417/14* (2013.01); *C12N 5/0647* (2013.01); *A61K 35/00* (2013.01); *C12N 2501/999* (2013.01)

(58) Field of Classification Search
None
See application file for complete search history.

(56) References Cited

U.S. PATENT DOCUMENTS

| | | | |
|---|---|---|---|
| 5,199,942 A | 4/1993 | Gillis | |
| 5,399,493 A | 3/1995 | Emerson et al. | |
| 5,437,994 A | 8/1995 | Emerson et al. | |
| 5,610,056 A * | 3/1997 | Nakahata ......... | A61K 38/204 424/93.7 |
| 5,646,043 A | 7/1997 | Emerson et al. | |
| 5,670,147 A | 9/1997 | Emerson et al. | |
| 5,670,351 A | 9/1997 | Emerson et al. | |
| 6,060,052 A | 5/2000 | Murray et al. | |
| 6,326,198 B1 | 12/2001 | Emerson et al. | |
| 6,326,205 B1 | 12/2001 | Murray et al. | |

(Continued)

FOREIGN PATENT DOCUMENTS

| | | |
|---|---|---|
| JP | 6-505151 A | 6/1994 |
| JP | 6-508613 A | 9/1994 |

(Continued)

OTHER PUBLICATIONS

Aggarwal et al. 2012. Hematopoietic stem cells: transcriptional regulation, ex vivo expansion and clinical application. Curr Mol Med 12: 34-49; author manuscript available online at http://www.ncbi.nlm.nih.gov/pmc/articles/PMC3286491/pdf/nihms356893.pdf.*

Kanji S et al. 2011. Plasticity and maintenance of hematopoietic stem cells during development. Recent Pat Biotechnol. 5: 40-53; author manuscript available online at http://www.ncbi.nlm.nih.gov/pmc/articles/PMC3294454/pdf/nihms-356918.pdf.*

Nishino T et al. 2009. Ex vivo expansion of human hematopoietic stem cells by a small-molecule agonist of c-MPL. Exp Hematol 37: 1364-1377.*

Nishino T et al. 2012. New approaches to expand hematopoietic stem and progenitor cells. Expert Op Biol Therap 12: 743-756.*

(Continued)

*Primary Examiner* — Lora E Barnhart Driscoll
(74) *Attorney, Agent, or Firm* — Oblon, McClelland, Maier & Neustadt, L.L.P.

(57) ABSTRACT

An expansion agent for hematopoietic stem cells and/or hematopoietic progenitor cells useful for improvement in the efficiency of gene transfer into hematopoietic stem cells for gene therapy useful for treatment of various hematopoietic disorders is provided.

A method for expanding hematopoietic stem cells and/or hematopoietic progenitor cells, which comprises culturing hematopoietic stem cells and/or hematopoietic progenitor cells ex vivo in the presence of a compound represented by the formula (I) (wherein X, Y, X, $Ar^1$, $R^1$, $R^2$, $R^3$, $R^4$, $R^5$, $R^6$ and $R^7$ are defined in the description), a tautomer or pharmaceutically acceptable salt of the compound or a solvate thereof.

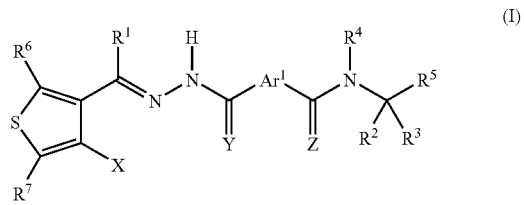

(I)

14 Claims, 2 Drawing Sheets

(56) References Cited

U.S. PATENT DOCUMENTS

| | | | |
|---|---|---|---|
| 6,887,704 | B2 | 5/2005 | Peled et al. |
| 6,962,698 | B1 | 11/2005 | Peled et al. |
| 7,344,881 | B2 | 3/2008 | Peled et al. |
| 7,351,841 | B2 | 4/2008 | Owada et al. |
| 2002/0022270 | A1 | 2/2002 | Emerson et al. |
| 2004/0091475 | A1 | 5/2004 | Tsuchiya et al. |
| 2006/0094694 | A1 | 5/2006 | Owada et al. |
| 2006/0222643 | A1 | 10/2006 | Tsunoda et al. |
| 2007/0166825 | A1 | 7/2007 | Hatsuyama et al. |
| 2008/0027068 | A1 | 1/2008 | Owada et al. |
| 2009/0118500 | A1 | 5/2009 | Miyaji et al. |
| 2009/0131659 | A1 | 5/2009 | Miyaji et al. |
| 2011/0092496 | A1 | 4/2011 | Miyaji et al. |

FOREIGN PATENT DOCUMENTS

| | | | |
|---|---|---|---|
| JP | 2000-23674 | | 1/2000 |
| JP | 2000-513924 A | | 10/2000 |
| JP | 2001-161350 | | 6/2001 |
| JP | 2002-502617 | | 1/2002 |
| JP | 2004-222502 A | | 8/2004 |
| JP | 2005-204539 A | | 8/2005 |
| JP | 2006-527187 A | | 11/2006 |
| WO | WO 97/12978 A1 | | 4/1997 |
| WO | WO 97/16535 A2 | | 5/1997 |
| WO | WO 97/16535 A3 | | 5/1997 |
| WO | WO 99/40783 | | 8/1999 |
| WO | WO 02/33072 A1 | | 4/2002 |
| WO | WO 2005/056604 A1 | | 6/2005 |
| WO | WO 2006/064957 A1 | | 6/2006 |
| WO | WO 2006062247 | * | 6/2006 ............ A61P 7/04 |
| WO | WO 2006062249 | * | 6/2006 ............ A61P 7/04 |
| WO | WO 2007/010954 A1 | | 1/2007 |
| WO | WO 2007/108559 A1 | | 9/2007 |
| WO | WO 2007/145227 A1 | | 12/2007 |

OTHER PUBLICATIONS

U.S. Appl. No. 13/376,280, filed Dec. 5, 2011, Nishino, et al.
Li Lu, et al., "The Selective Enhancing Influence of Hemin and Products of Human Erythrocytes on Colony Formation by Human Multipotential ($CFU_{GEMM}$) and Erythroid ($BFU_E$) Progenitor Cells In Vitro", Exp. Hematol. vol. 11, No. 8, 1983, pp. 721-729.
Akihiko Taguchi, et al., "Administration on CD34+ cells after stroke enhances neurogenesis via angiogenesis in a mouse model", The Journal of Clinical Investigation, vol. 114, No. 3, Aug. 2004, pp. 330-338.
Donald Orlic, et al., "Bone marrow cells regenerate infracted myocardium", Nature, vol. 410, Apr. 2001, pp. 701-705.
Eriko Tateishi-Yuyama, et al., "Therapeutic angiogenesis for patients with limb ischaemia by autologous transplantation of bone-marrow cells: a pilot study and a randomised controlled trial", The Lancet, vol. 360, (Articles), Aug. 10, 2002, pp. 427-435.
Joanne Kurtzberg, et al., "Placental Blood as a Source of Hematopoietic Stem Cells for Transplantation into unrelated Recipients", The New England Journal of Medicine, vol. 335, No. 3, 1996, pp. 157-166.
Amit C. Nathwani, et al., "A review of gene therapy for haematological disorders", British Journal of Haematology, 128, 2004, pp. 3-17.
Hideo Ema, et al., "Colony Formation of Clone-Sorted Human Hematopoietic Progenitors", Blood, vol. 75, No. 10, 1990, pp. 1941-1946.
Lori Ishizawa, et al., "Immunomagnetic Separation of $CD34^+$ Cells from Human Bone Marrow, Cord Blood, and Mobilized Blood", Journal of Hematotherapy 2, 1993, pp. 333-338.
Aliza Cassel, et al., "Retroviral-mediated gene transfer into CD34-enriched human peripheral blood stem cells", Experimental Hematology 21, 1993, pp. 585-591.
Mickie Bhatia, et al., "Purification of primitive human hematopoietic cells capable of repopulating immune-deficient mice", Proc. Natl. Acad. Sci. USA, vol. 94, May 1997, pp. 5320-5325.

André Larochelle, et al,. "Identification of primitive human hematopoietic cells capable of repopulating NOD/SCID mouse bone marrow: Implications for gene therapy", Nature Medicine, vol. 2, No. 12, Dec. 1996, pp. 1329-1337.
Ami J. Shah, et al., "Flt3 Ligand Induces Proliferation of Quiescent human Bone Marrow $CD34^+CD38^-$ Cells and Maintains Progenitor Cells in Vitro", Blood, vol. 87, No. 9, May 1, 1996, pp. 3563-3570.
John E. Dick, et al., "Assay of Human Stem Cells by Repopulation of NOD/SCID Mice", Hematopoietic Stem Cells, Stem Cells, 15, (suppl 1), 1997, pp. 199-207.
Takahiro Suzuki, et al., "Highly Efficient Ex Vivo Expansion of Human Hematopoietic Stem Cells Using Delta1-Fc Chimeric Protein", Stem Cells, 24, 2006, pp. 2456-2465.
Ian McNiece, et al., "Ex vivo expanded-peripheral blood progenitor cells provide rapid neutrophil recovery after high-dose chemotherapy in patients with breast cancer", Blood, vol. 96, No. 9, Nov. 1, 2000, pp. 3001-3007.
Kenneth Kaushansky, "Thrombopoietin and the Hematopoietic Stem Cell", Ann. N.Y. Acad. Sci. 1044, 2005, pp. 139-141.
Yutaka Kawano, et al., "Ex vivo expansion of G-CSF-mobilized peripheral blood $CD133^+$ progenitor cells on coculture with human stromal cells", Experimental Hematology 34, 2006, pp. 150-158.
Hiroshi Kawada, et al., "Rapid ex vivo expansion of human umbilical cord hematopoietic progenitors using a novel culture system", Experimental Hematology 27, Elsevier, 1999, pp. 904-915.
John P. Chute, et al., "Inhibition of aldehyde dehydrogenase and retinoid signaling induces the expansion of human hematopoietic stem cells", Proc. Natl. Acad. Sci., vol. 13, No. 31, Aug. 1, 2006, pp. 11707-11712.
Mohammed Milhem, et al., "Modification of hematopoietic stem cell fate by 5aza 2'deoxycytidine and trichostatin A", Blood, vol. 103. No. 11, Jun. 1, 2004, pp. 4102-4110.
Anskar Y. H. Leung, et al., "All-trans retinoic acid (ATRA) enhances maintenance of primitive human hematopoietic progenitors and skews system towards myeloid differentiation in a stroma-noncontact culture system", Experimental Hematology 33, 2005, pp. 422-427.
G. Astori, et al., "Evaluation of ex vivo expansion and engraftment in NOD-SCID mice of umbilical cord blood CD34+ cells using the DIDECO 'Pluricell System' ", Bone Marrow Transplantation, 35, 2005, pp. 1101-1106.
Mr. Koller, et al., "Clinical-scale human umbilical cord blood cell expansion in a novel automated perfusion culture system", Bone Marrow Transplantation, 21, 1998, pp. 653-663.
Manfred R. Koller, et al., "Large-Scale Expansion of Human Stem and Progenitor Cells From Bone Marrow Mononuclear Cells in Continuous Perfusion Cultures", Blood, vol. 82, No. 2, (Rapid communication), Jul. 15, 1993, pp. 378-384.
Venkateshwar A. Reddy, et al., "Granulocyte inducer C/EBPα inactivates the myeloid master regulator PU.1: possible role in lineage decisions", Blood, vol. 100, No. 2, Jul. 15, 2002, pp. 483-490.
Richard M. Schwartz, et al., "Rapid medium perfusion rate significantly increases the productivity and longevity bone marrow cultures", Proc. Natl. Acad. Sci., vol. 88, Aug. 1991, pp. 6760-6764.
M. Verma, et al., "Gene therapy-promises, problems and prospects", Nature, vol. 389, Sep. 18, 1997, pp. 239-242.
International Search Report issued Feb. 3, 2009 in PCT/JP2008/072207.
Extended European Search Report issued Jun. 25, 2012 in European patent application No. 08858085.7.
Asako Hatsuyama, et al., "Kanzen Muketsu Baiyokei de Zofuku Shita Saitaiketsu Zoketu Kansaibo no Tokucho", Rinsho Ketsueki, 44(8), 2003, p. 729 and cover page.
Office Action issued on Aug. 20, 2013 in the corresponding Japanese Patent Application No. 2009-544761 (with English Translation).
Ole J. Borge, e t al., "Ability of Early Acting Cytokines to Directly Promote Survival and Suppress Apoptosis of Human Primitive $CD34^+CD38^-$ Bone Marrow Cells With Multilineage Potential at the Single-Cell Level: Key Role of Thrombopoietin", Blood Journal, vol. 90, No. 6, 1997, p. 2282-2292.

(56) References Cited

OTHER PUBLICATIONS

Gary L. Gilmore, et al., "Ex vivo expansion of human umbilical cord blood and peripheral blood CD34⁺ hematopoietic stem cells", Experimental Hematology, vol. 90, No. 11, 2000, pp. 1297-1305.

Tomasz Oldak, et al., "Optimisation of transfection conditions of CD34⁺ hematopoietic cells derived from human umbilical cord blood", Acta Biochimica Polonica, vol. 49, No. 3, 2002, pp. 625-632.

* cited by examiner

METHOD FOR EXPANDING HEMATOPOIETIC STEM CELLS USING HETEROCYCLIC COMPOUND

JOINT RESEARCH AGREEMENT

The claimed invention was made by, on behalf of, and/or in connection with one or more of the following parties to a joint university corporation research agreement: Nissan Chemical Industries Ltd. and ReproCell Incorporated. The agreement was in effect on and before the date the claimed invention was made, and the claimed invention was made as a result of activities undertaken within the scope of the agreement.

TECHNICAL FIELD

The present invention relates to a method for expanding hematopoietic stem cells and/or hematopoietic progenitor cells using a low molecular weight compound having a blood cell expanding effect, in particular, to a method for expanding hematopoietic stem cells and/or hematopoietic progenitor cells in a culture medium containing various cytokines and/or growth factors in the presence of the compound, a gene therapy using the expansion method and a material for cell therapy using the hematopoietic stem cells and/or hematopoietic progenitor cells obtained by the expansion method.

BACKGROUND ART

Blood contains various lineages of blood cells having biological functions, such as the erythrocytic lineage associated with oxygen delivery, the megakaryocytic lineage generating thrombocytes, the granulocytic lineage associated with prevention of infections, the myeloid lineage such as monocytes and/or macrophages and the lymphocytic lineage responsible for immunity such as T cells and B cells. All these blood cells differentiate and mature from the common origin, hematopoietic stem cells, and are maintained and generated in an individual throughout its life. Hematopoietic stem cells are defined as cells having both pluripotency which allows them to differentiate into functional cells such as lymphocytes, erythrocytes and leukocytes and the ability to regenerate themselves while maintaining the pluripotency (self-renewal).

Previous studies have revealed that hematopoietic stem cells first diverge two ways into the myeloid lineage and the lymphoid lineage, then differentiate into myeloid stem cells (mixed colony forming cells, CFU-GEMM) and into lymphoid stem cells, respectively. Further, myeloid stem cells differentiate into erythrocytes via erythroid burst forming cells (BFU-E) and erythroid colony forming cells (CFU-E), into thrombocytes via megakaryocyte colony forming cells (CFU-MEG), into monocytes, neutrophils and basophils via granulocyte-macrophage colony forming cells (CFU-GM), and into eosinophils via eosinophil colony forming cells (CFU-EO), while lymphoid stem cells differentiate into T cells via T lymphoid progenitor cells and into B cells via B lymphoid progenitor cells. Among them, cells forming pluripotential colonies with diameters of at least 1 mm are called HPP-CFU colony forming cells and are known as the least differentiated hematopoietic progenitor cells, similarly to mixed colony forming cells (CFU-GEMM). These myeloid stem cells and various hematopoietic progenitor cells derived from them are identified by the properties of colonies they form on soft agar, semisolid methylcellulose media or the like in the presence of various cytokines (Non-Patent Document 1).

In recent years, as a curative therapy for a number of intractable diseases such as various blood diseases attributed to hematopoietic dysfunction and immune dysfunction, cancer, immunodeficiency, autoimmune diseases and inborn error of metabolism, autologous or allogeneic transplantation of hematopoietic stem cells have been carried out. Quite recently, the effectiveness of hematopoietic stem cell transplantation in treating cerebral infarction, myocardial infarction and obstructive arteriosclerosis was reported (Non-Patent Documents 2, 3 and 4). Among them, bone marrow transplantation has been used in many cases of treatment and most established as a standard hematopoietic cell transplantation therapy. However, because for bone marrow transplantation, the human leukocyte antigens (HLA) of the bone marrow donor and the transplant recipient have to match closely, there is a problem that bone marrow from donors are in short supply. Besides, the need for at least 4 days of hospitalization and pain, fever and bleeding caused by collection of a large amount of bone marrow are a heavy burden to donors.

In addition to bone marrow, peripheral blood is also used as an alternative source of hematopoietic stem cells nowadays. Hematopoietic stem cells mobilized from the bone marrow to peripheral blood by administration of granulocyte colony stimulating factor (G-CSF) to a human are used for transplantation after enrichment using a blood cell separator. However, donors for peripheral blood hematopoietic stem cell transplantation have to bear a heavy burden of the need for administration of G-CSF for 4 to 6 consecutive days which may cause side effects (such as blood coagulation and spleen hypertrophy). Besides, because the efficiency of the mobilization of hematopoietic stem cells from the bone marrow to peripheral blood by G-CSF varies from donor to donor, hematopoietic stem cells are not obtained sufficiently in some cases.

Just recently, it was found that cord blood contains as many hematopoietic stem cells as bone marrow and is useful for hematopoietic stem cell transplantation (Non-Patent Document 5). Because cord blood transplantation does not require complete HLA matching and is less likely to cause severe acute graft-versus-host disease (GVHD) than bone marrow and peripheral blood transplantation, cord blood is established as useful and has been used more frequently. However, because cord blood is obtained in a small amount from one donor and does not contain many hematopoietic stem cells, its use is mainly limited to children.

Furthermore, hematopoietic stem cells are also considered as useful cells for gene therapy of fatal genetic diseases with no effective cure, HIV infection, chronic granulomatosis and germ cell tumor. However, in order to transfect hematopoietic stem cells with a retrovirus vector carrying a target gene efficiently, it is necessary to artificially grow hematopoietic stem cells, which are usually in the stationary phase, by releasing them into the cell cycle. Besides, there is a problem that for long-lasting expression of a transgene, the transfected hematopoietic stem cells have to be kept undifferentiated in culture. Therefore, a cell expansion method for efficient gene transfer has been demanded (Non-Patent Document 6).

To solve the above-mentioned problems with hematopoietic stem cell transplantation and gene therapy, a technique for expanding hematopoietic stem cells and/or hematopoietic progenitor cells ex vivo is demanded, and various culture methods have been attempted so far.

Here, hematopoietic stem cells and hematopoietic progenitor cells, which are to be cultured, are explained. It was revealed that in human, hematopoietic stem cells and various hematopoietic progenitor cells derived from them are found in populations of CD34$^+$ cells expressing the CD34 molecule as a cell surface antigen, and hence hematopoietic stem cells can be enriched as a CD34$^+$ cell population (Non-Patent Document 7). Specifically speaking, they are often enriched by mixing a cell population to be separated with a CD34 antibody labeled with magnetic beads and magnetically collecting CD34$^+$ cells (Non-Patent Documents 8 and 9). CD34$^+$ cell populations contain less than 10% of CD34$^+$CD38$^-$ cell populations not expressing the CD38 molecule as a cell surface antigen. It has come to be considered that hematopoietic stem cells are more enriched in CD34$^+$CD38$^-$ cell populations than in CD34$^+$ cell populations (Non-Patent Documents 10 and 11). In order to determine the proportion of undifferentiated hematopoietic progenitor cells in a cell population, HPP-CFU colony forming cells are usually counted as mentioned above (Non-Patent Document 12). In recent years, it has become possible to experimentally assay human hematopoietic stem cells for bone marrow repopulating ability by using NOD/SCID mice obtained by crossing diabetic mice and immunodeficient mice. The cells detected by this assay are called SCID-repopulating cells (SRC) and considered the closest to human hematopoietic stem cells (Non-Patent Document 13).

Conventional techniques for expanding hematopoietic stem cells and/or hematopoietic progenitor cells will also be explained. As mentioned above, since hematopoietic stem cells are more enriched in CD34$^+$ cells, CD34$^+$ cells are mainly used as the starting cells for expansion. Expansion of hematopoietic stem cells and is hematopoietic progenitor cells from CD34$^+$ cells in culture in the presence of a cytokine or a growth factor such as stem cell factor (SCF), interleukin 3 (I-3), interleukin 6 (IL-6), interleukin 6 (IL-6)/soluble IL-6 receptor complex, interleukin 11 (IL-11), granulocyte colony stimulating factor (G-CSF), granulocyte-macrophage colony stimulating factor (GM-CSF), flk2/flt3 ligand (FL), thrombopoietin (TPO) and erythropoietin or Notch ligand (such as Delta 1) has been reported (Patent Documents 1, 2 and Non-Patent Documents 12, 14 and 15). Among them, TPO is especially excellent in hematopoietic stem cell expansion effect and used for in most of cases of expansion (Non-Patent Document 16). Hematopoietic stem cells and hematopoietic progenitor cells expand in culture in the presence of such various cytokines and growth factors, but hematopoietic stem cells expand only by several times. Besides, these cytokines and growth factors are all produced as recombinant proteins, it may be difficult to obtain them for expansion stably in a large amount at low cost quickly.

For ex vivo expansion of hematopoietic stem cells, coculture systems using a different type of cells as feeder cells in the presence of various cytokines were reported. For example, expansion of hematopoietic stem cells in coculture with human bone marrow stromal cells was attempted (Non-Patent Document 17). An attempt to expand CD34$^+$ cells in the presence of TPO, FL and SCF using mouse bone marrow cell line HESS-5 was also reported (Non-Patent Document 18). However, these coculture systems use foreign cells, there is a risk that cells infected with an unknown pathogen whose existence has not been confirmed may also be transplanted to patients. Furthermore, when stromal cells from a different kind of animal are used, the stromal cells have to be separated completely from CD34$^+$ cells because otherwise there is a risk of causing immune response in the recipient after transplantation.

In addition, ex vivo expansion of hematopoietic stem cells in culture in the presence of various cytokines such as TPO combined with low molecular weight compounds, not just various cytokines only, has been reported. Examples of such low molecular weight compounds include copper chelators, the combination of a histone deacetylase inhibitor and a DNA methylase inhibitor, all-trans retinoic acid, aldehyde dehydrogenase inhibitors (Non-Patent Documents 19, 20 and 21 and Patent Document 3). However, addition of any of them is not effective enough since hematopoietic stem cells expand by only several times, or cells have to be cultured for about 3 weeks.

Patent Document 1: JP-A-2001-161350
Patent Document 2: JP-A-2000-23674
Patent Document 3: JP-A-2002-502617
Non-Patent Document 1: Lu, L. et al.; Exp. Hematol., 11, 721-9, 1983
Non-Patent Document 2: Taguchi, A et al.; J Clin Invest., 114, 330-8. 2004
Non-Patent Document 3: Orlic, D et al.; Nature, 410, 701-5. 2001
Non-Patent Document 4: Tateishi-Yuyama, E et al.; Lancet, 360, 427-35. 2002
Non-Patent Document 5: Kurtzbert, J. et al.; New Eng. J. Med., 335, 157-66, 1996
Non-Patent Document 6: Nathwani, A C. et al.; Br J. Haematol., 128, 3-17, 2005
Non-Patent Document 7: Ema, H. et al.; Blood, 75, 1941-6, 1990
Non-Patent Document 8: Ishizawa, L. et al.; J Hemathor., 2, 333-8, 1993
Non-Patent Document 9: Cassel, A. et al.; Exp. Hematol., 21, 585-91, 1993
Non-Patent Document 10: Bhatia, M. et al.; Proc. Natl. Acad. Sci. USA 94:5320-25, 1997
Non-Patent Document 11: Larochelle, A. et al.; Nat. Med., 2, 1329-37, 1996
Non-Patent Document 12: Shah, A J et al.; Blood., 87, 3563-3570, 2000
Non-Patent Document 13: Dick, J E et al.; Stem Cells., 15, 199-203, 1997
Non-Patent Document 14: Suzuki, T et al.; Stem Cells., 24, 2456-2465, 2006
Non-Patent Document 15: McNiece et al., Blood.; 96, 3001-3007, 2000
Non-Patent Document 16: Kaushansky, K et al.; Ann NY Acad Sci., 1044, 139-141, 2005
Non-Patent Document 17: Kuwano, Y et al.; Exp Hematol., 34, 150-8, 2006
Non-Patent Document 18: Kawada, H et al.; Exp Hematol., 5, 904-15, 1999
Non-Patent Document 19: Chute, J P et al.; Proc Natl Acad Sci USA., 103, 11707-12, 2006
Non-Patent Document 20: Milhem, M et al.; Blood., 103, 4102-10, 2004
Non-Patent Document 21: Leung, A Y et al.; Exp Hematol., 33, 422-7, 2005

DISCLOSURE OF THE INVENTION

Object to be Accomplished by the Invention

An object of the present invention is to expand hematopoietic stem cells and/or hematopoietic progenitor cells ex vivo efficiently in a short term using a biologically safe and inexpensively obtainable low molecular weight compound. Another object of the present invention is to use an index more efficient than conventional ones in determining the expansion effect of such a low molecular weight compound on hematopoietic stem cells and/or hematopoietic progenitor cells. A still another object of the present invention is to provide an expansion agent for hematopoietic stem cells and/or hematopoietic progenitor cells useful for improvement in the efficiency of gene transfer into hematopoietic stem cells for gene therapy useful for treatment of various hematopoietic disorders caused by dysfunctional hematopoietic stem cells and/or hematopoietic progenitor cells.

Means to Accomplish the Object

The present inventors conducted extensive search for compounds having expansion activity to find a method for expanding human hematopoietic stem cells and/or hematopoietic progenitor cells ex vivo. As a result, they found that the compounds represented by the following formula show excellent expansion activity on $CD34^+CD38^-$ cells, HPP-CFU colony forming cells or SRC even in the absence of TPO and are highly useful as an expansion agent for human hematopoietic stem cells and/or hematopoietic progenitor cells and accomplished the present invention.

Namely, the present invention relates:
(1) A method for expanding hematopoietic stem cells and/or hematopoietic progenitor cells, which comprises culturing hematopoietic stem cells and/or hematopoietic progenitor cells ex vivo in the presence of a compound represented by the formula (I), a tautomer or pharmaceutically acceptable salt of the compound or a solvate thereof:

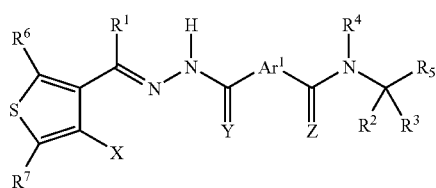

(I)

wherein each of $R^1$, $R^2$, $R^3$ and $R^4$ independently means a hydrogen atom or a $C_{1-10}$ alkyl group (the $C_{1-10}$ alkyl group may optionally be substituted with one or more halogen atoms),
$R^5$ means a $C_{2-14}$ aryl group (the $C_{2-14}$ aryl group is substituted with —$V^1$ (wherein $V^1$ means a hydrogen atom, a hydroxyl group, a protected hydroxyl group, an amino group, a protected amino group, a thiol group, a protected thiol group, a nitro group, a cyano group, a halogen atom, a carboxyl group, a carbamoyl group, a sulfamoyl group, a sulfo group, a formyl group, a $C_{1-3}$ alkyl group, a $C_{1-3}$ alkoxy group (the $C_{1-3}$ alkyl group and the $C_{1-3}$ alkoxy group are substituted with one or more halogen atoms), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkoxy group, a $C_{1-10}$ alkylcarbonyl group, a $C_{1-10}$ alkylcarbonylamino group, a mono- or di-$C_{1-10}$ alkylamino group, a $C_{1-10}$ alkylsulfonyl group, a $C_{1-10}$ alkylaminosulfonyl group, a $C_{1-10}$ alkylaminocarbonyl group, a $C_{1-10}$ alkylsulfonylamino group or a $C_{1-10}$ thioalkyl group) and, when it is a nitrogen-containing $C_{2-14}$ aryl group, may be an N-oxide thereof), a hydrogen atom or a $C_{1-6}$ alkyl group (the $C_{1-6}$ alkyl group may be substituted with one or more hydroxyl groups, one or more halogen atoms, one or more mono- or di-$C_{1-10}$ alkylamino groups, one or more $C_{1-3}$ alkoxy groups (the $C_{1-3}$ alkoxy groups may be substituted with one or more halogen atoms) or —$NR^9R^{10}$ (wherein $R^9$ and $R^{10}$ mean, together with each other, —$(CH_2)_{m1}$-G-$(CH_2)_{m2}$— (wherein G is an oxygen atom, a sulfur atom, $CR^{11}R^{12}$ (wherein each of $R^{11}$ and $R^{12}$ independently means a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{13}$ (wherein $R^{13}$ means a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may optionally be substituted with one or more substituents selected from carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups (the $C_{2-14}$ aryl groups and the $C_{2-14}$ aryloxy groups may be substituted with one or more $C_{1-6}$ alkyl groups (the $C_{1-6}$ alkyl groups may be substituted with one or more halogen atoms) or one or more halogen atoms)) or a $C_{2-14}$ aryl group (the $C_{2-14}$ aryl group may optionally be substituted with one or more substituents selected from $C_{1-10}$ alkyl groups (the $C_{1-10}$ alkyl groups may be substituted with one or more halogen atoms), $C_{2-6}$ alkenyl groups, $C_{2-6}$ alkynyl groups, carboxyl groups, nitro groups, cyano groups, halogen atoms, $C_{1-10}$ alkoxy groups, $C_{1-10}$ alkylcarbonyl groups, $C_{1-10}$ alkylcarbonyloxy groups, $C_{1-10}$ alkoxycarbonyl groups, $C_{1-10}$ alkylcarbonylamino groups, amino groups, mono- or di-$C_{1-10}$ alkylamino groups, hydroxyl groups, protected hydroxyl groups, $C_{2-14}$ aryl groups and $C_{2-14}$ aryloxy groups)), and each of m1 and m2 means an integer of from 0 to 5, provided m1+m2 is 3, 4 or 5))),
$R^6$ means a hydrogen atom or a $C_{1-10}$ alkyl group (the $C_{1-10}$ alkyl group may optionally be substituted with one or more halogen atoms),
$R^7$ means a $C_{2-14}$ aryl group (the $C_{2-14}$ aryl group is substituted with one or more substitutents independently represented by —$V^3$ (wherein $V^3$ is the same as $V^1$, and $V^1$ is the same as defined above)),
$Ar^1$ means a $C_{2-14}$ arylene group (the $C_{2-14}$ arylene group is substituted with one or more substituted independently represented by —$V^4$ (wherein $V^4$ is the same as $V^1$, and $V^1$ is the same as defined above)), and
X means $OR^8$ (wherein $R^8$ means a hydrogen atom, a $C_{1-10}$ alkyl group or a $C_{1-10}$ alkylcarbonyl group (the $C_{1-10}$ alkyl group and the $C_{1-10}$ alkylcarbonyl group are optionally substituted with one or more substituents independently represented by —$V^5$ (wherein $V^5$ is the same as $V^1$, and $V^1$ is the same as defined above))), and each of Y and Z independently means an oxygen atom or a sulfur atom.
(2) The method for expanding hematopoietic stem cells and/or hematopoietic progenitor cells according to (1), wherein $R^1$ is a hydrogen atom or a $C_{1-6}$ alkyl group (the $C_{1-6}$ alkyl group may optionally be substituted with one or more halogen atoms),
$R^2$, $R^3$ and $R^6$ are hydrogen atoms,
$R^4$ is a hydrogen atom or a $C_{1-6}$ alkyl group, Ar¹ is represented by the formula (II) or the formula (III):

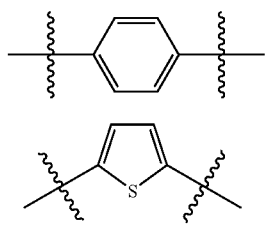

R⁷ is a phenyl group (the phenyl group may optionally be substituted with one or more $C_{1-10}$ alkyl groups (the $C_{1-10}$ alkyl groups may be substituted with one or more halogen atoms), one or more halogen atoms, one or more $C_{1-10}$ alkoxy groups or one or more $C_{1-3}$ alkoxy groups (the $C_{1-3}$ alkoxy groups are optionally substituted with one or more halogen atoms)), R⁵ is a $C_{2-14}$ aryl group (the $C_{2-14}$ aryl group is substituted with —V⁵ (wherein V⁵ means a hydrogen atom, a hydroxyl group, a protected hydroxyl group, an amino group, a protected amino group, a thiol group, a protected thiol group, a nitro group, a cyano group, a halogen atom, a carboxyl group, a carbamoyl group, a sulfamoyl group, a sulfo group, a formyl group, a $C_{1-3}$ alkyl group, a $C_{1-3}$ alkoxy group (the $C_{1-3}$ alkyl group and the $C_{1-3}$ alkoxy group are substituted with one or more halogen atoms), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkoxy group, a $C_{1-10}$ alkylcarbonyl group, a $C_{1-10}$ alkylcarbonylamino group, a mono- or di-$C_{1-10}$ alkylamino group, a $C_{1-10}$ alkylsulfonyl group, a $C_{1-10}$ alkylaminosulfonyl group, a $C_{1-10}$ alkylaminocarbonyl group, a $C_{1-10}$ alkylsulfonylamino group or a $C_{1-10}$ thioalkyl group) and, when it is a nitrogen-containing $C_{2-14}$ aryl group, may be an N-oxide thereof), X is OH, and Y and Z are oxygen atoms.

(3) The method for expanding hematopoietic stem cells and/or hematopoietic progenitor cells according to (2), wherein R¹ is a hydrogen atom or a $C_{1-3}$ alkyl group, and Ar¹ is represented by the formula (III).

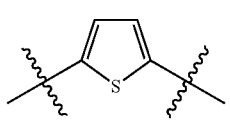

(4) The method for expanding hematopoietic stem cells and/or hematopoietic progenitor cells according to (3), wherein R⁵ is a $C_{2-14}$ aryl group (the $C_{2-14}$ aryl group is substituted with one or more hydrogen atoms, one or more nitro groups, one or more cyano groups, one or more halogen atoms, one or more carboxyl groups, one or more carbamoyl groups, one or more sulfamoyl groups, one or more sulfo groups, one or more formyl groups, one or more $C_{1-3}$ alkyl groups, one or more $C_{1-3}$ alkoxy groups (the $C_{1-3}$ alkyl groups and the $C_{1-3}$ alkoxy groups are substituted with one or more halogen atoms), one or more $C_{1-10}$ alkyl groups, one or more $C_{1-10}$ alkylcarbonyloxy groups, one or more $C_{1-10}$ alkoxycarbonyl groups, one or more $C_{1-10}$ alkoxy groups, one or more $C_{1-10}$ alkylcarbo- nyl groups, one or more $C_{1-10}$ alkylcarbonylamino groups, one or more mono- or di-$C_{1-10}$ alkylamino groups, one or more $C_{1-10}$ alkylsulfonyl groups, one or more $C_{1-10}$ alkylaminosulfonyl groups, one or more $C_{1-10}$ alkylaminocarbonyl groups, one or more $C_{1-10}$ alkylsulfonylamino groups or one or more $C_{1-10}$ thioalkyl groups) and, when it is a nitrogen-containing $C_{2-14}$ aryl group, may be an N-oxide thereof.

(5) The method for expanding hematopoietic stem cells and/or hematopoietic progenitor cells according to (3), wherein R⁵ is a $C_{2-14}$ aryl group (the $C_{2-14}$ aryl group is substituted with one or more hydrogen atoms, one or more cyano groups, one or more halogen atoms, one or more carbamoyl groups, one or more sulfamoyl groups, one or more $C_{1-3}$ alkylsulfonyl groups, one or more $C_{1-3}$ alkyl groups, one or more $C_{1-3}$ alkoxy groups (the $C_{1-3}$ alkyl groups and the $C_{1-3}$ alkoxy groups are substituted with one or more halogen atoms), one or more $C_{1-3}$ alkyl groups or one or more $C_{1-3}$ alkoxy groups and, when it is a nitrogen-containing $C_{2-14}$ aryl group, may be an N-oxide thereof).

(6) The method for expanding hematopoietic stem cells and/or hematopoietic progenitor cells according to (3), wherein R⁵ is a $C_{2-14}$ aryl group (the $C_{2-14}$ aryl group is substituted with one or more hydrogen atoms, one or more halogen atoms, one or more carbamoyl groups, one or more sulfamoyl groups, one or more $C_{1-3}$ alkylsulfonyl groups, one or more $C_{1-3}$ alkyl groups or one or more $C_{1-3}$ alkoxy groups and, when it is a nitrogen-containing $C_{2-14}$ aryl group, may be an N-oxide thereof).

(7) The method for expanding hematopoietic stem cells and/or hematopoietic progenitor cells according to (1), wherein each of R¹ and R⁴ is independently a hydrogen atom or a $C_{1-3}$ alkyl group, R², R³ and R⁶ are hydrogen atoms, Ar¹ is represented by the formula (III):

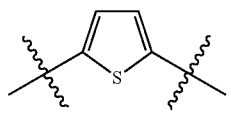

R⁷ is a phenyl group (the phenyl group is optionally substituted with one or more $C_{1-10}$ alkyl groups (the $C_{1-10}$ alkyl groups may be substituted with one or more halogen atoms), one or more halogen atoms, one or more $C_{1-10}$ alkoxy groups or one or more $C_{1-3}$ alkoxy groups (the $C_{1-3}$ alkoxy groups are optionally substituted with one or more halogen atoms)), R⁵ is a hydrogen atom or a $C_{1-6}$ alkyl group (the $C_{1-6}$ alkyl group may be substituted with one or more hydroxyl groups, one or more halogen atoms, one or more $C_{1-3}$ alkoxy groups, one or more dimethyl amino groups or one or more of the following groups), X is OH, and Y and Z are oxygen atoms.

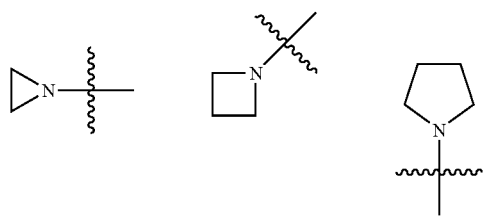

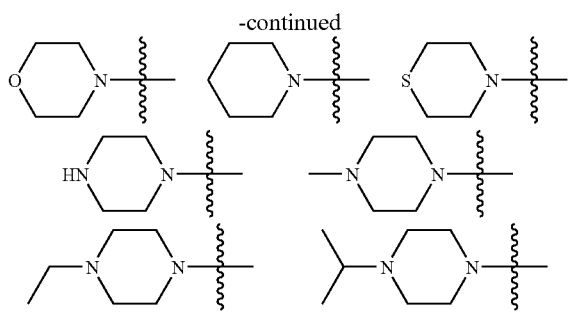

(8) The method for expanding hematopoietic stem cells and/or hematopoietic progenitor cells according to any one of (1) to (7), wherein the hematopoietic stem cells and/or hematopoietic progenitor cells to be expanded are CD34$^+$CD38$^-$ cells.

(9) The method for expanding hematopoietic stem cells and/or hematopoietic progenitor cells according to any one of (1) to (7), wherein the hematopoietic stem cells and/or hematopoietic progenitor cells to be expanded are HPP-CFU colony forming cells.

(10) The method for expanding hematopoietic stem cells and/or hematopoietic progenitor cells according to any one of (1) to (7), wherein the hematopoietic stem cells and/or hematopoietic progenitor cells to be expanded are SRC.

(11) The method for expanding hematopoietic stem cells and/or hematopoietic progenitor cells according to any one of (1) to (10), which involves addition of at least one blood cell stimulating factor.

(12) The method for expanding hematopoietic stem cells and/or hematopoietic progenitor cells according to (11), wherein the blood cell stimulating factor is selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).

(13) The method for expanding hematopoietic stem cells and/or hematopoietic progenitor cells according to (11), wherein the blood cell stimulating factor is stem cell factor (SCF) and/or flk/flt3 ligand (FL).

(14) The method for expanding hematopoietic stem cells and/or hematopoietic progenitor cells according to any one of (1) to (13), wherein the hematopoietic stem cells and/or hematopoietic progenitor cells are obtained from the bone marrow, the liver, the spleen or peripheral or cord blood.

(15) The method for expanding hematopoietic stem cells and/or hematopoietic progenitor cells according to (14), wherein the hematopoietic stem cells and/or hematopoietic progenitor cells are obtained from cord blood.

(16) The method for expanding hematopoietic stem cells and/or hematopoietic progenitor cells according to (15), wherein hematopoietic stem cells and/or hematopoietic progenitor cells obtained from cord blood are cultured in the presence of stem cell factor (SCF) and/or flk2/flt3 ligand (FL).

(17) A reagent or reagent kit for expanding hematopoietic stem cells and/or hematopoietic progenitor cells, which comprising the compound as defined in any one of (1) to (7), a tautomer or pharmaceutically acceptable salt of the compound or a solvate thereof, as an active ingredient.

(18) A method for transferring a gene into hematopoietic stem cells and/or hematopoietic progenitor cells, which comprises culturing hematopoietic stem cells and/or hematopoietic progenitor cells ex vivo in the presence of the compound as defined in any one of (1) to (7), a tautomer or pharmaceutically acceptable salt of the compound or a solvate thereof.

(19) The method for transferring a gene into hematopoietic stem cells and/or hematopoietic progenitor cells according to (18), which involves addition of at least one blood cell stimulating factor.

(20) The method for transferring a gene into hematopoietic stem cells and/or hematopoietic progenitor cells according to (19), wherein the blood cell stimulating factor is selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).

(21) The method for transferring a gene into hematopoietic stem cells and/or hematopoietic progenitor cells according to any one of (18) to (20), wherein the hematopoietic stem cells and/or hematopoietic progenitor cells are obtained from the bone marrow, the liver, the spleen or peripheral or cord blood.

(22) Hematopoietic stem cells and/or hematopoietic progenitor cells expanded by the method as defined in any one of (1) to (16).

(23) Hematopoietic stem cells and/or hematopoietic progenitor cells into which a gene is transferred by the method as defined in any one of (18) to (20).

(24) A material for cell therapy by transplanting hematopoietic stem cells and/or hematopoietic progenitor cells expanded by the method as defined in any one of (1) to (16) into a human for treatment of a disease.

(25) A material for cell therapy by transplanting hematopoietic stem cells and/or hematopoietic progenitor cells into which a gene is transferred by the method as defined in any one of (18) to (20) into a human for treatment of a disease.

(26) The material for cell therapy according to (24) or (25), wherein the disease to be treated is leukemia, aplastic anemia, myelodysplastic syndrome, malignant lymphoma, multiple myeloma, myeloproliferative disease, a genetic blood disease, a solid tumor, an autoimmune disease, immunodeficiency, cerebral infarction, myocardial infarction or obstructive arteriosclerosis.

Effects of the Invention

According to the method of the present invention, it is possible to expand hematopoietic stem cells and/or hematopoietic progenitor cells by culturing them ex vivo. Hematopoietic stem cells and/or hematopoietic progenitor cells expanded by the method of the present invention can be used as a cell transplant for treatment of diseases. The method of the present invention also makes it possible to provide a cell transplant (graft) soon as required even from a transplant source which can be obtained in a limited amount, by expanding hematopoietic stem cells and/or hematopoietic progenitor cells easily.

The low molecular weight compound to be used in the present invention can be produced by an ordinary process for organic synthesis and is obtained without using any substances from an animal other than human or a microorganism. Therefore, it is possible to prevent contamination with an unknown pathogen or a biomaterial from an animal other than human or a microorganism, as compared with expansion of hematopoietic stem cells using a protein such as cytokines and growth factors obtained by gene recombination technology. Namely, hematopoietic stem cells and/or hematopoietic progenitor cells obtained by the method of the present invention can avoid infection, contamination with foreign genes or immune response to foreign proteins. While being proteins, cytokines and growth factors can be stored or used within very narrow optimal ranges in terms of pH, heat and ion strength, the low molecular weight compound in the present invention can be used and stored under relatively broad ranges of conditions. In addition, because the low molecular weight compound in the present invention can be produced inexpensively and continuously unlike proteins, it is possible to eventually reduce treatment cost.

BEST MODE FOR CARRYING OUT THE INVENTION

Figure 1:
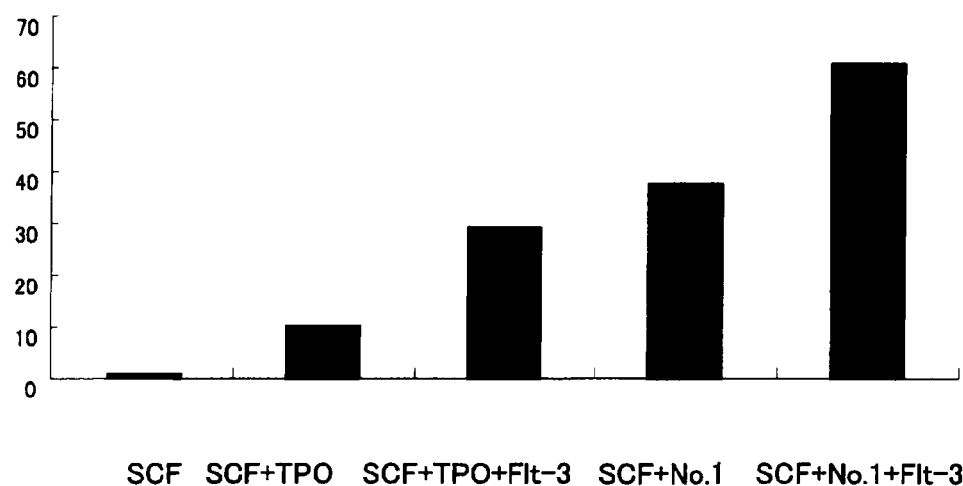
FIG. 1 A graph showing that $CD34^+CD38^-$ cells were expanded more remarkably in a culture of $CD34^+$ cells in the presence of the compound of the present invention than in the presence of TPO.

Now, the present invention will be described in further detail.

The terms used herein are defined as follows.

Hematopoietic stem cells are defined as cells having both pluripotency which allows them to differentiate into blood cells of all lineages and the ability to regenerate themselves while maintaining the pluripotency. Multipotential hematopoietic progenitor cells are cells which can differentiate into a plurality of blood cell lineages, though not into all blood cell lineages, but have no self-renewal ability. Unipotential hematopoietic progenitor cells are cells which can differentiate into only one blood cell lineage and have no self-renewal ability. Hematopoietic progenitor cells are a group of cells which covers both multipotential and unipotential hematopoietic progenitor cells. For example, the hematopoietic progenitor cells in the present invention may be granulocyte-macrophage colony forming cells (CFU-GM), eosinophil colony forming cells (EO-CFC), erythroid burst forming cells (BFU-E) as erythroid progenitor cells, megakaryocyte colony forming cells (CFU-MEG) or myeloid stem cells (mixed colony forming cells, CFU-GEMM). Among them, cells forming pluripotential colonies with diameters of at least 1 mm are called HPP-CFU colony forming cells and are defined as the least differentiated hematopoietic progenitor cells, similarly to mixed colony forming cells (CFU-GEMM).

$CD34^+$ means expressing CD (cluster of differentiation) 34 antigen on the cell surface. This antigen is a marker for hematopoietic stem cells and/or hematopoietic progenitor cells and disappears as the cell differentiates. Populations of $CD34^+$ cells are enriched with hematopoietic stem cells and/or hematopoietic progenitor cells.

$CD38^-$ means not expressing CD38 antigen on the cell surface. The expression of this antigen increases as blood cells differentiate. $CD34^+CD38^-$ cells mean cells expressing CD34 antigen but not expressing CD38 antigen. $CD34^+CD38^-$ cells are characterized as a group of cells containing more hematopoietic stem cells than $CD34^+$ cells.

It has become possible to experimentally assay human hematopoietic stem cells for bone marrow repopulating ability by using NOD/SCID mice obtained by crossing diabetic mice and immunodeficient mice. The cells detected by this assay are called SCID-repopulating cells (SRC) and considered the closest to human hematopoietic stem cells.

In the present invention, differentiation into hematopoietic stem cells and/or hematopoietic progenitor cells covers conversion of hematopoietic stem cells to hematopoietic progenitor cells, conversion of multipotential hematopoietic progenitor cells to unipotential hematopoietic progenitor cells and conversion of hematopoietic progenitor cells to cells having specific functions, i.e., mature blood cells such as erythrocytes, leukocytes and megakaryocytes.

Therefore, in the present invention, hematopoietic stem cell and/or hematopoietic progenitor cell expansion activity means the ability to proliferate hematopoietic stem cells and/or hematopoietic progenitor cells having the above-mentioned functions and increase hematopoietic stem cells and/or hematopoietic progenitor cells having the same functions. In the present invention, hematopoietic stem cell and/or hematopoietic progenitor cell differentiating activity means the ability to induce differentiation of hematopoietic stem cells and/or hematopoietic progenitor cells into hematopoietic progenitor cells having the above-mentioned functions and/or mature blood cells (such as erythrocytes, leukocytes and megakaryocytes).

The low molecular weight compound used in the present invention acts on hematopoietic stem cells and/or hematopoietic progenitor cells and shows such an activity that it helps hematopoietic stem cells and/or hematopoietic progenitor cells proliferate and survive when they are cultured ex vivo. The low molecular weight compound is capable of proliferate hematopoietic stem cells and/or hematopoietic progenitor cells with minimal differentiation. In some cases of treatment by transplantation of hematopoietic stem cells such as peripheral stem cells and cord blood stem cells, hematopoietic stem cells and/or hematopoietic progenitor cells as the transplant cannot be obtained in sufficient numbers to carry out the transplantation. Use of the low molecular weight compound makes it possible to expand collected hematopoietic stem cells and hematopoietic progenitor cells ex vivo and obtain hematopoietic stem cells and hematopoietic progenitor cells in the amount required to carry out the transplantation even in such cases. Specifically speaking, it is possible to expand hematopoietic stem cells with minimal differentiation by culturing them in a medium containing the low molecular weight compound and use them for transplantation. It is also possible to expand hematopoietic stem cells more efficiently by further adding various cytokines or growth factors, by coculturing them with stromal cells, or by further adding other low molecular weight compounds which act on hematopoietic stem cells and/or hematopoietic progenitor cells.

In the method of the present invention, the collected cells to be cultured for transplantation may be an isolated population of either hematopoietic stem cells or hematopoietic progenitor cells or a population containing both of them. The cells may contain either hematopoietic stem cells or hematopoietic progenitor cells and further contain other mature blood cells.

The source of the hematopoietic stem cells and/or hematopoietic progenitor cells in the method of the present invention may be any tissue as long as it contains hematopoietic stem cells, and it may be human bone marrow, peripheral blood, peripheral blood containing hematopoietic stem cells mobilized by a cytokine, spleen, liver or cord blood.

The hematopoietic stem cells and/or hematopoietic progenitor cells can be cultured in a culture vessel generally used for animal cell culture such as a Petri dish, a flask, a plastic bag, a Teflon (registered trademark) bag, optionally after preliminary coating with an extracellular matrix or a cell adhesion molecule. The material for such a coating may be collagens I to XIX, fibronectin, vitronectin, laminins 1 to 12, nitrogen, tenascin, thrombospondin, von Willebrand factor, osteopontin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, Sepharose, alginic acid gel, hydrogel or a fragment thereof. Such a coating material may be a recombinant material having an artificially modified amino acid sequence. The hematopoietic stem cells and/or hematopoietic progenitor cells may be cultured by using a bioreactor which can mechanically control the medium composition, pH and the like and obtain high density culture (Schwartz R M, Proc. Natl. Acad. Sci. U.S.A., 88:6760, 1991; Koller M R, Bone Marrow Transplant, 21:653, 1998; Koller, M R, Blood, 82: 378, 1993; Astori G, Bone Marrow Transplant, 35: 1101, 2005).

The nutrient medium to be used in the method of the present invention may be a natural medium, a semi-synthetic medium or a synthetic medium in terms of composition, and may be a solid medium, a semisolid medium or a liquid medium in terms of shape, and any nutrient medium used for animal cell culture, especially for hematopoietic stem cell and/or hematopoietic progenitor cell culture, may be used. As such a nutrient medium, Dulbecco's Modified Eagles's Medium (DMEM), Ham's Nutrient Mixture H12 Mixture F12, McCoy's 5A medium, Eagles's Minimum Essential Medium (EMEM), αMEM medium (alpha Modified Eagles's Minimum Essential Medium), RPMI1640 medium, Isocove's Modified Dulbecco's Medium (IMDM), Stem-Pro34 (Invitrogen), X-VIVO 10 (Cambrex), X-VIVO 15 (Cambrex), HPGM (Cambrex), StemSpan H3000 (Stemcell Technologies), StemSpan SFEM (Stemcell Technologies), Stemline II (Sigma-Aldrich) or QBSF-60 (Quality Biological) may be mentioned.

Such a medium may contain sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transfferin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. The cytokines to be added to the medium may be interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 14 (IL-14), interleukin 15 (IL-15), interleukin 18 (IL-18), interleukin 21 (IL-21), interferon-α (IFN-α), interferon-β (IFN-β), interferon-× (IFN-×), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia inhibitory factor (LIF), oncostatin M (OM), erythropoietin (EPO) and thrombopoietin (TPO), but are not restricted to those mentioned above. The growth factors to be added to the medium may be transforming growth factor-β (TGF-β), macrophage inflammatory protein-1α (MIP-1α), epidermal growth factor (EGF), fibroblast growth factor (FGF), nerve growth factor (NGF), hepatocyte growth factor (HGF), protease nexin I, protease nexin II, platelet-derived growth factor (PDGF), cholinergic differentiation factor (CDF), chemokines, Notch ligand (such as Delta 1), Wnt protein, angiopoietin-like protein 1 (Angpt1), insulin-like growth factor (IGF) and insulin-like growth factor binding protein (IGFBP), but are not restricted to those mentioned above. Besides, recombinant cytokines or growth factors having an artificially modified amino acid sequence such as IL-6/soluble IL-6 receptor complex, and Hyper IL-6 (IL-6/soluble IL-6 receptor fusion protein) may also be added.

Among the above-mentioned cytokines and growth factors, preferred are stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO), erythropoietin (EPO), Notch ligand (Delta 1) and the like, and more preferred are stem cell factor (SCF), flk2/flt3 ligand (FL), thrombopoietin (TPO) and the like. Cytokines and growth factors are usually added to culture at a concentration of 0.1 ng/mL to 1000 ng/mL, preferably from 1 ng/mL to 100 ng/mL.

In addition, at least one chemical substance known to be effective for expansion of hematopoietic stem cells may be added to the medium singly or in combination. Examples of such substances include copper chelators represented by tetraethylenepentamine, histone deacetylase inhibitors represented by trichostain A, DNA methylase inhibitors represented by 5-aza-2'-deoxycytidine, retinoic acid receptor ligands represented by all-trans retinoic acid, aldehyde dehydrogenase inhibitors represented by dimethylaminobenzaldehyde, but they are not restricted to those mentioned above.

The chemical components and biological components mentioned above may be used not only by adding them to the medium but also by immobilizing them onto the surface of the substrate or support used for the culture, specifically speaking, by dissolving a component to be used in an appropriate solvent, coating the substrate or support with the resulting solution and then washing away an excess of the component. Such a component to be used may be added to the substrate or support preliminarily coated with a substance which binds to the component.

When the low molecular weight compound of the present invention is added to such a medium as mentioned above, it is first dissolved in an appropriate solvent and added to the medium so that the concentration of the compound will be from 1 ng/mL to 100 µg/mL, preferably from 3 ng/mL to 30

μg/mL, more preferably from 30 ng/mL to 10 μg/mL, particularly preferably from 300 ng/mL to 3 μg/mL. Examples of the appropriate solvent include dimethyl sulfoxide (DMSO) and various alcohols, but it is not restricted thereto. The low molecular weight compound of the present invention may be immobilized on the surface of the substrate or support used for the culture. The low molecular weight compound of the present invention may be provided or stored in a certain form, for example, in a solid form as a tablet, a pill, a capsule or a granule, in a liquid form as a solution or suspension in an appropriate solvent or resolvent, or in the form bound to the substrate or support. When it is formulated into such a form, additives such as a preservative like p-hydroxybenzoates, an excipient like lactose, glucose, sucrose and mannitol; a lubricant like magnesium stearate and talc; a binder like polyvinyl alcohol, hydroxypropylcellulose and gelatin, a surfactant like fatty acid esters, a plasticizer like glycerin may be added. The additives are not restricted to those mentioned above and a person skilled in the art can use any additives of choice.

The hematopoietic stem cells and/or hematopoietic progenitor cells are cultured usually at a temperature of from 25 to 39° C., preferably from 33 to 39° C., in the atmosphere having a $CO_2$ concentration of from 4 to 10 vol %, preferably from 4 to 6 vol %, usually for a period of from 3 to 35 days, preferably from 5 to 21 days, more preferably from 7 to 14 days.

In the method of the present invention, when the hematopoietic stem cells and/or hematopoietic progenitor cells are cocultured with stromal cells, collected bone marrow cells may be grown directly in culture. Alternatively, it is possible to separate collected bone marrow into stromal cells, hematopoietic stem cells and/or hematopoietic progenitor cells, and coculture the hematopoietic stem cells and/or hematopoietic progenitor cells with stromal cells from an individual other than the bone marrow donor. It is also possible to first grow stromal cells only and add and grow hematopoietic stem cells and/or hematopoietic progenitor cells in coculture in such a medium under such conditions as mentioned above.

Hematopoietic stem cells and/or hematopoietic progenitor cells expanded by the method of the present invention can be used as a cell transplant. Because hematopoietic stem cells can differentiate into blood cells of all lineages, they may be transplanted after differentiated into a certain type of blood cells ex vivo. Hematopoietic stem cells and/or hematopoietic progenitor cells expanded by the method of the present invention may be transplanted as they are, or after enrichment using a cell surface antigen as an index, for example, by a magnetic bead method or by a cell sorting method. Such a cell surface antigen molecule may be CD2, CD3, CD4, CD8, CD13, CD14, CD15, CD16, CD19, CD24, CD33, CD34, CD38, CD41, CD45, CD56, CD66, CD90, CD133 or glycophorin A, but is not restricted thereto. The expanded hematopoietic stem cells and/or hematopoietic progenitor cells may be transplanted to its donor or another individual.

Namely, hematopoietic stem cells and/or hematopoietic progenitor cells expanded by the method of the present invention can be used as a transplant for hematopoietic stem cell therapy as a substitute for conventional bone marrow or cord blood transplantation. The transplantation of hematopoietic stem cells and hematopoietic progenitor cells expanded by using the low molecular compound of the present invention is carried out in the same manner as conventional bone marrow or cord blood transplantation, except for the cells to be used. The transplant may be a composition containing a buffer solution, an antibiotic, a pharmaceutical in addition to hematopoietic stem cells and/or hematopoietic progenitor cells expanded by the method of the present invention.

The hematopoietic stem cell and/or hematopoietic progenitor cell transplant obtained by the method of the present invention is useful for treatment of not only various types of leukemia but also various diseases. For example, in a case of treatment of a solid cancer patient by chemotherapy or radiotherapy which may cause myelosuppression as a side effect, the patient can recover from hematopoietic damage quickly if the hematopoietic stem cells and/or hematopoietic progenitor cells in bone marrow collected from the patient preliminarily to the treatment are expanded ex vivo and returned to the patient after the treatment. Thus, a more intense chemotherapy becomes available with an improved therapeutic effect. It is also possible to alleviate a deficiency in a certain type of blood cells in a patient by differentiating hematopoietic stem cells and/or hematopoietic progenitor cells obtained by the method of the present invention into such a type of blood cells and returning them into the patient. The method of the present invention is effective against diseases accompanying decrease in hematopoietic cells and/or hematopoietic insufficiency, diseases accompanying increase in hematopoietic cells, diseases accompanying hematopoietic dysfunction, decrease in immunocytes, increase in immunocytes, diseases accompanying autoimmunity, immune dysfunction and ischemic diseases.

As specific examples, chronic granulomatosis, severe combined immunodeficiency syndrome, adenylate deaminase (ADA) deficiency, agammaglobulinemia, Wiskott-Aldrich syndrome, Chediak-Higashi syndrome, immunodeficiency syndrome such as acquired immunodeficiency syndrome (AIDS), C3 deficiency, congenital anemia such as thalassemia, hemolytic anemia due to enzyme deficiency and sicklemia, lysosomal storage disease such as Gaucher's disease and mucopolysaccharidosis, adrenoleukodystrophy, various kinds of cancers and tumors, especially blood cancers such as acute or chronic leukemia, Fanconi syndrome, aplastic anemia, malignant lymphoma, Hodgkin's disease, multiple myeloma, chronic hepatopathy, renal failure, massive blood transfusion of bank blood or during operation, hepatitis B, hepatitis C, severe infections, systemic lupus erythematodes, articular rheumatism, xerodermosteosis, systemic sclerosis, polymyositis, dermatomyositis, mixed connective tissue disease, polyarteritis nodosa, Hashimoto's disease, Basedow's disease, myasthenia gravis, insulin dependent diabetes mellitus, autoimmune hemolytic anemia, snake bite, hemolytic uremic syndrome, hypersplenism, bleeding, Bernard-Soulier syndrome, Glanzmann's thrombasthenia, uremia, myelodysplastic syndrome, polycythemia rubra vera, erythremia, essential thrombocythemia, myeloproliferative disease, cerebral infarction, myocardial infarction, obstructive arteriosclerosis and the like may be mentioned.

Hematopoietic stem cells and/or hematopoietic progenitor cells expanded by the method of the present invention can be used for gene therapy. Gene therapy using hematopoietic stem cells has been difficult because the transfer of a target gene into hematopoietic stem cells at the stationary phase is inefficient, and hematopoietic stem cells differentiate in culture during a gene transfer procedure. However, use of the low molecular weight compound of the present invention in culture makes it possible to expand hematopoietic stem cells while suppressing differentiation of hematopoietic stem cells and improve the gene transfer efficiency considerably. In gene therapy, a therapeutic gene is transfected into hematopoietic stem cells and/or hematopoietic progenitor cells using the low molecular weight compound of the present invention, and the resulting transfected cells are transplanted into patients. The therapeutic gene to be transfected is appropriately selected among genes for hormones, cytokines, receptors, enzymes, polypeptides and the like according to the disease (Advance in Pharmacology 40, Academic Press, 1997). Specific examples of the gene include genes for insulin, amylase, proteases, lipases, trypsinogen, chymotrypsinogen, carboxypeptidases, ribonucleases, deoxyribonucleases, phospholipase A2, esterases, α1-antitrypsin, blood coagulation factors (VII, VIII, IX and the like), protein C, protein S, antithrombin, UDP glucuronyl transferase, ornithine transcarbamoylase, hemoglobin, NADPH oxidase, glucocerebrosidase, α-galactosidase, α-glucosidase, α-iduronidase, chytochrome P450 enzymes, adenosine deaminase, Bruton's kinase, complements C1 to C4, JAK3, common cytokine receptor γ chain, Ataxia Telangiectasia Mutated (ATM), Cystic Fibrosis (CF), myocilin, thymic humoral factor, thymopoietin, gastrin, selectins, cholecystokinin, serotinin, substance P, Major Histocompatibility Complex (MHC), multiple drug resistance factor (MDR-1) and the like.

In addition, RNA genes suppressing expression of disease genes are effective as therapeutic genes and can be used in the method of the present invention. For example, antisense RNA, siRNA, shRNA decoy RNA, ribozymes and the like may be mentioned.

For transfer of a therapeutic gene into hematopoietic stem cells and/or hematopoietic progenitor cells, ordinary gene transfer methods for animal cells, such as those using vectors for animal cells such as retrovirus vectors like murine stem cell vector (MSCV) and Moloney murine leukemia virus (MmoLV), adenovirus vectors, adeno-associated (AAV) vectors, herpes simplex virus and lentivirus vectors (for vectors for gene therapy, see Verma, I. M., Nature, 389:239, 1997), calcium phosphate coprecipitation, DEAE-dextran transfection, electroporation, a liposome method, lipofection, microinjection or the like may be used. Among them, retrovirus vectors, adeno-associated vectors or lentivirus vectors are preferred because their integration into the chromosomal DNA is expected to allow eternal expression of the gene.

For example, an adeno-associated virus (AAV) vector is prepared as follows. First, 293 cells are transfected with a vector plasmid obtained by inserting a therapeutic gene between the ITRs at both ends of wild-type adeno-associated virus DNA and a helper plasmid for supplementing virus proteins and subsequently infected with an adenovirus as a helper virus to induce production of virus particles containing AAV vectors. Instead of the adenovirus, a plasmid for expression of an adenovirus gene which functions as a helper may be transfected. Next, hematopoietic stem cells and/or hematopoietic progenitor cells are infected with the virus particles. It is preferred to insert an appropriate promoter, enhancer, insulator or the like upstream of the target gene in the vector DNA to regulate expression of the gene thereby. Introduction of a marker gene such as a drug resistance gene in addition to the therapeutic gene makes it easy to select cells carrying the therapeutic gene. The therapeutic gene may be a sense gene or an antisense gene.

When hematopoietic stem cells and/or hematopoietic progenitor cells are transfected with a therapeutic gene, the cells are cultured by an appropriate method selected from the culture methods mentioned above for expansion of hematopoietic stem cells and/or hematopoietic progenitor cells by the person in charge. The gene transfer efficiency can be evaluated by a standard method in the art.

The transplant for gene therapy may be a composition containing a buffer solution, an antibiotic, a pharmaceutical in addition to hematopoietic stem cells and/or hematopoietic progenitor cells expanded by the method of the present invention.

The diseases to be treated by gene therapy targeting blood cells include chronic granulomatosis, severe combined immunodeficiency syndrome, adenylate deaminase (ADA) deficiency, agammaglobulinemia, Wiskott-Aldrich syndrome, Chediak-Higashi syndrome, immunodeficiency syndrome such as acquired immunodeficiency syndrome (AIDS), hepatitis B, hepatitis C, congenital anemia such as thalassemia, hemolytic anemia due to enzyme deficiency, Fanconi's anemia and sicklemia, lysosomal storage disease such as Gaucher's disease and mucopolysaccharidosis, adrenoleukodystrophy, various kinds of cancers and tumors.

Preferred embodiments of expansion and transfection of hematopoietic stem cells and/or hematopoietic progenitor cells and transplantation of the expanded or transfected hematopoietic stem cells and/or hematopoietic progenitor cells according to the present invention will be described below.

First, for expansion of hematopoietic stem cells and/or hematopoietic progenitor cells, cord blood, bone marrow, peripheral blood or the like is collected, and a cell population enriched with hematopoietic stem cells and/or hematopoietic progenitor cells is separated from it. As such a cell population, $CD34^+$ cells, $CD133^+$ cells may be mentioned. For example, $CD34^+$ cells can be separated by density centrifugation combined with magnetic cell sorting (MACS) or flow cytometry. For example, CPD (citrate-phosphate-dextran)-treated blood is fractioned by density centrifugation to separate and collect a mononuclear cell enriched fraction (hereinafter referred to as nucleated cell fraction). As density centrifugation, dextran or Ficoll density centrifugation, Ficoll-pague density gradient centrifugation, Percoll discontinuous density gradient centrifugation or Lymphoprep density gradient centrifugation may be mentioned. Then, magnetic beads coated with an anti-human CD34 monoclonal antibody (Miltenyi Biotec; hereinafter referred to CD34 antibody magnetic beads) and the collected nucleated cell fraction are mixed and incubated at from 2 to 8° C. (for about 30 minutes) to bind $CD34^+$ cells to the antibody magnetic beads. The antibody magnetic bead/$CD34^+$ cell complexes are separated and collected by a specialized magnetic cell separator such as autoMACS system (Miltenyi Biotec). The $CD34^+$ cells thus obtained are cultured using the low molecular weight compound of the present invention. The conditions, incubator and medium for culturing $CD34^+$ cells, the species and amount of the low molecular weight compound, the kinds and amounts of additives and the incubation time and temperature may be selected appropriately from those disclosed herein by the person in charge, but are not restricted thereto. $CD34^+$ cells are transfected with a gene which is obtained by cloning a target gene into a vector by a standard method in the art, and incubating the vector and $CD34^+$ cells in the presence of the low molecular weight compound of the present invention. The kinds of the target gene and the vector, the transfection method and the culture method may be selected appropriately from those disclosed herein by the person in charge, but are not restricted thereto.

After culturing, the total cell count is measured by trypan blue assay or the like, while the cell culture is stained with an anti CD34 antibody and an anti CD38 antibody labeled with a fluorescent dye such as FITC (fluorescein isothiocyanate), PE (phycoerythrin) or APC (allophycocyanin), and the proportion of CD34⁺CD38⁻ cells is analyzed by flow cytometry. Thus, it is possible to determine how much hematopoietic stem cells and hematopoietic progenitor cells are expanded in the cell culture. The proportion of the least differentiated cells can be determined by subjecting part of the cell culture to colony assay and counting the resulting HPP-CFC colonies. The transgene can be detected by analyzing DNA or RNA extracted from the cells by southern blotting, northern blotting, RT-PCR (Reverse Transcriptase Polymerase Chain Reaction) or the like. The efficiency of transfer of the target gene is determined by detecting the protein expressed by a the transgene by ELISA (Enzyme Linked ImmunoSorvent Assay) or flow cytometry using a specific antibody or by measuring the functional activity of the protein by an enzyme assay.

Expanded or transfected hematopoietic stem cells and/or hematopoietic progenitor cells may be infused by drip, for example, in the case of treatment of leukemia, into patients pretreated with an anticancer drug, total body irradiation or an immunosuppressive drug for eradication of cancer cells or for facilitation of donor cell engraftment. The disease to be treated, the pretreatment and the cell transplantation method are selected appropriately by the person in charge. The engraftment of so transplanted hematopoietic stem cells and/or hematopoietic progenitor cells in the recipient, the recovery of hematopoiesis, the presence of side effects of the transplantation and the therapeutic effect of the transplantation can be judged by an ordinary assay used in transplantation therapy.

As described above, the present invention makes it possible to expand hematopoietic stem cells and/or hematopoietic progenitor cells and to carryout transplantation therapy and gene therapy safely and easily in a short term by using the expanded cells.

Because the method of the present invention can expand hematopoietic stem cells and/or hematopoietic progenitor cells efficiently, the compound of the present invention can be used as a reagent for research on hematopoietic stem cells and/or hematopoietic progenitor cells. For example, in a study to elucidate the factor regulating differentiation and growth of hematopoietic stem cells by identifying the colony forming cells in a culture of hematopoietic stem cells and analyzing the change in cell surface differentiation markers and gene expression, when hematopoietic stem cells are cultured in the presence of a putative factor, addition of the compound of the present invention makes it possible to expand the hematopoietic stem cells and/or hematopoietic progenitor cells to be analyzed efficiently. The incubation conditions, the incubator and the culture medium, the species and amount of the compound of the present invention, the kinds and amounts of additives and the incubation time and temperature used to elucidate such a factor may be selected appropriately from those disclosed herein by the person in charge. The colony forming cells emerging in the culture can be observed under a microscope normally used in the art, optionally after staining them using an antibody specific for the colony forming cells. The change in gene expression caused by such a putative factor can be detected by analyzing DNA or RNA extracted from the cells by southern blotting, northern blotting, RT-PCR or the like. The cell surface differentiation markers can be detected by ELISA or flow cytometry using a specific antibody to examine the effect of the putative factor on differentiation and growth of the cells.

Now, the compound to be used in the present invention will be described in terms of the definitions of terms used for it and its best mode.

In the compound to be used in the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Py" denotes pyridyl, "Naphthyl" denotes naphthyl, "Me" denotes methyl, "Et" denotes ethyl, "Pr" denotes propyl, and "Bu" denotes butyl.

First, the terms in the respective substituents $R^1$ to $R^{13}$ and $V^1$ to $V^5$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned.

A $C_{1-6}$ alkyl group may be linear, branched or a $C_{3-6}$ cycloalkyl group, and as specific examples, in addition to those mentioned above, n-butyl, 1-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-10}$ alkyl group may be linear, branched or a $C_{3-10}$ cycloalkyl group, and as specific examples, in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl and the like may be mentioned.

As a $C_{2-6}$ alkynyl group, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-1-propyl-2-propynyl and the like may be mentioned.

A $C_{2-6}$ alkenyl group may be linear, branched or a $C_{3-6}$ cycloalkenyl group, and as specific examples, ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl and the like may be mentioned.

A $C_{2-14}$ aryl group may be a $C_{6-14}$ aryl group containing no hetero atoms as ring constituting atoms, a $C_{2-9}$ aromatic heterocyclic group or a $C_{2-14}$ fused polycyclic group, and a $C_{2-9}$ aromatic heterocyclic group may be a 5 to 7-membered $C_{2-6}$ heteromonocyclic group or 8 to 10-membered $C_{6-9}$ fused heterobicyclic group containing from 1 to 3 oxygen atoms, nitrogen atoms or sulfur atoms singly or in combination.

As a $C_{6-14}$ aryl group containing no hetero atoms, a phenyl group, a 1-indenyl group, a 2-indenyl group, a 3-indenyl group, a 4-indenyl group, a 5-indenyl group, a 6-indenyl group, a 7-indenyl group, an α-naphthyl group, a 6-naphthyl group, a 1-tetrahydronaphthyl group, a 2-tetrahydronaphthyl group, a 5-tetrahydronaphthyl group, a 6-tetrahydronaphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

As a 5 to 7-membered $C_{2-6}$ heteromonocyclic group, a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 1-1,2,4-triazole group, a 3-1,2,4-triazole group, a 5-1,2,4-triazole group, a 1-1,2,3-triazole group, a 4-1,2,3-triazole group, a 5-1,2,3-triazole group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like may be mentioned.

As a 8 to 10-membered $C_{5-9}$ fused heterocyclic group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pteridinyl group, a 4-pteridinyl group, a 6-pteridinyl group, a 7-pteridinyl group or the like may be mentioned.

A $C_{2-14}$ fused polycyclic group is a fused bicyclic or fused tricyclic group consisting of a $C_{6-14}$ aryl group containing no hetero atoms and at most 12 carbon atoms as mentioned above or a C$_{2-9}$ aromatic heterocyclic group fused with a C$_{2-9}$ heterocyclyl group, and:

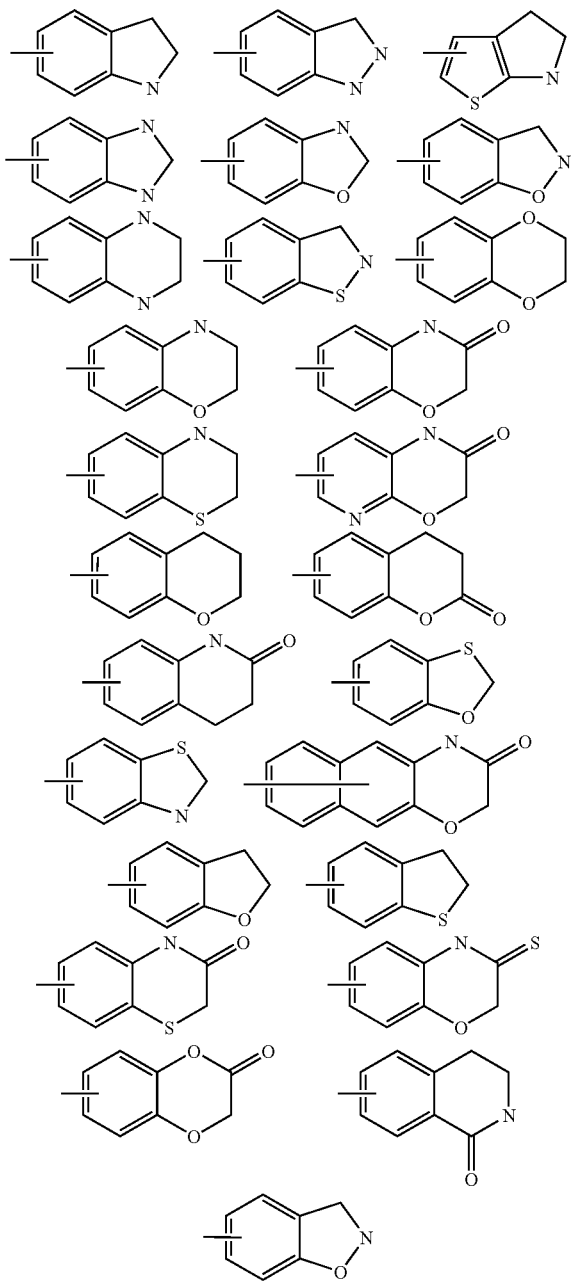

may be mentioned specifically.

An N-oxide of an nitrogen-containing C$_{2-14}$ aryl group is a group obtained by oxidizing a nitrogen atom in the C$_{2-14}$ aryl group with oxygen, and specifically, a 1-pyrrole-N-oxide group, a 2-pyrrole-N-oxide group, 3-pyrrole-N-oxide, a 1-imidazole-N-oxide group, a 2-imidazole-N-oxide group, a 4-imidazole-N-oxide group, a 1-pyrazole-N-oxide group, a 3-pyrazole-N-oxide group, a 4-pyrazole-N-oxide group, a 2-thiazole-N-oxide group, a 4-thiazole-N-oxide group, a 5-thiazole-N-oxide group, a 3-isothiazole-N-oxide group, a 4-isothiazole-N-oxide group, a 5-isothiazole-N-oxide group, a 2-oxazole-N-oxide group, a 4-oxazole-N-oxide group, a 5-oxazole-N-oxide group, a 3-isooxazole-N-oxide group, a 4-isooxazole-N-oxide group, a 5-isooxazole-N-oxide group, a 2-pyridine-N-oxide group, a 3-pyridine-N-oxide group, a 4-pyridine-N-oxide group or the like may be mentioned.

A C$_{1-10}$ alkylcarbonyl group may linear, branched or a C$_{3-10}$ cycloalkylcarbonyl group, and as specific examples, methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl, 1-methyl-1-ethyl-n-pentylcarbonyl, 1-heptylcarbonyl, 2-heptylcarbonyl, 1-ethyl-1,2-dimethyl-n-propylcarbonyl, 1-ethyl-2,2-dimethyl-n-propylcarbonyl, 1-octylcarbonyl, 3-octylcarbonyl, 4-methyl-3-n-heptylcarbonyl, 6-methyl-2-n-heptylcarbonyl, 2-propyl-1-n-heptylcarbonyl, 2,4,4-trimethyl-1-n-pentylcarbonyl, 1-nonylcarbonyl, 2-nonylcarbonyl, 2,6-dimethyl-4-n-heptylcarbonyl, 3-ethyl-2,2-dimethyl-3-n-pentylcarbonyl, 3,5,5-trimethyl-1-n-hexylcarbonyl, 1-decylcarbonyl, 2-decylcarbonyl, 4-decylcarbonyl, 3,7-dimethyl-1-n-octylcarbonyl, 3,7-dimethyl-3-n-octylcarbonyl or the like may be mentioned.

A C$_{1-10}$ thioalkyl group may linear, branched or a C$_{3-10}$ cyclothioalkyl group, and as specific examples, methylthio, ethylthio, n-propylthio, i-propylthio, c-propylthio, n-butylthio, i-butylthio, s-butylthio, t-butylthio, c-butylthio, 1-methyl-c-propylthio, 2-methyl-c-propylthio, n-pentylthio, 1-methyl-n-butylthio, 2-methyl-n-butylthio, 3-methyl-n-butylthio, 1,1-dimethyl-n-propylthio, 1,2-dimethyl-n-propylthio, 2,2-dimethyl-n-propylthio, 1-ethyl-n-propylthio, c-pentylthio, 1-methyl-c-butylthio, 2-methyl-c-butylthio, 3-methyl-c-butylthio, 1,2-dimethyl-c-propylthio, 2,3-dimethyl-c-propylthio, 1-ethyl-c-propylthio, 2-ethyl-c-propylthio, n-hexylthio, 1-methyl-n-pentylthio, 2-methyl-n-pentylthio, 3-methyl-n-pentylthio, 4-methyl-n-pentylthio, 1,1-dimethyl-n-butylthio, 1,2-dimethyl-n-butylthio, 1,3-dimethyl-n-butylthio, 2,2-dimethyl-n-butylthio, 2,3-dimethyl-n-butylthio, 3,3-dimethyl-n-butylthio, 1-ethyl-n-butylthio, 2-ethyl-n-butylthio, 1,1,2-trimethyl-n-propylthio, 1,2,2-trimethyl-n-propylthio, 1-ethyl-1-methyl-n-propylthio, 1-ethyl-2-methyl-n-propylthio, c-hexylthio, 1-methyl-c-pentylthio, 2-methyl-c-pentylthio, 3-methyl-c-pentylthio, 1-ethyl-c-butylthio, 2-ethyl-c-butylthio, 3-ethyl-c-butylthio, 1,2-dimethyl-c-butylthio, 1,3-dimethyl-c-butylthio, 2,2-dimethyl-c-butylthio, 2,3-dimethyl-c-butylthio, 2,4-dimethyl-c-butylthio, 3,3-dimethyl-c-butylthio, 1-n-propyl-c-propylthio, 2-n-propyl-c-propylthio, 1-i-propyl-c-propylthio, 2-i-propyl-c-propylthio, 1,2,2-trimethyl-c-propylthio, 1,2,3-trimethyl-c-propylthio, 2,2,3-trimethyl-c-propylthio, 1-ethyl-2-methyl-c-propylthio, 2-ethyl-1-methyl-c-propylthio, 2-ethyl-2-methyl-c-propylthio, 2-ethyl-3-methyl-c-propylthio, 1-methyl-1-ethyl-n-pentylthio, 1-heptylthio, 2-heptylthio, 1-ethyl-1,2-dimethyl-n-propylthio, 1-ethyl-2,2-dimethyl-n-propylthio, 1-octylthio, 3-octylthio, 4-methyl-3-n-heptylthio, 6-methyl-2-n-heptylthio, 2-propyl-1-n-heptylthio, 2,4,4-trimethyl-1-n-pentylthio, 1-nonylthio, 2-nonylthio, 2,6-dimethyl-4-n-heptylthio, 3-ethyl-2,2-dimethyl-3-n-pentylthio, 3,5,5-trimethyl-1-n-hexylthio, 1-decylthio, 2-decylthio, 4-decylthio, 3,7-dimethyl-1-n-octylthio, 3,7-dimethyl-3-n-octylthio or the like may be mentioned.

A $C_{1-3}$ alkylsulfonyl group may be linear, branched or a $C_3$ cycloalkylsulfonyl group, and as specific examples, methylsulfonyl, ethylsulfonyl, n-propylsulfonyl, propylsulfonyl, c-propylsulfonyl or the like may be mentioned.

A $C_{1-10}$ alkylsulfonyl group may be linear, branched or a $C_{3-10}$ cycloalkylsulfonyl group, and as specific examples, in addition to those mentioned above, n-butylsulfonyl, i-butylsulfonyl, s-butylsulfonyl, t-butylsulfonyl, c-butylsulfonyl, 1-methyl-c-propylsulfonyl, 2-methyl-c-propylsulfonyl, n-pentylsulfonyl, 1-methyl-n-butylsulfonyl, 2-methyl-n-butylsulfonyl, 3-methyl-n-butylsulfonyl, 1,1-dimethyl-n-propylsulfonyl, 1,2-dimethyl-n-propylsulfonyl, 2,2-dimethyl-n-propylsulfonyl, 1-ethyl-n-propylsulfonyl, c-pentylsulfonyl, 1-methyl-c-butylsulfonyl, 2-methyl-c-butylsulfonyl, 3-methyl-c-butylsulfonyl, 1,2-dimethyl-c-propylsulfonyl, 2,3-dimethyl-c-propylsulfonyl, 1-ethyl-c-propylsulfonyl, 2-ethyl-c-propylsulfonyl, n-hexylsulfonyl, 1-methyl-n-pentylsulfonyl, 2-methyl-n-pentylsulfonyl, 3-methyl-n-pentylsulfonyl, 4-methyl-n-pentylsulfonyl, 1,1-dimethyl-n-butylsulfonyl, 1,2-dimethyl-n-butylsulfonyl, 1,3-dimethyl-n-butylsulfonyl, 2,2-dimethyl-n-butylsulfonyl, 2,3-dimethyl-n-butylsulfonyl, 3,3-dimethyl-n-butylsulfonyl, 1-ethyl-n-butylsulfonyl, 2-ethyl-n-butylsulfonyl, 1,1,2-trimethyl-n-propylsulfonyl, 1,2,2-trimethyl-n-propylsulfonyl, 1-ethyl-1-methyl-n-propylsulfonyl, 1-ethyl-2-methyl-n-propylsulfonyl, c-hexylsulfonyl, 1-methyl-c-pentylsulfonyl, 2-methyl-c-pentylsulfonyl, 3-methyl-c-pentylsulfonyl, 1-ethyl-c-butylsulfonyl, 2-ethyl-c-butylsulfonyl, 3-ethyl-c-butylsulfonyl, 1,2-dimethyl-c-butylsulfonyl, 1,3-dimethyl-c-butylsulfonyl, 2,2-dimethyl-c-butylsulfonyl, 2,3-dimethyl-c-butylsulfonyl, 2,4-dimethyl-c-butylsulfonyl, 3,3-dimethyl-c-butylsulfonyl, 1-n-propyl-c-propylsulfonyl, 2-n-propyl-c-propylsulfonyl, 1-i-propyl-c-propylsulfonyl, 2-1-propyl-c-propylsulfonyl, 1,2,2-trimethyl-c-propylsulfonyl, 1,2,3-trimethyl-c-propylsulfonyl, 2,2,3-trimethyl-c-propylsulfonyl, 1-ethyl-2-methyl-c-propylsulfonyl, 2-ethyl-1-methyl-c-propylsulfonyl, 2-ethyl-2-methyl-c-propylsulfonyl, 2-ethyl-3-methyl-c-propylsulfonyl, 1-methyl-1-ethyl-n-pentylsulfonyl, 1-heptylsulfonyl, 2-heptylsulfonyl, 1-ethyl-1,2-dimethyl-n-propylsulfonyl, 1-ethyl-2,2-dimethyl-n-propylsulfonyl, 1-octylsulfonyl, 3-octylsulfonyl, 4-methyl-3-n-heptylsulfonyl, 6-methyl-2-n-heptylsulfonyl, 2-propyl-1-n-heptylsulfonyl, 2,4,4-trimethyl-1-n-pentylsulfonyl, 1-nonylsulfonyl, 2-nonylsulfonyl, 2,6-dimetyl-4-n-heptylsulfonyl, 3-ethyl-2,2-dimethyl-3-n-pentylsulfonyl, 3,5,5-trimethyl-1-n-hexylsulfonyl, 1-decylsulfonyl, 2-decylsulfonyl, 4-decylsulfonyl, 3,7-dimethyl-1-n-octylsulfonyl, 3,7-dimethyl-3-n-octylsulfonyl or the like may be mentioned.

A $C_{1-10}$ alkylsulfonylamino group may be linear, branched or a $C_{3-10}$ cycloalkylsulfonylamino group, and as specific examples, methylsulfonylamino, ethylsulfonylamino, n-propylsulfonylamino, i-propylsulfonylamino, c-propylsulfonylamino, n-butylsulfonylamino, i-butylsulfonylamino, s-butylsulfonylamino, t-butylsulfonylamino, c-butylsulfonylamino, 1-methyl-c-propylsulfonylamino, 2-methyl-c-propylsulfonylamino, n-pentylsulfonylamino, 1-methyl-n-butylsulfonylamino, 2-methyl-n-butylsulfonylamino, 3-methyl-n-butylsulfonylamino, 1,1-dimethyl-n-propylsulfonylamino, 1,2-dimethyl-n-propylsulfonylamino, 2,2-dimethyl-n-propylsulfonylamino, 1-ethyl-n-propylsulfonylamino, c-pentylsulfonylamino, 1-methyl-c-butylsulfonylamino, 2-methyl-c-butylsulfonylamino, 3-methyl-c-butylsulfonylamino, 1,2-dimethyl-c-propylsulfonylamino, 2,3-dimethyl-c-propylsulfonylamino, 1-ethyl-c-propylsulfonylamino, 2-ethyl-c-propylsulfonylamino, n-hexylsulfonylamino, 1-methyl-n-pentylsulfonylamino, 2-methyl-n-pentylsulfonylamino, 3-methyl-n-pentylsulfonylamino, 4-methyl-n-pentylsulfonylamino, 1,1-dimethyl-n-butylsulfonylamino, 1,2-dimethyl-n-butylsulfonylamino, 1,3-dimethyl-n-butylsulfonylamino, 2,2-dimethyl-n-butylsulfonylamino, 2,3-dimethyl-n-butylsulfonylamino, 3,3-dimethyl-n-butylsulfonylamino, 1-ethyl-n-butylsulfonylamino, 2-ethyl-n-butylsulfonylamino, 1,1,2-trimethyl-n-propylsulfonylamino, 1,2,2-trimethyl-n-propylsulfonylamino, 1-ethyl-1-methyl-n-propylsulfonylamino, 1-ethyl-2-methyl-n-propylsulfonylamino, c-hexylsulfonylamino, 1-methyl-c-pentylsulfonylamino, 2-methyl-c-pentylsulfonylamino, 3-methyl-c-pentylsulfonylamino, 1-ethyl-c-butylsulfonylamino, 2-ethyl-c-butylsulfonylamino, 3-ethyl-c-butylsulfonylamino, 1,2-dimethyl-c-butylsulfonylamino, 1,3-dimethyl-c-butylsulfonylamino, 2,2-dimethyl-c-butylsulfonylamino, 2,3-dimethyl-c-butylsulfonylamino, 2,4-dimethyl-c-butylsulfonylamino, 3,3-dimethyl-c-butylsulfonylamino, 1-n-propyl-c-propylsulfonylamino, 2-n-propyl-c-propylsulfonylamino, 1-i-propyl-c-propylsulfonylamino, 2-i-propyl-c-propylsulfonylamino, 1,2,2-trimethyl-c-propylsulfonylamino, 1,2,3-trimethyl-c-propylsulfonylamino, 2,2,3-trimethyl-c-propylsulfonylamino, 1-ethyl-2-methyl-c-propylsulfonylamino, 2-ethyl-1-methyl-c-propylsulfonylamino, 2-ethyl-2-methyl-c-propylsulfonylamino, 2-ethyl-3-methyl-c-propylsulfonylamino, 1-methyl-1-ethyl-n-pentylsulfonylamino, 1-heptylsulfonylamino, 2-heptylsulfonylamino, 1-ethyl-1,2-dimethyl-n-propylsulfonylamino, 1-ethyl-2,2-dimethyl-n-propylsulfonylamino, 1-octylsulfonylamino, 3-octylsulfonylamino, 4-methyl-3-n-heptylsulfonylamino, 6-methyl-2-n-heptylsulfonylamino, 2-propyl-1-n-heptylsulfonylamino, 2,4,4-trimethyl-1-n-pentylsulfonylamino, 1-nonylsulfonylamino, 2-nonylsulfonylamino, 2,6-dimethyl-4-n-heptylsulfonylamino, 3-ethyl-2,2-dimethyl-3-n-pentylsulfonylamino, 3,5,5-trimethyl-1-n-hexylsulfonylamino, 1-decylsulfonylamino, 2-decylsulfonylamino, 4-decylsulfonylamino, 3,7-dimethyl-1-n-octylsulfonylamino, 3,7-dimethyl-3-n-octylsulfonylamino, c-heptylsulfonylamino, c-octylsulfonylamino, 1-methyl-c-hexylsulfonylamino, 2-methyl-c-hexylsulfonylamino, 3-methyl-c-hexylsulfonylamino, 1,2-dimethyl-c-hexylsulfonylamino, 1-ethyl-c-hexylsulfonylamino, 1-methyl-c-pentylsulfonylamino, 2-methyl-c-pentylsulfonylamino, 3-methyl-c-pentylsulfonylamino or the like may be mentioned.

A $C_{1-3}$ alkoxy group may be linear, branched or a $C_3$ cycloalkoxy group, and as specific examples, methoxy, ethoxy, n-propoxy, i-propoxy, c-propoxy or the like may be mentioned.

A $C_{1-10}$ alkoxy group may be linear, branched or a $C_{3-10}$ cycloalkoxy group, and as specific examples, in addition to those mentioned above, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy, 1-methyl-1-ethyl-n-pentyloxy, 1-heptyloxy, 2-heptyloxy, 1-ethyl-1,2-dimethyl-n-propyloxy, 1-ethyl-2,2-dimethyl-n-propyloxy, 1-octyloxy, 3-octyloxy, 4-methyl-3-n-heptyloxy, 6-methyl-2-n-heptyloxy, 2-propyl-1-n-heptyloxy, 2,4,4-trimethyl-1-n-pentyloxy, 1-nonyloxy, 2-nonyloxy, 2,6-dimethyl-4-n-heptyloxy, 3-ethyl-2,2-dimethyl-3-n-pentyloxy, 3,5,5-trimethyl-1-n-hexyloxy, 1-decyloxy, 2-decyloxy, 4-decyloxy, 3,7-dimethyl-1-n-octyloxy, 3,7-dimethyl-3-n-octyloxy or the like may be mentioned.

A $C_{1-10}$ alkoxycarbonyl group may be linear, branched or a $C_{3-10}$ cycloalkoxycarbonyl group, and as specific examples, methoxycarbonyl, ethoxycarbonyl, n-propoxycarbonyl, i-propoxycarbonyl, c-propoxycarbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i-propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl, 1-methyl-1-ethyl-n-pentyloxycarbonyl, 1-heptyloxycarbonyl, 2-heptyloxycarbonyl, 1-ethyl-1,2-dimethyl-n-propyloxycarbonyl, 1-ethyl-2,2-dimethyl-n-propyloxycarbonyl, 1-octyloxycarbonyl, 3-octyloxycarbonyl, 4-methyl-3-n-heptyloxycarbonyl, 6-methyl-2-n-heptyloxycarbonyl, 2-propyl-1-n-heptyloxycarbonyl, 2,4,4-trimethyl-1-n-pentyloxycarbonyl, 1-nonyloxycarbonyl, 2-nonyloxycarbonyl, 2,6-dimethyl-4-n-heptyloxycarbonyl, 3-ethyl-2,2-dimethyl-3-n-pentyloxycarbonyl, 3,5,5-trimethyl-1-n-hexyloxycarbonyl, 1-decyloxycarbonyl, 2-decyloxycarbonyl, 4-decyloxycarbonyl, 3,7-dimethyl-1-n-octyloxycarbonyl, 3,7-dimethyl-3-n-octyloxycarbonyl or the like may be mentioned.

A $C_{1-10}$ alkylcarbonyloxy group may be linear, branched or a $C_{3-10}$ cycloalkylcarbonyloxy group, and as specific examples, methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3-dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-trimethyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonylxoy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propylcarbonyloxy, 1-i-propyl-c-propylcarbonyloxy, 2-i-propyl-c-propylcarbonyloxy, 1,2,2-trimethyl-c-propylcarbonyloxy, 1,2,3-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c- propylcarbonyloxy, 2-ethyl-3-methyl-c-propylcarbonyloxy, 1-methyl-1-ethyl-n-pentylcarbonyloxy, 1-heptylcarbonyloxy, 2-heptylcarbonyloxy, 1-ethyl-1,2-dimethyl-n-propylcarbonyloxy, 1-ethyl-2,2-dimethyl-n-propylcarbonyloxy, 1-octylcarbonyloxy, 3-octylcarbonyloxy, 4-methyl-3-n-heptylcarbonyloxy, 6-methyl-2-n-heptylcarbonyloxy, 2-propyl-1-n-heptylcarbonyloxy, 2,4,4-trimethyl-1-n-pentylcarbonyloxy, 1-nonylcarbonyloxy, 2-nonylcarbonyloxy, 2,6-dimethyl-4-n-heptylcarbonyloxy, 3-ethyl-2,2-dimethyl-3-n-pentylcarbonyloxy, 3,5,5-trimethyl-1-n-hexylcarbonyloxy, 1-decylcarbonyloxy, 2-decylcarbonyloxy, 4-decylcarbonyloxy, 3,7-dimethyl-1-n-octylcarbonyloxy, 3,7-dimethyl-3-n-octylcarbonyloxy or the like may be mentioned.

A $C_{1-10}$ alkylcarbonylamino group may be linear, branched or a $C_{3-10}$ cycloalkylcarbonylamino group, and as specific examples, methylcarbonylamino, ethylcarbonylamino, n-propylcarbonylamino, i-propylcarbonylamino, c-propylcarbonylamino, n-butylcarbonylamino, i-butylcarbonylamino, s-butylcarbonylamino, t-butylcarbonylamino, c-butylcarbonylamino, 1-methyl-c-propylcarbonylamino, 2-methyl-c-propylcarbonylamino, n-pentylcarbonylamino, 1-methyl-n-butylcarbonylamino, 2-methyl-n-butylcarbonylamino, 3-methyl-n-butylcarbonylamino, 1,1-dimethyl-n-propylcarbonylamino, 1,2-dimethyl-n-propylcarbonylamino, 2,2-dimethyl-n-propylcarbonylamino, 1-ethyl-n-propylcarbonylamino, c-pentylcarbonylamino, 1-methyl-c-butylcarbonylamino, 2-methyl-c-butylcarbonylamino, 3-methyl-c-butylcarbonylamino, 1,2-dimethyl-c-propylcarbonylamino, 2,3-dimethyl-c-propylcarbonylamino, 1-ethyl-c-propylcarbonylamino, 2-ethyl-c-propylcarbonylamino, n-hexylcarbonylamino, 1-methyl-n-pentylcarbonylamino, 2-methyl-n-pentylcarbonylamino, 3-methyl-n-pentylcarbonylamino, 4-methyl-n-pentylcarbonylamino, 1,1-dimethyl-n-butylcarbonylamino, 1,2-dimethyl-n-butylcarbonylamino, 1,3-dimethyl-n-butylcarbonylamino, 2,2-dimethyl-n-butylcarbonylamino, 2,3-dimethyl-n-butylcarbonylamino, 3,3-dimethyl-n-butylcarbonylamino, 1-ethyl-n-butylcarbonylamino, 2-ethyl-n-butylcarbonylamino, 1,1,2-trimethyl-n-propylcarbonylamino, 1,2,2-trimethyl-n-propylcarbonylamino, 1-ethyl-1-methyl-n-propylcarbonylamino, 1-ethyl-2-methyl-n-propylcarbonylamino, c-hexylcarbonylamino, 1-methyl-c-pentylcarbonylamino, 2-methyl-c-pentylcarbonylamino, 3-methyl-c-pentylcarbonylamino, 1-ethyl-c-butylcarbonylamino, 2-ethyl-c-butylcarbonylamino, 3-ethyl-c-butylcarbonylamino, 1,2-dimethyl-c-butylcarbonylamino, 1,3-dimethyl-c-butylcarbonylamino, 2,2-dimethyl-c-butylcarbonylamino, 2,3-dimethyl-c-butylcarbonylamino, 2,4-dimethyl-c-butylcarbonylamino, 3,3-dimethyl-c-butylcarbonylamino, 1-n-propyl-c-propylcarbonylamino, 2-n-propyl-c-propylcarbonylamino, 1-i-propyl-c-propylcarbonylamino, 2-i-propyl-c-propylcarbonylamino, 1,2,2-trimethyl-c-propylcarbonylamino, 1,2,3-trimethyl-c-propylcarbonylamino, 2,2,3-trimethyl-c-propylcarbonylamino, 1-ethyl-2-methyl-c-propylcarbonylamino, 2-ethyl-1-methyl-c-propylcarbonylamino, 2-ethyl-2-methyl-c-propylcarbonylamino, 2-ethyl-3-methyl-c-propylcarbonylamino, 1-methyl-1-ethyl-n-pentylcarbonylamino, 1-heptylcarbonylamino, 2-heptylcarbonylamino, 1-ethyl-1,2-dimethyl-n-propylcarbonylamino, 1-ethyl-2,2-dimethyl-n-propylcarbonylamino, 1-octylcarbonylamino, 3-octylcarbonylamino, 4-methyl-3-n-heptylcarbonylamino, 6-methyl-2-n-heptylcarbonylamino, 2-propyl-1-n-heptylcarbonylamino, 2,4,4-trimethyl-1-n-pentylcarbonylamino, 1-nonylcarbonylamino, 2-nonylcarbonylamino, 2,6-dimethyl-4-n-heptylcarbonylamino, 3-ethyl-2,2-dimethyl-3-n-pentylcarbonylamino, 3,5,5-trimethyl-1-n-hexylcarbonylamino, 1-decylcarbonylamino, 2-decylcarbonylamino, 4-decylcarbonylamino, 3,7-dimethyl-1-n-octylcarbonylamino, 3,7-dimethyl-3-n-octylcarbonylamino or the like may be mentioned.

A $C_{1-10}$ monoalkylamino group may be linear, branched or a $C_{3-10}$ cycloalkylamino group, and specific examples, methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n-pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2-ethyl-3-methyl-c-propylamino, 1-methyl-1-ethyl-n-pentylamino, 1-heptylamino, 2-heptylamino, 1-ethyl-1,2-dimethyl-n-propylamino, 1-ethyl-2,2-dimethyl-n-propylamino, 1-octylamino, 3-octylamino, 4-methyl-3-n-heptylamino, 6-methyl-2-n-heptylamino, 2-propyl-1-n-heptylamino, 2,4,4-trimethyl-1-n-pentylamino, 1-nonylamino, 2-nonylamino, 2,6-dimethyl-4-n-heptylamino, 3-ethyl-2,2-dimethyl-3-n-pentylamino, 3,5,5-trimethyl-1-n-hexylamino, 1-decylamino, 2-decylamino, 4-decylamino, 3,7-dimethyl-1-n-octylamino, 3,7-dimethyl-3-n-octylamino or the like may be mentioned.

A di-$C_{1-10}$ alkylamino group may be symmetric or asymmetric. A symmetric di-$C_{1-10}$ alkylamino group may be linear, branched or a $C_{3-10}$ cycloalkylamino group, and as specific examples, dimethylamino, diethylamino, di-n-propylamino, di-i-propylamino, di-c-propylamino, di-n-butylamino, di-i-butylamino, di-s-butylamino, di-t-butylamino, di-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2-dimethyl-n-propyl)amino, di-(1-ethyl-n-propyl)amino, di-c-pentylamino, di-(1-methyl-c-butyl)amino, di-(2-methyl-c-butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, di-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(1, 3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-c-propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, di-(1,2,3-trimethyl-c-propyl)amino, di-(2,2,3-trimethyl-c-propyl)amino, di-(1-ethyl-2-methyl-c-propyl)amino, di-(2-ethyl-1-methyl-c-propyl)amino, di-(2-ethyl-2-methyl-c-propyl)amino, di-(2-ethyl-3-methyl-c-propyl)amino, di-(1-methyl-1-ethyl-n-pentyl)amino, di-(1-heptyl)amino, di-(2-heptyl)amino, di-(1-ethyl-1,2-dimethyl-n-propyl)amino, di-(1-ethyl-2,2-dimethyl-n-propyl)amino, di-(1-octyl)amino, di-(3-octyl)amino, di-(4-methyl-3-n-heptyl)amino, di-(6-methyl-2-n-heptyl)amino, di-(2-propyl-1-n-heptyl)amino, di-(2,4,4-trimethyl-1-n-pentyl)amino, di-(1-nonyl)amino, di-(2-nonyl)amino, di-(2,6-dimethyl-4-n-heptyl)amino, di-(3-ethyl-2,2-dimethyl-3-n-pentyl)amino, di-(3,5,5-trimethyl-1-n-hexyl)amino, di-(1-decyl)amino, di-(2-decyl)amino, di-(4-decyl)amino, di-(3,7-dimethyl-1-n-octyl)amino, di-(3,7-dimethyl-3-n-octyl)amino or the like may be mentioned.

An asymmetric di-$C_{1-10}$ alkylamino group may be linear, branched or a $C_{3-10}$ cycloalkylamino group, and as specific examples, (methyl, ethyl)amino, (methyl, n-propyl)amino, (methyl, i-propyl)amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl)amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl)amino, (ethyl, c-pentyl)amino, (ethyl, n-hexyl)amino, (ethyl, c-hexyl)amino, (n-propyl, i-propyl)amino, (n-propyl, c-propyl)amino, (n-propyl, n-butyl)amino, (n-propyl, i-butyl)amino, (n-propyl, s-butyl)amino, (n-propyl, t-butyl)amino, (n-propyl, n-pentyl)amino, (n-propyl, c-pentyl)amino, (n-propyl, n-hexyl)amino, (n-propyl, c-hexyl)amino, (i-propyl, c-propyl)amino, (i-propyl, n-butyl)amino, (i-propyl, i-butyl)amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (c-propyl, n-butyl)amino, (c-propyl, i-butyl)amino, (c-propyl, s-butyl)amino, (c-propyl, t-butyl)amino, (c-propyl, n-pentyl)amino, (c-propyl, c-pentyl)amino, (c-propyl, n-hexyl)amino, (c-propyl, c-hexyl)amino, (n-butyl, i-butyl)amino, (n-butyl, s-butyl)amino, (n-butyl, t-butyl)amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl)amino, (i-butyl, n-pentyl)amino, (i-butyl, c-pentyl)amino, (i-butyl, n-hexyl)amino, (i-butyl, c-hexyl)amino, (s-butyl, t-butyl)amino, (s-butyl, n-pentyl)amino, (s-butyl, c-pentyl)amino, (s-butyl, n-hexyl)amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl)amino, (n-pentyl, n-hexyl)amino, (n-pentyl, c-hexyl)amino, (c-pentyl, n-hexyl)amino, (c-pentyl, c-hexyl)amino, (n-hexyl, c-hexyl) amino, (methyl, n-heptyl)amino, (methyl, n-octyl)amino, (methyl, n-nonanyl)amino, (methyl, n-decyl)amino, (ethyl, n-heptyl)amino, (ethyl, n-octyl)amino, (ethyl, n-nonanyl) amino, (ethyl, n-decyl)amino or the like may be mentioned.

A $C_{1-10}$ alkylaminocarbonyl group may be linear, branched or a $C_{1-10}$ cycloalkylaminocarbonyl group and may be a di-$C_{1-10}$ alkylaminocarbonyl group, and as specific examples, methylaminocarbonyl, ethylaminocarbonyl, n-propylaminocarbonyl, i-propylaminocarbonyl, c-propylaminocarbonyl, n-butylaminocarbonyl, i-butylaminocarbonyl, s-butylaminocarbonyl, t-butylaminocarbonyl, c-butylaminocarbonyl, 1-methyl-c-propylaminocarbonyl, 2-methyl-c-propylaminocarbonyl, n-pentylaminocarbonyl, 1-methyl-n-butylaminocarbonyl, 2-methyl-n-butylaminocarbonyl, 3-methyl-n-butylaminocarbonyl, 1,1-dimethyl-n-propylaminocarbonyl, 1,2-dimethyl-n-propylaminocarbonyl, 2,2-dimethyl-n-propylaminocarbonyl, 1-ethyl-n-propylaminocarbonyl, c-pentylaminocarbonyl, 1-methyl-c-butylaminocarbonyl, 2-methyl-c-butylaminocarbonyl, 3-methyl-c-butylaminocarbonyl, 1,2-dimethyl-c-propylaminocarbonyl, 2,3-dimethyl-c-propylaminocarbonyl, 1-ethyl-c-propylaminocarbonyl, 2-ethyl-c-propylaminocarbonyl, n-hexylaminocarbonyl, 1-methyl-n-pentylaminocarbonyl, 2-methyl-n-pentylaminocarbonyl, 3-methyl-n-pentylaminocarbonyl, 4-methyl-n-pentylaminocarbonyl, 1,1-dimethyl-n-butylaminocarbonyl, 1,2-dimethyl-n-butylaminocarbonyl, 1,3-dimethyl-n-butylaminocarbonyl, 2,2-dimethyl-n-butylaminocarbonyl, 2,3-dimethyl-n-butylaminocarbonyl, 3,3-dimethyl-n-butylaminocarbonyl, 1-ethyl-n-butylaminocarbonyl, 2-ethyl-n-butylaminocarbonyl, 1,1,2-trimethyl-n-propylaminocarbonyl, 1,2,2-trimethyl-n-propylaminocarbonyl, 1-ethyl-1-methyl-n-propylaminocarbonyl, 1-ethyl-2-methyl-n-propylaminocarbonyl, c-hexylaminocarbonyl, 1-methyl-c-pentylaminocarbonyl, 2-methyl-c-pentylaminocarbonyl, 3-methyl-c-pentylaminocarbonyl, 1-ethyl-c-butylaminocarbonyl, 2-ethyl-c-butylaminocarbonyl, 3-ethyl-c-butylaminocarbonyl, 1,2-dimethyl-c-butylaminocarbonyl, 1,3-dimethyl-c-butylaminocarbonyl, 2,2-dimethyl-c-butylaminocarbonyl, 2,3-dimethyl-c-butylaminocarbonyl, 2,4-dimethyl-c-butylaminocarbonyl, 3,3-dimethyl-c-butylaminocarbonyl, 1-n-propyl-c-propylaminocarbonyl, 2-n-propyl-c-propylaminocarbonyl, 1-i-propyl-c-propylaminocarbonyl, 2-i-propyl-c-propylaminocarbonyl, 1,2,2-trimethyl-c-propylaminocarbonyl, 1,2,3-trimethyl-c-propylaminocarbonyl, 2,2,3-trimethyl-c-propylaminocarbonyl, 1-ethyl-2-methyl-c-propylaminocarbonyl, 2-ethyl-1-methyl-c-propylaminocarbonyl, 2-ethyl-2-methyl-c-propylaminocarbonyl, 2-ethyl-3-methyl-c-propylaminocarbonyl, 1-methyl-1-ethyl-n-pentylaminocarbonyl, 1-heptylaminocarbonyl, 2-heptylaminocarbonyl, 1-ethyl-1,2-dimethyl-n-propylaminocarbonyl, 1-ethyl-2,2-dimethyl-n-propylaminocarbonyl, 1-octylaminocarbonyl, 3-octylaminocarbonyl, 4-methyl-3-n-heptylaminocarbonyl, 6-methyl-2-n-heptylaminocarbonyl, 2-propyl-1-n-heptylaminocarbonyl, 2,4,4-trimethyl-1-n-pentylaminocarbonyl, 1-nonylaminocarbonyl, 2-nonylaminocarbonyl, 2,6-dimethyl-4-n-heptylaminocarbonyl, 3-ethyl-2,2-dimethyl-3-n-pentylaminocarbonyl, 3,5,5-trimethyl-1-n-hexylaminocarbonyl, 1-decylaminocarbonyl, 2-decylaminocarbonyl, 4-decylaminocarbonyl, 3,7-dimethyl-1-n-octylaminocarbonyl, 3,7-dimethyl-3-n-octylaminocarbonyl or the like may be mentioned.

A di-$C_{1-10}$ alkylaminocarbonyl group may be symmetric or asymmetric. A symmetric di-$C_{1-10}$ alkylaminocarbonyl group may be linear, branched or a $C_{3-10}$ cycloalkylaminocarbonyl group, and as specific examples, dimethylaminocarbonyl, diethylaminocarbonyl, di-n-propylaminocarbonyl, di-i-propylaminocarbonyl, di-c-propylaminocarbonyl, di-n-butylaminocarbonyl, di-i-butylaminocarbonyl, di-s-butylaminocarbonyl, di-t-butylaminocarbonyl, di-c-butylaminocarbonyl, di-(1-methyl-c-propyl)aminocarbonyl, di-(2-methyl-c-propyl)aminocarbonyl, di-n-pentylaminocarbonyl, di-(1-methyl-n-butyl)aminocarbonyl, di-(2-methyl-n-butyl)aminocarbonyl, di-(3-methyl-n-butyl)aminocarbonyl, di-(1,1-dimethyl-n-propyl)aminocarbonyl, di-(1,2-dimethyl-n-propyl)aminocarbonyl, di-(2,2-dimethyl-n-propyl)aminocarbonyl, di-(1-ethyl-n-propyl)aminocarbonyl, di-c-pentylaminocarbonyl, di-(1-methyl-c-butyl)aminocarbonyl, di-(2-methyl-c-butyl)aminocarbonyl, di-(3-methyl-c-butyl)aminocarbonyl, di-(1,2-dimethyl-c-propyl)aminocarbonyl, di-(2,3-dimethyl-c-propyl)aminocarbonyl, di-(1-ethyl-c-propylaminocarbonyl, di-(2-ethyl-c-propyl)aminocarbonyl, di-n-hexylaminocarbonyl, di-(1-methyl-n-pentyl)aminocarbonyl, di-(2-methyl-n-pentyl)aminocarbonyl, di-(3-methyl-n-pentyl)aminocarbonyl, di-(4-methyl-n-pentyl)aminocarbonyl, di-(1,1-dimethyl-n-butyl)aminocarbonyl, di-(1,2-dimethyl-n-butyl)aminocarbonyl, di-(1,3-dimethyl-n-butyl)aminocarbonyl, di-(2,2-dimethyl-n-butyl)aminocarbonyl, di-(2,3-dimethyl-n-butyl)aminocarbonyl, di-(3,3-dimethyl-n-butyl)aminocarbonyl, di-(1-ethyl-n-butyl)aminocarbonyl, di-(2-ethyl-n-butyl)aminocarbonyl, di-(1,1,2-trimethyl-n-propyl)aminocarbonyl, di-(1,2,2-trimethyl-n-propyl)aminocarbonyl, di-(1-ethyl-1-methyl-n-propyl)aminocarbonyl, di-(1-ethyl-2-methyl-n-propyl)aminocarbonyl, di-c-hexylaminocarbonyl, di-(1-methyl-c-pentyl)aminocarbonyl, di-(2-methyl-c-pentyl)aminocarbonyl, di-(3-methyl-c-pentyl)aminocarbonyl, di-(1-ethyl-c-butyl)aminocarbonyl, di-(2-ethyl-c-butyl)aminocarbonyl, di-(3-ethyl-c-butyl)aminocarbonyl, di-(1,2-dimethyl-c-butyl)aminocarbonyl, di-(1,3-dimethyl-c-butyl)aminocarbonyl, di-(2,2-dimethyl-c-butyl)aminocarbonyl, di-(2,3-dimethyl-c-butyl)aminocarbonyl, di-(2,4-dimethyl-c-butyl)aminocarbonyl, di-(3,3-dimethyl-c-butyl)aminocarbonyl, di-(1-n-propyl-c-propyl)aminocarbonyl, di-(2-n-propyl-c-propyl)aminocarbonyl, di-(1-i-propyl-c-propyl)aminocarbonyl, di-(2-i-propyl-c-propyl)aminocarbonyl, di-(1,2,2-trimethyl-c-propyl)aminocarbonyl, di-(1,2,3-trimethyl-c-propyl)aminocarbonyl, di-(2,2,3-trimethyl-c-propyl)aminocarbonyl, di-(1-ethyl-2-methyl-c-propyl)aminocarbonyl, di-(2-ethyl-1-methyl-c-propyl)aminocarbonyl, di-(2-ethyl-2-methyl-c-propyl)aminocarbonyl, di-(2-ethyl-3-methyl-c-propyl)aminocarbonyl, di-(1-methyl-1-ethyl-n-pentyl)aminocarbonyl, di-(1-heptyl)aminocarbonyl, di-(2-heptyl)aminocarbonyl, di-(1-ethyl-1,2-dimethyl-n-propyl)aminocarbonyl, di-(1-ethyl-2,2-dimethyl-n-propyl)aminocarbonyl, di-(1-octyl)aminocarbonyl, di-(3-octyl)aminocarbonyl, di-(4-methyl-3-n-heptyl)aminocarbonyl, di-(6-methyl-2-n-heptyl)aminocarbonyl, di-(2-propyl-1-n-heptyl)aminocarbonyl, di-(2,4,4-trimethyl-1-n-pentyl)aminocarbonyl, di-(1-nonyl)aminocarbonyl, di-(2-nonyl)aminocarbonyl, di-(2,6-dimethyl-4-n-heptyl)aminocarbonyl, di-(3-ethyl-2,2-dimethyl-3-n-pentyl)aminocarbonyl, di-(3,5,5-trimethyl-1-n-hexyl)aminocarbonyl, di-(1-decyl)aminocarbonyl, di-(2-decyl)aminocarbonyl, di-(4-decyl)aminocarbonyl, di-(3,7-dimethyl-1-n-octyl)aminocarbonyl, di-(3,7-dimethyl-3-n-octyl)aminocarbonyl or the like may be mentioned.

An asymmetric $C_{1-10}$ dialkylaminocarbonyl group may be linear, branched or a $C_{3-10}$ cycloalkylaminocarbonyl group, and as specific examples, (methyl, ethyl)aminocarbonyl, (methyl, n-propyl)aminocarbonyl, (methyl, i-propyl)aminocarbonyl, (methyl, c-propyl)aminocarbonyl, (methyl, n-butyl)aminocarbonyl, (methyl, i-butyl)aminocarbonyl, (methyl, s-butyl)aminocarbonyl, (methyl, t-butyl)aminocarbonyl, (methyl, n-pentyl)aminocarbonyl, (methyl, c-pentyl)aminocarbonyl, (methyl, n-hexyl)aminocarbonyl, (methyl, c-hexyl)aminocarbonyl, (ethyl, n-propyl)aminocarbonyl, (ethyl, i-propyl)aminocarbonyl, (ethyl, c-propyl)aminocarbonyl, (ethyl, n-butyl)aminocarbonyl, (ethyl, i-butyl)aminocarbonyl, (ethyl, s-butyl)aminocarbonyl, (ethyl, t-butyl)aminocarbonyl, (ethyl, n-pentyl)aminocarbonyl, (ethyl, c-pentyl)aminocarbonyl, (ethyl, n-hexyl)aminocarbonyl, (ethyl, c-hexyl)aminocarbonyl, (n-propyl, i-propyl)aminocarbonyl, (n-propyl, c-propyl)aminocarbonyl, (n-propyl, n-butyl)aminocarbonyl, (n-propyl, i-butyl)aminocarbonyl, (n-propyl, s-butyl)aminocarbonyl, (n-propyl, t-butyl)aminocarbonyl, (n-propyl, n-pentyl)aminocarbonyl, (n-propyl, c-pentyl)aminocarbonyl, (n-propyl, n-hexyl)aminocarbonyl, (n-propyl, c-hexyl)aminocarbonyl, (i-propyl, c-propyl)aminocarbonyl, (i-propyl, n-butyl)aminocarbonyl, (i-propyl, i-butyl)aminocarbonyl, (i-propyl, s-butyl)aminocarbonyl, (i-propyl, t-butyl)aminocarbonyl, (i-propyl, n-pentyl)aminocarbonyl, (i-propyl, c-pentyl)aminocarbonyl, (i-propyl, n-hexyl)aminocarbonyl, (i-propyl, c-hexyl)aminocarbonyl, (c-propyl, n-butyl)aminocarbonyl, (c-propyl, i-butyl)aminocarbonyl, (c-propyl, s-butyl)aminocarbonyl, (c-propyl, t-butyl)aminocarbonyl, (c-propyl, n-pentyl)aminocarbonyl, (c-propyl, c-pentyl)aminocarbonyl, (c-propyl, n-hexyl)aminocarbonyl, (c-propyl, c-hexyl)aminocarbonyl, (n-butyl, i-butyl)aminocarbonyl, (n-butyl, s-butyl)aminocarbonyl, (n-butyl, t-butyl)aminocarbonyl, (n-butyl, n-pentyl)aminocarbonyl, (n-butyl, c-pentyl)aminocarbonyl, (n-butyl, n-hexyl)aminocarbonyl, (n-butyl, c-hexyl)aminocarbonyl, (i-butyl, s-butyl)aminocarbonyl, (i-butyl, t-butyl)aminocarbonyl, (i-butyl, n-pentyl)aminocarbonyl, (i-butyl, c-pentyl)aminocarbonyl, (i-butyl, n-hexyl)aminocarbonyl, (i-butyl, c-hexyl)aminocarbonyl, (s-butyl, t-butyl)aminocarbonyl, (s-butyl, n-pentyl)aminocarbonyl, (s-butyl, c-pentyl)aminocarbonyl, (s-butyl, n-hexyl)aminocarbonyl, (s-butyl, c-hexyl)aminocarbonyl, (t-butyl, n-pentyl)aminocarbonyl, (t-butyl, c-pentyl)aminocarbonyl, (t-butyl, n-hexyl)aminocarbonyl, (t-butyl, c-hexyl)aminocarbonyl, (n-pentyl, c-pentyl)aminocarbonyl, (n-pentyl, n-hexyl)aminocarbonyl, (n-pentyl, c-hexyl)aminocarbonyl, (c-pentyl, n-hexyl)aminocarbonyl, (c-pentyl, c-hexyl)aminocarbonyl, (n-hexyl, c-hexyl)aminocarbonyl, (methyl, n-heptyl)aminocarbonyl, (methyl, n-octyl)aminocarbonyl, (methyl, n-nonanyl)aminocarbonyl, (methyl, n-decyl)aminocarbonyl, (ethyl, n-heptyl)aminocarbonyl, (ethyl, n-octyl)aminocarbonyl, (ethyl, n-nonanyl)aminocarbonyl, (ethyl, n-decyl)aminocarbonyl or the like may be mentioned.

A $C_{1-10}$ alkylaminosulfonyl group may be linear, branched, a $C_{3-10}$ cycloalkylsulfonylamino group or a di-$C_{1-10}$ alkylaminosulfonyl group, and as specific examples, methylaminosulfonyl, ethylaminosulfonyl, n-propylaminosulfonyl, i-propylaminosulfonyl, c-propylaminosulfonyl, n-butylaminosulfonyl, i-butylaminosulfonyl, s-butylaminosulfonyl, t-butylaminosulfonyl, c-butylaminosulfonyl, 1-methyl-c-propylaminosulfonyl, 2-methyl-c-propylaminosulfonyl, n-pentylaminosulfonyl, 1-methyl-n-butylaminosulfonyl, 2-methyl-n-butylaminosulfonyl, 3-methyl-n-butylaminosulfonyl, 1,1-dimethyl-n-propylaminosulfonyl, 1,2-dimethyl-n-propylaminosulfonyl, 2,2-dimethyl-n-propylaminosulfonyl, 1-ethyl-n-propylaminosulfonyl, c-pentylaminosulfonyl, 1-methyl-c-butylaminosulfonyl, 2-methyl-c-butylaminosulfonyl, 3-methyl-c-butylaminosulfonyl, 1,2-dimethyl-c-propylaminosulfonyl, 2,3-dimethyl-c-propylaminosulfonyl, 1-ethyl-c-propylaminosulfonyl, 2-ethyl-c-propylaminosulfonyl, n-hexylaminosulfonyl, 1-methyl-n-pentylaminosulfonyl, 2-methyl-n-pentylaminosulfonyl, 3-methyl-n-pentylaminosulfonyl, 4-methyl-n-pentylaminosufonyl, 1,1-dimethyl-n-butylaminosufonyl, 1,2-dimethyl-n-butylaminosufonyl, 1,3-dimethyl-n-butylaminosufonyl, 2,2-dimethyl-n-butylaminosufonyl, 2,3-dimethyl-n-butylaminosufonyl, 3,3-dimethyl-n-butylaminosufonyl, 1-ethyl-n-butylaminosufonyl, 2-ethyl-n-butylaminosufonyl, 1,1,2-trimethyl-n-propylaminosulfonyl, 1,2,2-trimethyl-n-propylaminosulfonyl, 1-ethyl-1-methyl-n-propylaminosulfonyl, 1-ethyl-2-methyl-n-propylaminosulfonyl, c-hexylaminosulfonyl, 1-methyl-c-pentylaminosulfonyl, 2-methyl-c-pentylaminosulfonyl, 3-methyl-c-pentylaminosulfonyl, 1-ethyl-c-butylaminosulfonyl, 2-ethyl-c-butylaminosulfonyl, 3-ethyl-c-butylaminosulfonyl, 1,2-dimethyl-c-butylaminosulfonyl, 1,3-dimethyl-c-butylaminosulfonyl, 2,2-dimethyl-c-butylaminosulfonyl, 2,3-dimethyl-c-butylaminosulfonyl, 2,4-dimethyl-c-butylaminosulfonyl, 3,3-dimethyl-c-butylaminosulfonyl, 1-n-propyl-c-propylaminosulfonyl, 2-n-propyl-c-propylaminosulfonyl, 1-i-propyl-c-propylaminosulfonyl, 2-i-propyl-c-propylaminosulfonyl, 1,2,2-trimethyl-c-propylaminosulfonyl, 1,2,3-trimethyl-c-propylaminosulfonyl, 2,2,3-trimethyl-c-propylaminosulfonyl, 1-ethyl-2-methyl-c-propylaminosulfonyl, 2-ethyl-1-methyl-c-propylaminosulfonyl, 2-ethyl-2-methyl-c-propylaminosulfonyl, 1-methyl-1-ethyl-n-pentylaminosulfonyl, 1-heptylaminosulfonyl, 2-heptylaminosulfonyl, 1-ethyl-1,2-dimethyl-n-propylaminosulfonyl, 1-ethyl-2,2-dimethyl-n-propylaminosulfonyl, 1-octylaminosulfonyl, 3-octylaminosulfonyl, 4-methyl-3-n-heptylaminosulfonyl, 6-methyl-2-n-heptylaminosulfonyl, 2-propyl-1-n-heptylaminosulfonyl, 2,4,4-trimethyl-1-n-pentylaminosulfonyl, 1-nonylaminosulfonyl, 2-nonylaminosulfonyl, 2,6-dimethyl-4-n-heptylaminosulfonyl, 3-ethyl-2,2-dimethyl-3-n-pentylaminosulfonyl, 3,5,5-trimethyl-1-n-hexylaminosulfonyl, 1-decylaminosulfonyl, 2-decylaminosulfonyl, 4-decylaminosulfonyl, 3,7-dimetyl-1-n-octylaminosulfonyl, 3,7-dimetyl-3-n-octylaminosulfonyl, c-heptylaminosulfonyl, c-octylaminosulfonyl, 1-methyl-c-hexylaminosulfonyl, 2-methyl-c-hexylaminosulfonyl, 3-methyl-c-hexylaminosulfonyl, 1,2-dimethyl-c-hexylaminosulfonyl, 1-ethyl-c-hexylaminosulfonyl, 1-methyl-c-pentylaminosulfonyl, 2-methyl-c-pentylaminosulfonyl, 3-methyl-c-pentylaminosulfonyl or the like may be mentioned.

A di-$C_{1-10}$ alkylaminosulfonyl group may be symmetric or asymmetric. A symmetric di-$C_{1-10}$ dialkylaminosulfonyl group may be linear, branched or a $C_{3-10}$ cycloalkylaminosulfonyl group, and as specific examples, dimethylaminosulfonyl, diethylaminosulfonyl, di-n-propylaminosulfonyl, di-i-propylaminosulfonyl, di-c-propylaminosulfonyl, di-n-butylaminosulfonyl, di-i-butylaminosulfonyl, di-s-butylaminosulfonyl, di-t-butylaminosulfonyl, di-c-butylaminosulfonyl, di-(1-methyl-c-propyl)aminosulfonyl, di-(2-methyl-c-propyl)aminosulfonyl, di-n-pentylaminosulfonyl, di-(1-methyl-n-butyl)aminosulfonyl, di-(2-methyl-n-butyl)aminosulfonyl, di-(3-methyl-n-butyl)aminosulfonyl, di-(1,1-dimethyl-n-propyl)aminosulfonyl, di-(1,2-dimethyl-n-propyl)aminosulfonyl, di-(2,2-dimethyl-n-propyl)aminosulfonyl, di-(1-ethyl-n-propyl)aminosulfonyl, di-c-pentylaminosulfonyl, di-(1-methyl-c-butyl)aminosulfonyl, di-(2-methyl-c-butyl)aminosulfonyl, di-(3-methyl-c-butyl)aminosulfonyl, di-(1,2-dimethyl-c-propyl)aminosulfonyl, di-(2,3-dimethyl-c-propyl)aminosulfonyl, di-(1-ethyl-c-propyl)aminosulfonyl, di-(2-ethyl-c-propyl)aminosulfonyl, di-n-hexylaminosulfonyl, di-(1-methyl-n-pentyl)aminosulfonyl, di-(2-methyl-n-pentyl)aminosulfonyl, di-(3-methyl-n-pentyl)aminosulfonyl, di-(4-methyl-n-pentyl)aminosulfonyl, di-(1,1-dimethyl-n-butyl)aminosulfonyl, di-(1,2-dimethyl-n-butyl)aminosulfonyl, di-(1,3-dimethyl-n-butyl)aminosulfonyl, di-(2,2-dimethyl-n-butyl)aminosulfonyl, di-(2,3-dimethyl-n-butyl)aminosulfonyl, di-(3,3-dimethyl-n-butyl)aminosulfonyl, di-(1-ethyl-n-butyl)aminosulfonyl, di-(2-ethyl-n-butyl)aminosulfonyl, di-(1,1,2-trimethyl-n-propyl)aminosulfonyl, di-(1,2,2-trimethyl-n-propyl)aminosulfonyl, di-(1-ethyl-1-methyl-n-propyl)aminosulfonyl, di-(1-ethyl-2-methyl-n-propyl)aminosulfonyl, di-c-hexylaminosulfonyl, di-(1-methyl-c-pentyl)aminosulfonyl, di-(2-methyl-c-pentyl)aminosulfonyl, di-(3-methyl-c-pentyl)aminosulfonyl, di-(1-ethyl-c-butyl)aminosulfonyl, di-(2-ethyl-c-butyl)aminosulfonyl, di-(3-ethyl-c-butyl)aminosulfonyl, di-(1,2-dimethyl-c-butyl)aminosulfonyl, di-(1,3-dimethyl-c-butyl)aminosulfonyl, di-(2,2-dimethyl-c-butyl)aminosulfonyl, di-(2,3-dimethyl-c-butyl)aminosulfonyl, di-(2,4-dimethyl-c-butyl)aminosulfonyl, di-(3,3-dimethyl-c-butyl)aminosulfonyl, di-(1-n-propyl-c-propyl)aminosulfonyl, di-(2-n-propyl-c-propyl)aminosulfonyl, di-(1-i-propyl-c-propyl)aminosulfonyl, di-(2-i-propyl-c-propyl)aminosulfonyl, di-(1,2,2-trimethyl-c-propyl)aminosulfonyl, di-(1,2,3-trimethyl-c-propyl)aminosulfonyl, di-(2,2,3-trimethyl-c-propyl)aminosulfonyl, di-(1-ethyl-2-methyl-c-propyl)aminosulfonyl, di-(2-ethyl-1-methyl-c-propyl)aminosulfonyl, di-(2-ethyl-2-methyl-c-propyl)aminosulfonyl, di-(2-ethyl-3-methyl-c-propyl)aminosulfonyl, di-(1-methyl-1-ethyl-n-pentyl)aminosulfonyl, di-(1-heptyl)aminosulfonyl, di-(2-heptyl)aminosulfonyl, di-(1-ethyl-1,2-dimethyl-n-propyl)aminosulfonyl, di-(1-ethyl-2,2-dimethyl-n-propyl)aminosulfonyl, di-(1-octyl)aminosulfonyl, di-(3-octyl)aminosulfonyl, di-(4-methyl-3-n-heptyl)aminosulfonyl, di-(6-methyl-2-n-heptyl)aminosulfonyl, di-(2-propyl-1-n-heptyl)aminosulfonyl, di-(2,4,4-trimethyl-1-n-pentyl)aminosulfonyl, di-(1-nonyl)aminosulfonyl, di-(2-nonyl)aminosulfonyl, di-(2,6-dimethyl-4-n-heptyl)aminosulfonyl, di-(3-ethyl-2,2-dimethyl-3-n-pentyl)aminosulfonyl, di-(3,5,5-trimethyl-1-n-hexyl)aminosulfonyl, di-(1-decyl)aminosulfonyl, di-(2-decyl)aminosulfonyl, di-(4-decyl)aminosulfonyl, di-(3,7-dimethyl-1-n-octyl)aminosulfonyl, di-(3,7-dimethyl-3-n-octyl)aminosulfonyl or the like may be mentioned.

An asymmetric di-$C_{1-10}$ alkylaminosulfonyl group may be linear, branched or a $C_{3-10}$ cycloalkylaminosulfonyl group, and as specific examples, (methyl, ethyl)aminosulfonyl, (methyl, n-propyl)aminosulfonyl, (methyl, i-propyl)aminosulfonyl, (methyl, c-propyl)aminosulfonyl, (methyl, n-butyl)aminosulfonyl, (methyl, i-butyl)aminosulfonyl, (methyl, s-butyl)aminosulfonyl, (methyl, t-butyl)aminosulfonyl, (methyl, n-pentyl)aminosulfonyl, (methyl, c-pentyl)aminosulfonyl, (methyl, n-hexyl)aminosulfonyl, (methyl, c-hexyl)aminosulfonyl, (ethyl, n-propyl)aminosulfonyl, (ethyl, i-propyl)aminosulfonyl, (ethyl, c-propyl)aminosulfonyl, (ethyl, n-butyl)aminosulfonyl, (ethyl, i-butyl)aminosulfonyl, (ethyl, s-butyl)aminosulfonyl, (ethyl, t-butyl)aminosulfonyl, (ethyl, n-pentyl)aminosulfonyl, (ethyl, c-pentyl)aminosulfonyl, (ethyl, n-hexyl)aminosulfonyl, (ethyl, c-hexyl)aminosulfonyl, (n-propyl, i-propyl)aminosulfonyl, (n-propyl, c-propyl)aminosulfonyl, (n-propyl, n-butyl)aminosulfonyl, (n-propyl, i-butyl)aminosulfonyl, (n-propyl, s-butyl)aminosulfonyl, (n-propyl, t-butyl)aminosulfonyl, (n-propyl, n-pentyl)aminosulfonyl, (n-propyl, c-pentyl)aminosulfonyl, (n-propyl, n-hexyl)aminosulfonyl, (n-propyl, c-hexyl)aminosulfonyl, (i-propyl, c-propyl)aminosulfonyl, (i-propyl, n-butyl)aminosulfonyl, (i-propyl, i-butyl)aminosulfonyl, (i-propyl, s-butyl)aminosulfonyl, (i-propyl, t-butyl)aminosulfonyl, (i-propyl, n-pentyl)aminosulfonyl, (i-propyl, c-pentyl)aminosulfonyl, (i-propyl, n-hexyl)aminosulfonyl, (i-propyl, c-hexyl)aminosulfonyl, (c-propyl, n-butyl)aminosulfonyl, (c-propyl, i-butyl)aminosulfonyl, (c-propyl, s-butyl)aminosulfonyl, (c-propyl, t-butyl)aminosulfonyl, (c-propyl, n-pentyl)aminosulfonyl, (c-propyl, c-pentyl)aminosulfonyl, (c-propyl, n-hexyl)aminosulfonyl, (c-propyl, c-hexyl)aminosulfonyl, (n-butyl, i-butyl)aminosulfonyl, (n-butyl, s-butyl)aminosulfonyl, (n-butyl, t-butyl)aminosulfonyl, (n-butyl, n-pentyl)aminosulfonyl, (n-butyl, c-pentyl)aminosulfonyl, (n-butyl, n-hexyl)aminosulfonyl, (n-butyl, c-hexyl)aminosulfonyl, (i-butyl, s-butyl)aminosulfonyl, (i-butyl, t-butyl)aminosulfonyl, (i-butyl, n-pentyl)aminosulfonyl, (i-butyl, c-pentyl)aminosulfonyl, (i-butyl, n-hexyl)aminosulfonyl, (i-butyl, c-hexyl)aminosulfonyl, (s-butyl, t-butyl)aminosulfonyl, (s-butyl, n-pentyl)aminosulfonyl, (s-butyl, c-pentyl)aminosulfonyl, (s-butyl, n-hexyl)aminosulfonyl, (s-butyl, c-hexyl)aminosulfonyl, (t-butyl, n-pentyl)aminosulfonyl, (t-butyl, c-pentyl)aminosulfonyl, (t-butyl, n-hexyl)aminosulfonyl, (t-butyl, c-hexyl)aminosulfonyl, (n-pentyl, c-pentyl)aminosulfonyl, (n-pentyl, n-hexyl)aminosulfonyl, (n-pentyl, c-hexyl)aminosulfonyl, (c-pentyl, n-hexyl)aminosulfonyl, (c-pentyl, c-hexyl)aminosulfonyl, (n-hexyl, c-hexyl)aminosulfonyl, (methyl, n-heptyl)aminosulfonyl, (methyl, n-octyl)aminosulfonyl, (methyl, n-nonanyl)aminosulfonyl, (methyl, n-decyl)aminosulfonyl, (ethyl, n-heptyl)aminosulfonyl, (ethyl, n-octyl)aminosulfonyl, (ethyl, n-nonanyl)aminosulfonyl, (ethyl, n-decyl)aminosulfonyl or the like may be mentioned.

A $C_{2-14}$ arylene group is a bivalent group formed by removing a hydrogen atom from a ring-constituting atom in a $C_{2-14}$ aryl group, and as specific examples,

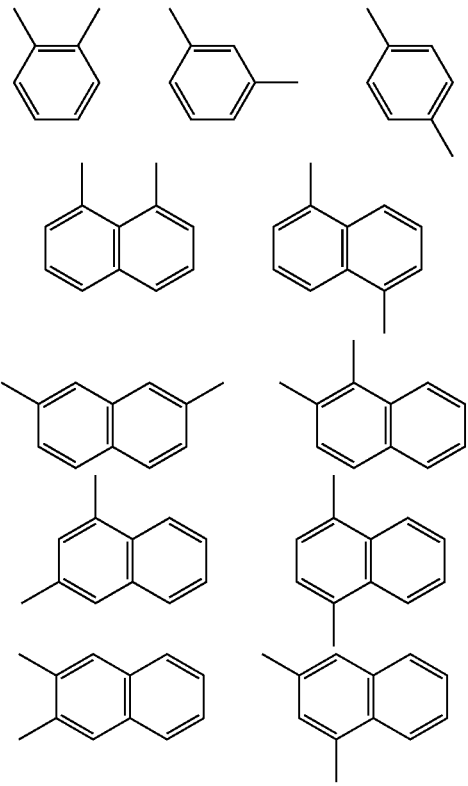

-continued

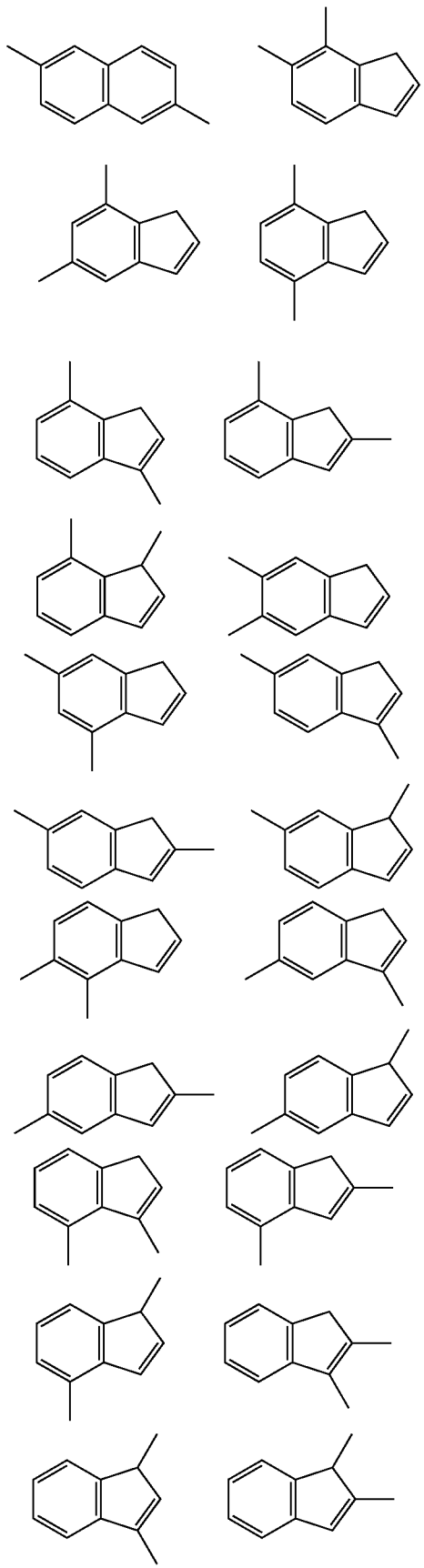

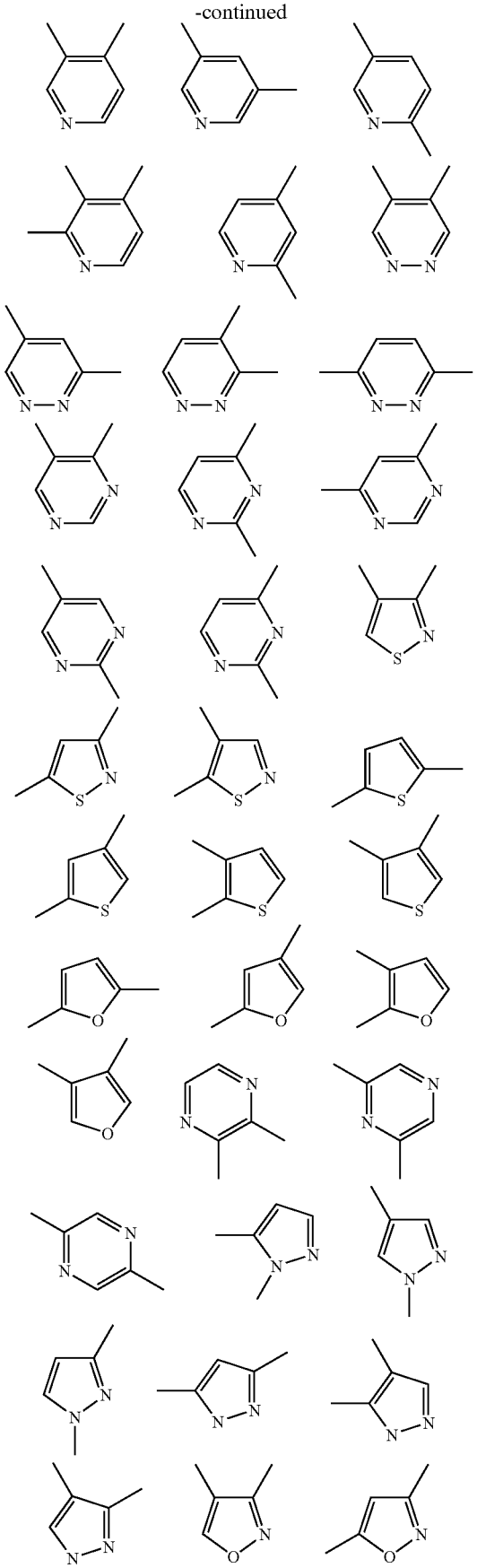
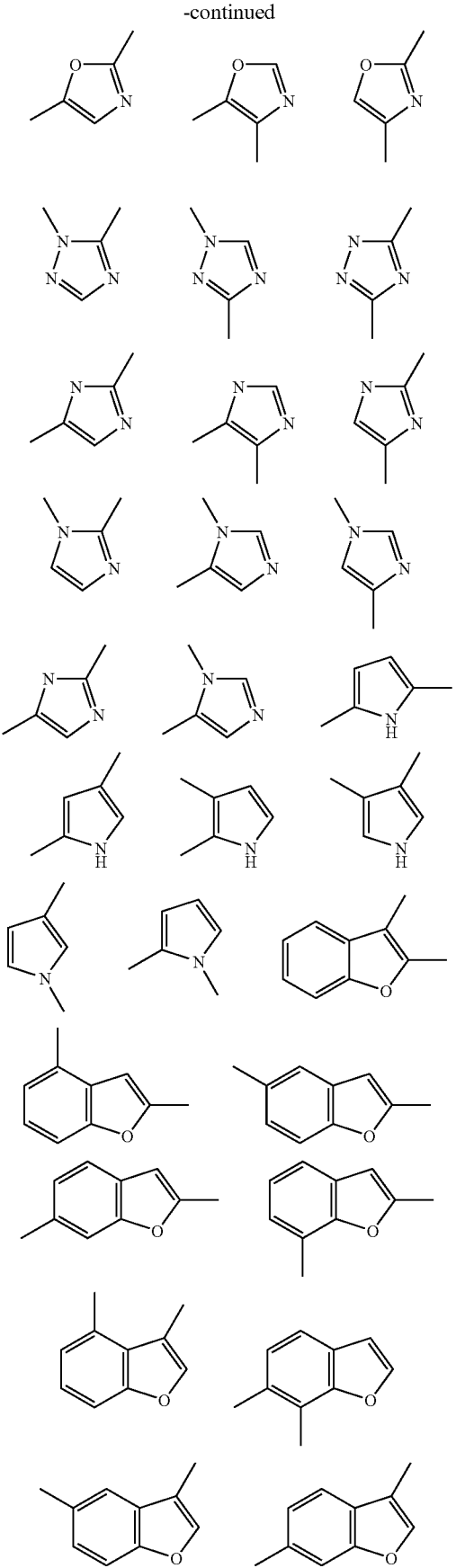

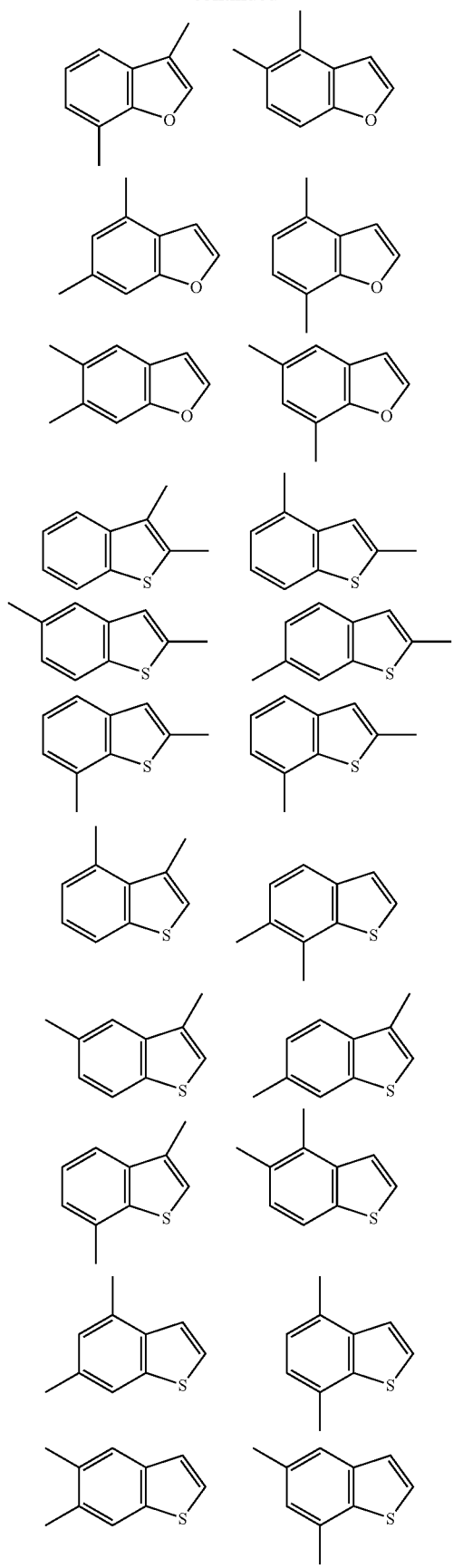
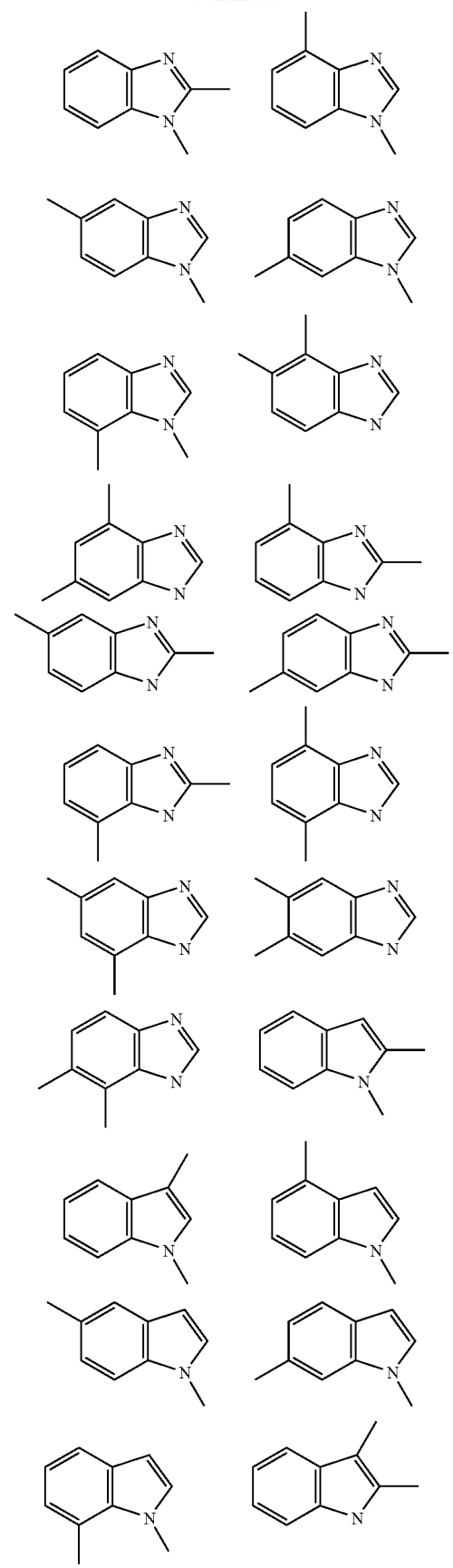

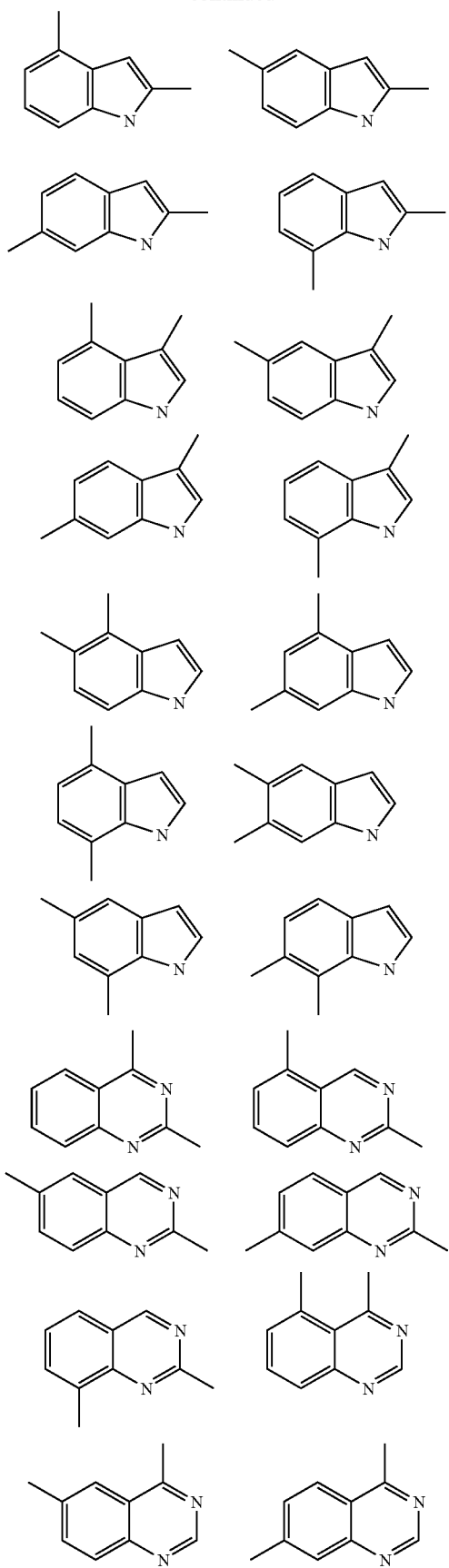
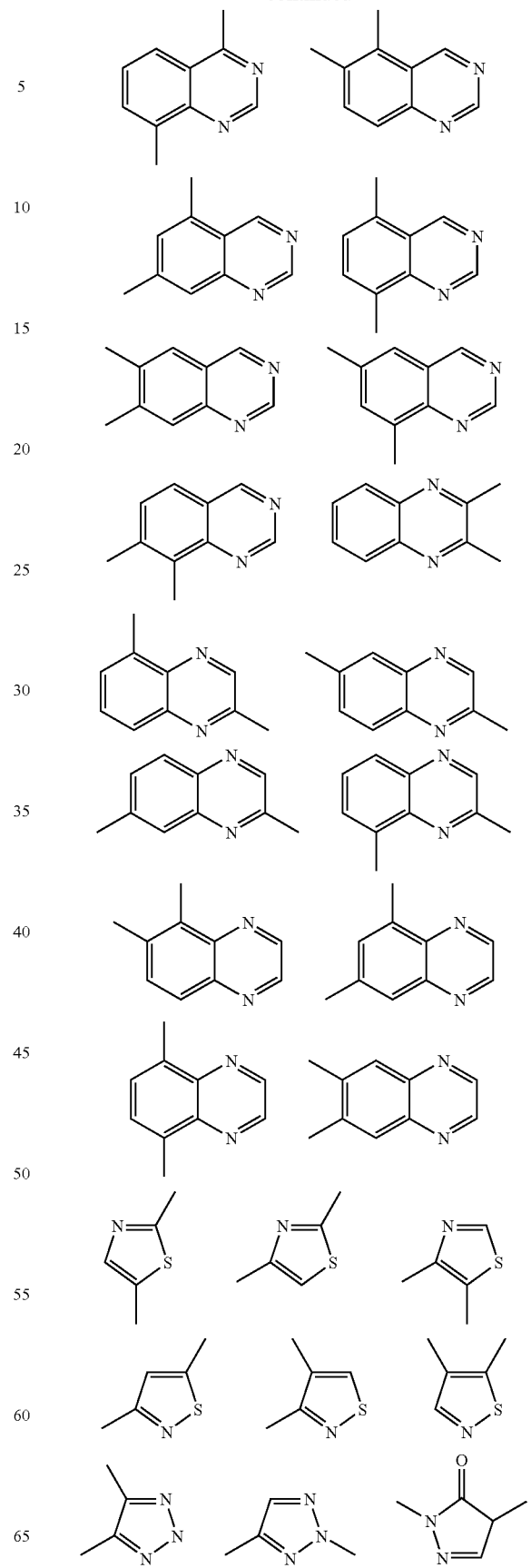

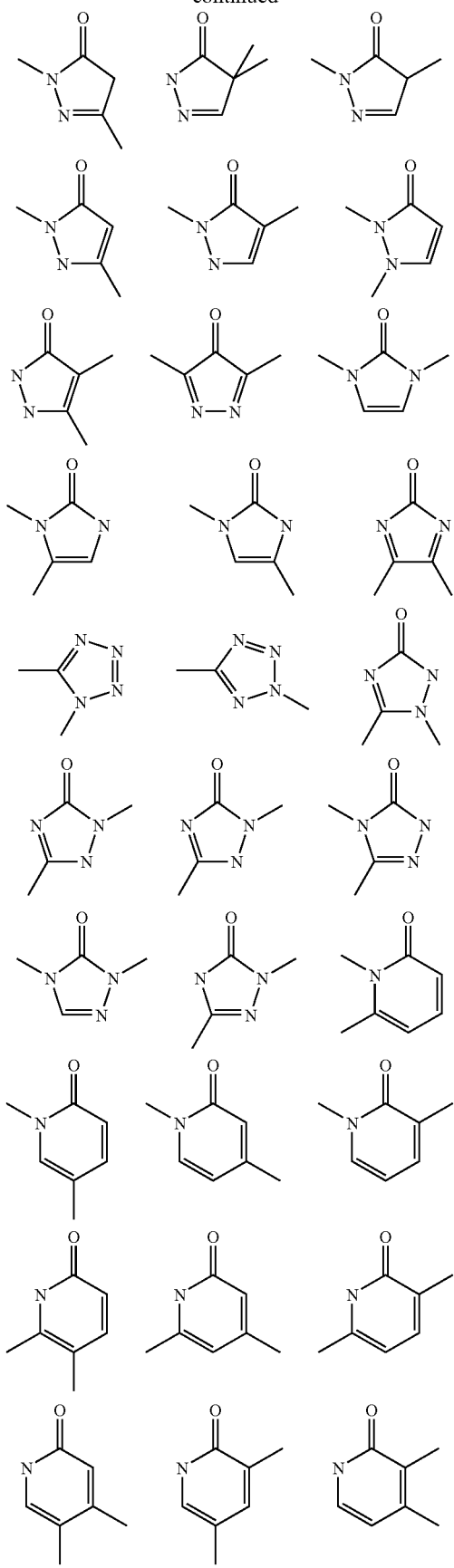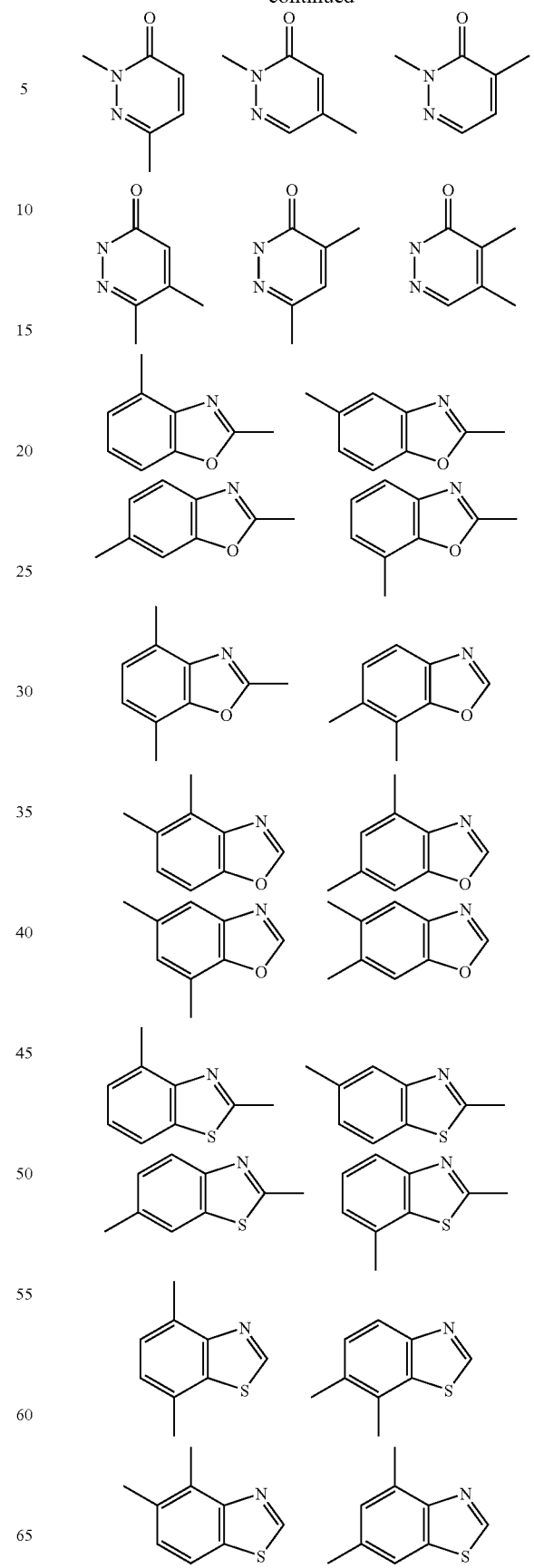

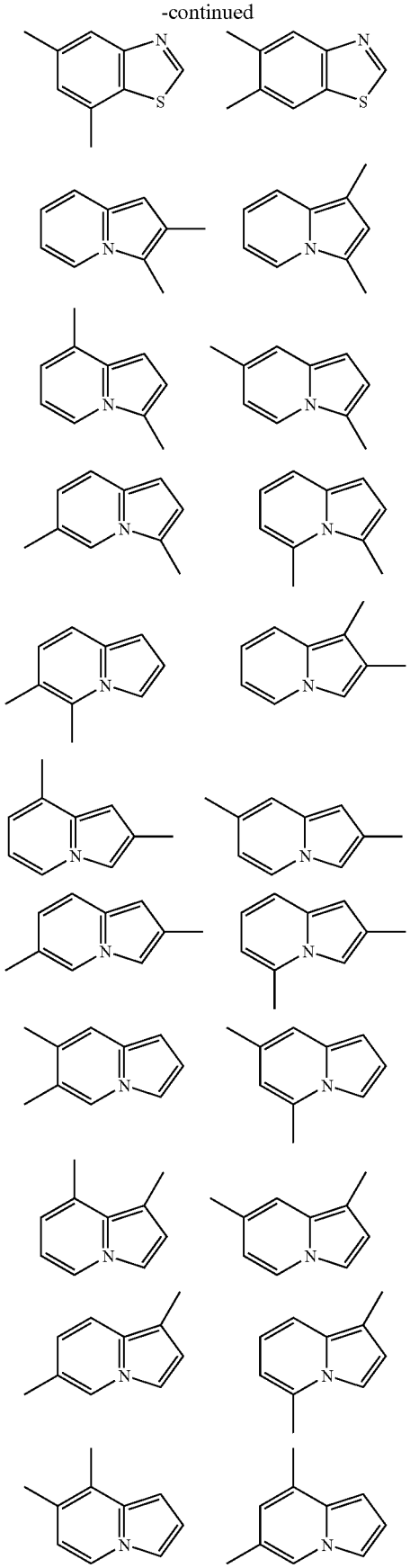
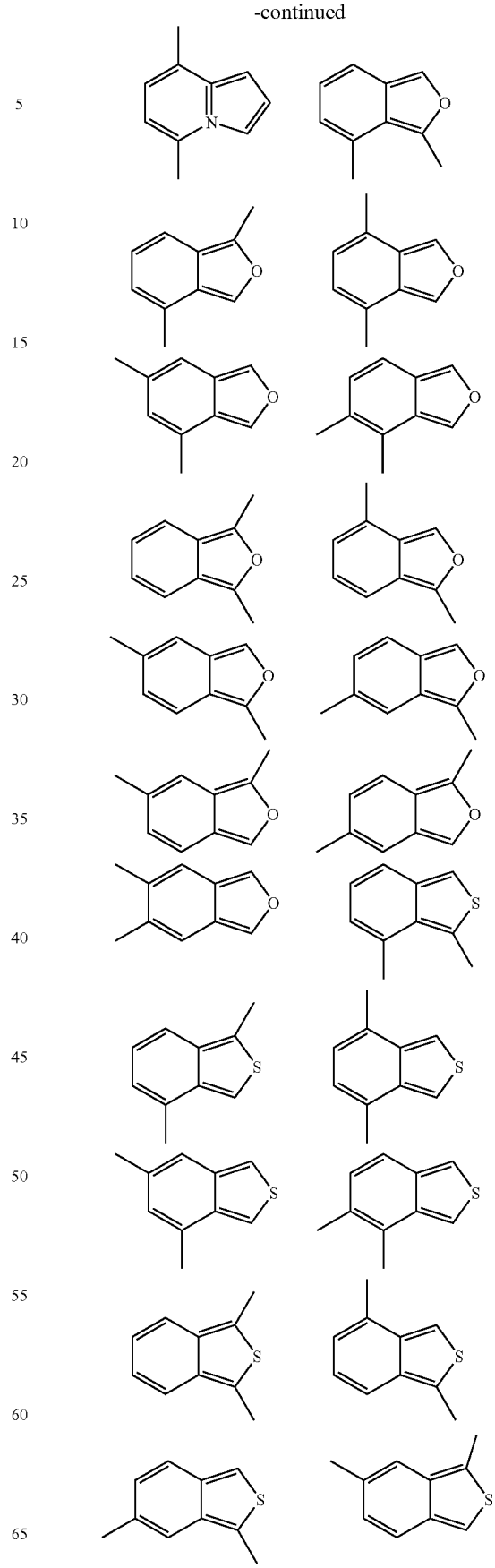

-continued
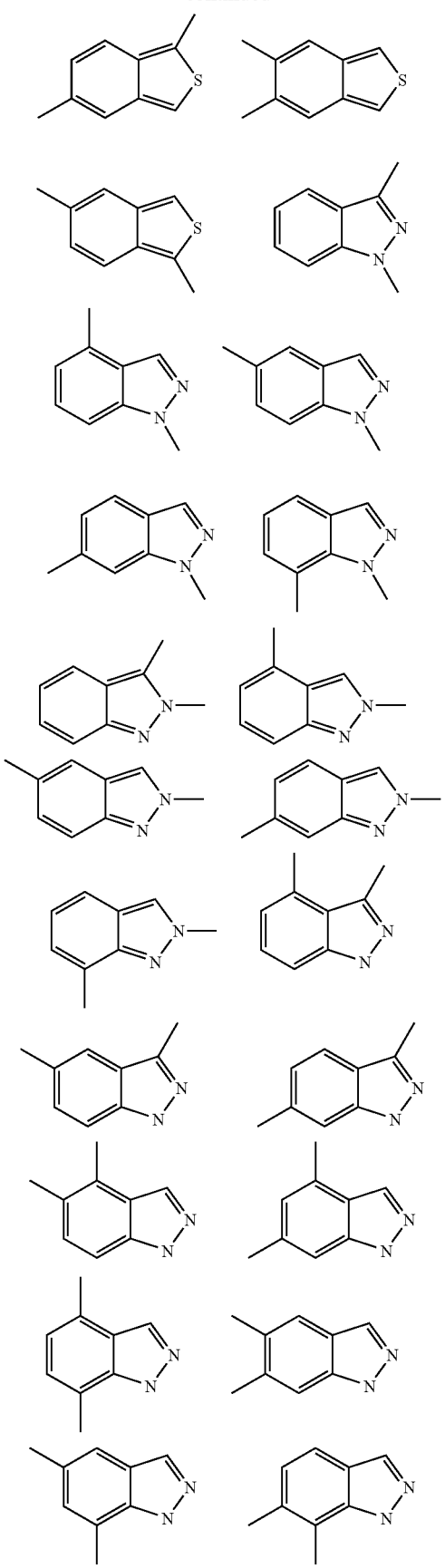
-continued
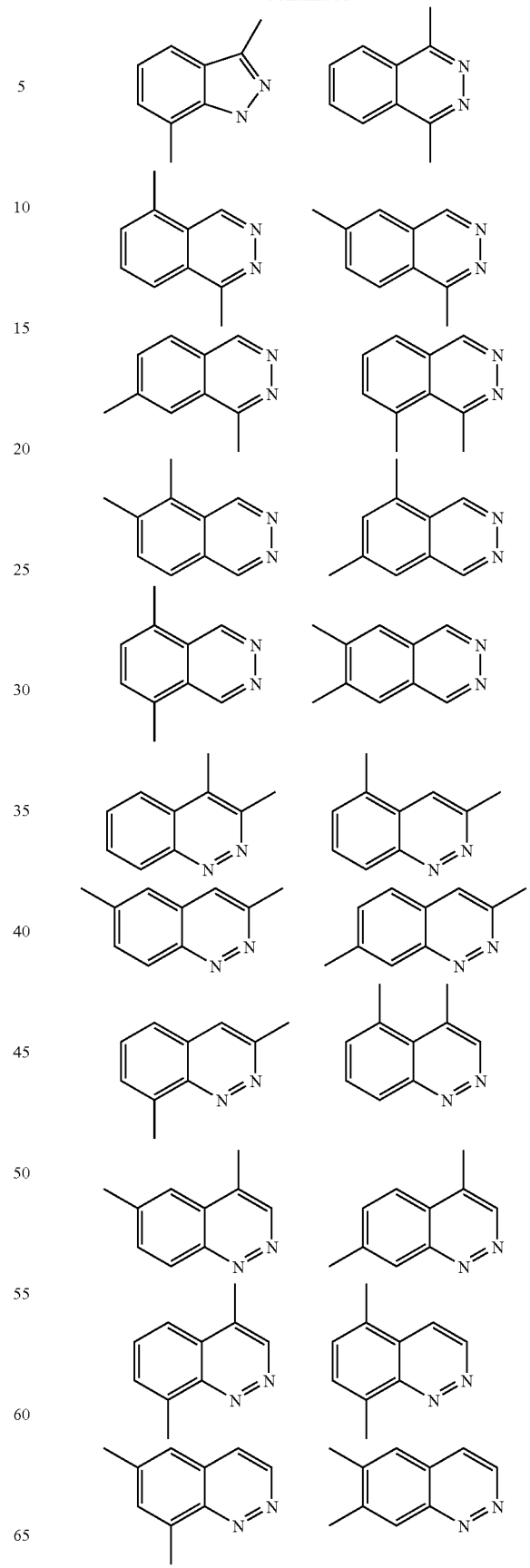

51
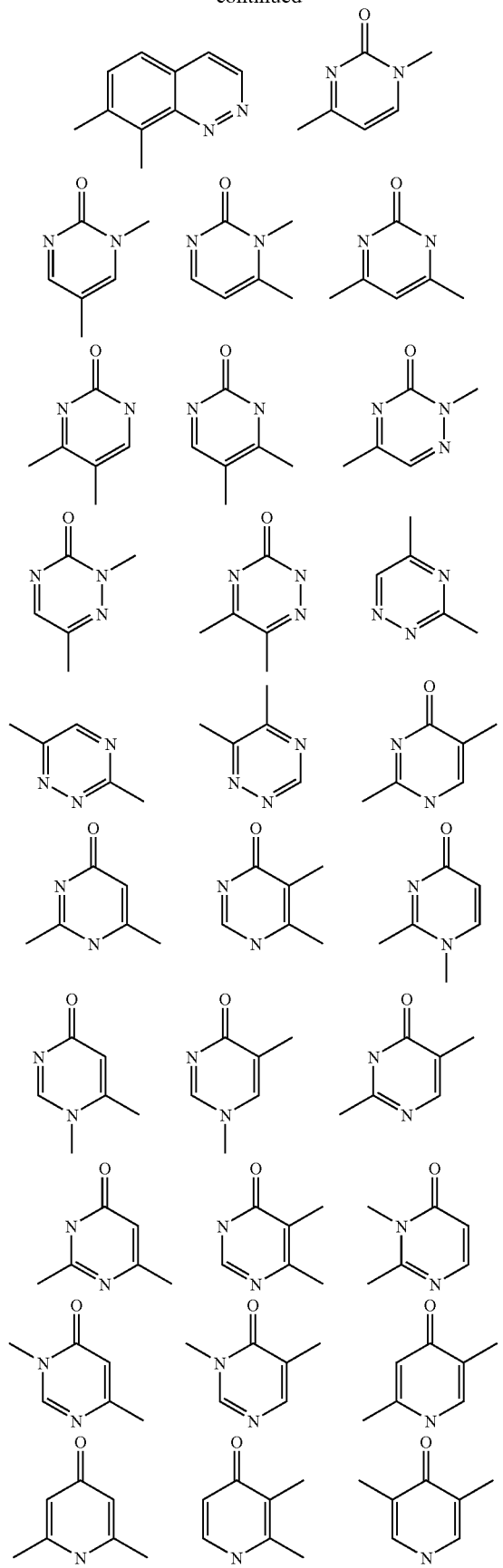
52
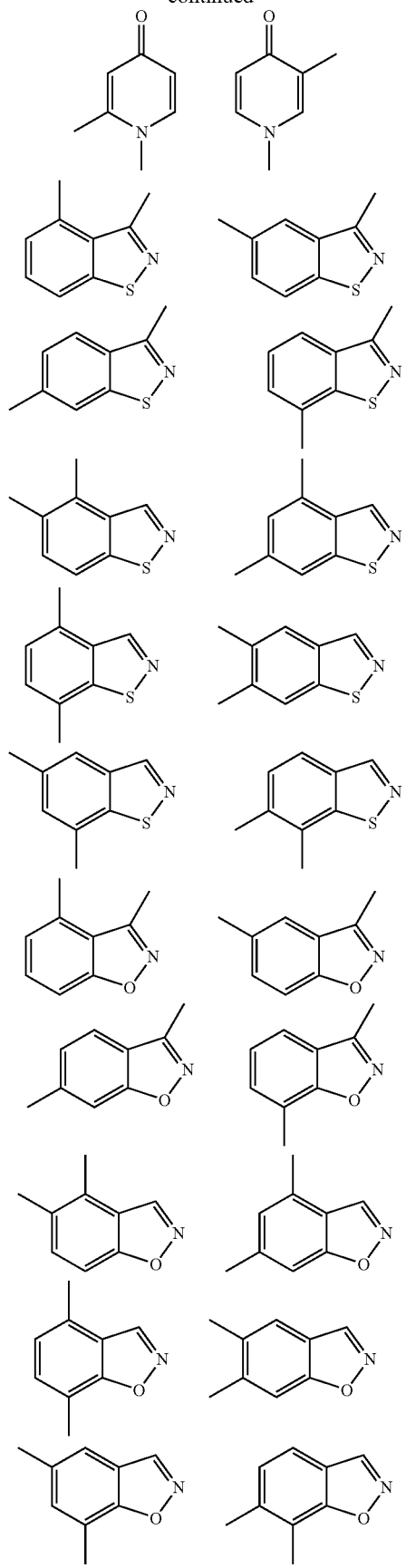

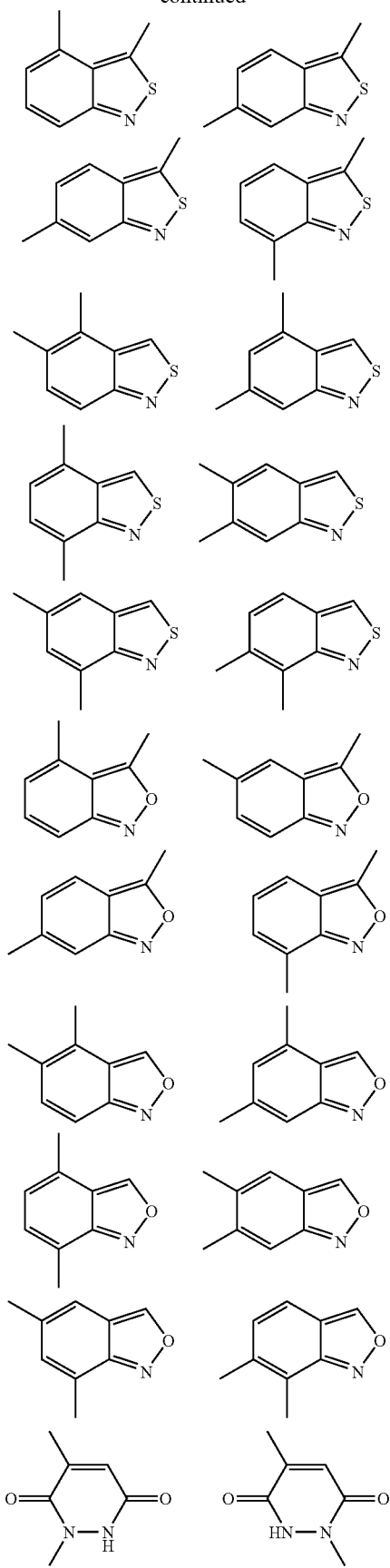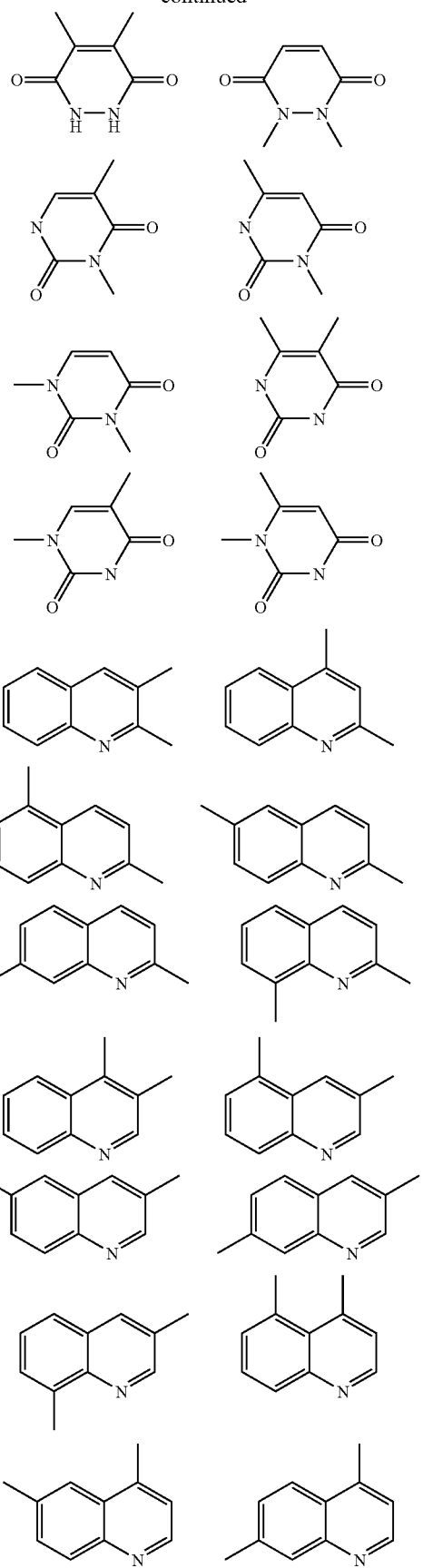

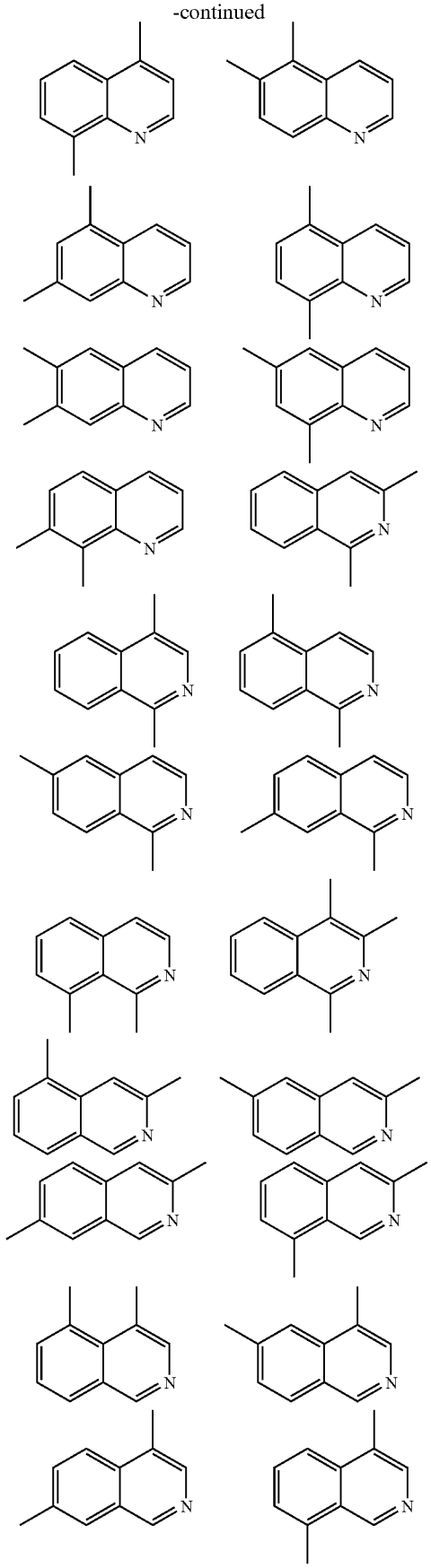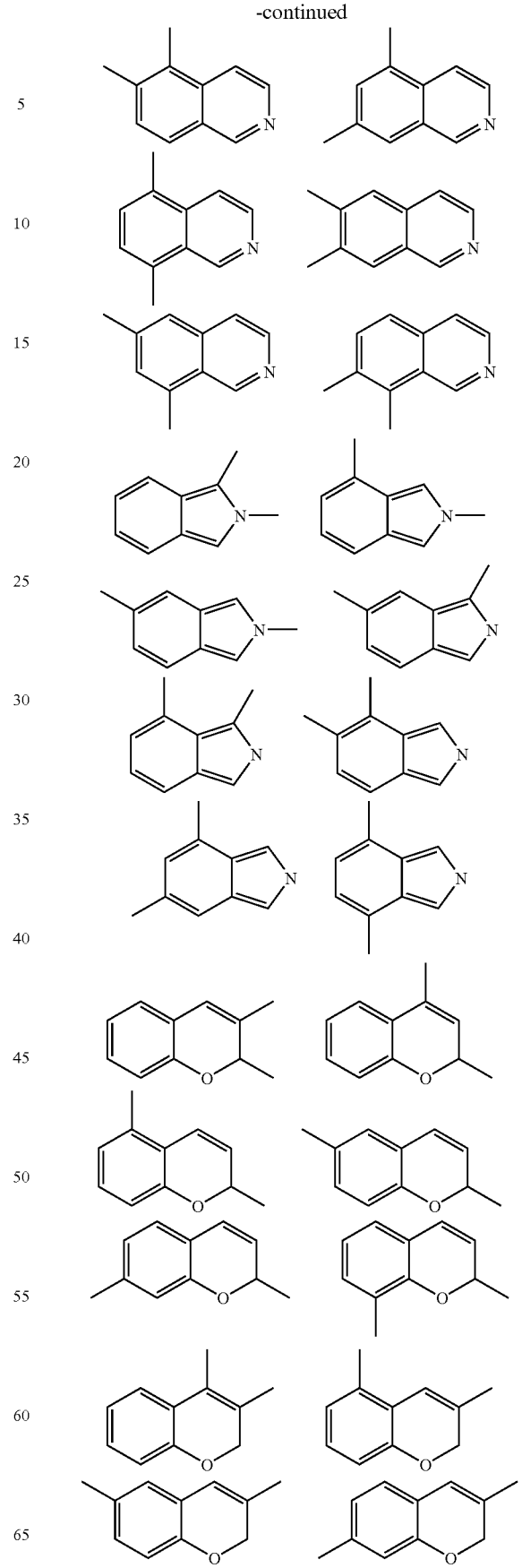

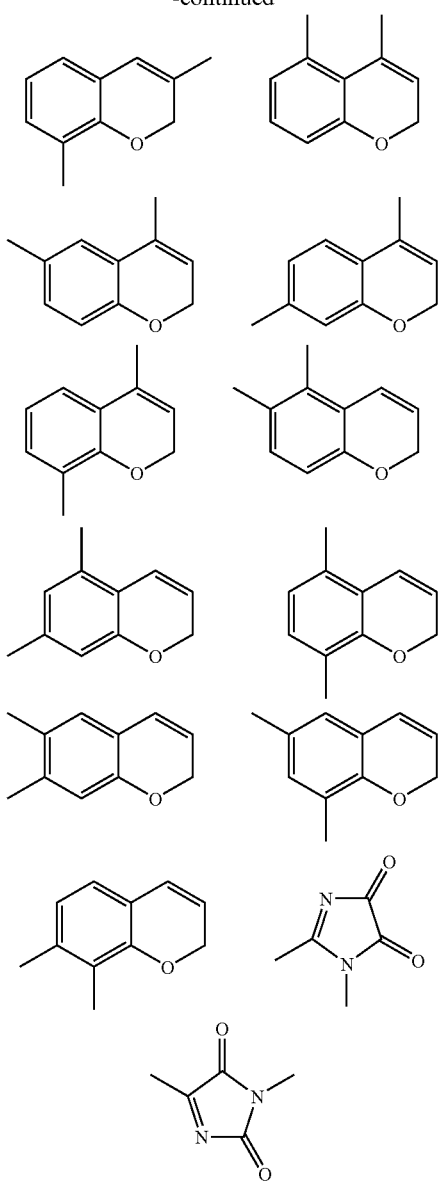
or the like may be mentioned,
A $C_{2-9}$ heterocyclyl group may be a monocyclic or fused bicyclic heterocyclic group containing at least one atom optionally selected from nitrogen atoms, oxygen atoms and sulfur atoms and from 2 to 9 carbon atoms, and specifically mentioned are:
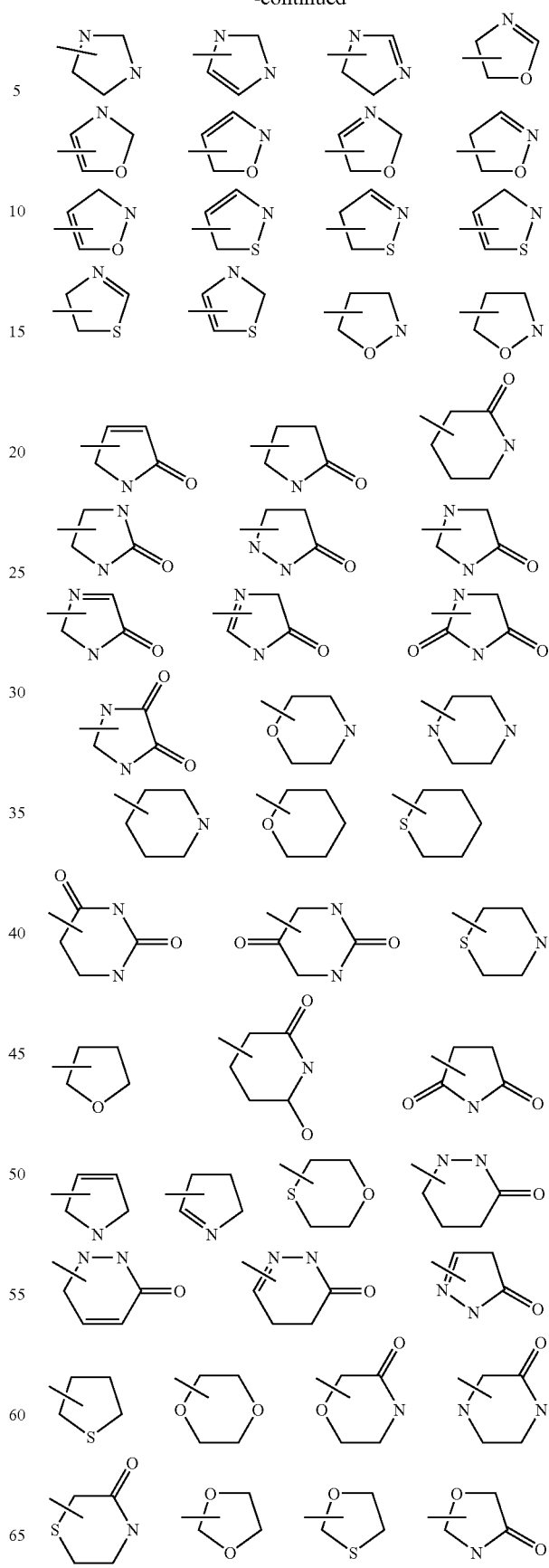

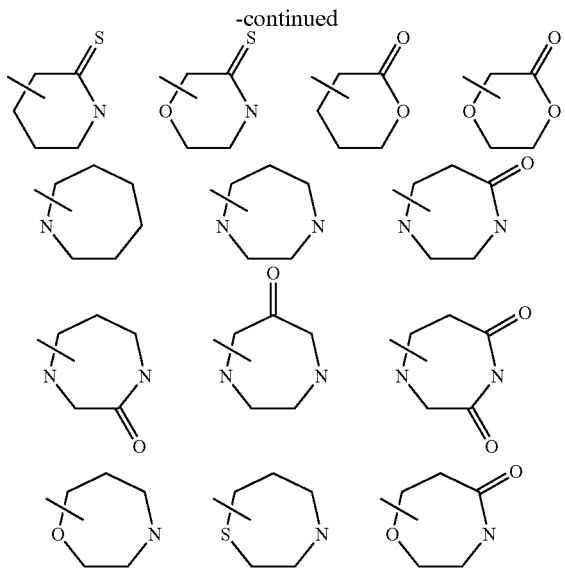

The protecting group in a protected hydroxyl group, a protected amino group or a protected thiol group may be a $C_{1-4}$ alkoxymethyl group (such as MOM: methoxymethyl, MEM: 2-methoxyethoxymethyl, ethoxymethyl, n-propoxymethyl, i-propoxymethyl, n-butoxymethyl, iBM: isobutyloxymethyl, BUM: t-butoxymethyl, POM: pivaloyloxymethyl, SEM: trimethylsilylethoxymethyl and the like, preferably a $C_{1-2}$ alkoxymethyl or the like), an aryloxymethyl (such as BOM: benzyloxymethyl, PMBM: p-methoxybenzyloxymethyl, P-AOM: p-anisyloxymethyl and the like, preferably benzyloxymethyl), a $C_{1-4}$ alkylaminomethyl group (such as dimethylaminomethyl), a substituted acetamidomethyl group (such as Acm: acetamidomethyl, Tacm: trimethylacetamidomethyl and the like), a substituted thiomethyl group (such as MTM: methylthiomethyl, PTM: phenylthiomethyl, Btm: benzylthiomethyl and the like), a carboxyl group, a $C_{1-7}$ acyl group (such as formyl, acetyl, fluoroacetyl, difluoroacetyl, trifluoroacetyl, chloroacetyl, dichloroacetyl, trichloroacetyl, propionyl, Pv: pivaloyl, tigloyl and the like), an arylcarbonyl group (such as benzoyl, p-bromobenzoyl, p-nitrobenzoyl, 2,4-dinitrobenzoyl, benzoylformyl, benzoylpropionyl, phenylpropionyl and the like), a $C_{1-4}$ alkoxycarbonyl group (such as methoxycarbonyl, ethoxycarbonyl, n-propoxycarbonyl, i-propoxycarbonyl, n-butoxycarbonyl, i-butoxycarbonyl, BOC: t-butoxycarbonyl, AOC: t-amyloxycarbonyl, VOC: vinyloxycarbonyl, AOC: allyloxycarbonyl, Teoc: 2-(trimethylsilyl)ethoxycarbonyl, Troc: 2,2,2-trichloroethoxycarbonyl and the like, preferably BOC and the like), an aryloxycarbonyl group (such as Z: benzyloxycarbonyl, p-nitrobenzyloxycarbonyl, MOZ: p-methoxybenzyloxycarbonyl and the like), a $C_{1-4}$ alkylaminocarbonyl group (such as methylcarbamoyl, Ec: ethylcarbamoyl, n-propylcarbamoyl and the like), an arylaminocarbonyl group (such as phenylcarbamoyl and the like), a trialkylsilyl group (such as TMS: trimethylsilyl, TES: triethylsilyl, TIPS: triisopropylsilyl, DEIPS: diethylisopropylsilyl, DMIPS: dimethylisopropylsilyl, DTBMS: di-t-butylmethylsilyl, IPDMS: isopropyldimethylsilyl, TBDMS: t-butyldimethylsilyl, TDS: thexyldimethylsilyl and the like, preferably t-butyldimethylsilyl and the like), a trialkylarylsilyl group (such as DPMS: diphenylmethylsilyl, TBDPS: t-butyldiphenylsilyl, TBMPS: t-butyldimethoxyphenylsilyl, TPS: triphenylsilyl and the like), an alkylsulfonyl group, (such as Ms: methanesulfonyl, ethanesulfonyl and the like) or an arylsulfonyl group (such as benzenesulfonyl, Ts: p-toluenesulfonyl, p-chlorobenzenesulfonyl, MBS: p-methoxybenzenesulfonyl, m-nitrobenzenesulfonyl, o-nitrobenzenesulfonyl, p-nitrobenzenesulfonyl, 2,4-nitrobenzenesulfonyl, iMds: 2,6-dimethoxy-4-methylbenzenesulfonyl, Mds: 2,6-dimethyl-4-methoxybenzenesulfonyl, Mtb: 2,4,6-trimethoxybenzenesulfonyl, Mte: 2,3,5,6-tetramethyl-4-methoxybenzenesulfonyl, Mtr: 2,3,6-trimethyl-4-methoxybenzenesulfonyl, Mts: 2,4,6-trimethylbenzenesulfonyl, Pme: pentamethylbenzenesulfonyl and the like).

In addition, a 1-methyl-1-methoxyethyl group, a 1-ethoxyethyl group, a 2,2,2-trichloroethyl group, a 2-trimethylsilylethoxy group, a t-butyl group, an allyl group, a benzyl group, a p-methoxybenzyl group, a 2,4-dinitrophenyl group, a p-chlorophenyl group, a p-methoxyphenyl group, a tetrahydropyranyl group, a tetrahydrofuranyl group or the like may be mentioned.

Preferred examples of the substituents in the compound to be used in the present invention are given below.

Preferred examples of $R^1$ are a hydrogen atom and a $C_{1-3}$ alkyl group (the $C_{1-3}$ alkyl group may be substituted with one or more halogen atoms), a more preferred example is a $C_{1-3}$ alkyl group, and a particularly preferred example is a methyl group.

Preferred examples of $R^2$, $R^3$ and $R^6$ are a hydrogen atom and a $C_{1-3}$ alkyl group (the $C_{1-3}$ alkyl group may be substituted with one or more halogen atoms), and a more preferred example is a hydrogen atom.

Preferred examples of $R^4$ are a hydrogen atom and a $C_{1-6}$ alkyl group (the $C_{1-6}$ alkyl group may be substituted with one or more halogen atoms), and more preferred examples are a hydrogen atom and a $C_{1-6}$ alkyl group.

Preferred examples of $R^5$ are a phenyl group, a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 1-1,2,4-triazole group, a 3-1,2,4-triazole group, a 5-1,2,4-triazole group, a 1-1,2,3-triazole group, a 4-1,2,3-triazole group, a 5-1,2,3-triazole group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group and a 3-1,2,5-thiadiazolyl group (the phenyl group, the 2-thienyl group, the 3-thienyl group, the 2-furyl group, the 3-furyl group, the 2-pyranyl group, the 3-pyranyl group, the 4-pyranyl group, the 1-pyrrolyl group, the 2-pyrrolyl group, the 3-pyrrolyl group, the 1-imidazolyl group, the 2-imidazolyl group, the 4-imidazolyl group, the 1-pyrazolyl group, the 3-pyrazolyl group, the 4-pyrazolyl group, the 2-thiazolyl group, the 4-thiazolyl group, the 5-thiazolyl group, the 3-isothiazolyl group, the 4-isothiazolyl group, the 5-isothiazolyl group, the 1-1,2,4-triazole group, the 3-1,2,4-triazole group, the 5-1,2,4-triazole group, the 1-1,2,3-triazole group, the 4-1,2,3-triazole group, the 5-1,2,3-triazole group, the 2-oxazolyl group, the 4-oxazolyl group, the 5-oxazolyl group, the 3-isoxazolyl group, the 4-isoxazolyl group, the 5-isoxazolyl group, the 2-pyridyl group, the 3-pyridyl group, the 4-pyridyl group, the 2-pyrazinyl group, the 2-pyrimidinyl group, the 4-pyrimidinyl group, the 5-pyrimidinyl group, the 3-pyridazinyl group, the 4-pyridazinyl group, the 2-1,3,4-oxadiazolyl group, the 2-1,3,4-thiadiazolyl group, the 3-1,2,4-oxadiazolyl group, the 5-1,2,4-oxadiazolyl group, the 3-1,2,4-thiadiazolyl group, the 5-1,2,4-thiadiazolyl group, the 3-1,2,5-oxadiazolyl group and the 3-1,2,5-thiadiazolyl group may optionally be substituted with one or more halogen atoms, one or more cyano groups, one or more carbamoyl groups, one or more sulfamoyl groups, one or more carboxyl groups, one or more $C_{1-3}$ alkylsulfonyl groups, one or more $C_{1-3}$ alkyl groups or one or more $C_{1-3}$ alkoxy groups), and the N-oxides of the above nitrogen-containing aryl groups).

More preferred examples of $R^5$ are a phenyl group, a 2-thienyl group, a 3-thienyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 1-1,2,4-triazole group, a 3-1,2,4-triazole group, a 5-1,2,4-triazole group, a 1-1,2,3-triazole group, a 4-1,2,3-triazole group, a 5-1,2,3-triazole group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group and a 4-pyridazinyl group (the phenyl group, the 2-thienyl group, the 3-thienyl group, the 1-imidazolyl group, the 2-imidazolyl group, the 4-imidazolyl group, the 1-pyrazolyl group, the 3-pyrazolyl group, the 4-pyrazolyl group, the 2-thiazolyl group, the 4-thiazolyl group, the 5-thiazolyl group, the 1-1,2,4-triazole group, the 3-1,2,4-triazole group, the 5-1,2,4-triazole group, the 1-1,2,3-triazole group, the 4-1,2,3-triazole group, the 5-1,2,3-triazole group, the 3-isoxazolyl group, the 4-isoxazolyl group, the 5-isoxazolyl group, the 2-pyridyl group, the 3-pyridyl group, the 4-pyridyl group, the 2-pyrazinyl group, the 2-pyrimidinyl group, the 4-pyrimidinyl group, the 5-pyrimidinyl group, the 3-pyridazinyl group and the 4-pyridazinyl group may optionally be substituted with one or more chlorine atoms, one or more cyano groups, one or more carbamoyl groups, one or more sulfamoyl groups, one or more carboxyl groups, one or more methylsulfonyl groups, one or more methyl groups, one or more ethyl groups or one or more methoxy groups), a 2-pyridyl-N-oxide group, a 3-pyridyl-N-oxide group and a 4-pyridyl-N-oxide group.

As preferred examples of $R^5$ also mentioned are a hydrogen atom and a $C_{1-10}$ alkyl group (the $C_{1-10}$ alkyl group may be substituted with one or more hydroxyl groups, one or more halogen atoms, one or more $C_{1-3}$ alkyl groups, one or more dimethylamino groups, one or more diethylamino groups or one or more of the following substituents).

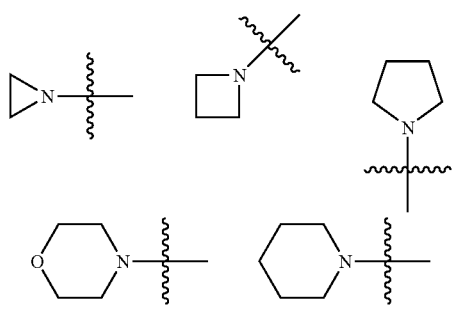

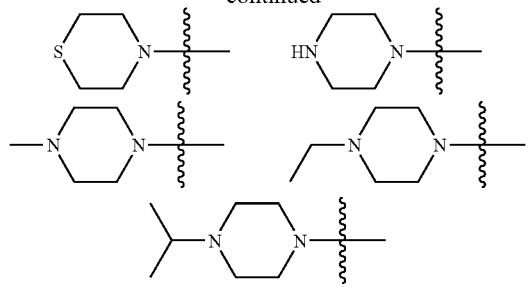

More preferred examples of $R^5$ are a hydrogen atom and a $C_{1-6}$ alkyl group (the $C_{1-6}$ alkyl group may be substituted with one or more hydroxyl groups, one or more halogen atoms, one or more methoxy groups, one or more ethoxy groups, one or more dimethylamino groups or one or more of the following substituents).

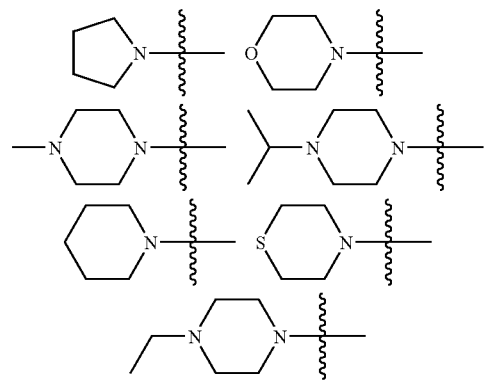

Preferred examples of $R^7$ are a $C_{2-14}$ aryl group (the $C_{2-14}$ aryl group may optionally be substituted with one or more $C_{1-10}$ alkyl groups (the $C_{1-10}$ alkyl groups may be substituted with one or more halogen atoms), one or more halogen atoms, one or more $C_{1-10}$ alkoxy groups or one or more $C_{1-3}$ alkoxy groups (the $C_{1-3}$ alkoxy groups are optionally substituted with one or more halogen atoms)), and a more preferred examples is a phenyl group (the phenyl group may optionally be substituted with one or more $C_{1-10}$ alkyl groups (the $C_{1-10}$ alkyl groups may be substituted with one or more halogen atoms), one or more halogen atoms, one or more $C_{1-10}$ alkoxy groups or one or more $C_{1-3}$ alkoxy groups (the $C_{1-3}$ alkoxy groups are optionally substituted with one or more halogen atoms)). A particularly preferred example is a phenyl group (the phenyl group may optionally be substituted with one or more $C_{1-6}$ alkyl groups, one or more halogen atoms or one or more $C_{1-3}$ alkoxy groups (the $C_{1-3}$ alkoxy groups are optionally substituted with one or more halogen atoms)).

Preferred examples of $Ar^1$ are the structures represented by the following formula (II) or (III);

(II)

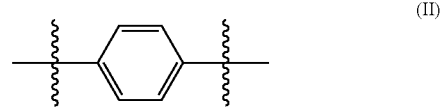

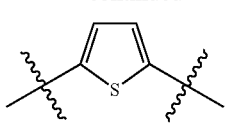

and more preferred is the structure represented by the formula (III).

Favorable compounds to be used for the present invention are as follows.

(1) Compounds represented by the formula (I), tautomers or pharmaceutically acceptable salts of the compounds or solvates thereof:

$$\text{(I)}$$

wherein each of $R^1$ and $R^4$ is independently a hydrogen atom or a $C_{1-6}$ alkyl group (the $C_{1-6}$ alkyl group may optionally be substituted with one or more halogen atoms),
$R^2$, $R^3$ and $R^6$ are hydrogen atoms,
$Ar^1$ is represented by the formula (II) or the formula (III):

$$\text{(II)}$$

$$\text{(III)}$$

$R^7$ is a phenyl group (the phenyl group is optionally substituted with one or more $C_{1-10}$ alkyl groups (the $C_{1-10}$ alkyl groups may be substituted with one or more halogen atoms), one or more halogen atoms, one or more $C_{1-10}$ alkoxy groups or one or more $C_{1-3}$ alkoxy groups (the $C_{1-3}$ alkoxy groups are optionally substituted with one or more halogen atoms)), $R^5$ is a $C_{2-14}$ aryl group (the $C_{2-14}$ aryl group is substituted with —$V^5$ (wherein $V^5$ means a hydrogen atom, a hydroxyl group, a protected hydroxyl group, an amino group, a protected amino group, a thiol group, a protected thiol group, a nitro group, a cyano group, a halogen atom, a carboxyl group, a carbamoyl group, a sulfamoyl group, a sulfo group, a formyl group, a $C_{1-3}$ alkyl group, a $C_{1-3}$ alkoxy group (the $C_{1-3}$ alkyl group and the $C_{1-3}$ alkoxy group are substituted with one or more halogen atoms), a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkoxycarbonyl group, a $C_{1-10}$ alkoxy group, a $C_{1-10}$ alkylcarbonyl group, a $C_{1-10}$ alkylcarbonylamino group, a mono- or di-$C_{1-10}$ alkylamino group, a $C_{1-10}$ alkylsulfonyl group, a $C_{1-10}$ alkylaminosulfonyl group, a $C_{1-10}$ alkylaminocarbonyl group, a $C_{1-10}$ alkylsulfonylamino group or a $C_{1-10}$ thioalkyl group) and, when it is a nitrogen-containing $C_{2-14}$ aryl group, may be an N-oxide thereof), X is OH, and Y and Z are oxygen atoms.

(2) The compounds according to (1), tautomers or pharmaceutically acceptable salts of the compounds or solvates thereof, wherein $R^1$ is a hydrogen atom or a $C_{1-3}$ alkyl group, and
$Ar^1$ is represented by the formula (III).

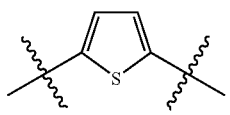

(3) The compounds according to (2), tautomers or pharmaceutically acceptable salts of the compounds or solvates thereof, wherein $R^5$ is a $C_{2-14}$ aryl group (the $C_{2-14}$ aryl group is substituted with one or more hydrogen atoms, one or more nitro groups, one or more cyano groups, one or more halogen atoms, one or more carboxyl groups, one or more carbamoyl groups, one or more sulfamoyl groups, one or more sulfo groups, one or more formyl groups, one or more $C_{1-3}$ alkyl groups, one or more $C_{1-3}$ alkoxy groups (the $C_{1-3}$ alkyl groups and the $C_{1-3}$ alkoxy groups are substituted with one or more halogen atoms), one or more $C_{1-10}$ alkyl groups, one or more $C_{1-10}$ alkylcarbonyloxy groups, one or more $C_{1-10}$ alkoxycarbonyl groups, one or more $C_{1-10}$ alkoxy groups, one or more $C_{1-10}$ alkylcarbonyl groups, one or more $C_{1-10}$ alkylcarbonylamino groups, one or more mono- or di-$C_{1-10}$ alkylamino groups, one or more $C_{1-10}$ alkylsulfonyl groups, one or more $C_{1-10}$ alkylaminosulfonyl groups, one or more $C_{1-10}$ alkylaminocarbonyl groups, one or more $C_{1-10}$ alkylsulfonylamino groups or one or more $C_{1-10}$ thioalkyl groups) and, when it is a nitrogen-containing $C_{2-14}$ aryl group, may be an N-oxide thereof).

(4) The compounds according to (2), tautomers or pharmaceutically acceptable salts of the compounds or solvates thereof, wherein $R^5$ is a $C_{2-14}$ aryl group (the $C_{2-14}$ aryl group is substituted with one or more hydrogen atoms, one or more cyano groups, one or more halogen atoms, one or more carbamoyl groups, one or more sulfamoyl groups, one or more $C_{1-3}$ alkylsulfonyl groups, one or more $C_{1-3}$ alkyl groups, one or more $C_{1-3}$ alkoxy groups (the $C_{1-3}$ alkyl groups and the $C_{1-3}$ alkoxy groups are substituted with one or more halogen atoms), one or more $C_{1-3}$ alkyl groups or one or more $C_{1-3}$ alkoxy groups and, when it is a nitrogen-containing $C_{2-14}$ aryl group, may be an N-oxide thereof).

(5) The compounds according to (2), tautomers or pharmaceutically acceptable salts of the compounds or solvates thereof, wherein $R^5$ is a $C_{2-14}$ aryl group (the $C_{2-14}$ aryl group is substituted with one or more hydrogen atoms, one or more halogen atoms, one or more carbamoyl groups, one or more sulfamoyl groups, one or more $C_{1-10}$ alkylsulfonyl groups, one or more $C_{1-3}$ alkyl groups or one or more $C_{1-3}$ alkoxy groups and, when it is a nitrogen-containing $C_{2-14}$ aryl group, may be an N-oxide thereof).

Compounds represented by the formula (I), tautomers or pharmaceutically acceptable salts of the compounds or solvates thereof:

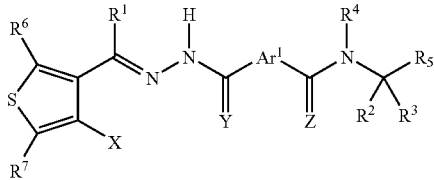

(I)

wherein each of R¹ and R⁴ is independently a hydrogen atom or a $C_{1-3}$ alkyl group, $R^2$, $R^3$ and $R^6$ are hydrogen atoms, $Ar^1$ is represented by the formula (III):

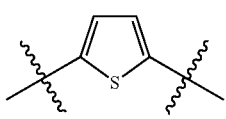

(III)

$R^7$ is a phenyl group (the phenyl group is optionally substituted with one or more $C_{1-10}$ alkyl groups (the $C_{1-10}$ alkyl groups may be substituted with one or more halogen atoms), one or more halogen atoms, one or more $C_{1-10}$ alkoxy groups or one or more $C_{1-3}$ alkoxy groups (the $C_{1-3}$ alkoxy groups are optionally substituted with one or more halogen atoms)), $R^5$ is a hydrogen atom or a $C_{1-6}$ alkyl group (the $C_{1-6}$ alkyl group may be substituted with one or more hydroxyl groups, one or more halogen atoms, one or more $C_{1-3}$ alkoxy groups, one or more dimethyl amino groups or one or more of the following groups), X is OH, and Y and Z are oxygen atoms.

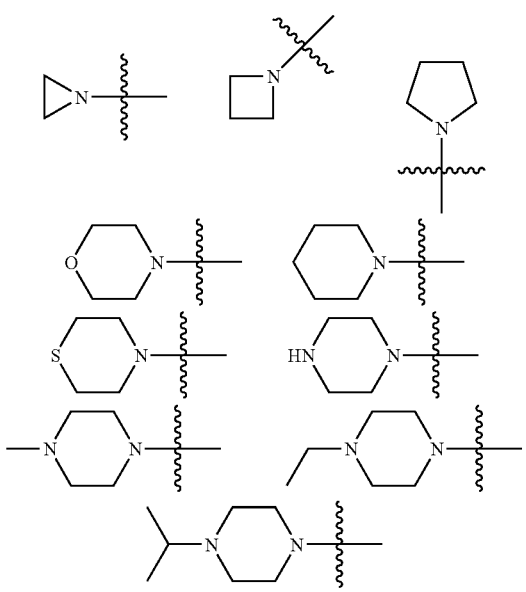

(7) Compounds wherein Ra, Ar and Q are any of the following combinations shown in Table 1, tautomers or pharmaceutically acceptable salts of the compounds or solvates thereof. The symbols in Table 1 denote the following substituents.

TABLE 1

| Ra | Ar | Q |
|---|---|---|
| Ra1 | Ar1 | Q1 |
| Ra1 | Ar1 | Q2 |
| Ra1 | Ar1 | Q3 |
| Ra1 | Ar1 | Q4 |
| Ra1 | Ar1 | Q5 |
| Ra1 | Ar1 | Q6 |
| Ra1 | Ar1 | Q7 |
| Ra1 | Ar1 | Q8 |
| Ra1 | Ar1 | Q9 |
| Ra1 | Ar1 | Q10 |
| Ra1 | Ar1 | Q11 |
| Ra1 | Ar1 | Q12 |
| Ra1 | Ar1 | Q13 |
| Ra1 | Ar1 | Q14 |
| Ra1 | Ar1 | Q15 |
| Ra1 | Ar1 | Q16 |
| Ra1 | Ar1 | Q17 |
| Ra1 | Ar1 | Q18 |
| Ra1 | Ar1 | Q19 |
| Ra1 | Ar1 | Q20 |
| Ra1 | Ar1 | Q21 |
| Ra1 | Ar1 | Q22 |
| Ra1 | Ar1 | Q23 |
| Ra1 | Ar1 | Q24 |
| Ra1 | Ar1 | Q25 |
| Ra1 | Ar1 | Q26 |
| Ra1 | Ar1 | Q27 |
| Ra1 | Ar1 | Q28 |
| Ra1 | Ar1 | Q29 |
| Ra1 | Ar1 | Q30 |
| Ra1 | Ar1 | Q31 |
| Ra1 | Ar1 | Q32 |
| Ra1 | Ar1 | Q33 |
| Ra1 | Ar1 | Q34 |
| Ra1 | Ar1 | Q35 |
| Ra1 | Ar1 | Q36 |
| Ra1 | Ar1 | Q37 |
| Ra1 | Ar1 | Q38 |
| Ra1 | Ar1 | Q39 |
| Ra1 | Ar1 | Q40 |
| Ra1 | Ar1 | Q41 |
| Ra1 | Ar1 | Q42 |
| Ra1 | Ar1 | Q43 |
| Ra1 | Ar1 | Q44 |
| Ra1 | Ar1 | Q45 |
| Ra1 | Ar1 | Q46 |
| Ra1 | Ar1 | Q47 |
| Ra1 | Ar1 | Q48 |
| Ra1 | Ar1 | Q49 |
| Ra1 | Ar1 | Q50 |
| Ra1 | Ar1 | Q51 |
| Ra2 | Ar1 | Q1 |
| Ra2 | Ar1 | Q2 |
| Ra2 | Ar1 | Q3 |
| Ra2 | Ar1 | Q4 |
| Ra2 | Ar1 | Q5 |
| Ra2 | Ar1 | Q6 |
| Ra2 | Ar1 | Q7 |
| Ra2 | Ar1 | Q8 |
| Ra2 | Ar1 | Q9 |
| Ra2 | Ar1 | Q10 |
| Ra2 | Ar1 | Q11 |
| Ra2 | Ar1 | Q12 |
| Ra2 | Ar1 | Q13 |
| Ra2 | Ar1 | Q14 |
| Ra2 | Ar1 | Q15 |

TABLE 1-continued

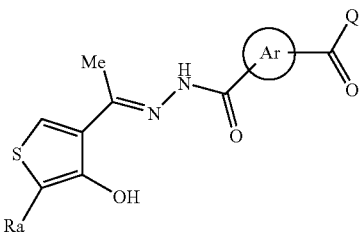

| Ra | Ar | Q |
|---|---|---|
| Ra2 | Ar1 | Q16 |
| Ra2 | Ar1 | Q17 |
| Ra2 | Ar1 | Q18 |
| Ra2 | Ar1 | Q19 |
| Ra2 | Ar1 | Q20 |
| Ra2 | Ar1 | Q21 |
| Ra2 | Ar1 | Q22 |
| Ra2 | Ar1 | Q23 |
| Ra2 | Ar1 | Q24 |
| Ra2 | Ar1 | Q25 |
| Ra2 | Ar1 | Q26 |
| Ra2 | Ar1 | Q27 |
| Ra2 | Ar1 | Q28 |
| Ra2 | Ar1 | Q29 |
| Ra2 | Ar1 | Q30 |
| Ra2 | Ar1 | Q31 |
| Ra2 | Ar1 | Q32 |
| Ra2 | Ar1 | Q33 |
| Ra2 | Ar1 | Q34 |
| Ra2 | Ar1 | Q35 |
| Ra2 | Ar1 | Q36 |
| Ra2 | Ar1 | Q37 |
| Ra2 | Ar1 | Q38 |
| Ra2 | Ar1 | Q39 |
| Ra2 | Ar1 | Q40 |
| Ra2 | Ar1 | Q41 |
| Ra2 | Ar1 | Q42 |
| Ra2 | Ar1 | Q43 |
| Ra2 | Ar1 | Q44 |
| Ra2 | Ar1 | Q45 |
| Ra2 | Ar1 | Q46 |
| Ra2 | Ar1 | Q47 |
| Ra2 | Ar1 | Q48 |
| Ra2 | Ar1 | Q49 |
| Ra2 | Ar1 | Q50 |
| Ra2 | Ar1 | Q51 |
| Ra3 | Ar1 | Q1 |
| Ra3 | Ar1 | Q2 |
| Ra3 | Ar1 | Q3 |
| Ra3 | Ar1 | Q4 |
| Ra3 | Ar1 | Q5 |
| Ra3 | Ar1 | Q6 |
| Ra3 | Ar1 | Q7 |
| Ra3 | Ar1 | Q8 |
| Ra3 | Ar1 | Q9 |
| Ra3 | Ar1 | Q10 |
| Ra3 | Ar1 | Q11 |
| Ra3 | Ar1 | Q12 |
| Ra3 | Ar1 | Q13 |
| Ra3 | Ar1 | Q14 |
| Ra3 | Ar1 | Q15 |
| Ra3 | Ar1 | Q16 |
| Ra3 | Ar1 | Q17 |
| Ra3 | Ar1 | Q18 |
| Ra3 | Ar1 | Q19 |
| Ra3 | Ar1 | Q20 |
| Ra3 | Ar1 | Q21 |
| Ra3 | Ar1 | Q22 |
| Ra3 | Ar1 | Q23 |
| Ra3 | Ar1 | Q24 |
| Ra3 | Ar1 | Q25 |
| Ra3 | Ar1 | Q26 |
| Ra3 | Ar1 | Q27 |
| Ra3 | Ar1 | Q28 |
| Ra3 | Ar1 | Q29 |
| Ra3 | Ar1 | Q30 |

TABLE 1-continued

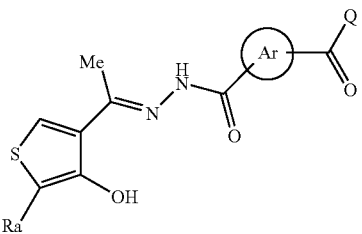

| Ra | Ar | Q |
|---|---|---|
| Ra3 | Ar1 | Q31 |
| Ra3 | Ar1 | Q32 |
| Ra3 | Ar1 | Q33 |
| Ra3 | Ar1 | Q34 |
| Ra3 | Ar1 | Q35 |
| Ra3 | Ar1 | Q36 |
| Ra3 | Ar1 | Q37 |
| Ra3 | Ar1 | Q38 |
| Ra3 | Ar1 | Q39 |
| Ra3 | Ar1 | Q40 |
| Ra3 | Ar1 | Q41 |
| Ra3 | Ar1 | Q42 |
| Ra3 | Ar1 | Q43 |
| Ra3 | Ar1 | Q44 |
| Ra3 | Ar1 | Q45 |
| Ra3 | Ar1 | Q46 |
| Ra3 | Ar1 | Q47 |
| Ra3 | Ar1 | Q48 |
| Ra3 | Ar1 | Q49 |
| Ra3 | Ar1 | Q50 |
| Ra3 | Ar1 | Q51 |
| Ra4 | Ar1 | Q1 |
| Ra4 | Ar1 | Q2 |
| Ra4 | Ar1 | Q3 |
| Ra4 | Ar1 | Q4 |
| Ra4 | Ar1 | Q5 |
| Ra4 | Ar1 | Q6 |
| Ra4 | Ar1 | Q7 |
| Ra4 | Ar1 | Q8 |
| Ra4 | Ar1 | Q9 |
| Ra4 | Ar1 | Q10 |
| Ra4 | Ar1 | Q11 |
| Ra4 | Ar1 | Q12 |
| Ra4 | Ar1 | Q13 |
| Ra4 | Ar1 | Q14 |
| Ra4 | Ar1 | Q15 |
| Ra4 | Ar1 | Q16 |
| Ra4 | Ar1 | Q17 |
| Ra4 | Ar1 | Q18 |
| Ra4 | Ar1 | Q19 |
| Ra4 | Ar1 | Q20 |
| Ra4 | Ar1 | Q21 |
| Ra4 | Ar1 | Q22 |
| Ra4 | Ar1 | Q23 |
| Ra4 | Ar1 | Q24 |
| Ra4 | Ar1 | Q25 |
| Ra4 | Ar1 | Q26 |
| Ra4 | Ar1 | Q27 |
| Ra4 | Ar1 | Q28 |
| Ra4 | Ar1 | Q29 |
| Ra4 | Ar1 | Q30 |
| Ra4 | Ar1 | Q31 |
| Ra4 | Ar1 | Q32 |
| Ra4 | Ar1 | Q33 |
| Ra4 | Ar1 | Q34 |
| Ra4 | Ar1 | Q35 |
| Ra4 | Ar1 | Q36 |
| Ra4 | Ar1 | Q37 |
| Ra4 | Ar1 | Q38 |
| Ra4 | Ar1 | Q39 |
| Ra4 | Ar1 | Q40 |
| Ra4 | Ar1 | Q41 |
| Ra4 | Ar1 | Q42 |
| Ra4 | Ar1 | Q43 |
| Ra4 | Ar1 | Q44 |
| Ra4 | Ar1 | Q45 |

TABLE 1-continued

| Ra | Ar | Q |
|---|---|---|
| Ra4 | Ar1 | Q46 |
| Ra4 | Ar1 | Q47 |
| Ra4 | Ar1 | Q48 |
| Ra4 | Ar1 | Q49 |
| Ra4 | Ar1 | Q50 |
| Ra4 | Ar1 | Q51 |
| Ra5 | Ar1 | Q1 |
| Ra5 | Ar1 | Q2 |
| Ra5 | Ar1 | Q3 |
| Ra5 | Ar1 | Q4 |
| Ra5 | Ar1 | Q5 |
| Ra5 | Ar1 | Q6 |
| Ra5 | Ar1 | Q7 |
| Ra5 | Ar1 | Q8 |
| Ra5 | Ar1 | Q9 |
| Ra5 | Ar1 | Q10 |
| Ra5 | Ar1 | Q11 |
| Ra5 | Ar1 | Q12 |
| Ra5 | Ar1 | Q13 |
| Ra5 | Ar1 | Q14 |
| Ra5 | Ar1 | Q15 |
| Ra5 | Ar1 | Q16 |
| Ra5 | Ar1 | Q17 |
| Ra5 | Ar1 | Q18 |
| Ra5 | Ar1 | Q19 |
| Ra5 | Ar1 | Q20 |
| Ra5 | Ar1 | Q21 |
| Ra5 | Ar1 | Q22 |
| Ra5 | Ar1 | Q23 |
| Ra5 | Ar1 | Q24 |
| Ra5 | Ar1 | Q25 |
| Ra5 | Ar1 | Q26 |
| Ra5 | Ar1 | Q27 |
| Ra5 | Ar1 | Q28 |
| Ra5 | Ar1 | Q29 |
| Ra5 | Ar1 | Q30 |
| Ra5 | Ar1 | Q31 |
| Ra5 | Ar1 | Q32 |
| Ra5 | Ar1 | Q33 |
| Ra5 | Ar1 | Q34 |
| Ra5 | Ar1 | Q35 |
| Ra5 | Ar1 | Q36 |
| Ra5 | Ar1 | Q37 |
| Ra5 | Ar1 | Q38 |
| Ra5 | Ar1 | Q39 |
| Ra5 | Ar1 | Q40 |
| Ra5 | Ar1 | Q41 |
| Ra5 | Ar1 | Q42 |
| Ra5 | Ar1 | Q43 |
| Ra5 | Ar1 | Q44 |
| Ra5 | Ar1 | Q45 |
| Ra5 | Ar1 | Q46 |
| Ra5 | Ar1 | Q47 |
| Ra5 | Ar1 | Q48 |
| Ra5 | Ar1 | Q49 |
| Ra5 | Ar1 | Q50 |
| Ra5 | Ar1 | Q51 |
| Ra6 | Ar1 | Q1 |
| Ra6 | Ar1 | Q2 |
| Ra6 | Ar1 | Q3 |
| Ra6 | Ar1 | Q4 |
| Ra6 | Ar1 | Q5 |
| Ra6 | Ar1 | Q6 |
| Ra6 | Ar1 | Q7 |
| Ra6 | Ar1 | Q8 |
| Ra6 | Ar1 | Q9 |
| Ra6 | Ar1 | Q10 |
| Ra6 | Ar1 | Q11 |
| Ra6 | Ar1 | Q12 |
| Ra6 | Ar1 | Q13 |
| Ra6 | Ar1 | Q14 |
| Ra6 | Ar1 | Q15 |
| Ra6 | Ar1 | Q16 |
| Ra6 | Ar1 | Q17 |
| Ra6 | Ar1 | Q18 |
| Ra6 | Ar1 | Q19 |
| Ra6 | Ar1 | Q20 |
| Ra6 | Ar1 | Q21 |
| Ra6 | Ar1 | Q22 |
| Ra6 | Ar1 | Q23 |
| Ra6 | Ar1 | Q24 |
| Ra6 | Ar1 | Q25 |
| Ra6 | Ar1 | Q26 |
| Ra6 | Ar1 | Q27 |
| Ra6 | Ar1 | Q28 |
| Ra6 | Ar1 | Q29 |
| Ra6 | Ar1 | Q30 |
| Ra6 | Ar1 | Q31 |
| Ra6 | Ar1 | Q32 |
| Ra6 | Ar1 | Q33 |
| Ra6 | Ar1 | Q34 |
| Ra6 | Ar1 | Q35 |
| Ra6 | Ar1 | Q36 |
| Ra6 | Ar1 | Q37 |
| Ra6 | Ar1 | Q38 |
| Ra6 | Ar1 | Q39 |
| Ra6 | Ar1 | Q40 |
| Ra6 | Ar1 | Q41 |
| Ra6 | Ar1 | Q42 |
| Ra6 | Ar1 | Q43 |
| Ra6 | Ar1 | Q44 |
| Ra6 | Ar1 | Q45 |
| Ra6 | Ar1 | Q46 |
| Ra6 | Ar1 | Q47 |
| Ra6 | Ar1 | Q48 |
| Ra6 | Ar1 | Q49 |
| Ra6 | Ar1 | Q50 |
| Ra6 | Ar1 | Q51 |

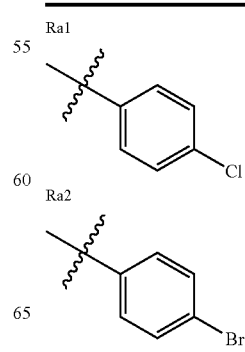

Ra1: 4-chlorophenyl

Ra2: 4-bromophenyl

TABLE 1-continued
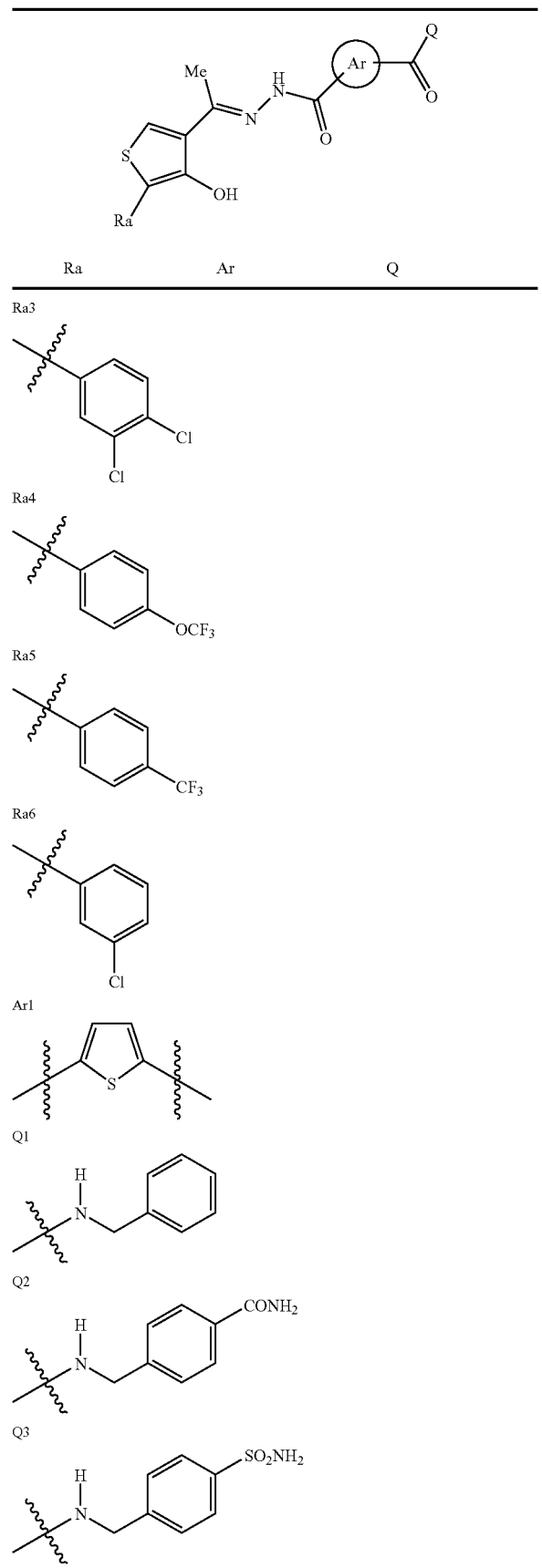
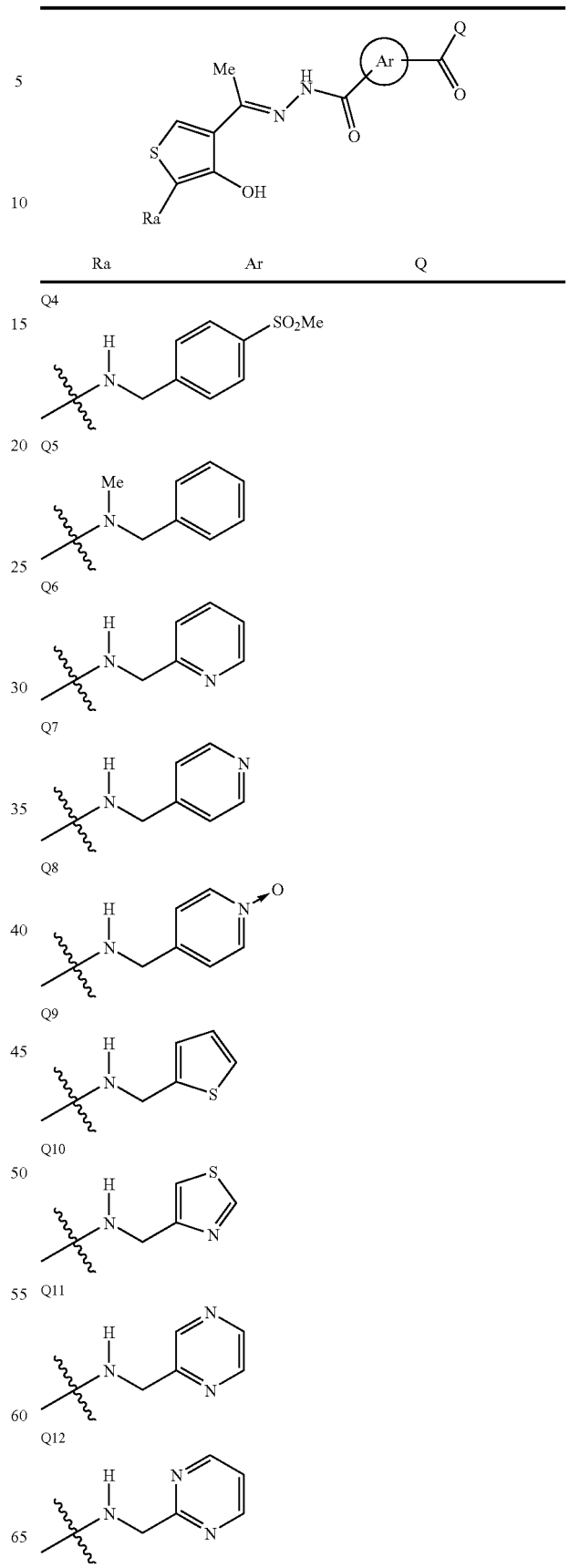

TABLE 1-continued
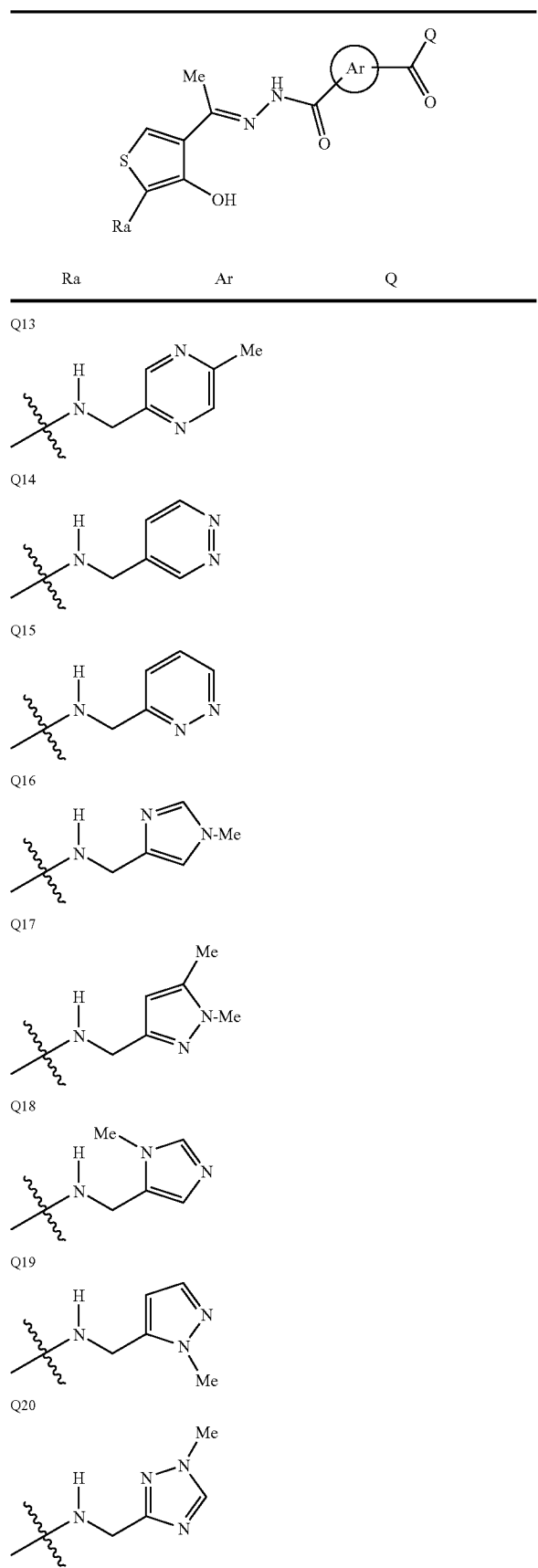
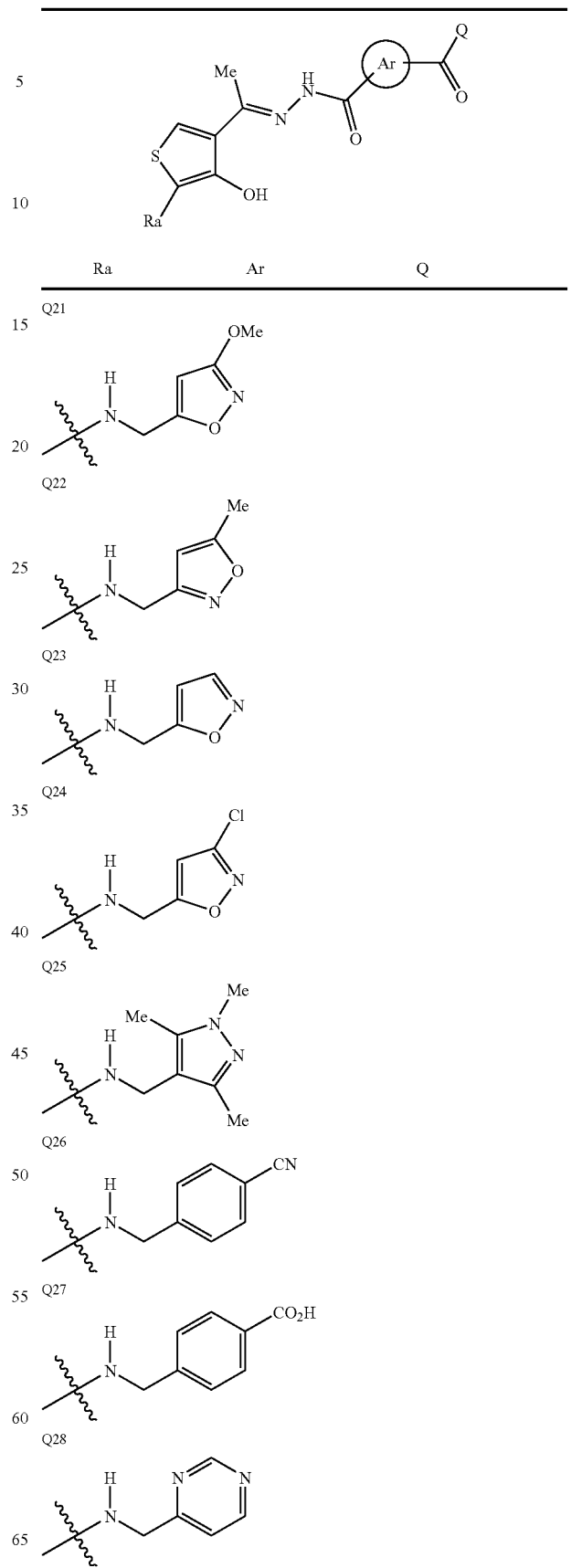

TABLE 1-continued
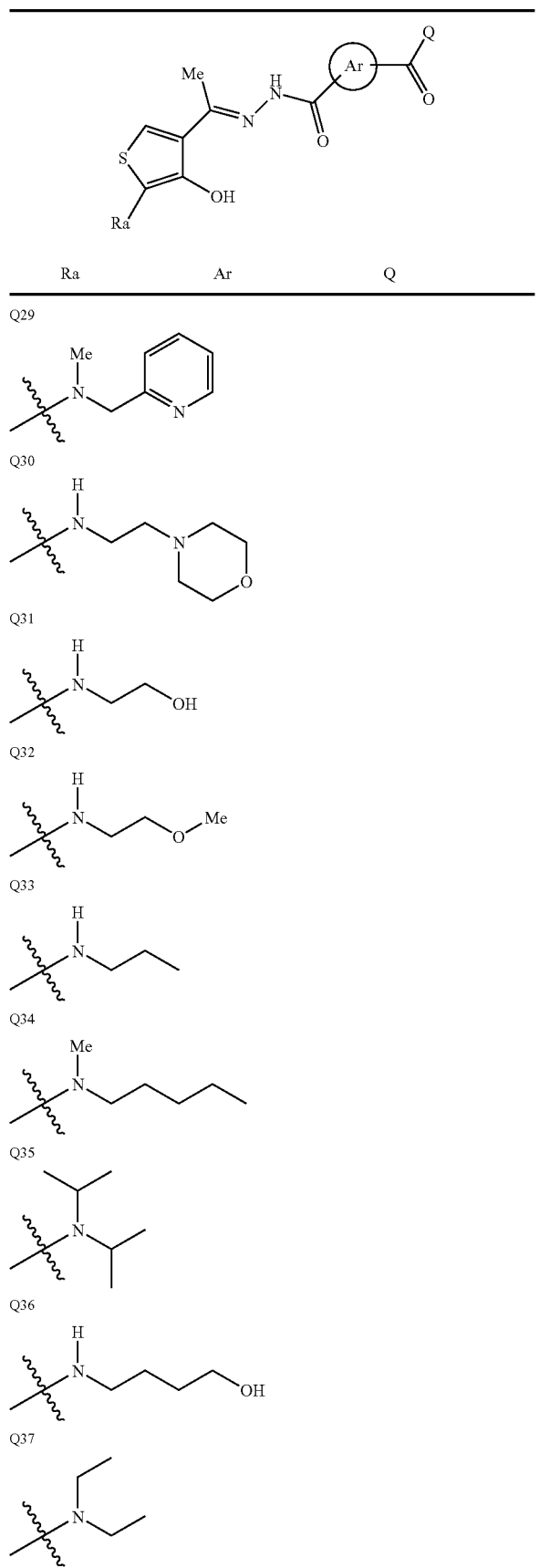
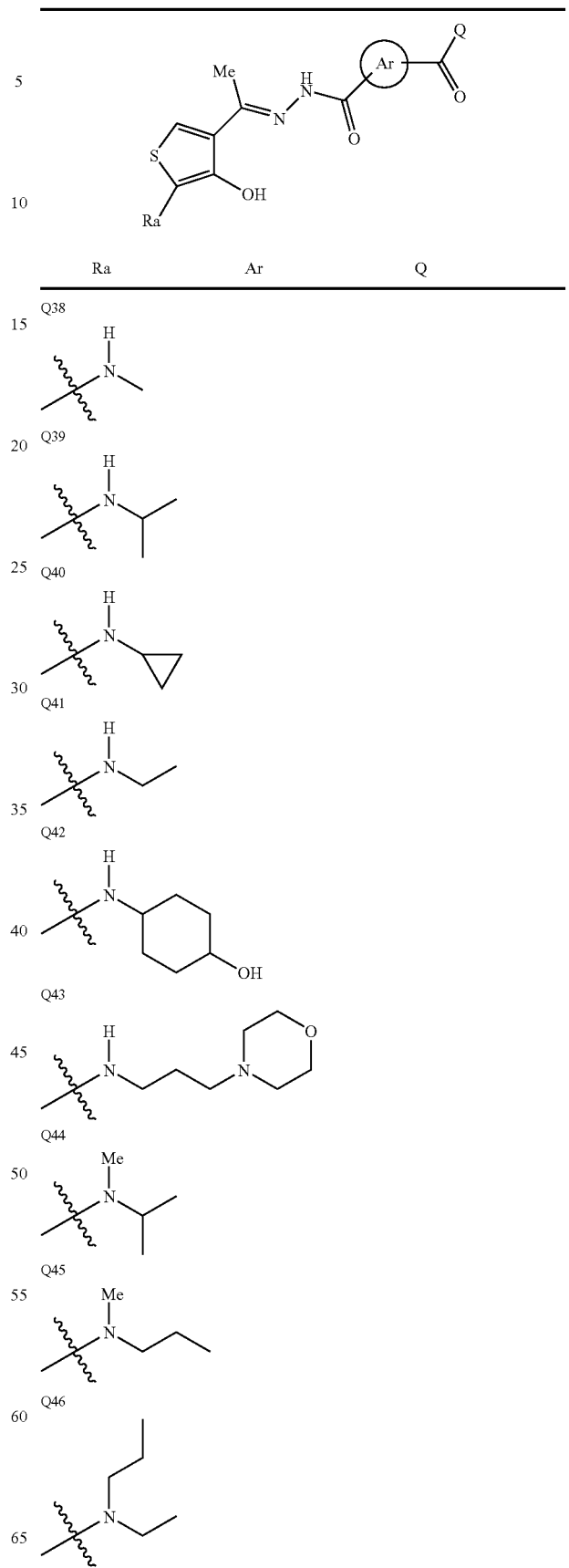

TABLE 1-continued

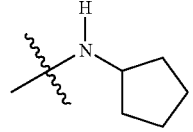 [SMILES: *NC1CCCC1]

| Ra | Ar | Q |
|---|---|---|

Q47 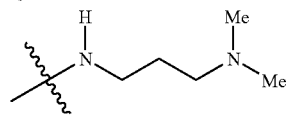

Q48 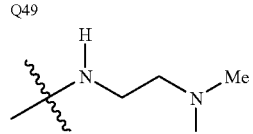

Q49 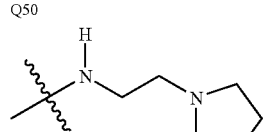

Q50 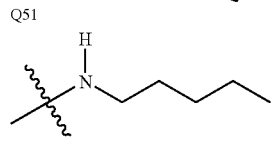

Q51 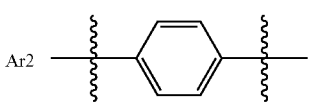

(8) The compounds shown in Table 1, wherein Ar¹ is converted to Ar2, tautomers or pharmaceutically acceptable salts of the compounds or solvates thereof.

Ar2 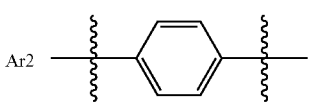

The compound of the present invention can be synthesized by reference to Patent Documents WO2004108683, WO2006064957, WO2007010954 and the like. The compound of the present invention represented by the formula (1) or a pharmaceutically acceptable salt thereof may be in the form of arbitrary crystals or an arbitrary hydrate, depending on the production conditions. The present invention covers these crystals, hydrates and mixtures. They may be in the form of a solvate with an organic solvent such as acetone, ethanol and tetrahydrofuran, and the present invention covers any of these forms.

The compound of the present invention represented by the formula (1) may be converted to a pharmaceutically acceptable salt or may be liberated from the resulting salt, if necessary. The pharmaceutically acceptable salt of the present invention may be, for example, a salt with an alkali metal (such as lithium, sodium and potassium), an alkaline earth metal (such as magnesium and calcium), ammonium, an organic base or an amino acid. It may be a salt with an inorganic acid (such as hydrochloric acid, hydrobromic acid, phosphoric acid and sulfuric acid) or an organic acid (such as acetic acid, citric acid, maleic acid, fumaric acid, benzenesulfonic acid and p-toluenesulfonic acid).

EXAMPLES

Now, the present invention will be described in further detail with reference to Examples. However, it should be understood that the present invention is by no means restricted by these specific Examples.

The $CO_2$ concentration (%) in the $CO_2$ incubator is expressed in the percentage of the volume of $CO_2$ in the atmosphere.

Example 1

Preparation of Hematopoietic Stem Cells from Human Cord Blood

From human cord blood donated by obstetric and gynecologic patients with informed consent (about 50 mL, containing heparin as an anticoagulant), a mononuclear cell fraction was obtained by the Ficoll method (density centrifugation using Lymphosepar I manufactured by Immuno-Biological Laboratories (IBL)). Subsequently, the mononuclear cell fraction was washed with PBS (Phosphate buffer saline) (−) containing 2% (v/v) fetal bovine serum (FBS, DS Pharma Biomedical), mixed with magnetic beads coated with an anti-human CD34 monoclonal antibody (Miltenyi Biotec) and incubated at 4° C. (for about 30 minutes). The antibody magnetic bead/$CD34^+$ cell complexes were separated and collected by using a MACS system (Miltenyi Biotec). When $CD34^+CD38^-$ cells were to be collected, the $CD34^+$ cells thus collected were treated with an CD34 antibody (APC, Becton, Dickinson and Company) and an CD38 antibody (PE, Becton, Dickinson and Company), and $CD34^+CD38^-$ cells were collected by using a flow cytometer JSAN (Bay Bioscience). Human cord blood-derived $CD34^+$ cells (Cambrex Bio Science Walkersville) were also purchased arbitrarily and used in the following assays.

Example 2

Expansion of $CD34^+CD38^-$ Cells from Human Cord Blood-Derived $CD34^+$ Cells

The human cord blood-derived $CD34^+$ cells collected or purchased in Example 1 were plated on a 24-well plate (TPP) (10000 cells/1/mL/well). As the culture medium, StemSpan SFEM (Stemcell Technologies) containing 50 ng/mL SCF (Peprotech) was used, and Compounds No. 1 to 133 dissolved in dimethyl sulfoxide were added in an amount of 0.1% (v/v) to a final concentration of 1 μg/mL.

After the cells were incubated in liquid culture at 37° C. for 7 days in a $CO_2$ incubator (5% $CO_2$), the number of viable cells was counted by trypan blue assay. The number of $CD34^+CD38^-$ cells was calculated as follows. After the incubation, the cells in the liquid culture was stained with a CD34 antibody (APC, Becton, Dickinson and Company) and a CD38 antibody (PE, Becton, Dickinson and Company), then washed with PBS(−) containing 2% (v/v) FBS and stained with propidium iodide (Sigma-Aldrich Japan)

added to a final concentration of 5 μg/mL. The stained cells were analyzed with a flow cytometer JSAN (Bay Bioscience) to determined the proportion of $CD34^+CD38^-$ cells, which was multiplied by the number of viable cells to calculate the number of $CD34^+CD38^-$ cells.

The results demonstrate that the compounds of the present invention showed excellent expansion activity on $CD34^+CD38^-$ cells and have expansion activity on hematopoietic stem cells and hematopoietic progenitor cells.

The expansion efficiencies in the presence of 1 μg/mL of compounds based on the number of $CD34^+CD38^-$ cells in the absence of them are shown in Tables 2 and 3 on a scale of A for expansion efficiencies of 10 or greater, B for expansion efficiencies of at least 5 and less than 10, and C for expansion efficiencies of at least 3 and less than 5.

TABLE 2

| Compound No. | Expansion efficiency |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | B |
| 21 | A |
| 22 | B |
| 23 | B |
| 24 | B |
| 25 | B |
| 26 | A |
| 27 | B |
| 28 | A |
| 29 | A |
| 30 | B |
| 31 | A |
| 32 | B |
| 33 | B |
| 34 | C |
| 35 | B |
| 36 | A |
| 37 | B |
| 38 | A |
| 39 | B |
| 40 | B |
| 41 | B |
| 42 | B |
| 43 | A |
| 44 | B |
| 45 | B |
| 46 | B |
| 47 | B |
| 48 | B |
| 49 | B |
| 50 | B |
| 51 | B |
| 52 | B |
| 53 | B |
| 54 | B |
| 55 | B |
| 56 | B |
| 57 | B |
| 58 | B |
| 59 | B |
| 60 | A |
| 61 | B |
| 62 | C |
| 63 | C |
| 64 | C |
| 65 | B |
| 66 | C |
| 67 | C |
| 68 | B |
| 69 | C |
| 70 | B |
| 71 | B |
| 72 | B |
| 73 | B |
| 74 | B |
| 75 | C |
| 76 | C |
| 77 | B |
| 78 | B |
| 79 | C |
| 80 | C |
| 81 | C |
| 82 | C |
| 83 | C |
| 84 | B |
| 85 | C |

TABLE 3

| Compound No. | Expansion efficiency |
|---|---|
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | C |
| 101 | A |
| 102 | A |
| 103 | A |
| 104 | A |
| 105 | B |
| 106 | A |
| 107 | A |
| 108 | A |
| 109 | A |
| 110 | A |
| 111 | A |
| 112 | A |
| 113 | A |
| 114 | A |
| 115 | A |
| 116 | A |
| 117 | A |
| 118 | A |
| 119 | A |
| 120 | A |
| 121 | B |
| 122 | A |
| 123 | A |
| 124 | A |
| 125 | A |
| 126 | A |
| 127 | A |
| 128 | A |

TABLE 3-continued
| Compound No. | Expansion efficiency |
|---|---|
| 129 | A |
| 130 | A |
| 131 | A |
TABLE 3-continued
| Compound No. | Expansion efficiency |
|---|---|
| 132 | A |
| 133 | A |
No. 1
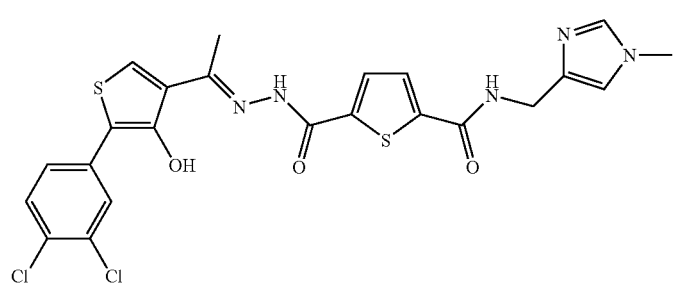
No. 2
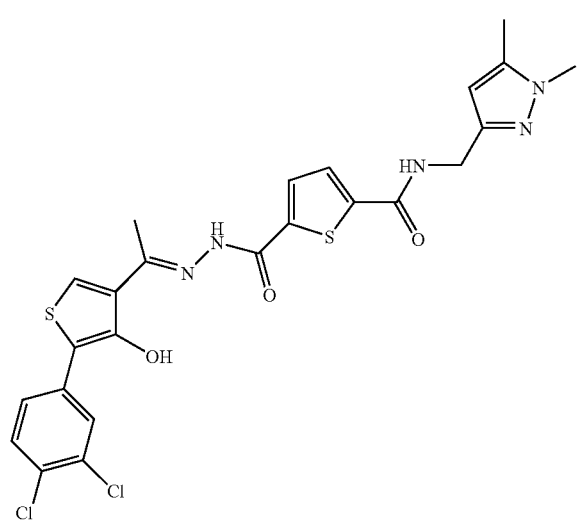
No. 3
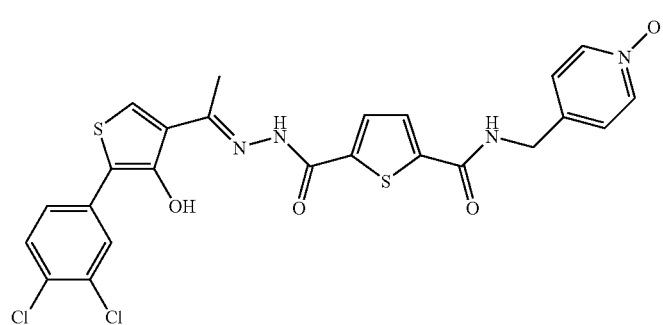
No. 4
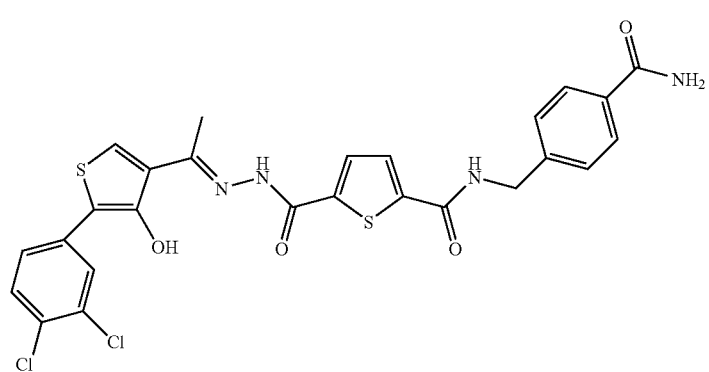

-continued
No. 5
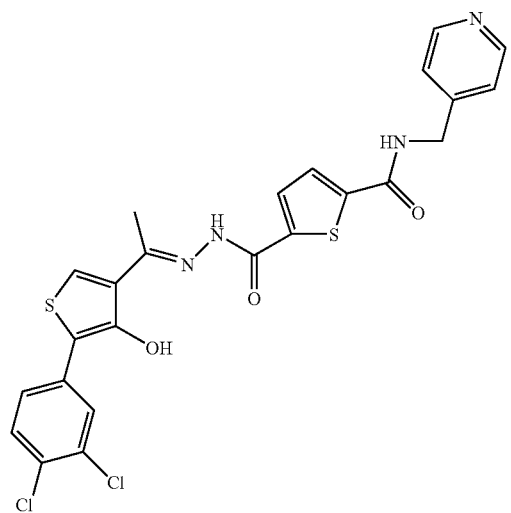
No. 6
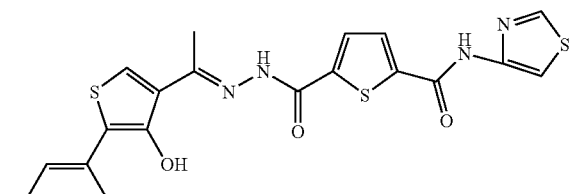
No. 7
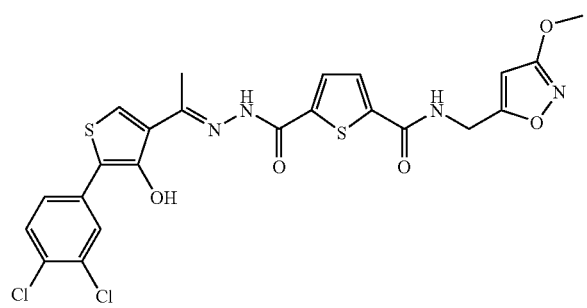
No. 8
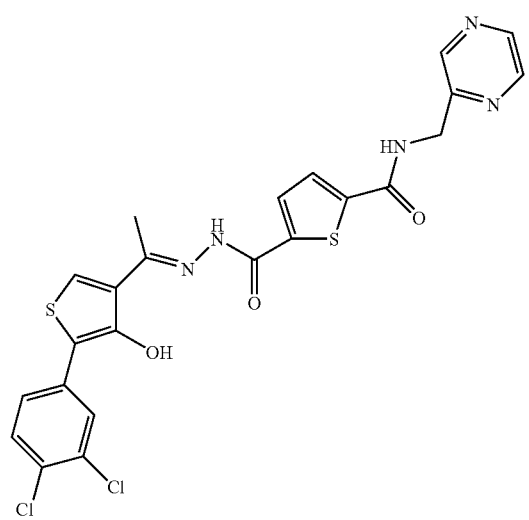
No. 9
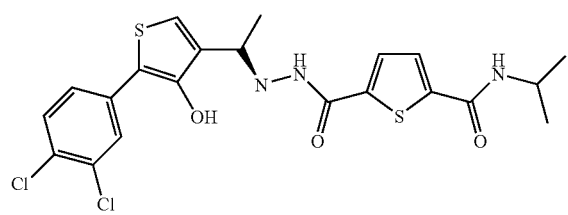
No. 10
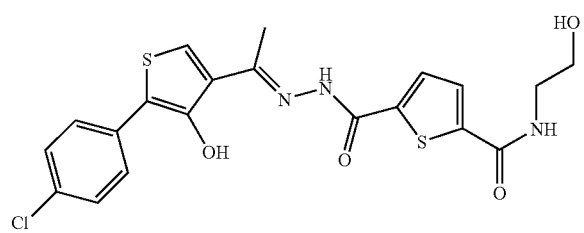
No. 11
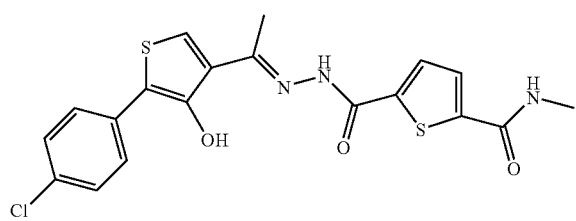

-continued
No. 12
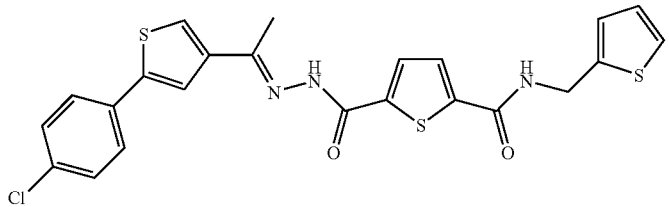
No. 13
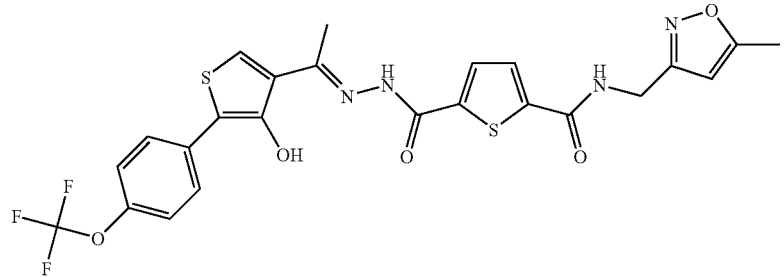
No.14
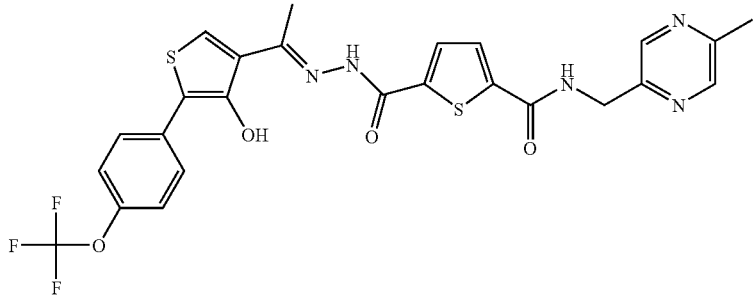
No.15
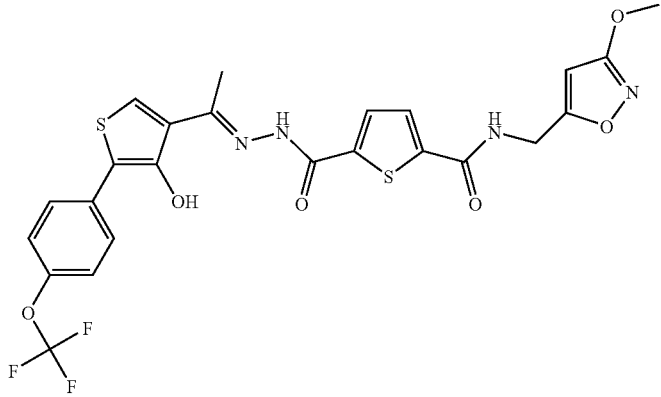
No.16
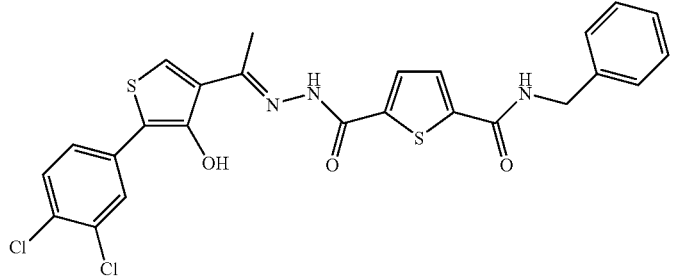

-continued
No.17
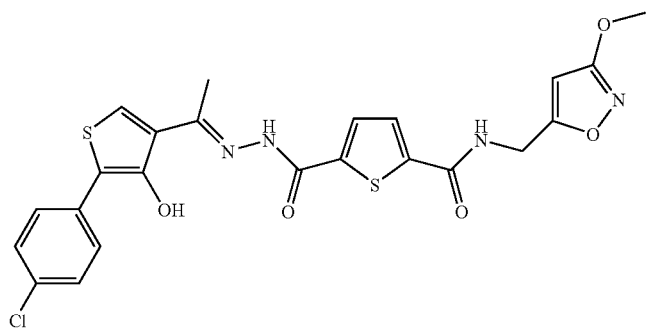
No.18
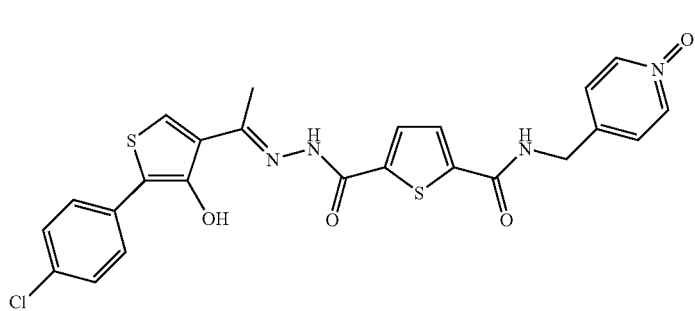
No. 19
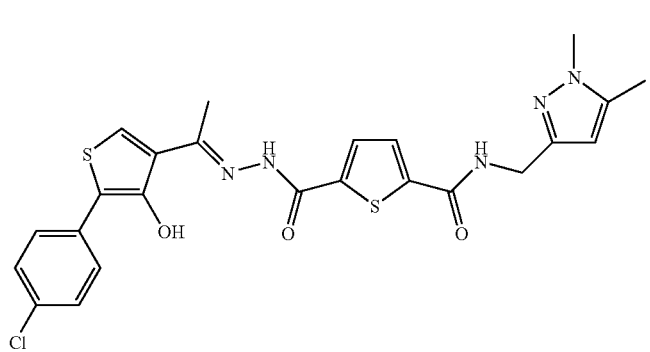
No. 20
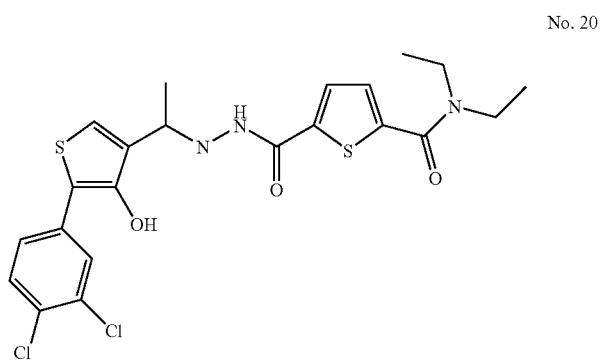
No. 21
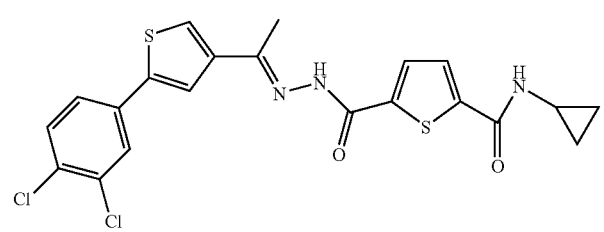

No. 22
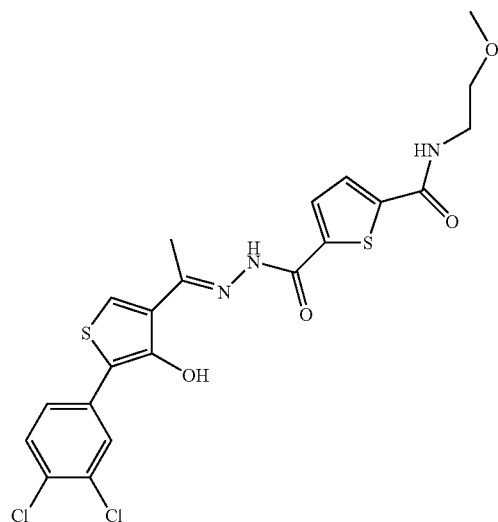
No. 23
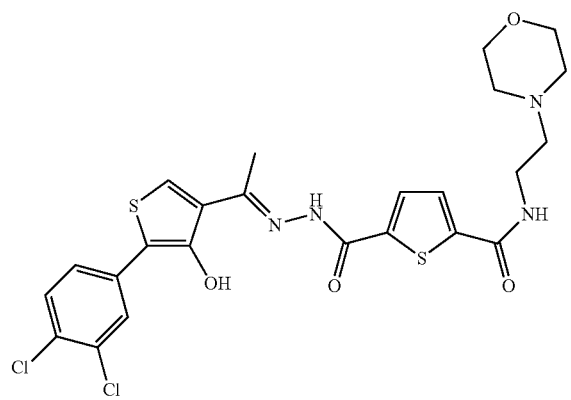
No. 24
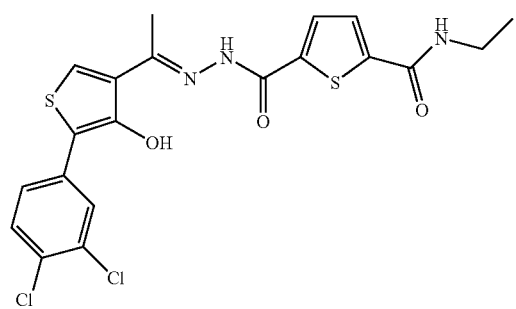
No. 25
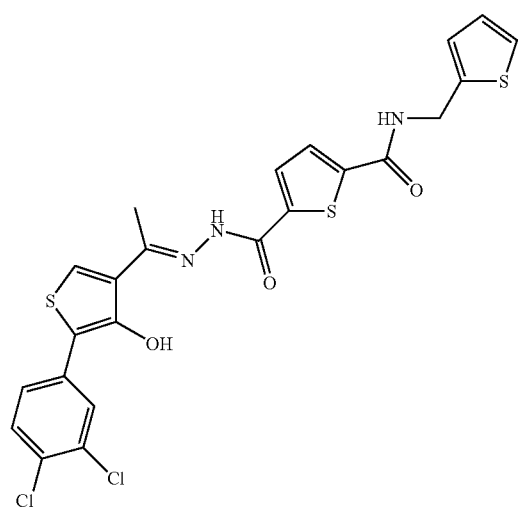
No. 26
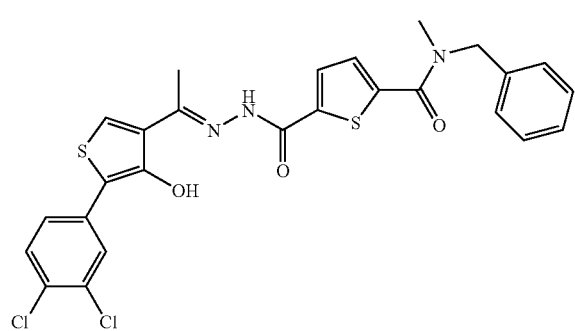

-continued
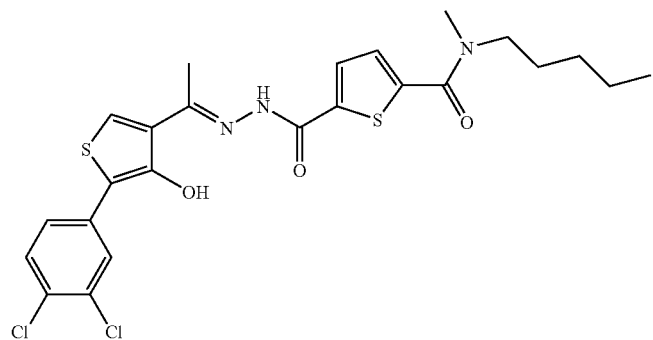
No. 27
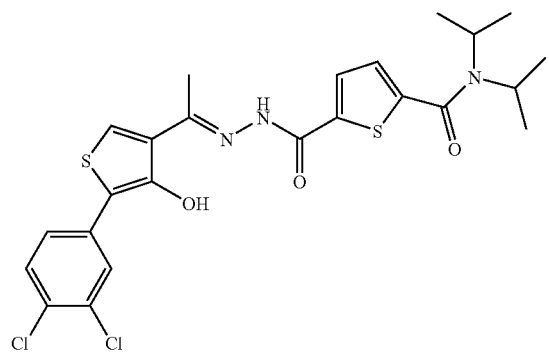
No. 28
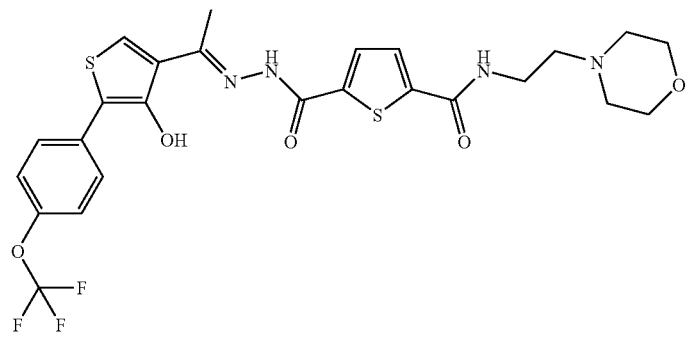
No. 29
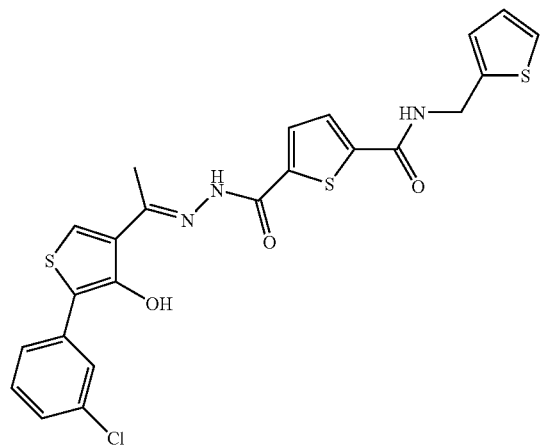
No. 30

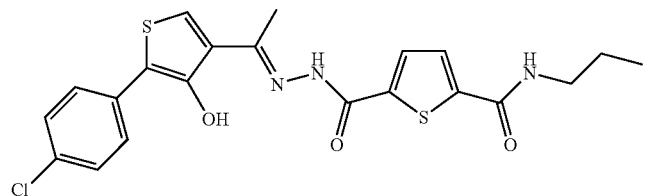
No. 31
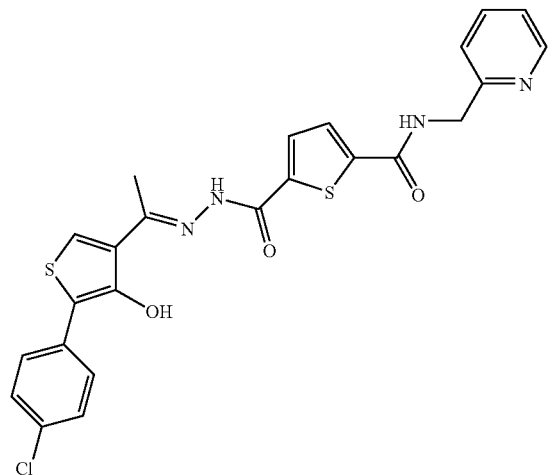
No. 32
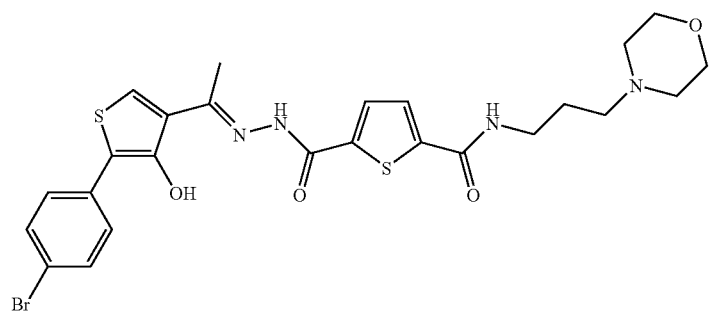
No. 33
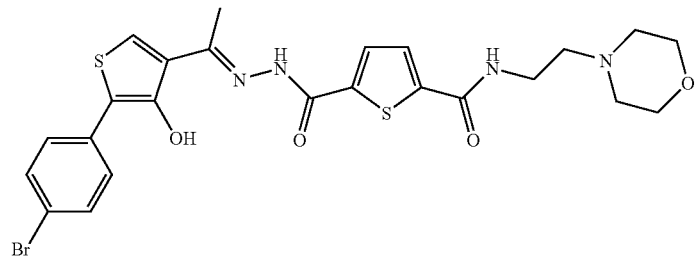
No. 34
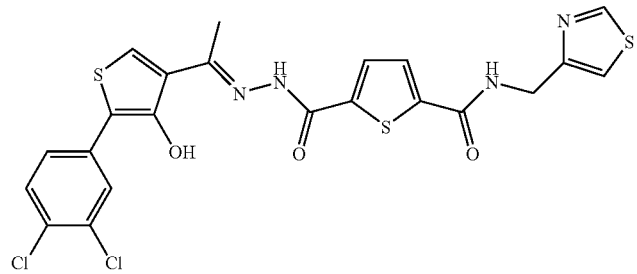
No. 35

-continued
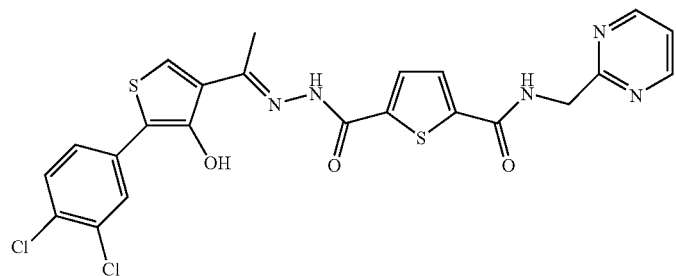
No. 36
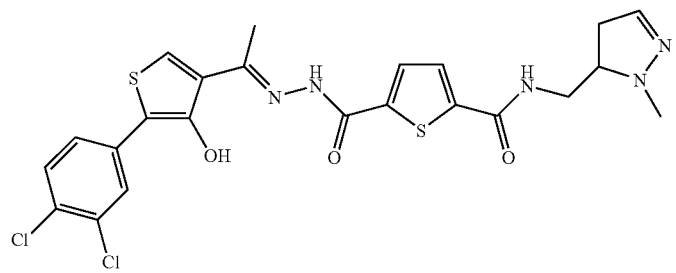
No. 37
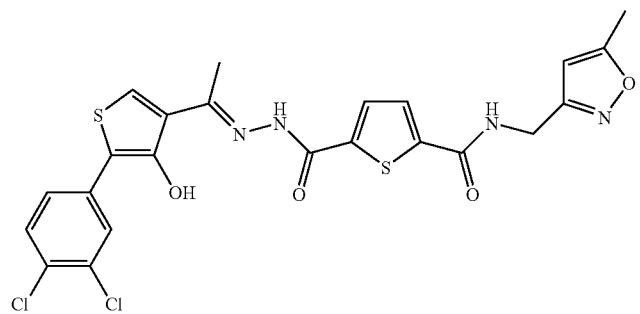
No. 38
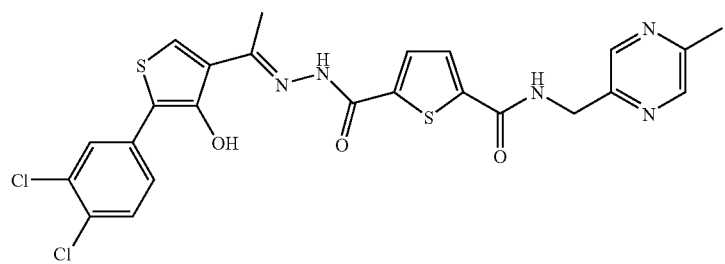
No. 39
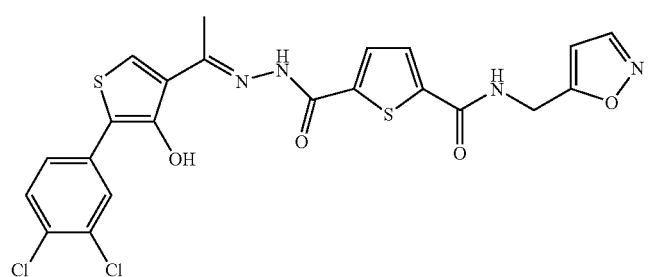
No. 40

-continued
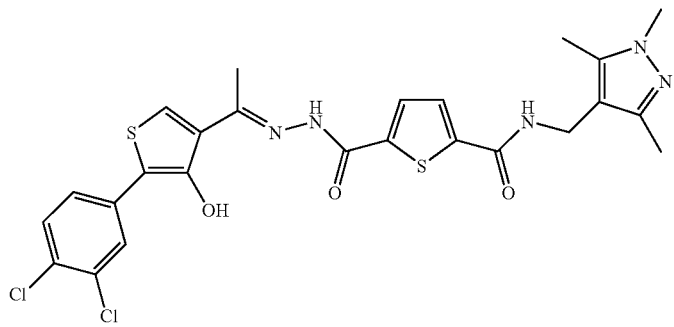
No. 41
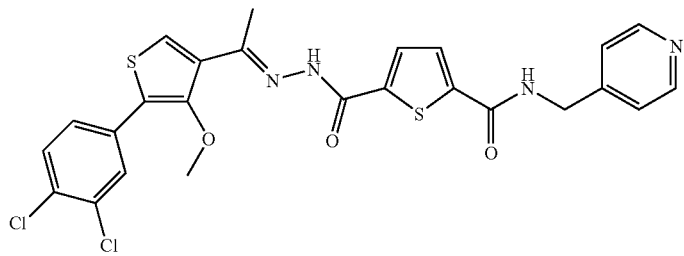
No. 42
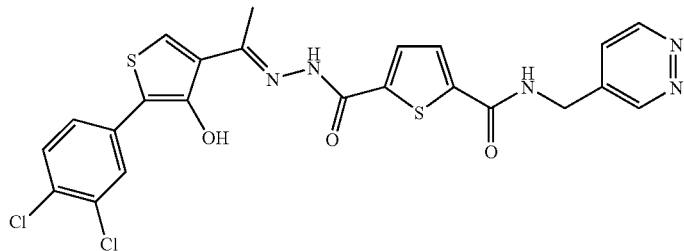
No. 43
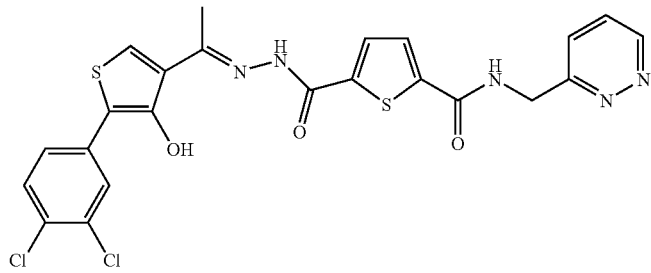
No. 44
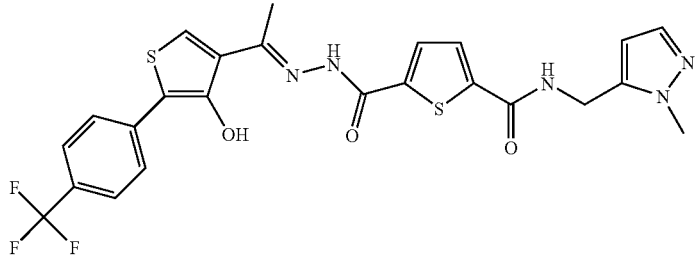
No. 45
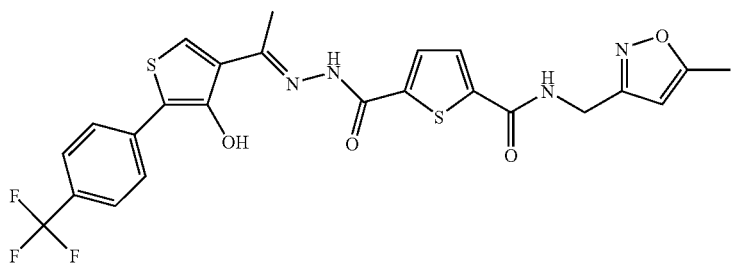
No. 46

-continued
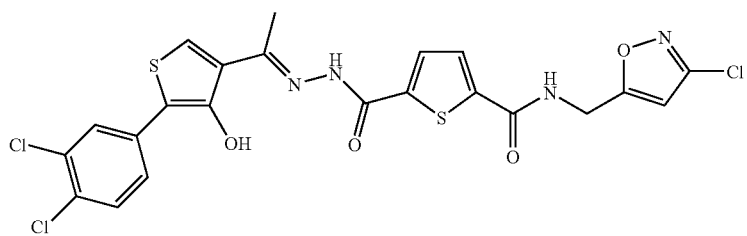
No. 47
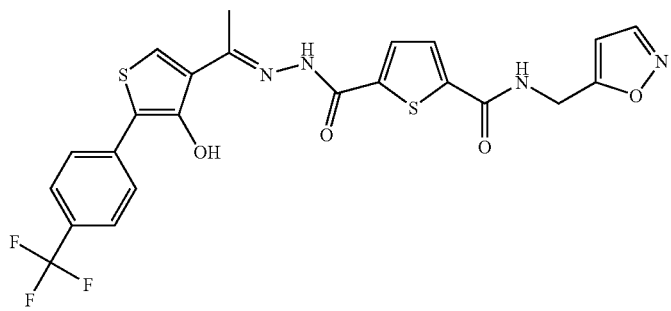
No. 48
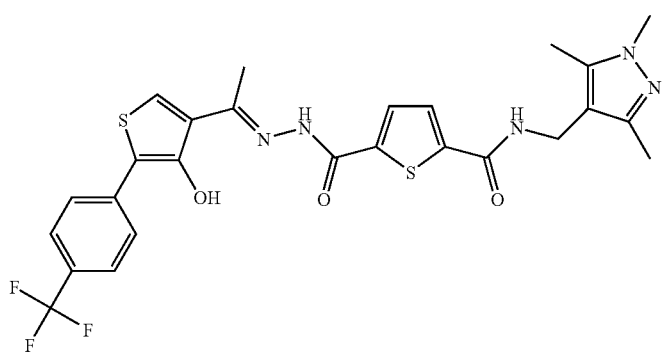
No. 49
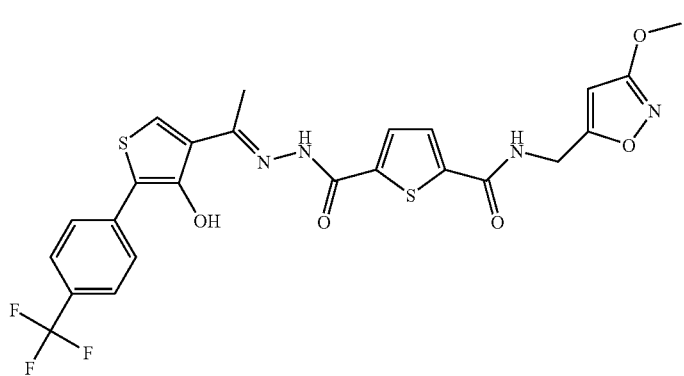
No. 50
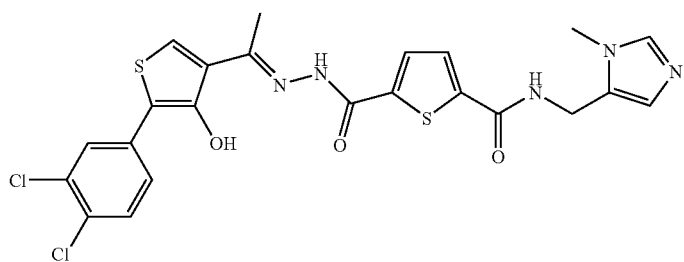
No. 51

-continued
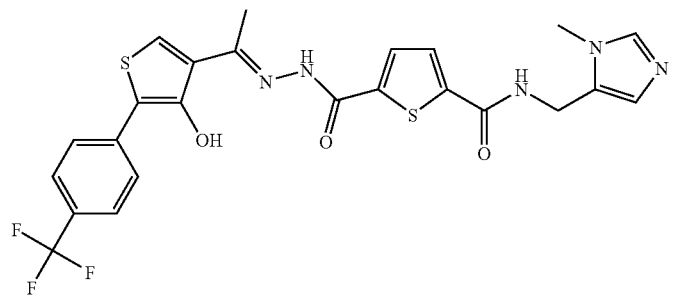
No. 52
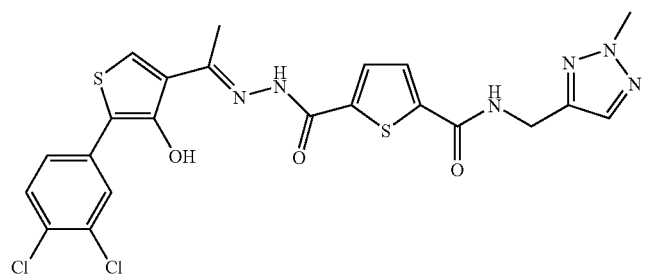
No. 53
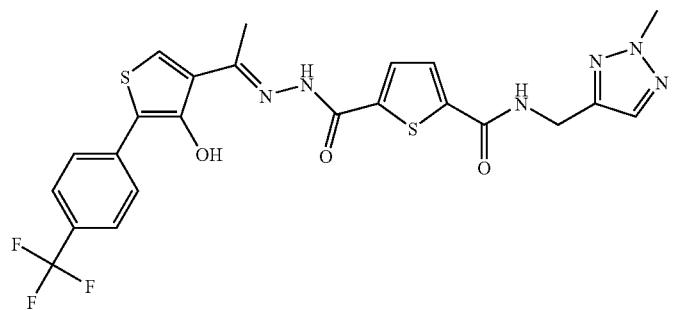
No. 54
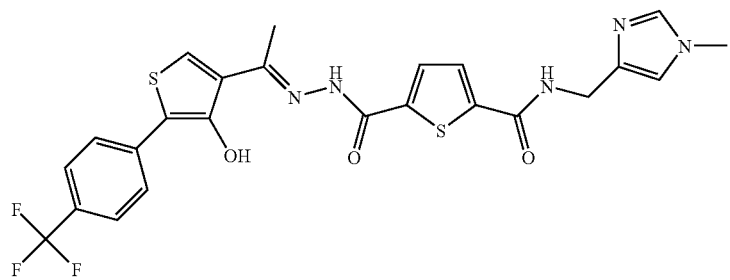
No. 55
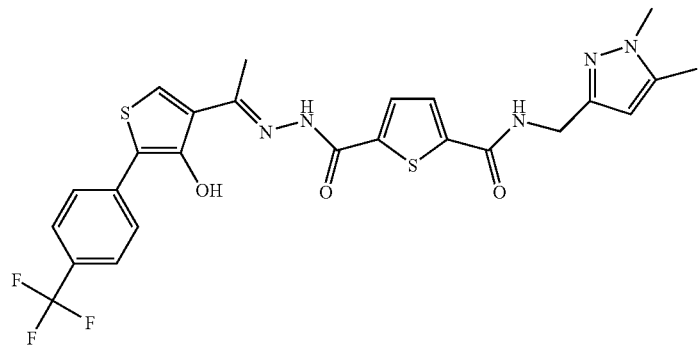
No. 56

No. 57
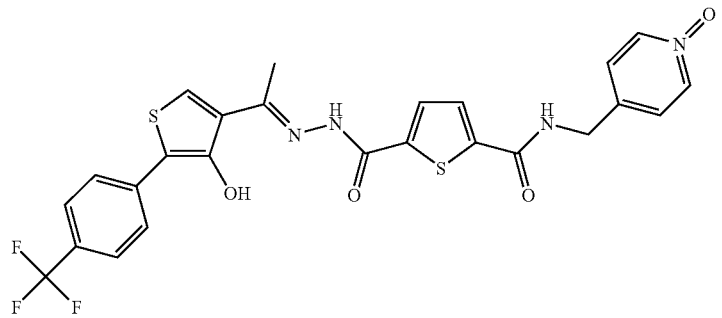
No. 58
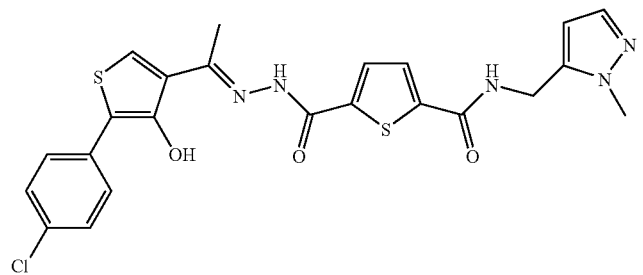
No. 59
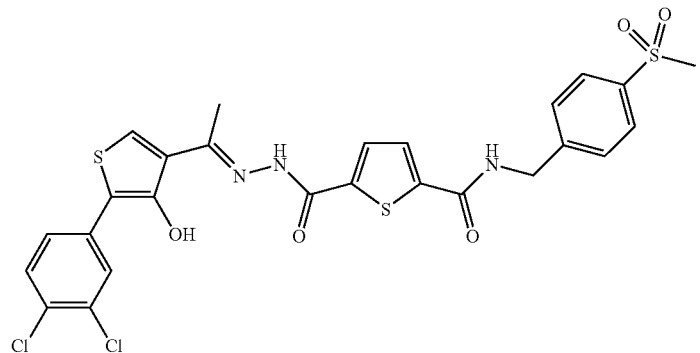
No. 60
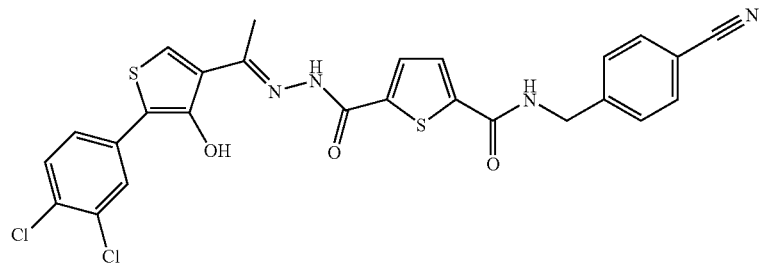
No. 61
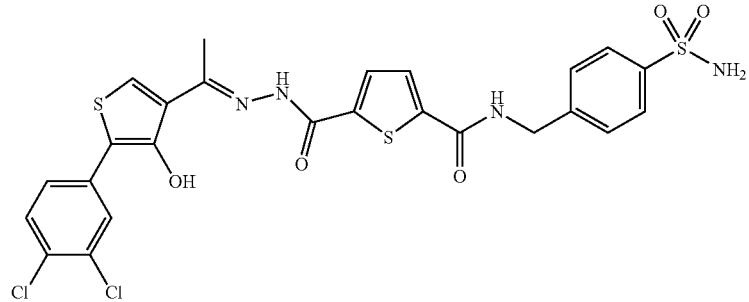

-continued
No. 62
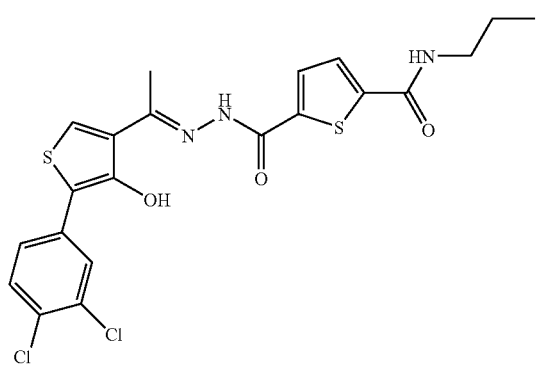
No. 63
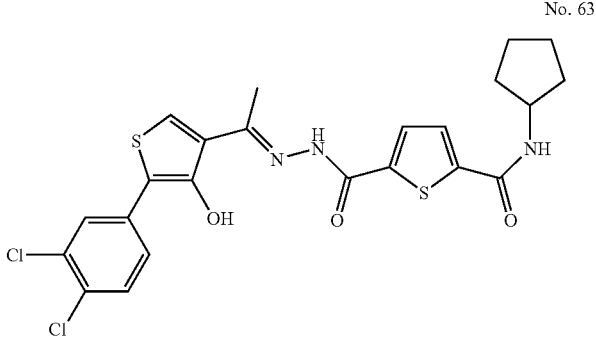
No. 64
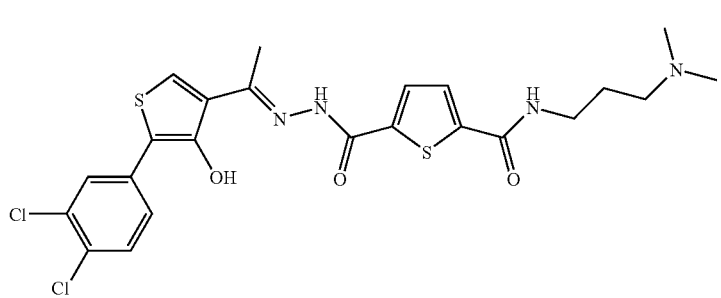
No. 65
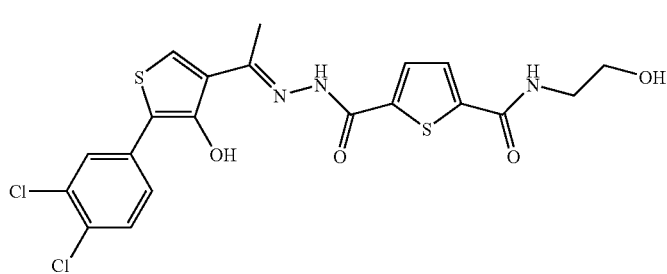
No. 66
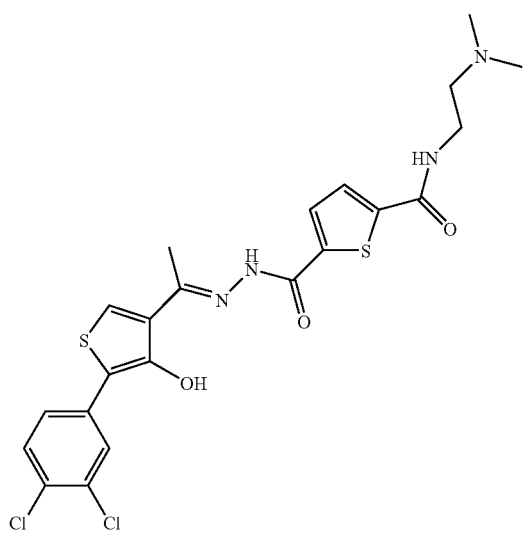
No. 67
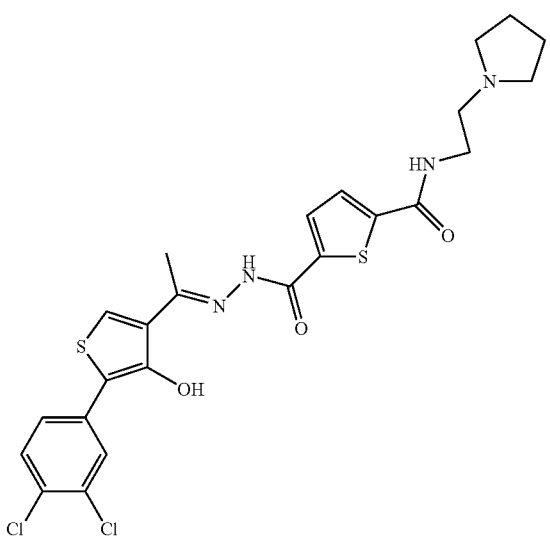

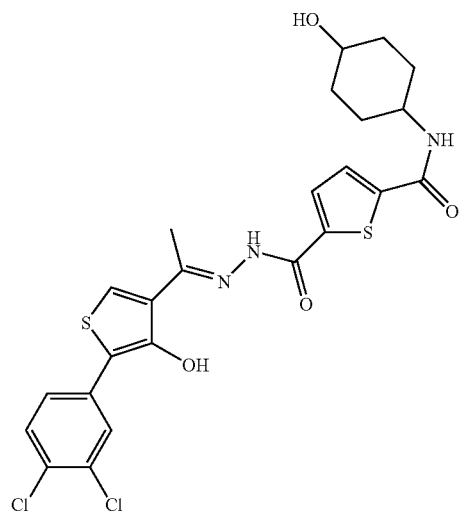
No. 68
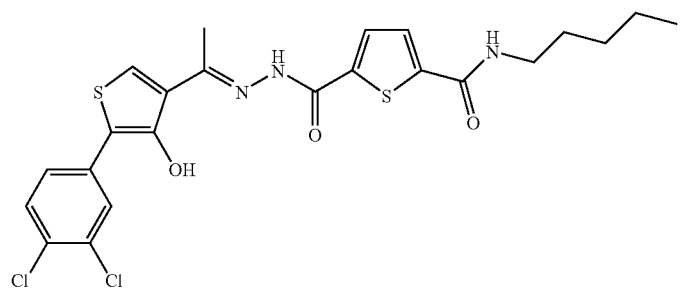
No. 69
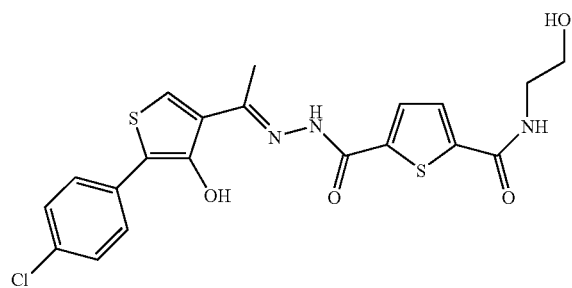
No. 70
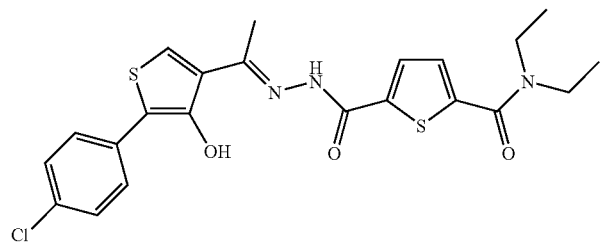
No. 71
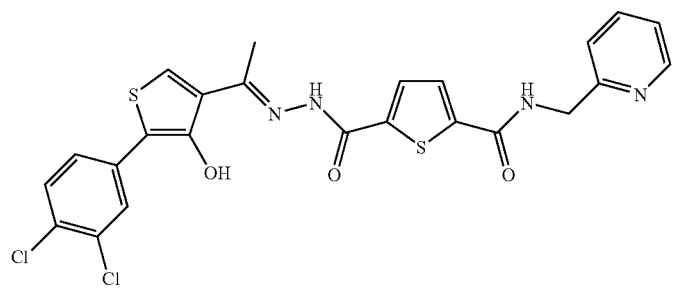
No. 72

-continued
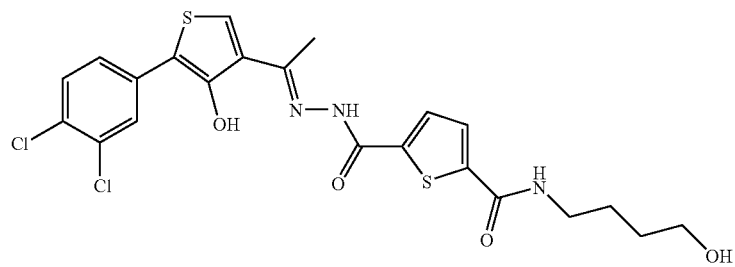
No. 73
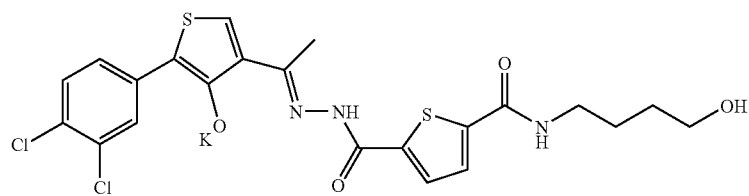
No. 74
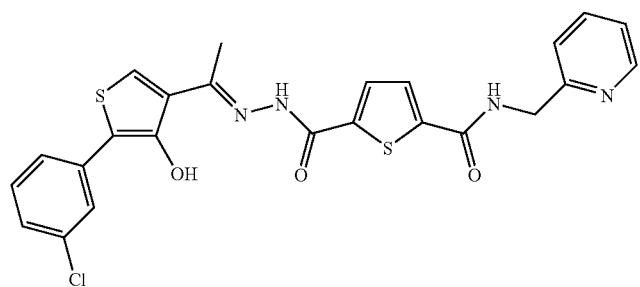
No. 75
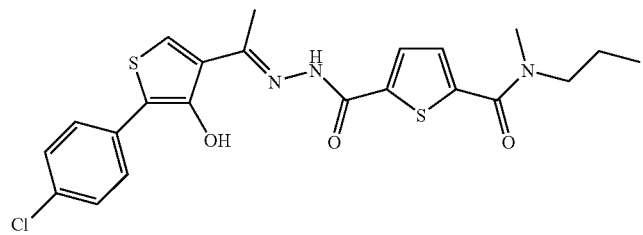
No. 76
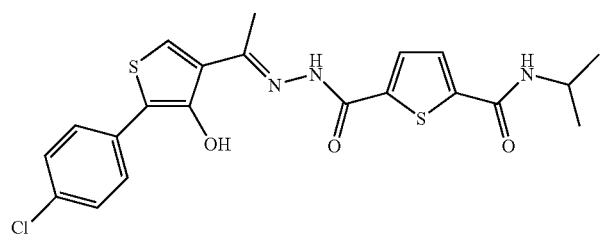
No. 77
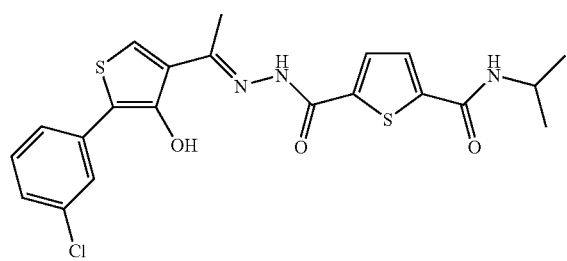
No. 78

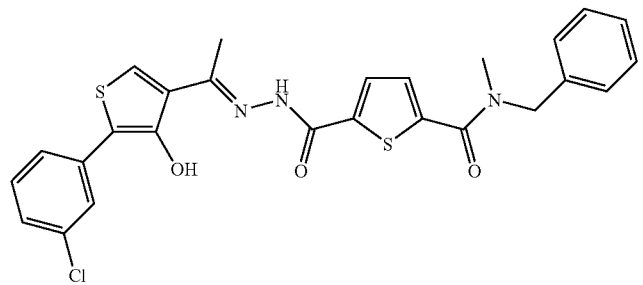
No. 79
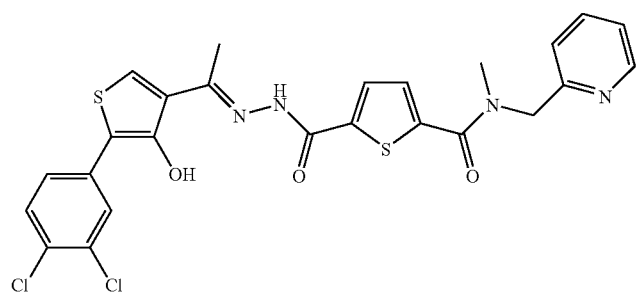
No. 80
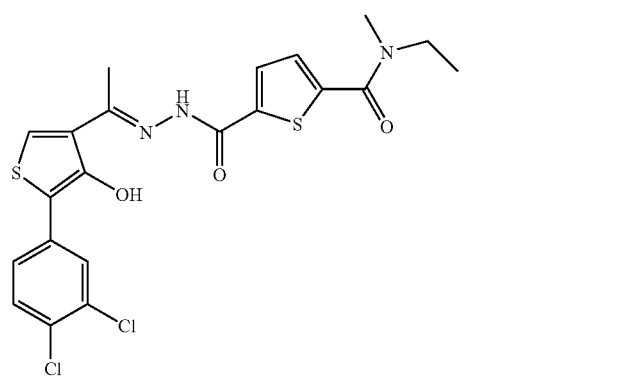
No. 81
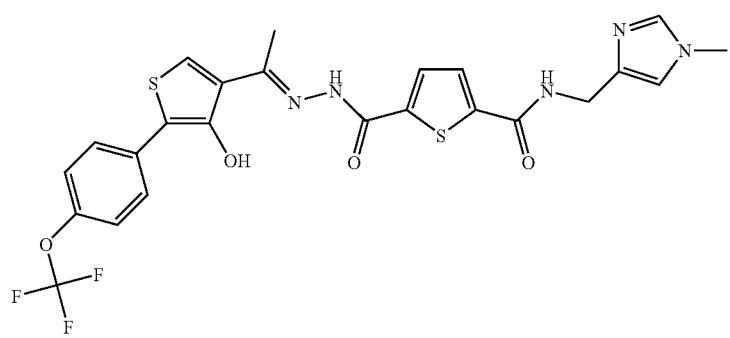
No. 82
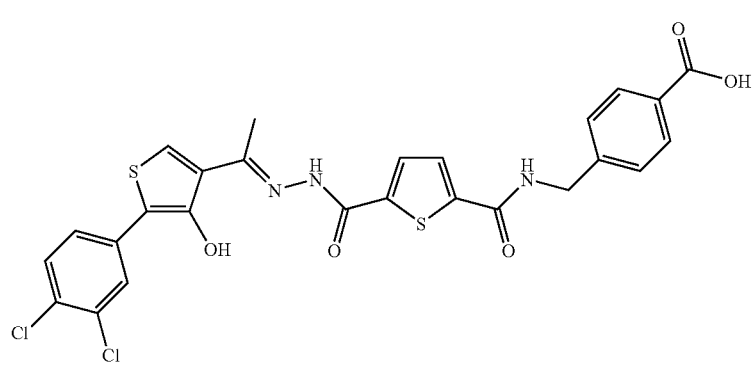
No. 83

-continued
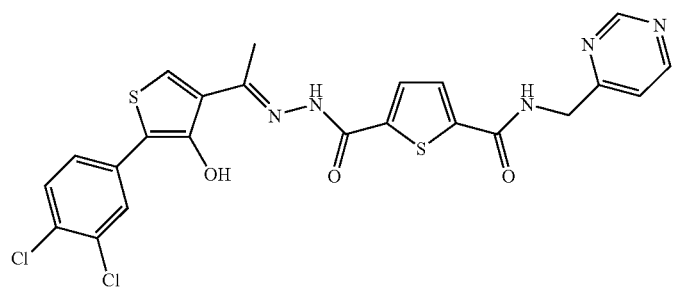
No. 84
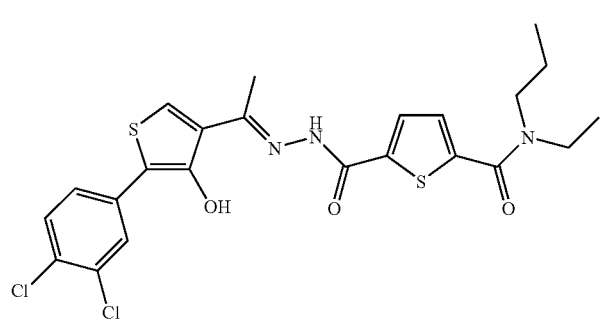
No. 85
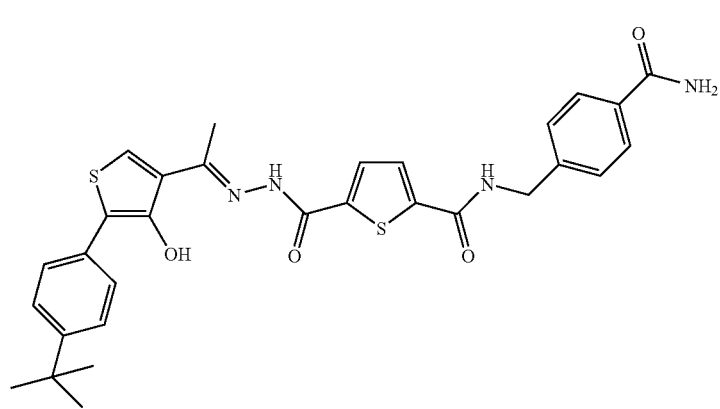
No. 86
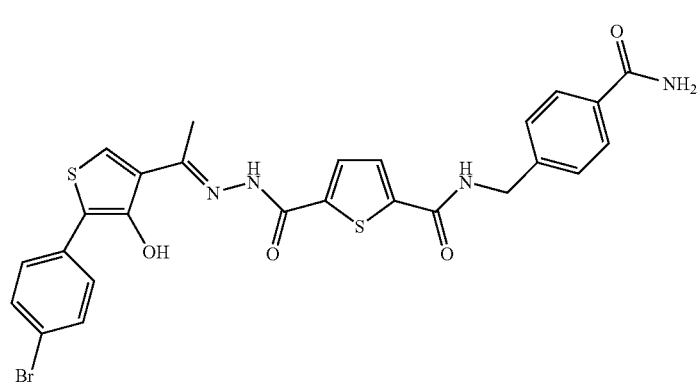
No. 87

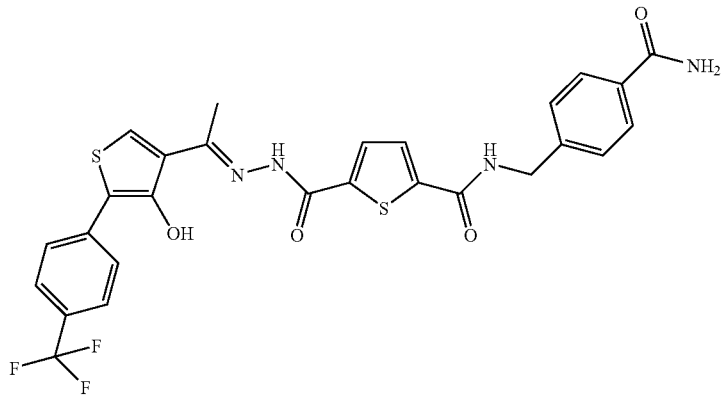
No. 88
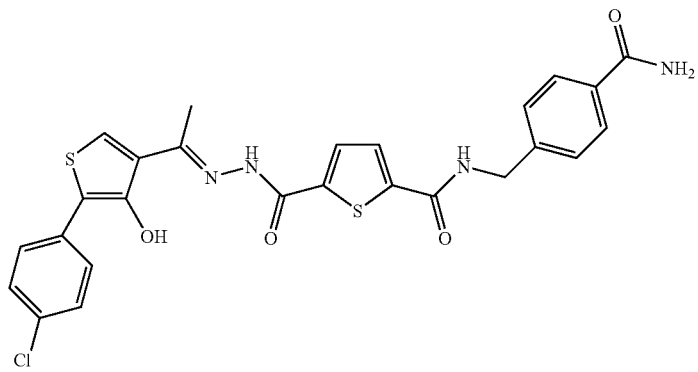
No. 89
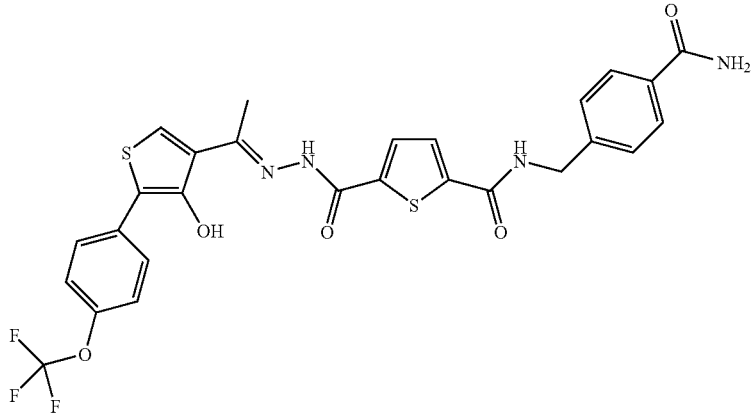
No. 90
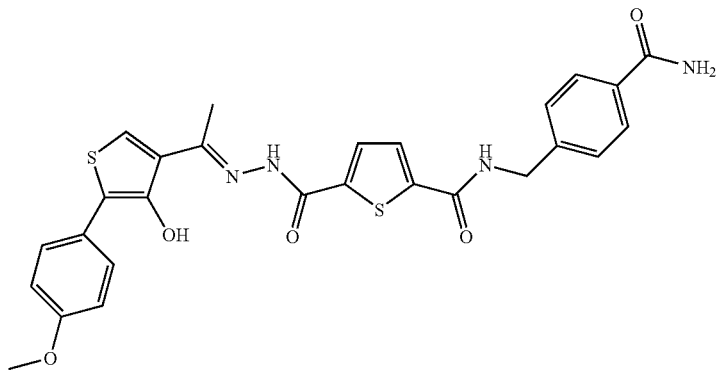
No. 91

-continued
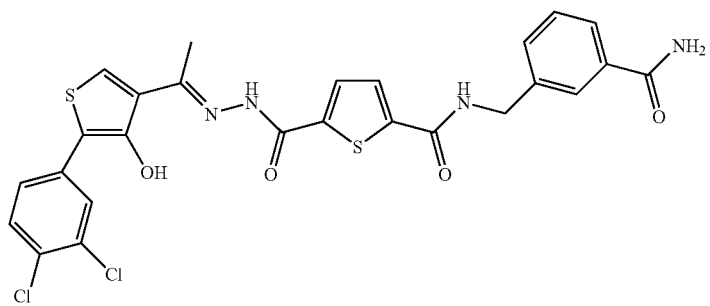
No. 92
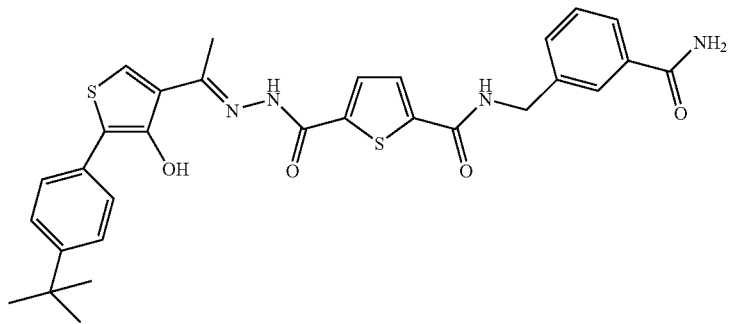
No. 93
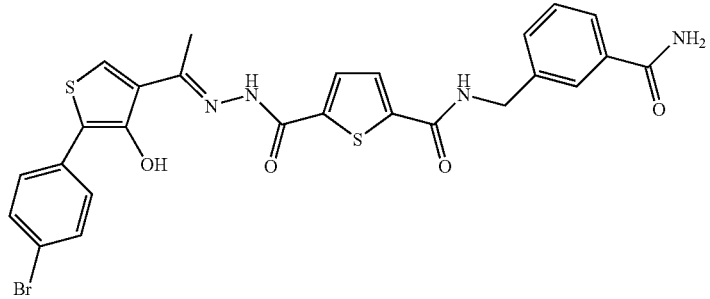
No. 94
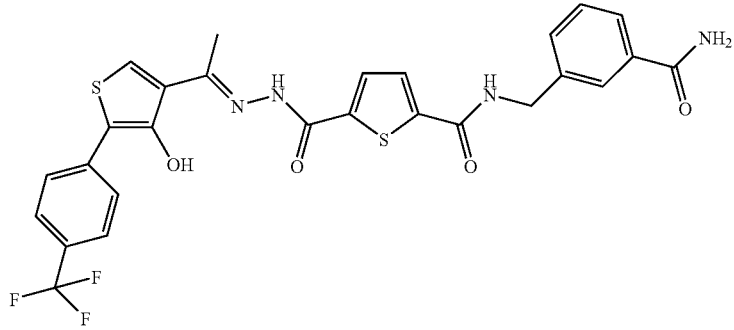
No. 95
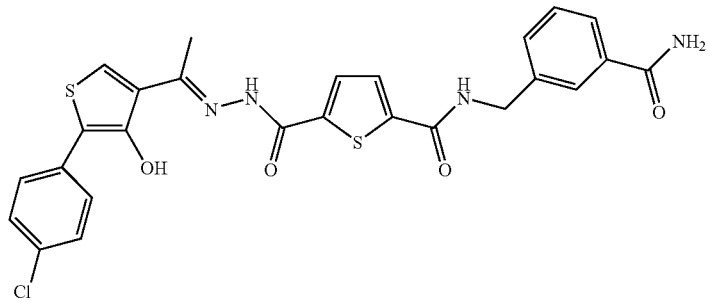
No. 96

-continued
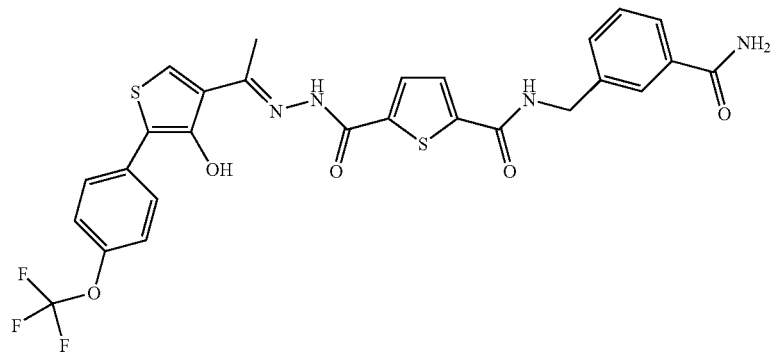
No. 97
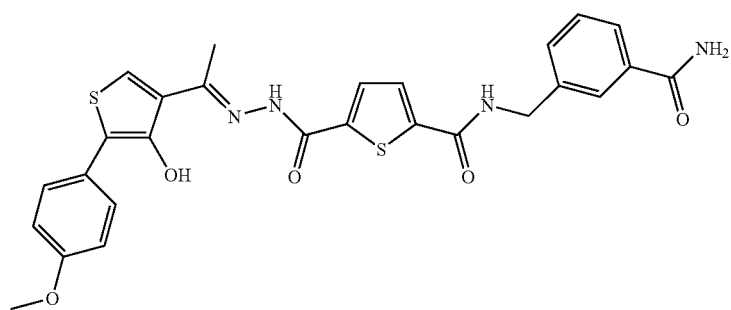
No. 98
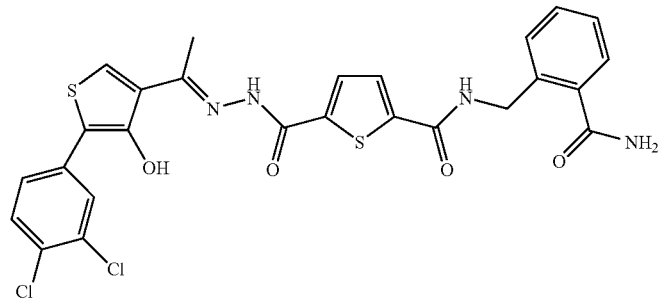
No. 99
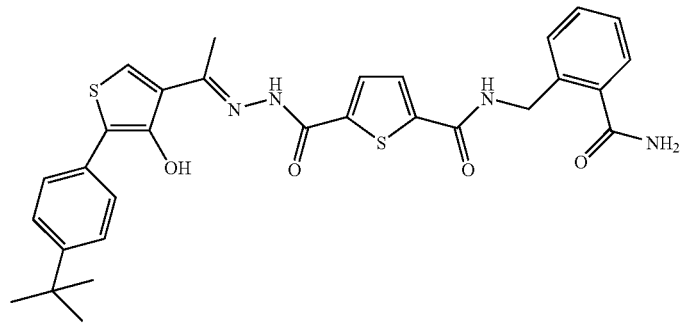
No. 100
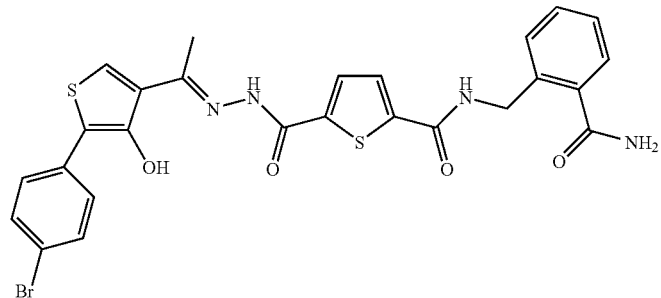
No. 101

-continued
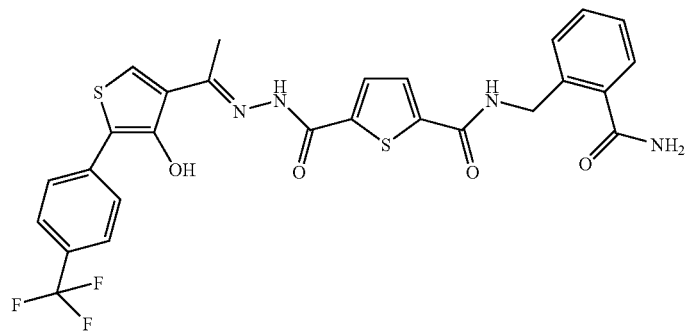
No. 102
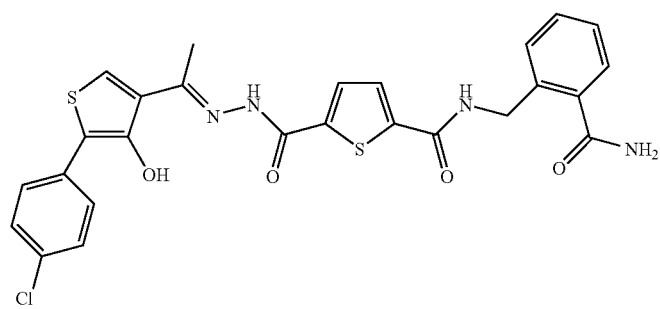
No. 103
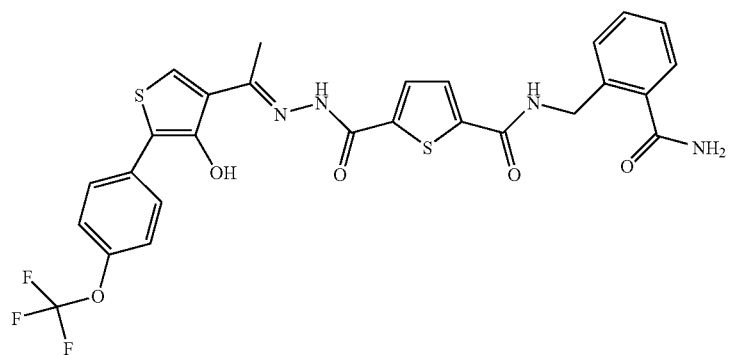
No. 104
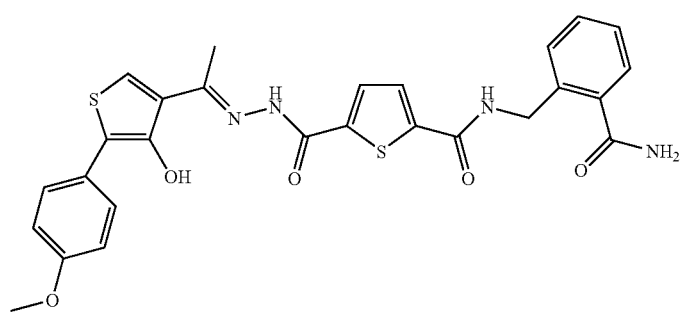
No. 105

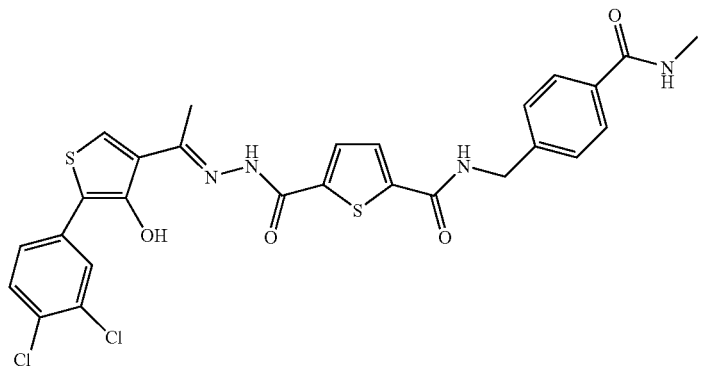
No. 106
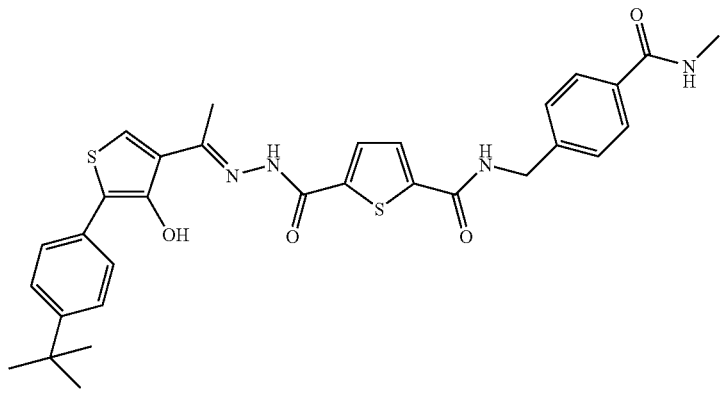
No. 107
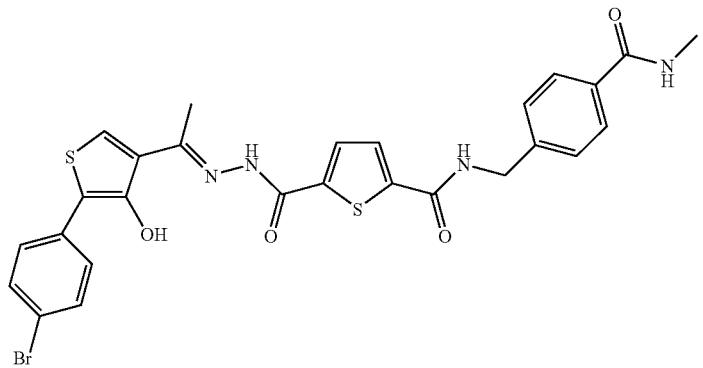
No. 108
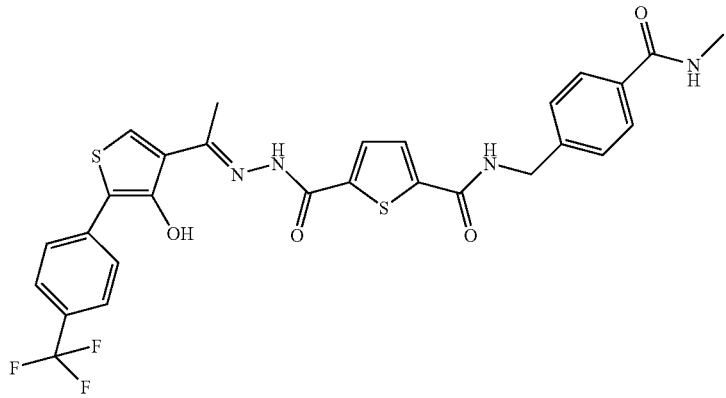
No. 109

-continued
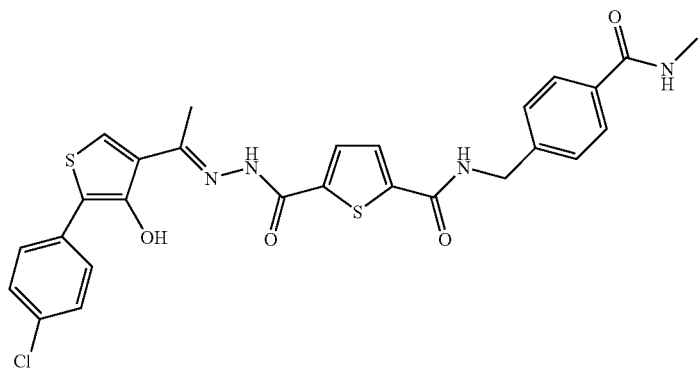
No. 110
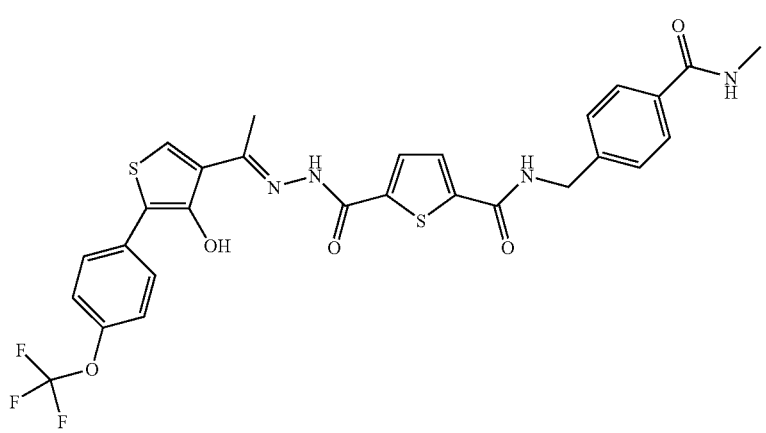
No. 111
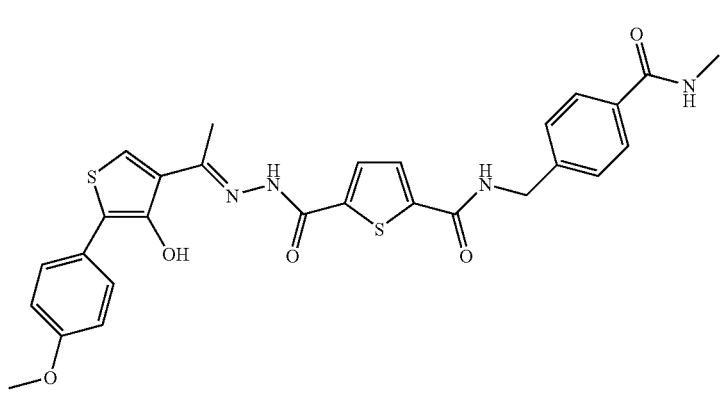
No. 112
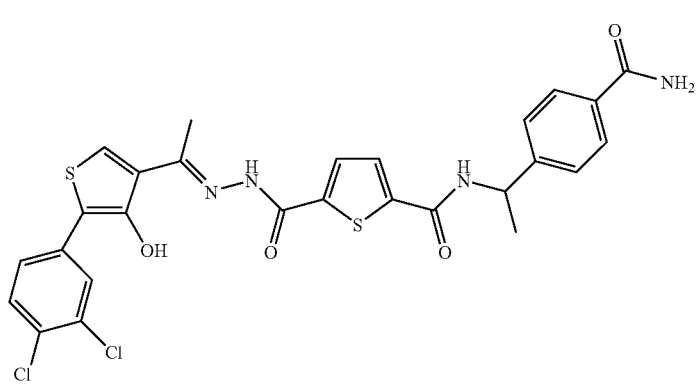
No. 113

-continued
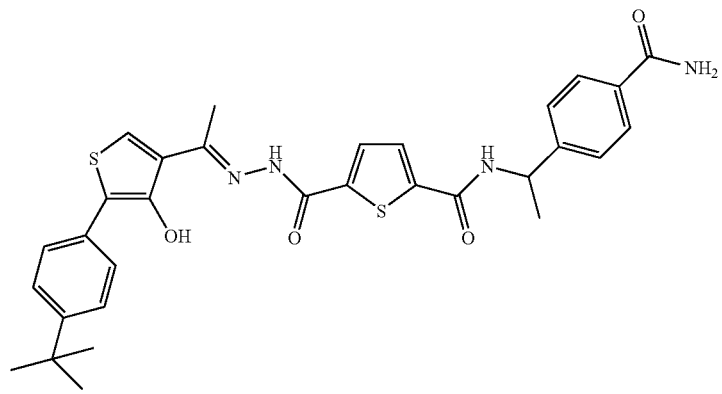
No. 114
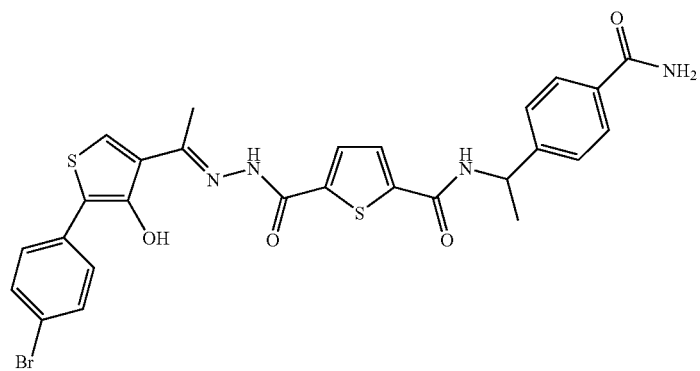
No. 115
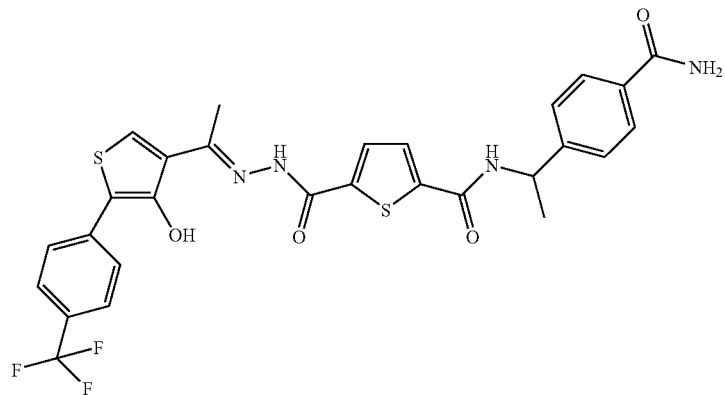
No. 116
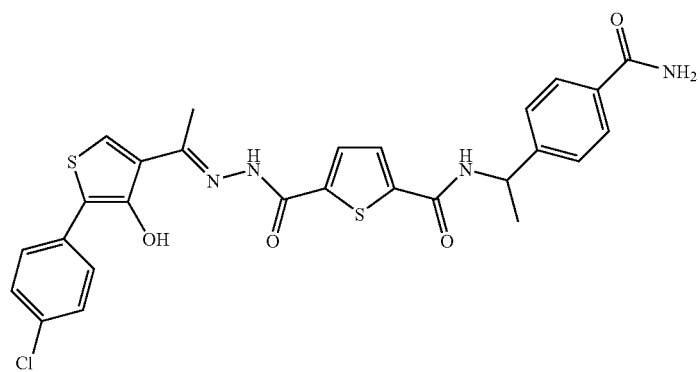
No. 117

-continued
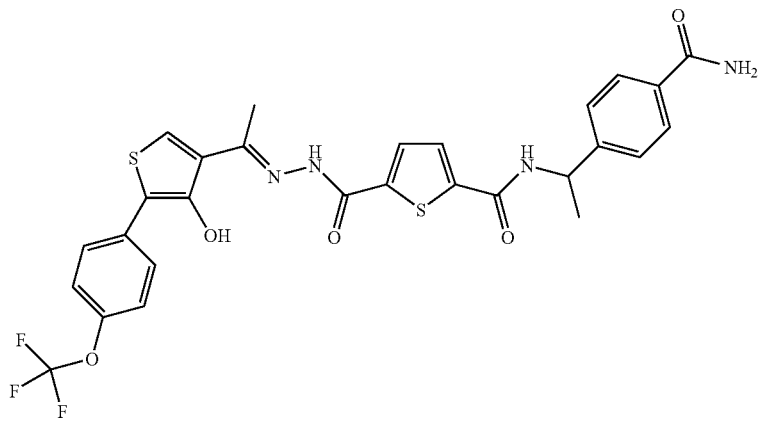
No. 118
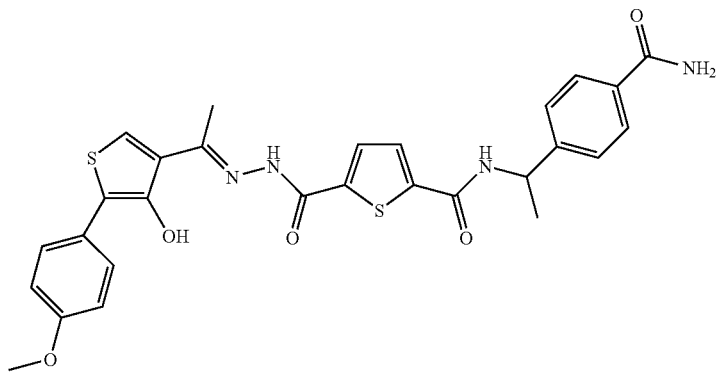
No. 119
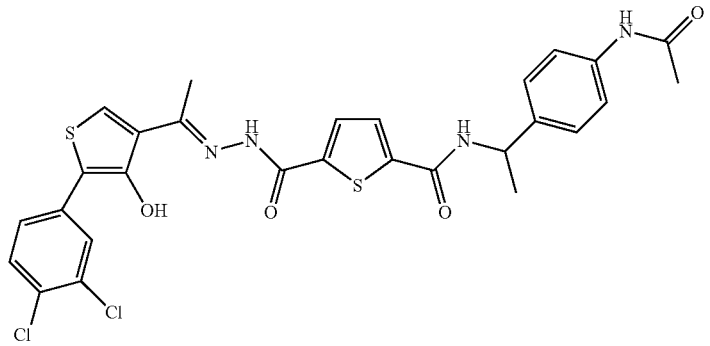
No. 120
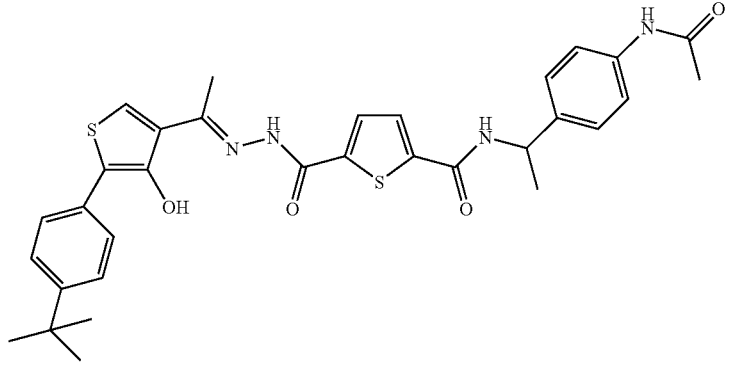
No. 121

-continued
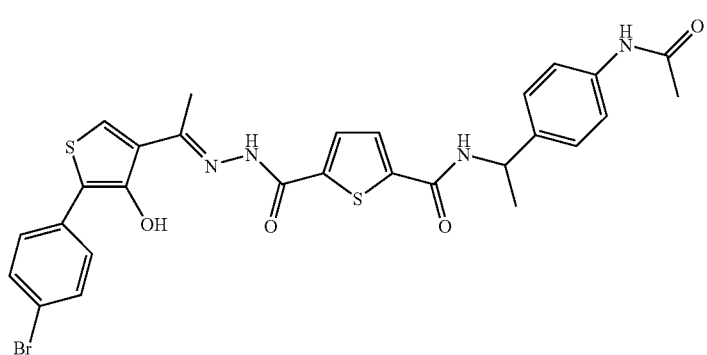
No. 122
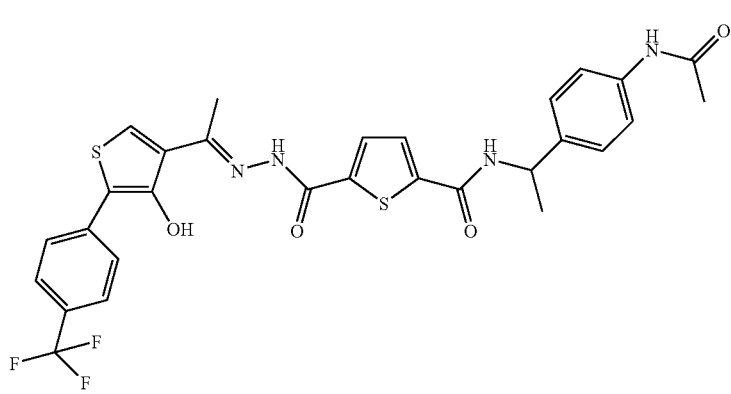
No. 123
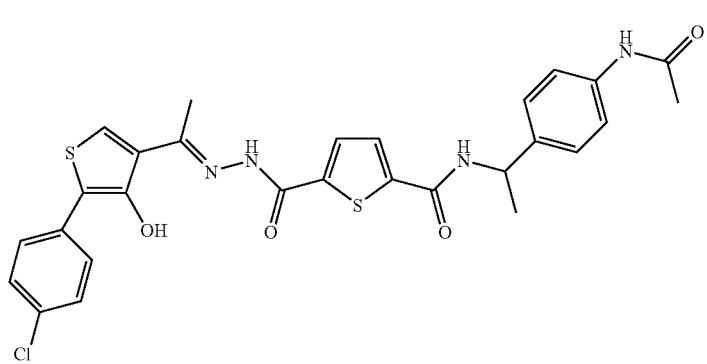
No. 124
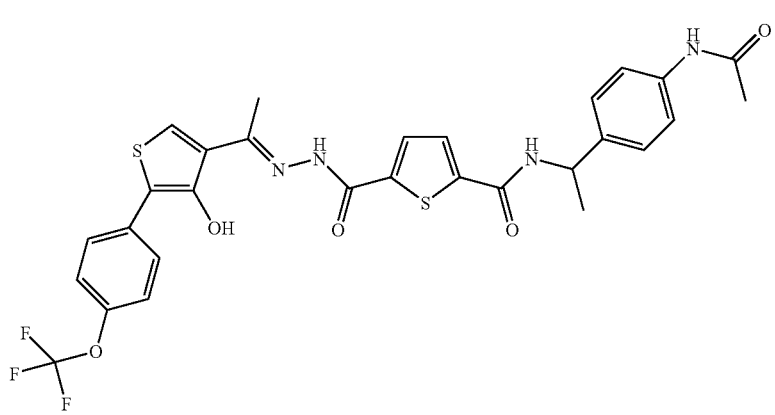
No. 125

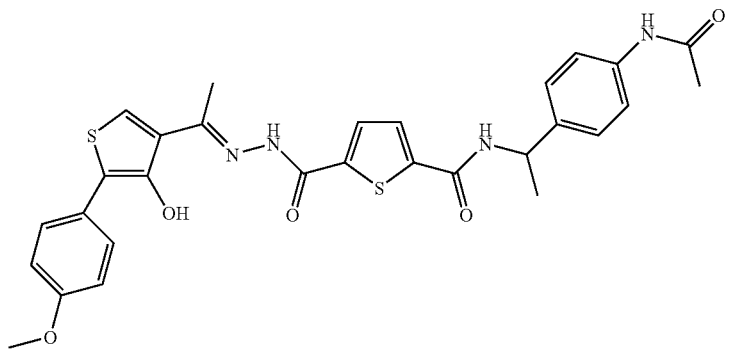
No. 126
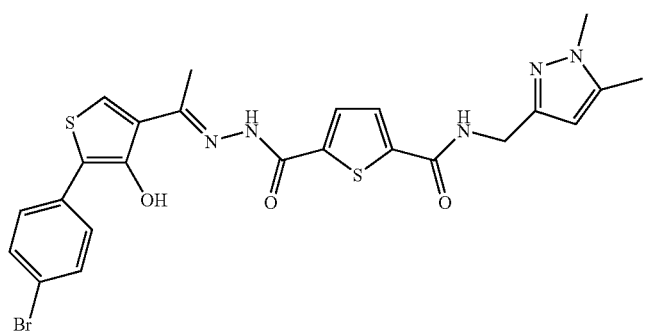
No. 127
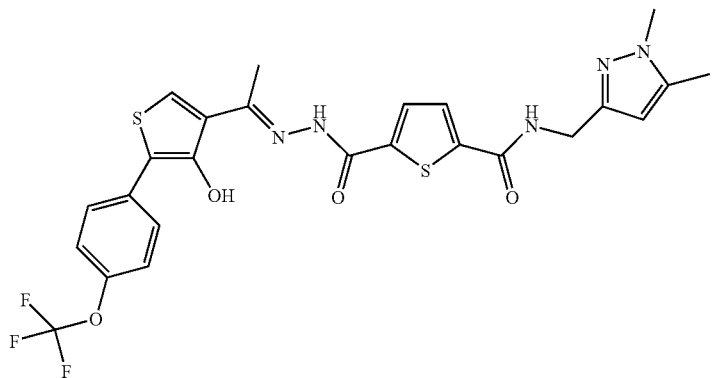
No. 128
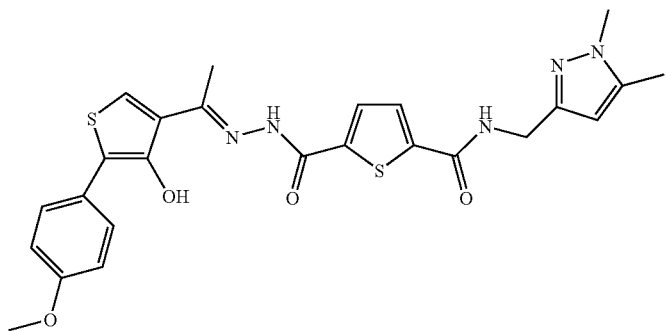
No. 129

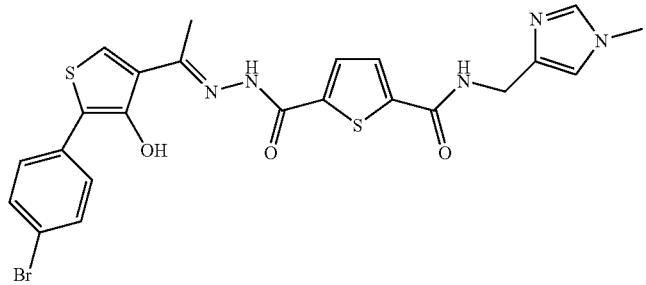
No. 130

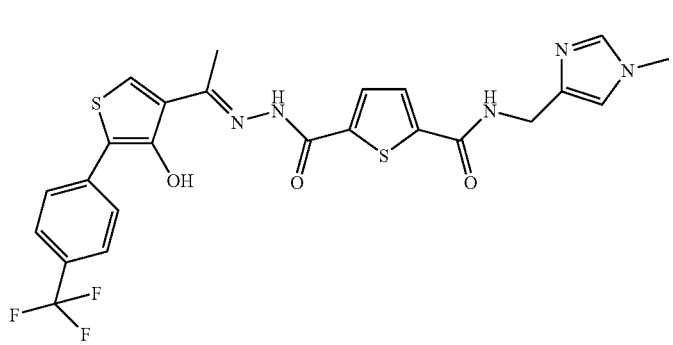
No. 131

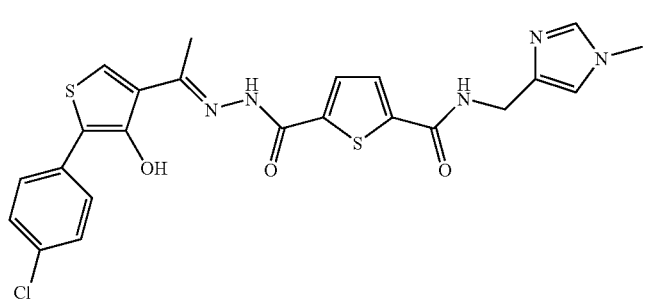
No. 132

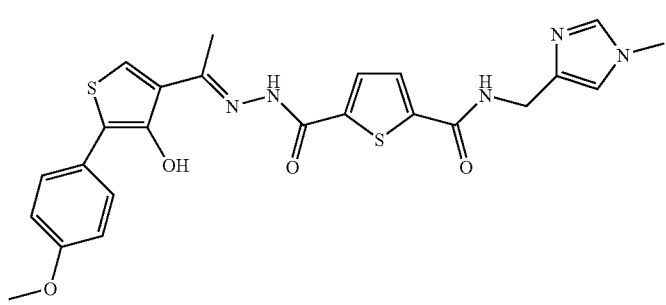
No. 133

Example 3

Expansion of CD34+CD38− Cells Using Human Cord Blood-Derived CD34+ Cells

The human cord blood-derived CD34+ cells collected or purchased in Example 1 were plated on a 24-well plate (TPP) (10000 cells/1 mL/well). As the culture medium, StemSpan SFEM (Stemcell Technologies) containing 50 ng/mL SCF (Peprotech) was used, and TPO (Peprotech), Flt-3 (Wako Pure Chemical Industries) and Compound No. 1 were added in combinations to final concentrations of 10 ng/mL, 100 ng/mL and 1 ρg/mL, respectively.

After the cells were incubated in liquid culture at 37° C. for 7 days in a $CO_2$ incubator (5% $CO_2$), the number of viable cells was counted by trypan blue assay. The number of CD34+CD38− cells was calculated in the same manner as in Example 2.

The results demonstrate that the compound of the present invention showed higher expansion activity on CD34+CD38− cells than 10 ng/mL TPO in the presence of SCF and in the presence of SCF and FL.

The expansion efficiencies in the presence of 1 μg/mL of the compound and various cytokines based on the number of CD34+CD38− cells in the absence of them are shown in FIG. 1.

Example 4

Expansion of CD34⁺CD38⁻ Cells Using Human Cord Blood-Derived CD34⁺ Cells

The human cord blood-derived CD34⁺ cells collected or purchased in Example 1 were plated on a 24-well plate (TPP) (10000 cells/1/mL/well). As the culture medium, αMEM (Invitrogen) containing 50 ng/mL SCF (Peprotech), 50 ng/mL Flt-3 (Wako Pure Chemical Industries), 50 ng/mL IL-6 (Wako Pure Chemical Industries) and 10% (V/V) FBS was used, and TPO (Peprotech) or Compound No. 4 was added to a final concentration of 10 ng/mL or 1 μg/mL, respectively.

After the cells were incubated in liquid culture at 37° C. for 7 days in a $CO_2$ incubator (5% $CO_2$), the number of viable cells was counted by trypan blue assay. The number of CD34⁺CD38⁻ cells was calculated in the same manner as in Example 2.

The results demonstrate that the compound of the present invention showed higher expansion activity on CD34⁺CD38⁻ cells than 10 ng/mL TPO.

Figure 2:
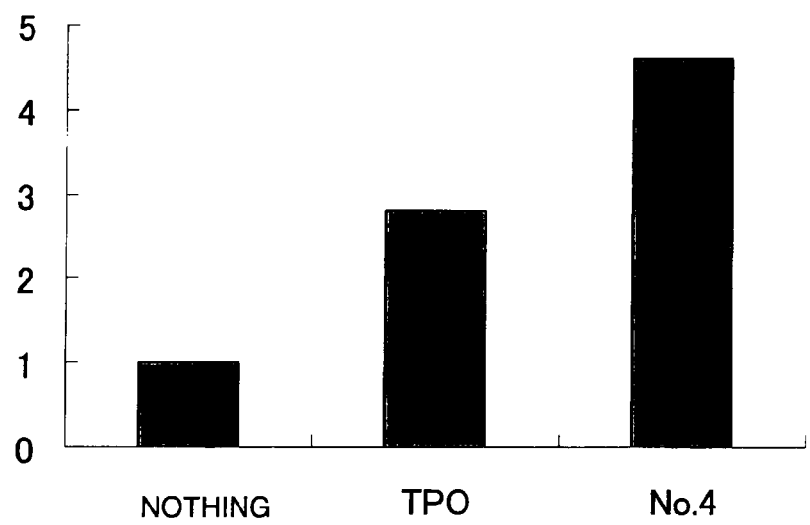
FIG. 2 A graph showing that $CD34^+CD38^-$ cells were expanded more remarkably in a culture of $CD34^+$ cells in the presence of the compound of the present invention than in the presence of TPO.

The expansion efficiencies in the presence of 10 ng/mL TPO and in the presence of 1 μg/mL of the compound based on the number of CD34⁺CD38⁻ cells in the absence of them are shown in FIG. 2.

Example 5

Expansion of HPP-CFU Using Human Cord Blood-Derived CD34⁺ Cells

The effects of Compounds No. 1, No. 2, and No. 4 of the present invention on hematopoietic progenitor cells were measured by blood cell colony forming assay. The liquid cell cultures obtained in Example 2 were poured into 3.5-cm Petri dishes with MethoCult GF H4435 culture medium (Stemcell Technologies) at 500 cells/dish and incubated in a $CO_2$ incubator (5% $CO_2$, 37° C.) for 12 days. The number of HPP-CFC colonies in each plate was counted under a microscope routinely. The assay was carried out at least in duplicate, and the numbers of HPP-CFC colonies were averaged.

The results demonstrate that the compounds of the present invention remarkably stimulated colony formation of HPP-CFU and have expansion activity on hematopoietic progenitor cells.

The results are shown in Table 4.

TABLE 4

| Compound No. | Number of HPP-CFC colonies |
|---|---|
| None | 4 |
| 1 | 41 |
| 2 | 35 |
| 4 | 45 |

Example 6

Expansion of CD34⁺CD38⁻ Cells Using Human Cord Blood-Derived CD34⁺CD38⁻ Cells The human cord blood-derived CD34⁺CD38⁻ cells collected in Example 1 were plated on a 24-well plate (TPP) (from 3000 to 10000 cells/1 mL/well). As the culture medium, StemSpan SFEM (Stemcell Technologies) containing 50 ng/mL SCF (Peprotech) was used, and TPO (Peprotech) or Compound No. 1, No. 2, No. 4 or No. 6 in dimethyl sulfoxide in an amount of 0.1% (v/v) was added to a final concentration of 10 μg/mL or 1 μg/mL, respectively. After the cells were incubated in liquid culture at 37° C. for 7 days in a $CO_2$ incubator (5% $CO_2$), the number of CD34⁺CD38⁻ cells was calculated in the same manner as in Example 2.

The results demonstrate that the compounds of the present invention showed expansion activity on CD34⁺CD38⁻ cells and have expansion activity on hematopoietic stem cells and hematopoietic progenitor cells.

The expansion efficiencies in the presence of 1 μg/mL of the compounds based on the number of CD34⁺CD38⁻ cells in the presence of 10 ng/mL TPO are shown in Table 5.

TABLE 5

| Compound No. | Expansion efficiency |
|---|---|
| None | 1 |
| 1 | 1.9 |
| 2 | 2.7 |
| 4 | 1.9 |
| 6 | 1.4 |

Example 7

Transplantation of Cell Culture into Immunodeficient (NOD/SCID) Mice

Cultured cells obtained in the same manner as in Example 2 in the presence of TPO (Peprotech) at a final concentration of 10 ng/mL or in the presence of Compound No. 1 or No. 4 at a final concentration of 1 μg/mL was transplanted into at least three 7- to 8-week-old NOD/SCID mice by tail vein injection at 4 to $5 \times 10^4$ cells/mouse in terms of the initial number of CD34⁺ cells after a sublethal dose of irradiation (2.75 to 3 Gy). Three weeks after the transplantation, the mice were killed, and the bone marrow cells were collected from both thighbones. Subsequently, the bone marrow cells were stained with a human CD45 antibody (APC, Becton, Dickinson and Company), then washed with PBS(−) containing 2% (v/v) FBS and stained with propidium iodide (Sigma-Aldrich Japan) added to a final concentration of 5 μg/mL. The stained cells were analyzed with a flow cytometer JSAN (Bay Bioscience) to determined the proportion of human CD45⁺ cells in the bone marrow cells. The results demonstrate that the compounds of the present invention has an excellent SRC expanding effect and have expansion activity on hematopoietic stem cells.

Figure 3:
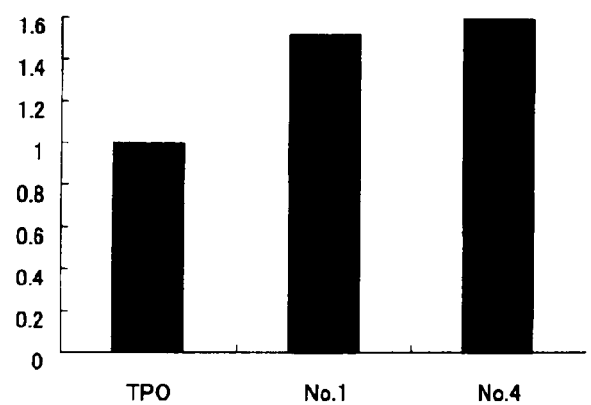
FIG. 3 A graph showing that SRC were expanded more remarkably from $CD34^+$ cells cultured in the presence of the compounds of the present invention than from those cultured in the presence of TPO, which was estimated by transplantation assay of $CD34^+$ cells into immunodeficient mice.

The proportions of human CD45⁺ cells from the cell cultures incubated in the presence of 1 μg/mL of Compound No. 1 or No. 4 based on the proportion of human CD45⁺ cells from the cell culture incubated in the presence of 10 ng/mL TPO are shown in FIG. 3.

Example 8

Transplantation of Cell Culture into Immunodeficient (NOD/SCID) Mice

Cultured cells were transplanted into NOD/SCID mice in the same manner as in Example 7, and the proportion of human CD45⁺ cells in bone marrow cells was calculated. As the culture medium for CD34⁺ cells, StemSpan SFEM (Stemcell Technologies) containing 100 ng/mL SCF (Peprotech) and 100 ng/mL Flt-3 (Wako Pure Chemical Industries) was used, and TPO (Peprotech) or Compound No. 1, No. 4 or No. 87 was added to a final concentration of 20 ng/mL or final concentrations of 1 μg/mL, respectively.

Figure 4:
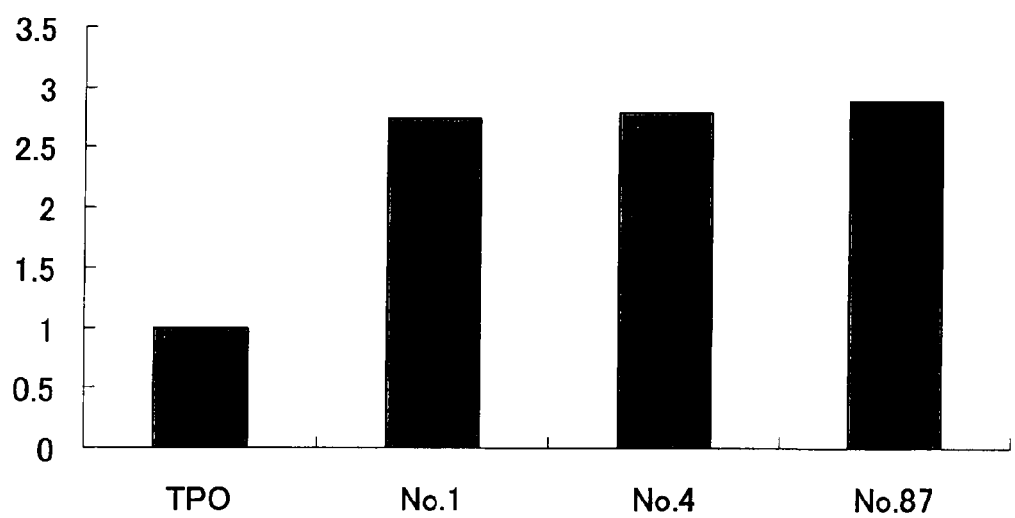
FIG. 4 A graph showing that SRC was expanded more remarkably from $CD34^+$ cells cultured in the presence of the compounds of the present invention than from those cultured in the presence of TPO after transplantation of $CD34^+$ cells into immunodeficient mice.

The proportions of human CD45$^+$ cells from the cell cultures incubated in the presence of 1 μg/mL of Compound No. 1, No. 4 or No. 87 based on the proportion of human CD45$^+$ cells from the cell culture incubated in the presence of 20 ng/mL TPO are shown in FIG. 4.

Example 9

Preparation of Retrovirus for Expression of NGFR 293 cells were inoculated into 10 cm-Petri dishes and incubated in liquid culture containing Doulbecco's modified Eagle's Medium (DMEM) containing 10% (v/v) FBS in a $CO_2$ incubator (5% $CO_2$) at 37° C. for 24 hours (1.5 to 2.5×106 cells/10 ml/dish). BES-buffered saline (Sigma-Aldrich Japan) containing 17 μg/mL of a retrovirus vector for expression of nerve growth factor receptor (NGFR) (a gift from Professor Atsushi Iwama at Chiba University, see Reddy V A et al. Blood, 100:483, 2002), 10 μg/mL pCL-10A1 vector (Nacalai Tesque) and 100 mM CaCl2 was added dropwise to the liquid culture, and the liquid culture was incubated in a $CO_2$ incubator (3% $CO_2$) at 35° C. for 12 to 16 hours. Then, the cells were washed with PBS(-) and incubated in liquid culture containing DMEM supplemented with 10% (v/v) FBS in a $CO_2$ incubator (5% $CO_2$) at 37° C. for 48 hours. The supernatant from the culture was filtered through a 0.45 μm filter to obtain a virus solution, which was stored in portions at -80° C. unless used immediately.

Example 10

Transfection of Human Cord Blood-Derived CD34$^+$ Cells with NGFR Gene

The human cord blood-derived CD34$^+$ cells collected or purchased in Example 1 were plated on 3 cm-Petri dishes (TPP) (100000 cells/3 ml/dish). As the culture medium, StemSpan SFEM (Stemcell Technologies) containing 20 ng/ml SCF (Peprotech) and 20 ng/mL Flt-3 (Wako Pure Chemical Industries) was used, and TPO (Peprotech) or Compound No. 1 or No. 4 in dimethyl sulfoxide in an amount of 0.1% (v/v) was added to a final concentration of 20 ng/mL or 0.3 μg/mL, respectively. A negative control culture was incubated in the absence of TPO and the compounds.

After the cells were incubated in liquid culture at 37° C. for 24 hours in a $CO_2$ incubator (5% $CO_2$), 2 ml of the culture medium was sucked out, and 2 ml of the solution of the retrovirus for expression of NGFR prepared in Example 7 (containing 5 μg/mL protamine sulfate (Sigma-Aldrich Japan), 20 ng/ml SCF (Peprotech) and 20 ng/mL Flt-3 (Wako Pure Chemical Industries)) was added. TPO (Peprotech) or Compound No. 1 or No. 4 in dimethyl sulfoxide in an amount of 0.1% (v/v) was further added to a final concentration of 20 μg/mL or 0.3 μg/mL, respectively, and centrifugation at 2000 g was carried out at 32° C. for 30 minutes. Then, the cells were incubated in liquid culture under the same conditions as mentioned above for 24 hours, 2 ml of the culture medium was sucked out, 2 ml of the same solution of the retrovirus for expression of NGFR was added together with TPO or either compound, and centrifugation at 2000 g was carried out at 32° C. for 30 minutes. Then, the cells were incubated in liquid culture under the same conditions as mentioned above for 24 hours, 2 ml of the culture medium was sucked out, and 2 ml of StemSpan SFEM (Stemcell Technologies) containing 20 ng/mL SCF (Peprotech) and 20 ng/mL Flt-3 (Wako Pure Chemical Industries) was added. Further, TPO (Peprotech) or Compound No. 1 or No. 4 in dimethyl sulfoxide in an amount of 0.1% (v/v) was further added to a final concentration of 20 μg/mL or 0.3 μg/mL, respectively. The cells were incubated in liquid culture under the same conditions as mentioned above for 24 hours, and the number of viable cells was counted by trypan blue assay (GIBCO).

The number of CD34$^+$ cells carrying NGFR introduced via the retrovirus vector (the number of CD34$^+$NGFR$^+$ cells) was calculated as follows. First, virus-treated cells were incubated with a biotin-labeled NGFR antibody (Becton, Dickinson and Company) at 4° C. for 1 hour and stained with PE-labeled avidin (Becton, Dickinson and Company) and a CD34 antibody (APC, Becton, Dickinson and Company). Then, the cells were washed with PBS(-) containing 2% (v/v) FBS and stained with propidium iodide (Sigma-Aldrich Japan) added to a final concentration of 5 μg/mL. The stained cells were analyzed with JSAN (Bay Bioscience) to determined the proportion of CD34$^+$NGFR$^+$ cells, which was multiplied by the number of viable cells to calculate the number of CD34$^+$NGFR$^+$ cells.

The results demonstrate that the compounds of the present invention showed higher expansion activity on CD34$^+$NGFR$^+$ cells than TPO and have the effect of facilitating gene transfer into hematopoietic stem cells and hematopoietic progenitor cells.

The cell expansion efficiencies in the presence of TPO or the compounds based on the number of CD34$^+$NGFR$^+$ cells in the absence of them are shown in Table 6.

TABLE 6

| Synthetic Example No. | Expansion efficiency |
| --- | --- |
| Nothing | 1 |
| TPO | 7.7 |
| 1 | 9.8 |
| 4 | 12.5 |

INDUSTRIAL APPLICABILITY

The method of the present invention can expand human hematopoietic stem cells and/or hematopoietic progenitor cells in an undifferentiated state by using a low molecular weight compound as an active ingredient. Cells expanded by the method of the present invention are useful as a hematopoietic cell transplant for diseases accompanying hematopoietic dysfunction, ischemia or immune dysfunction and hence its application to cell therapy and gene therapy is expected.

The entire disclosure of Japanese Patent Application No. 2007-316276 filed on Dec. 6, 2007 including specification, claims, drawings and summary is incorporated herein by reference in its entirety.

The invention claimed is:

1. A method for expanding hematopoietic stem cells and/or hematopoietic progenitor cells, which comprises culturing hematopoietic stem cells and/or hematopoietic progenitor cells ex vivo in a medium containing at least one compound represented by the following formula (I), a tautomer or pharmaceutically acceptable salt or a solvate thereof:

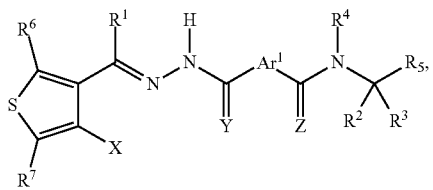

wherein
$R^1$ is a hydrogen atom or a $C_{1-3}$ alkyl group,
$R^2$, $R^3$ and $R^6$ are hydrogen atoms,
$R^4$ is a hydrogen atom or a $C_{1-6}$ alkyl group,
$Ar^1$ is represented by the formula (III):

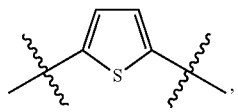

$R^5$ is a $C_{2-14}$ aryl group
substituted with:
(1) one or more hydrogen atoms,
(2) one or more halogen atoms,
(3) one or more carbamoyl groups,
(4) one or more sulfamoyl groups,
(5) one or more $C_{1-3}$ alkylsulfonyl groups,
(6) one or more $C_{1-3}$ alkyl groups
or
(7) one or more $C_{1-3}$ alkoxy groups,
and, when the $C_{2-14}$ aryl group is a nitrogen-containing $C_{2-14}$ aryl group, the $C_{2-14}$ aryl group may be an N-oxide thereof,
$R^7$ is a phenyl group which may optionally be substituted with:
(1) one or more $C_{1-10}$ alkyl groups which may be substituted with one or more halogen atoms,
(2) one or more halogen atoms,
(3) one or more $C_{1-10}$ alkoxy groups, or
(4) one or more $C_{1-3}$ alkoxy groups which may be optionally substituted with one or more halogen atoms,
X is OH, and
each of Y and Z is an oxygen atom.

2. The method for expanding hematopoietic stem cells and/or hematopoietic progenitor cells according to claim 1, wherein the hematopoietic stem cells and/or hematopoietic progenitor cells to be expanded are $CD34^+CD38^-$ cells.

3. The method for expanding hematopoietic stem cells and/or hematopoietic progenitor cells according to claim 1, further comprising:
combining at least one blood cell stimulating factor with the cells and the compound represented by the formula (I) in the culturing.

4. The method for expanding hematopoietic stem cells and/or hematopoietic progenitor cells according to claim 3, wherein the at least one blood cell stimulating factor is selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO), and erythropoietin (EPO).

5. The method for expanding hematopoietic stem cells and/or hematopoietic progenitor cells according to claim 3, wherein the blood cell stimulating factor is a stem cell factor (SCF) and/or a flk/flt3 ligand (FL).

6. The method for expanding hematopoietic stem cells and/or hematopoietic progenitor cells according to claim 1, wherein the hematopoietic stem cells and/or hematopoietic progenitor cells are obtained from bone marrow, liver, spleen, peripheral blood, or cord blood.

7. The method for expanding hematopoietic stem cells and/or hematopoietic progenitor cells according to claim 6, wherein the hematopoietic stem cells and/or hematopoietic progenitor cells are obtained from cord blood.

8. The method for expanding hematopoietic stem cells and/or hematopoietic progenitor cells according to claim 7, wherein hematopoietic stem cells and/or hematopoietic progenitor cells obtained from cord blood are cultured in the presence of a stem cell factor (SCF) and/or a flk2/flt3 ligand (FL).

9. The method for expanding hematopoietic stem cells and/or hematopoietic progenitor cells according to claim 1, wherein
each of $R^1$ and $R^4$ is independently a hydrogen atom or a $C_{1-3}$ alkyl group,
and
Y and Z are oxygen atoms.

10. The method for expanding hematopoietic stem cells and/or hematopoietic progenitor cells according to claim 1, wherein $R^5$ is a phenyl group substituted with a carbamoyl group.

11. A method for expanding hematopoietic stem cells and/or hematopoietic progenitor cells, which comprises culturing hematopoietic stem cells and/or hematopoietic progenitor cells ex vivo in a medium containing at least one compound selected from the group consisting of:

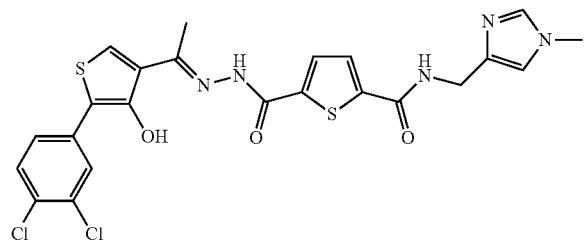 [SMILES: C/C(=N\NC(=O)c1ccc(C(=O)NCc2cn(C)cn2)s1)c1csc(-c2ccc(Cl)c(Cl)c2)c1O]

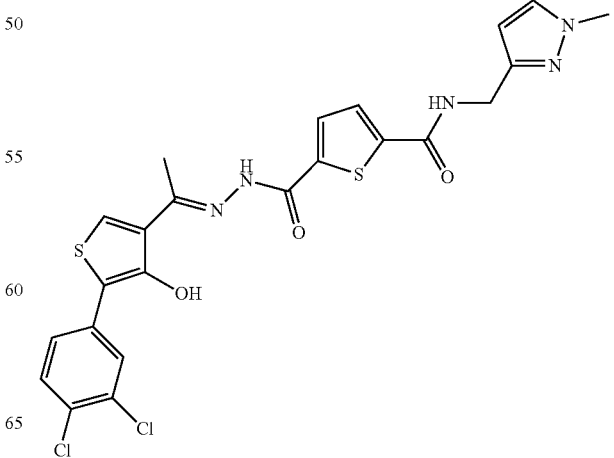

143
-continued
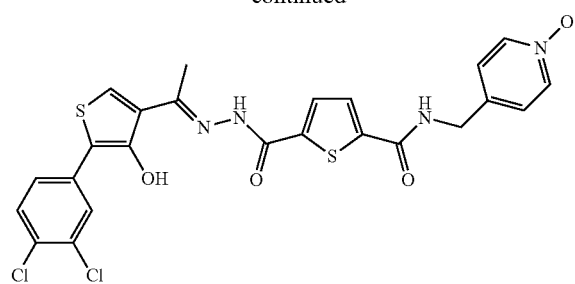
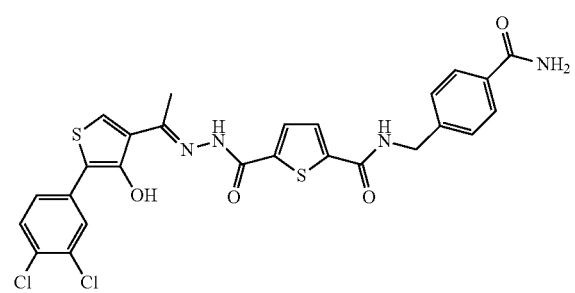
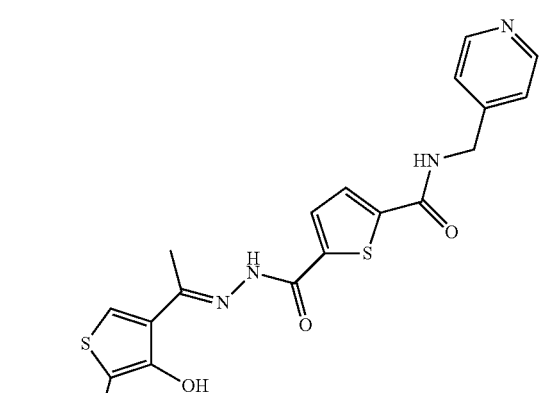
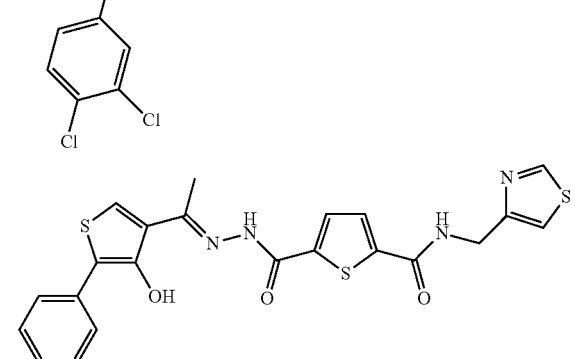
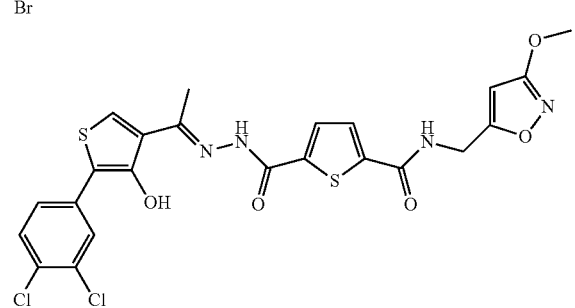
144
-continued
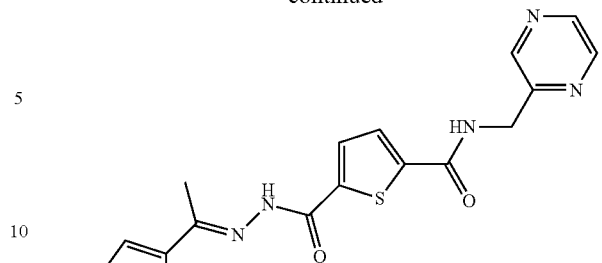
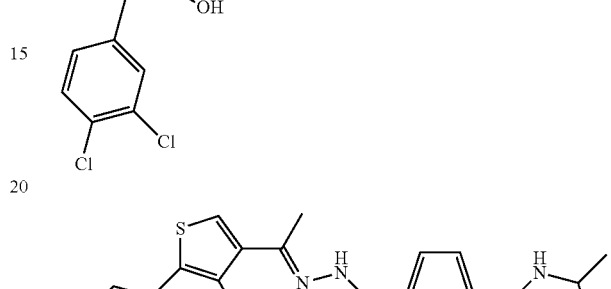
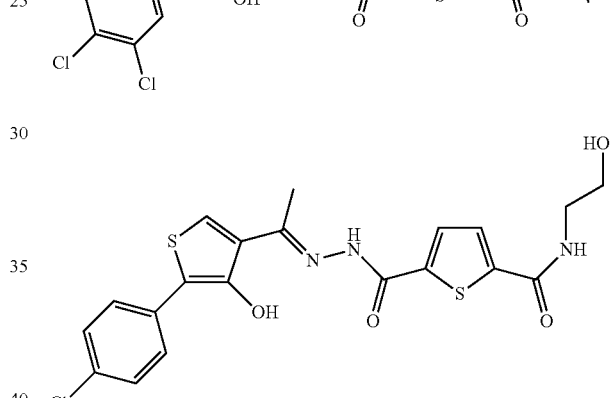
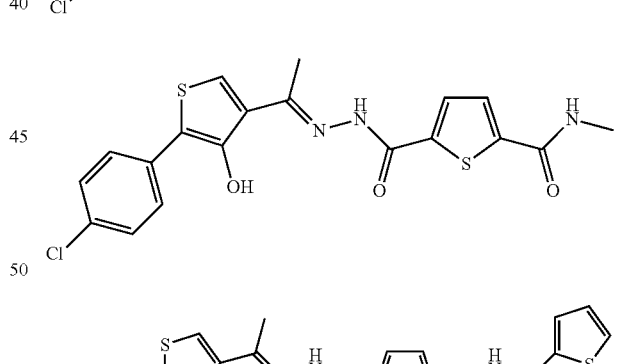
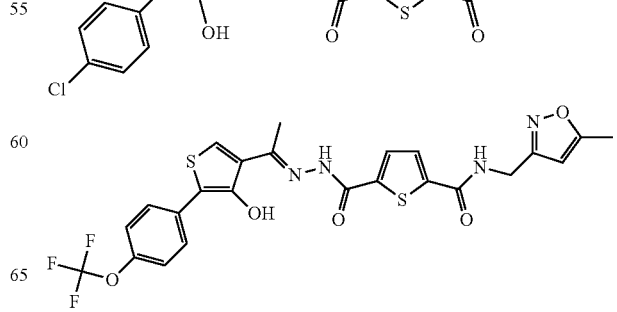

145
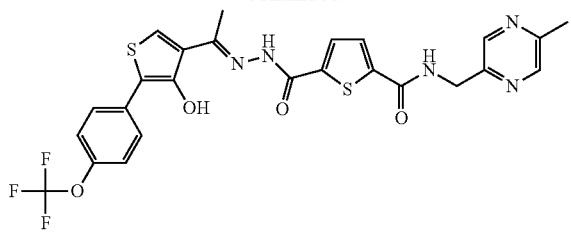
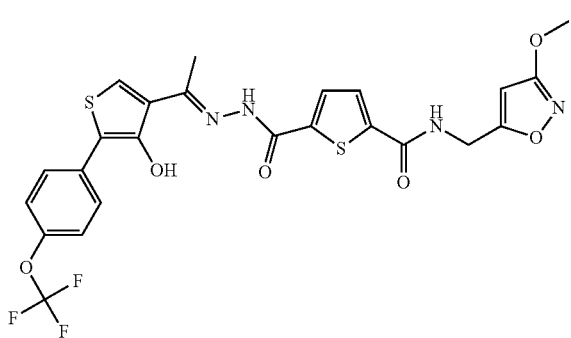
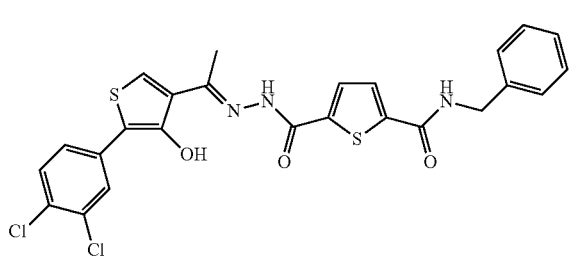
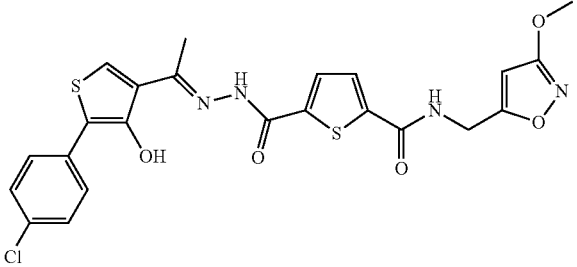
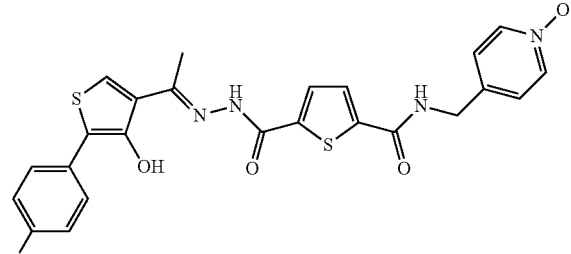
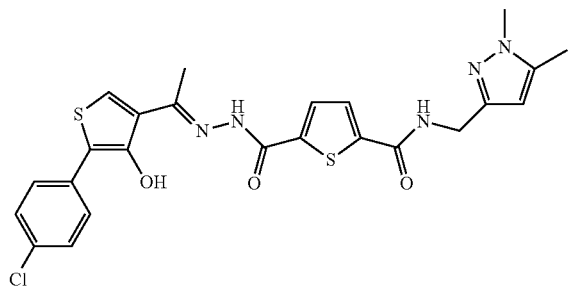
146
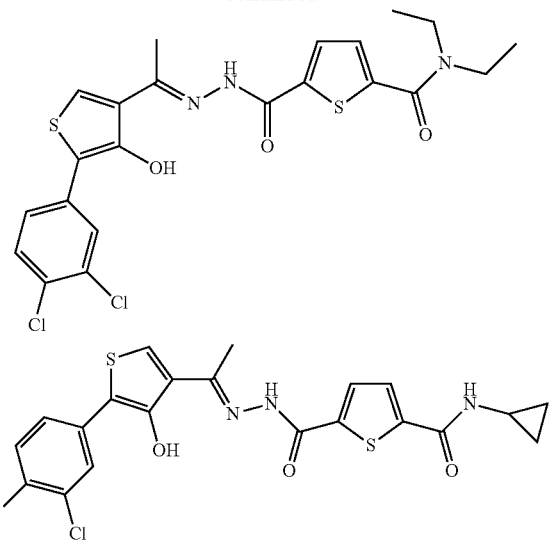
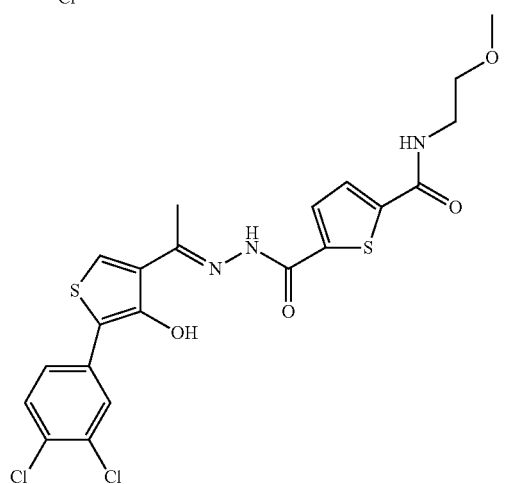
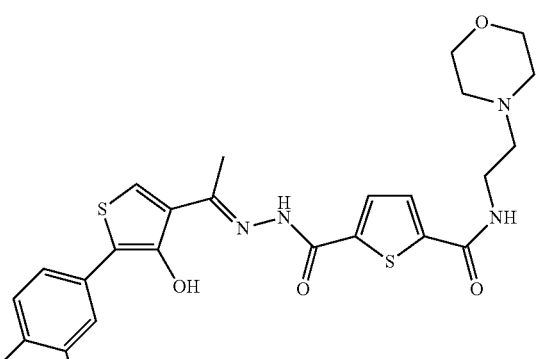
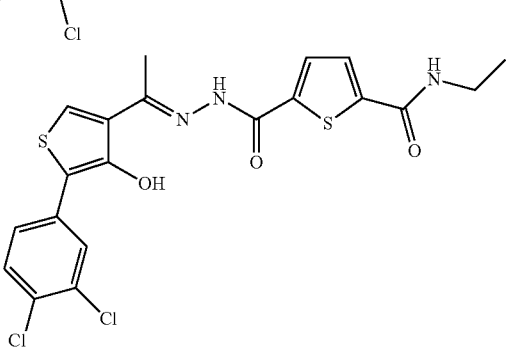

147
-continued
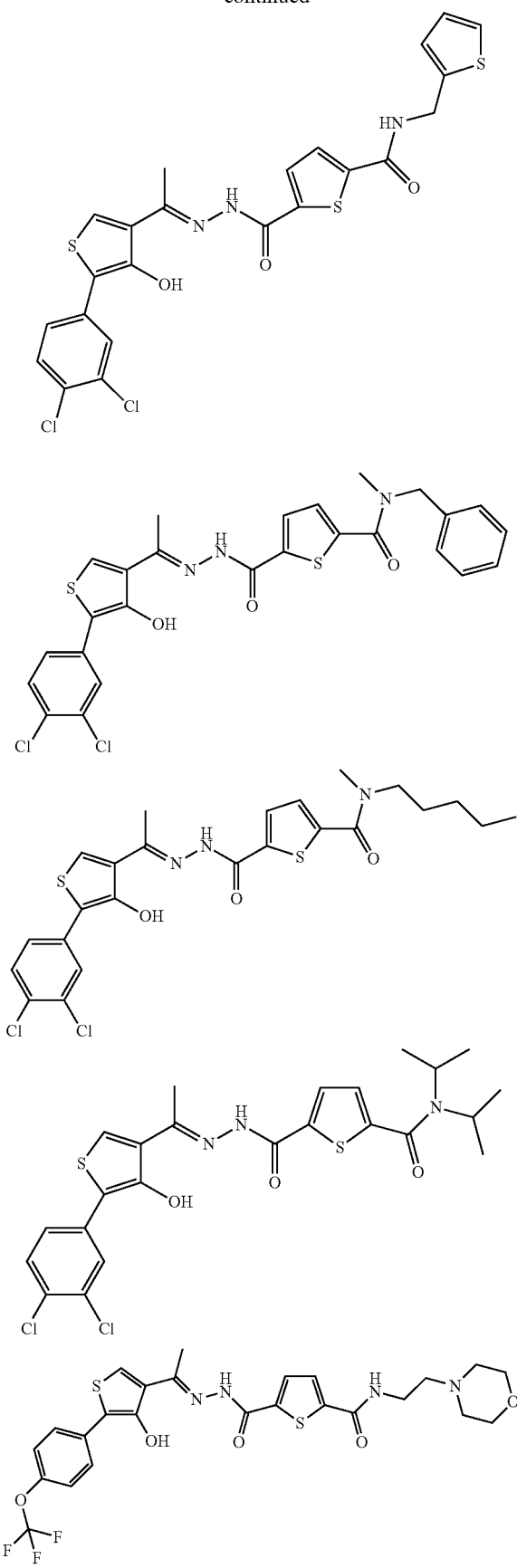
148
-continued
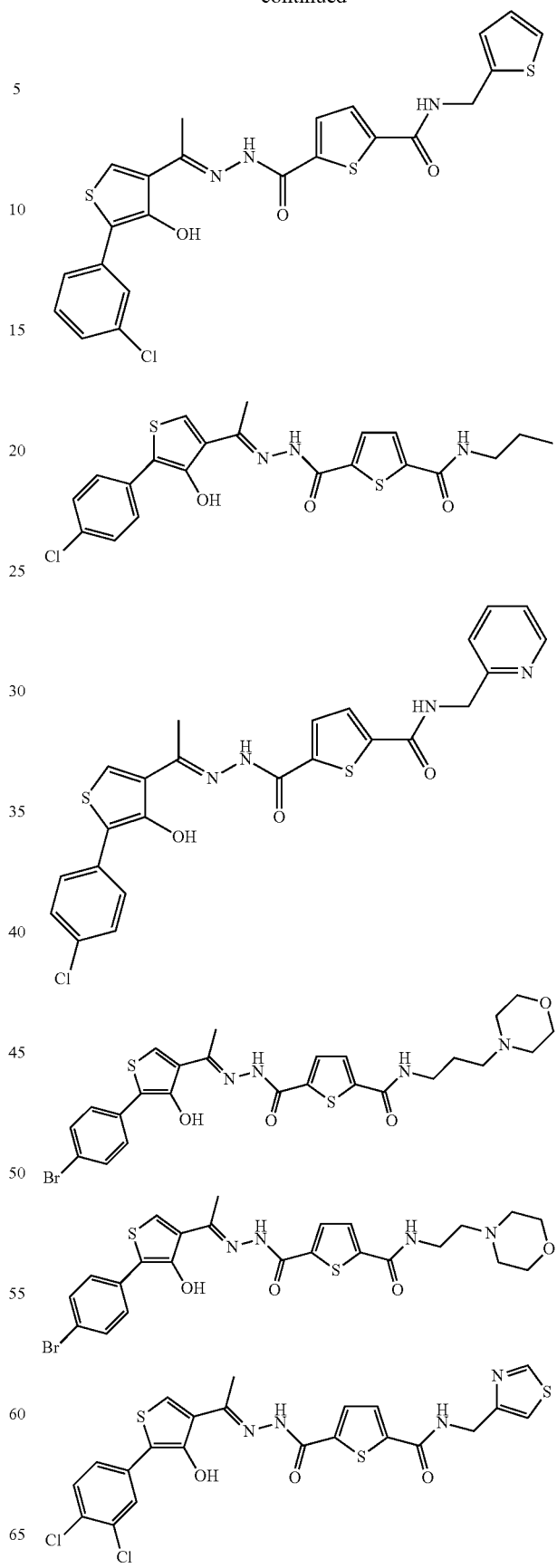

149
-continued
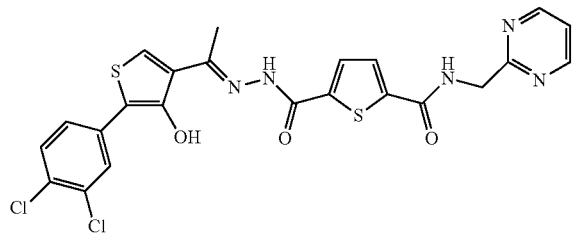
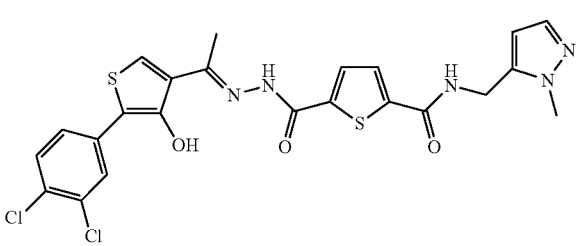
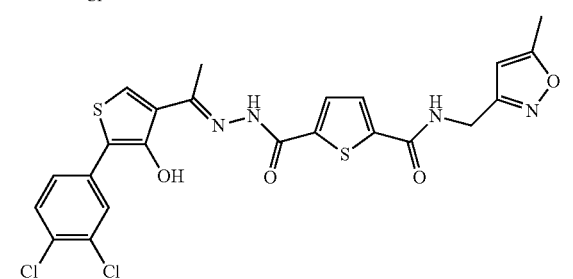
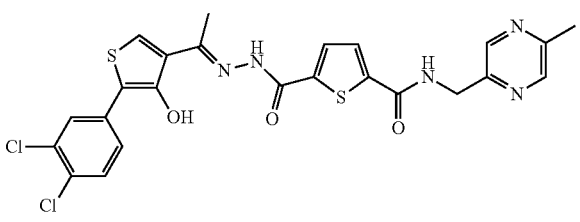
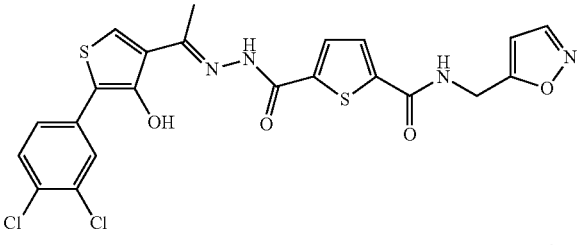
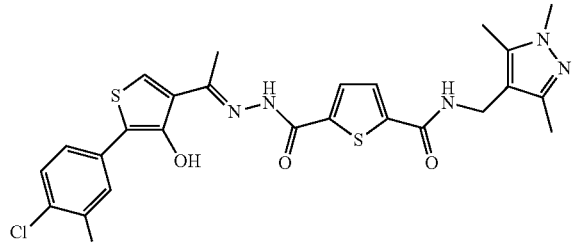
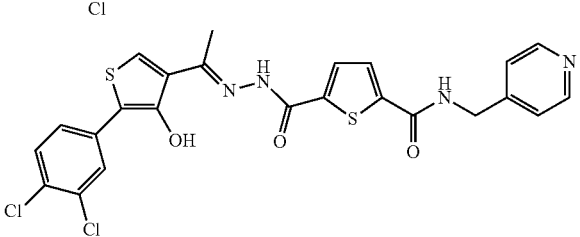
150
-continued
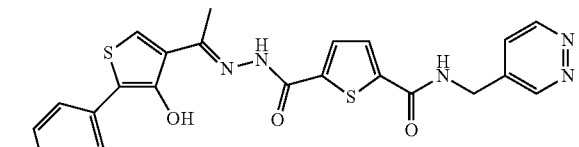
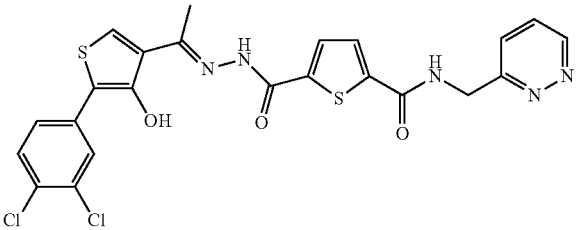
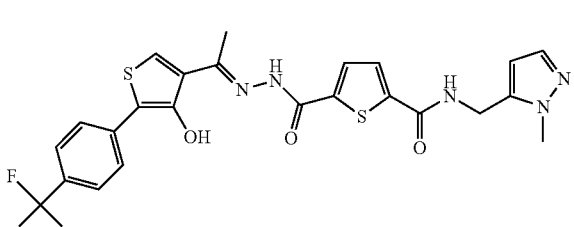
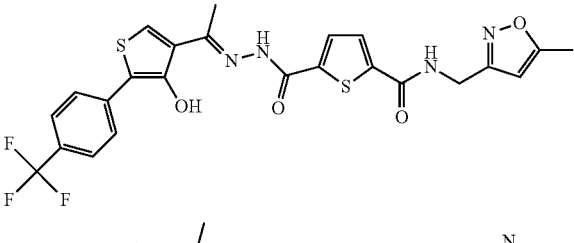
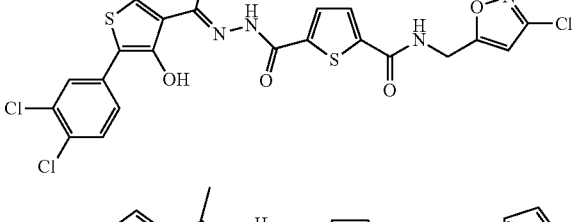
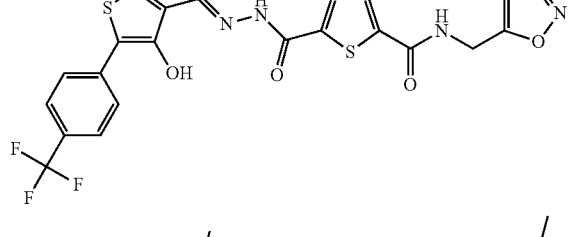

151
-continued
152
-continued
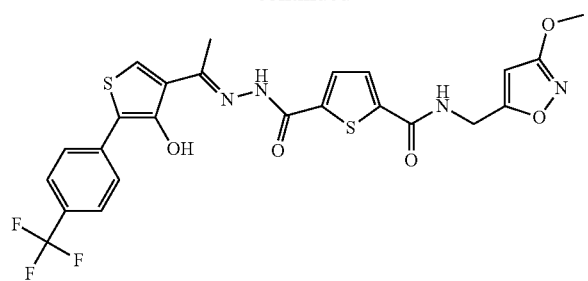
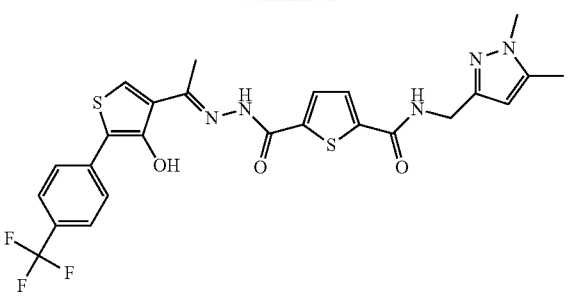

153
-continued
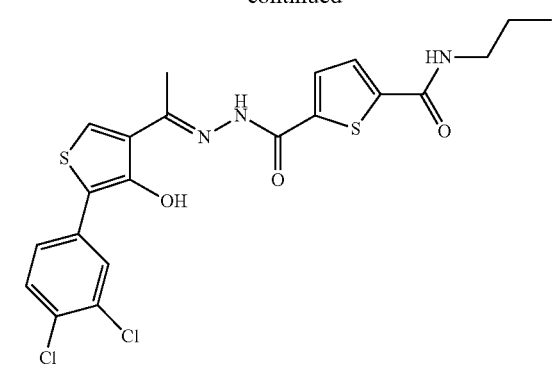
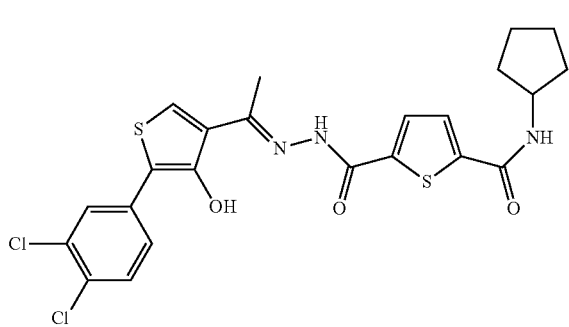
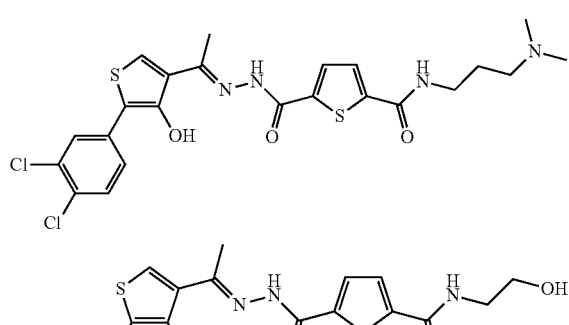
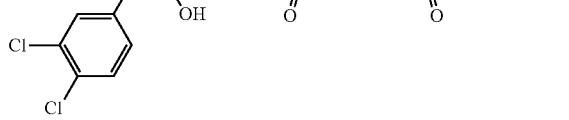
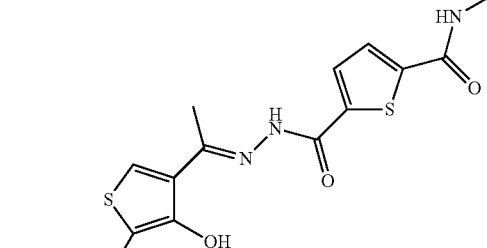
154
-continued
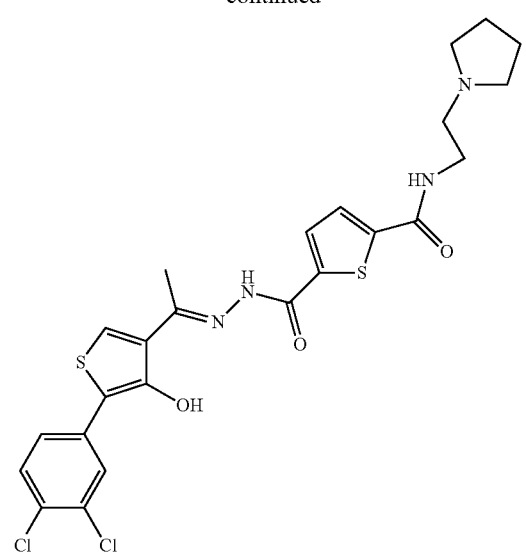
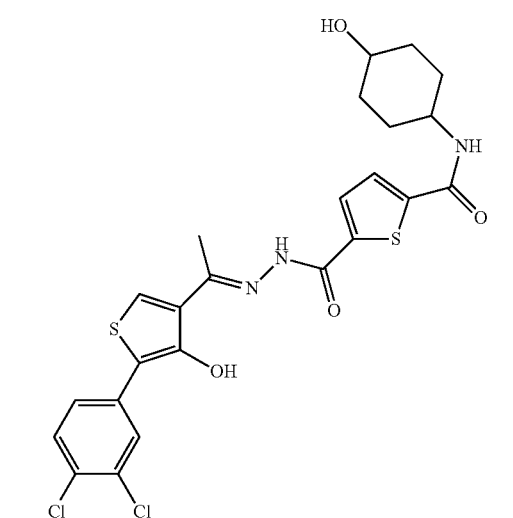
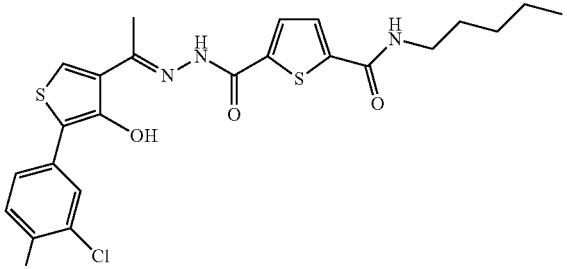
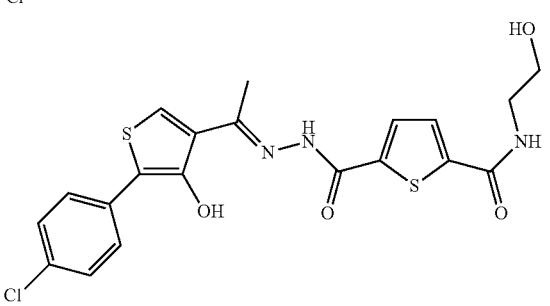

-continued
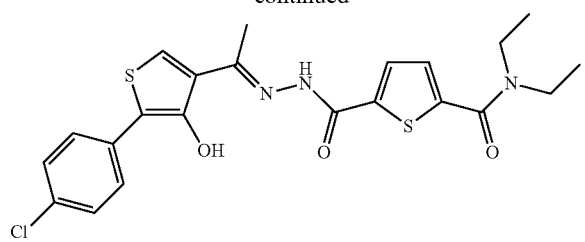
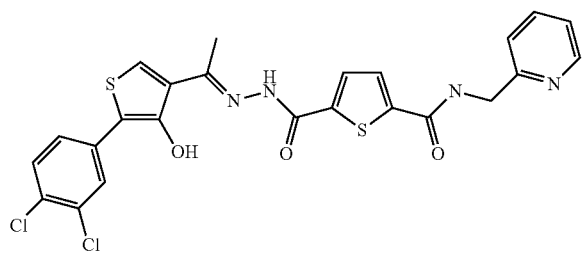
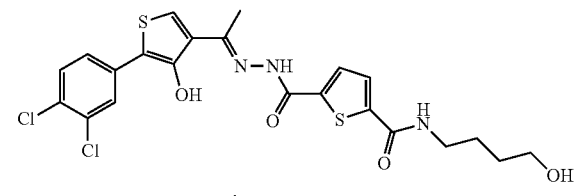
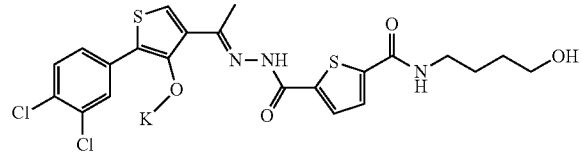
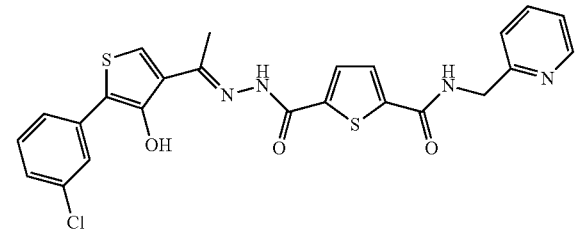
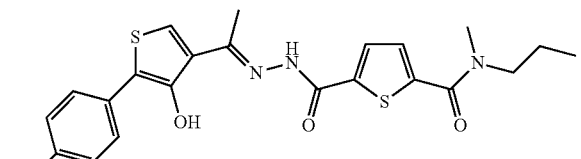
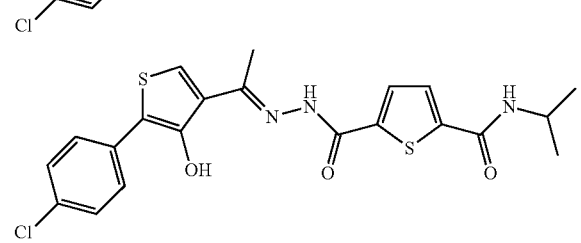
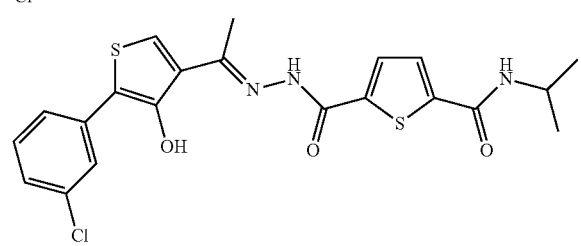
-continued
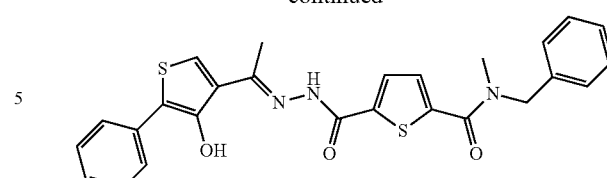
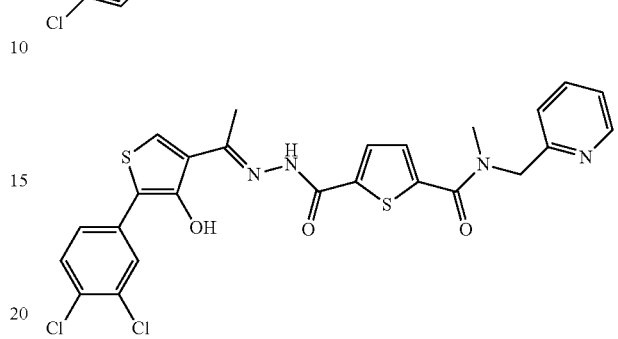
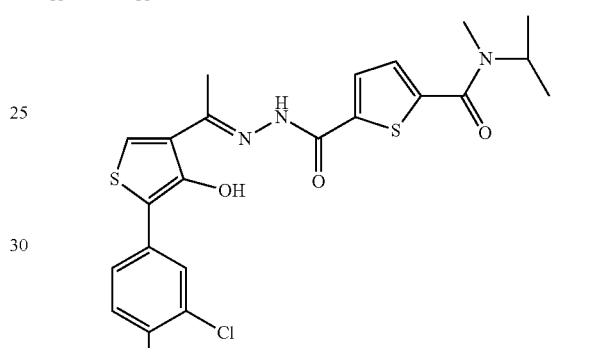
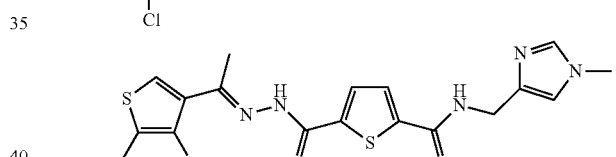
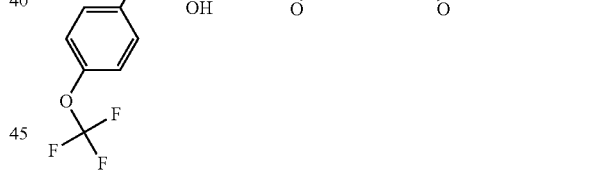
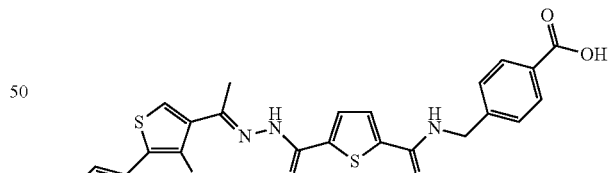
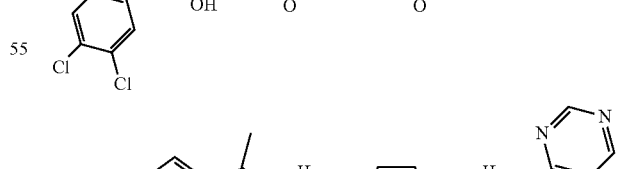
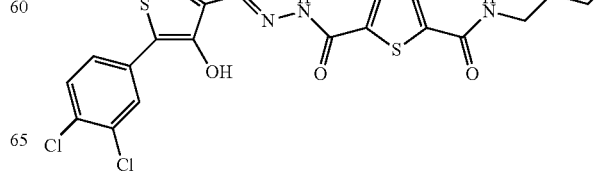

157
-continued
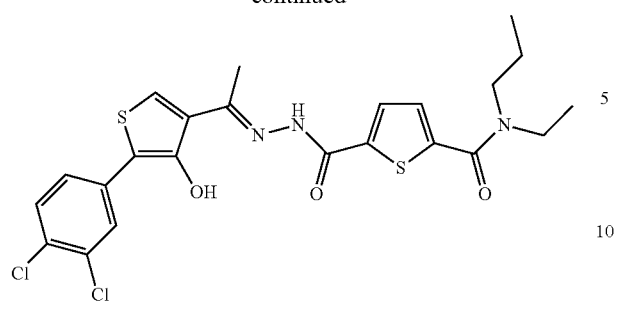
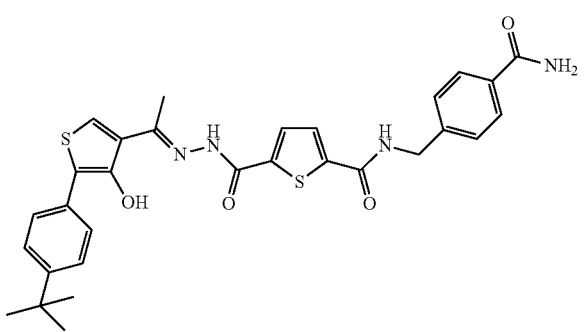
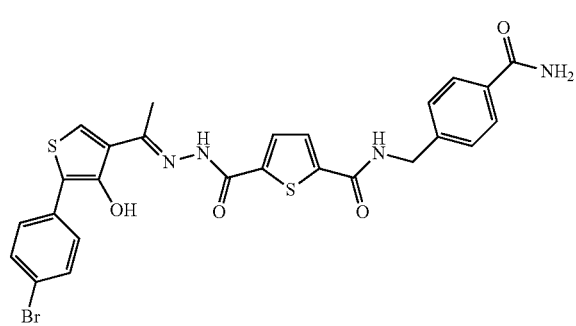 [SMILES: C/C(=N\NC(=O)c1ccc(C(=O)NCc2ccc(C(N)=O)cc2)s1)c1csc(-c2ccc(Br)cc2)c1O]
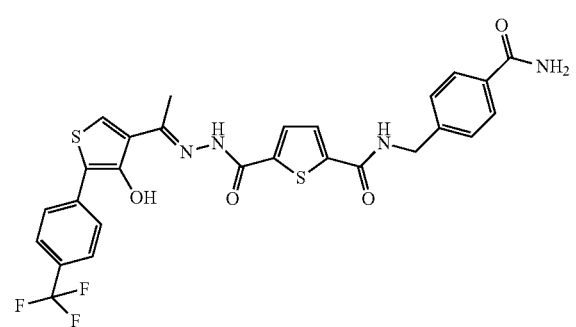
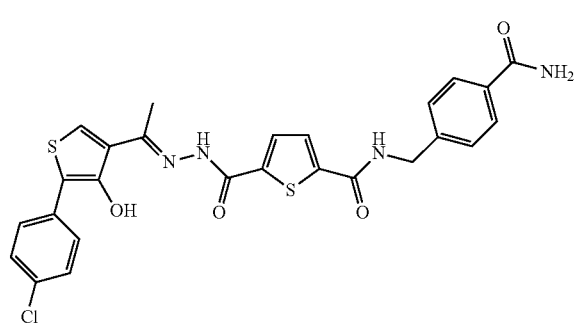
158
-continued
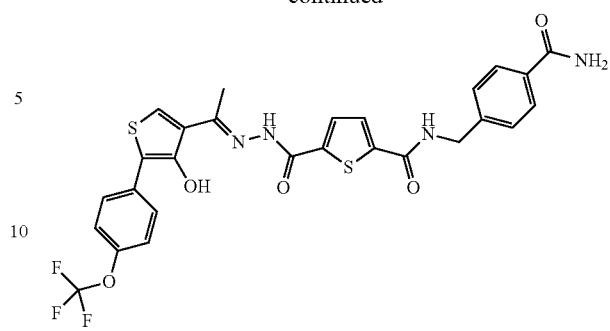
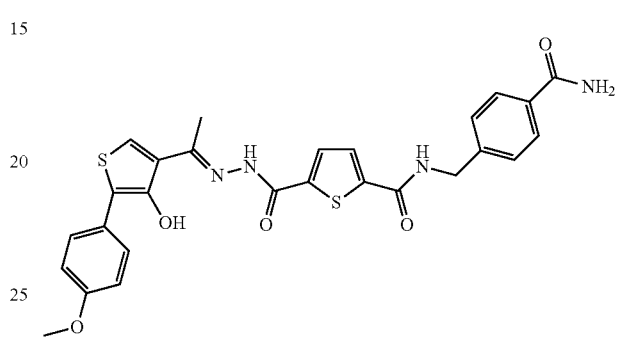
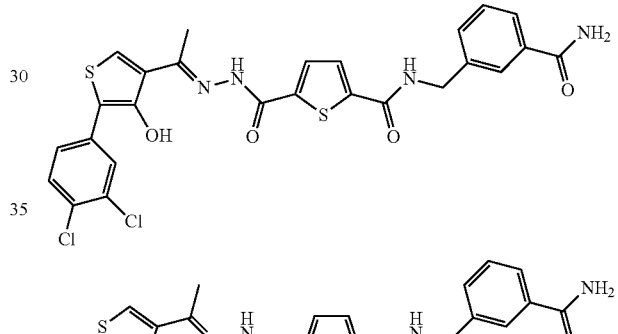
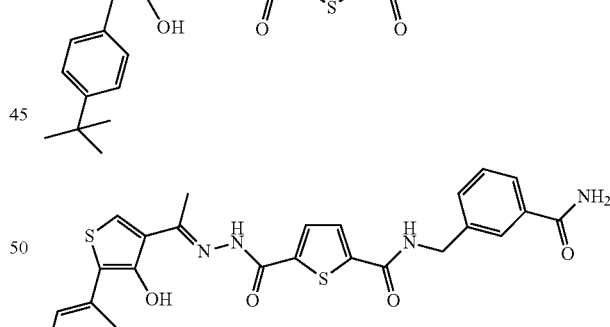
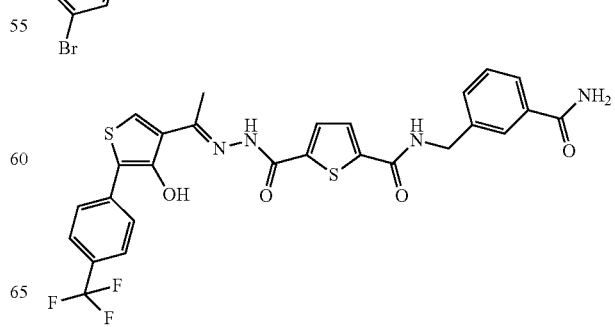

159
-continued
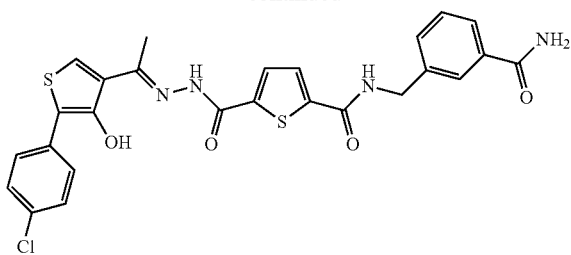
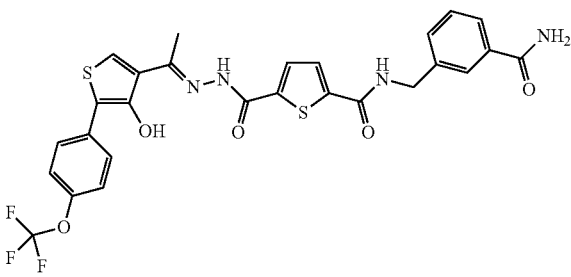
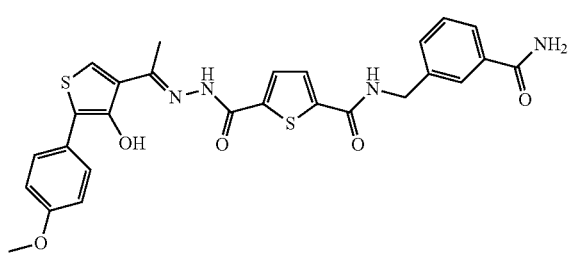
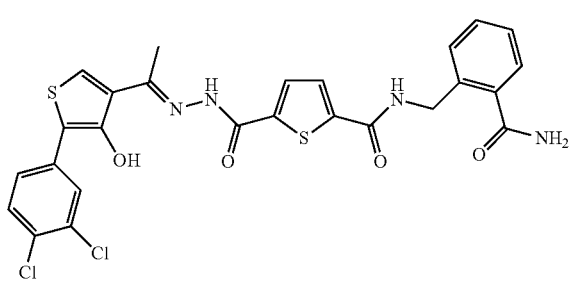
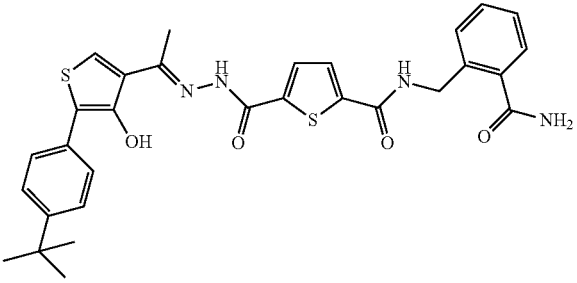
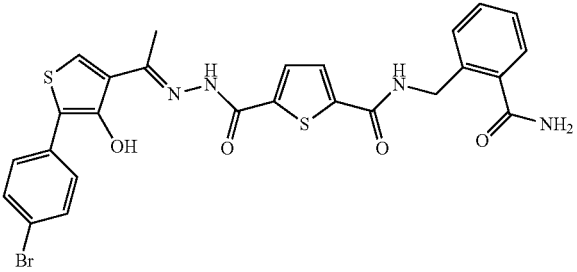
160
-continued
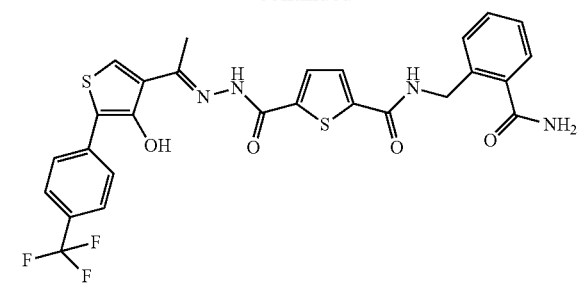
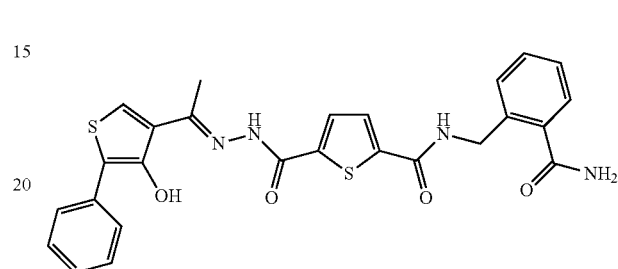
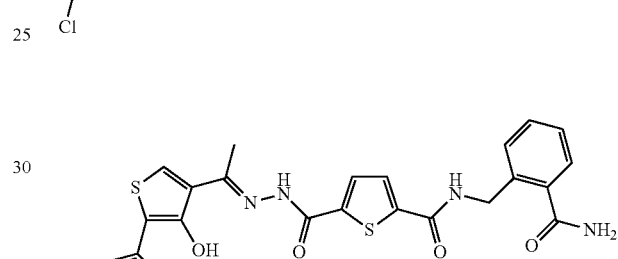
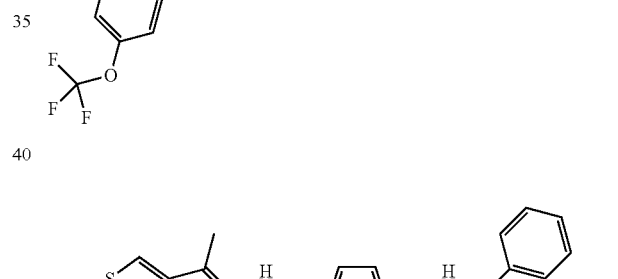
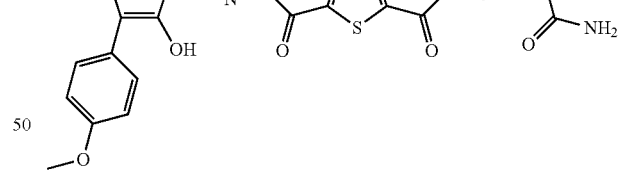
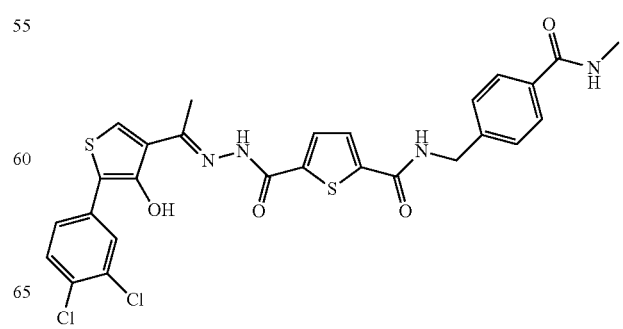

161
-continued
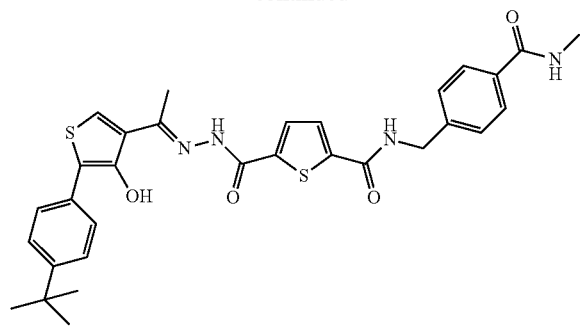
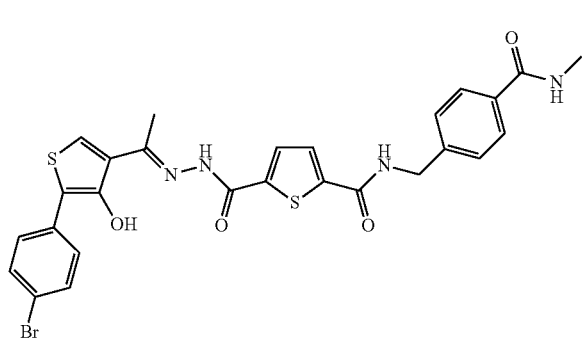
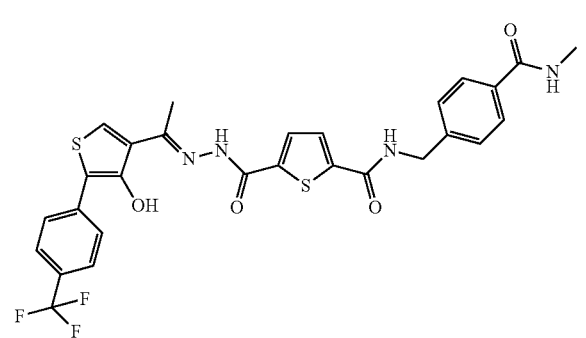
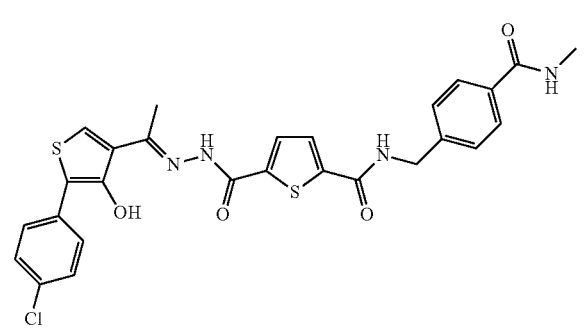
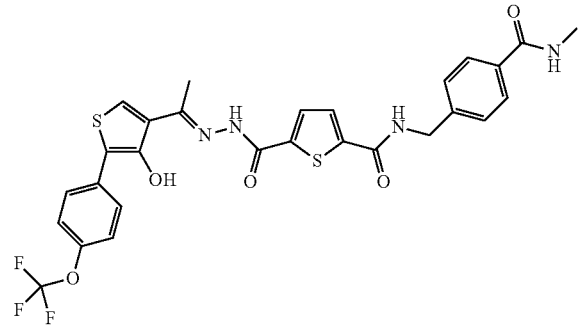
162
-continued
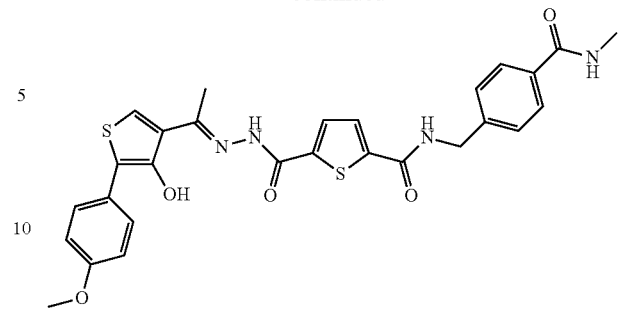
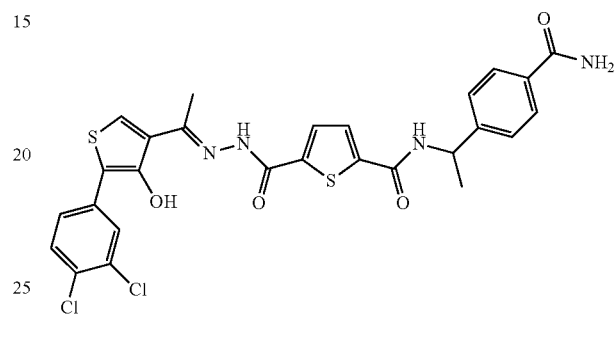
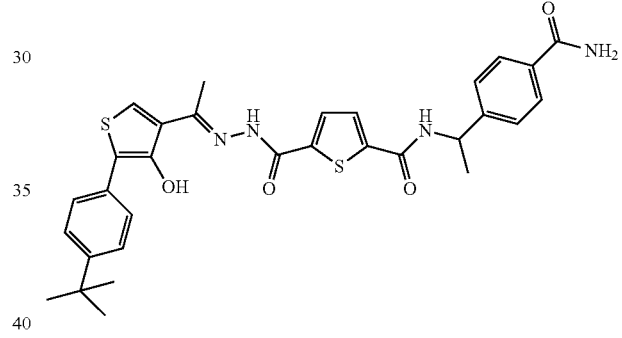
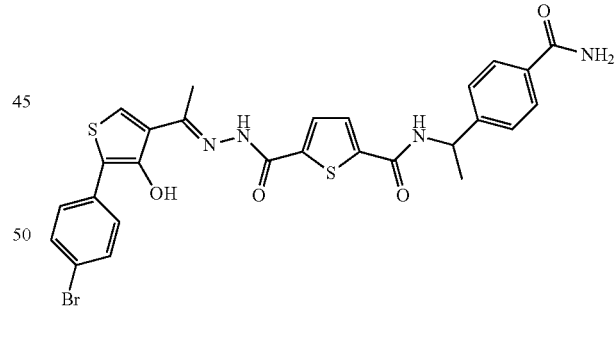
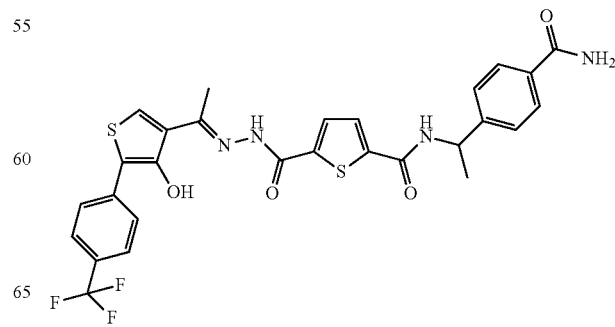

163
-continued
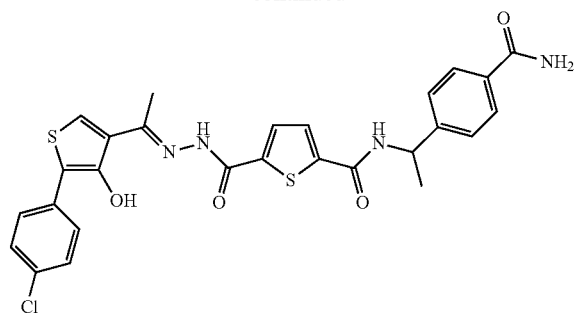
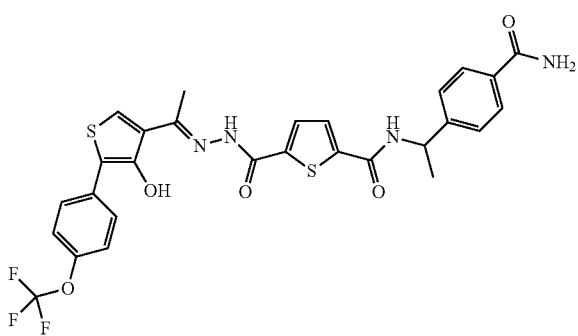
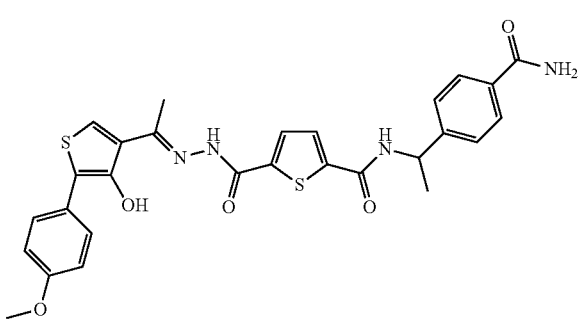
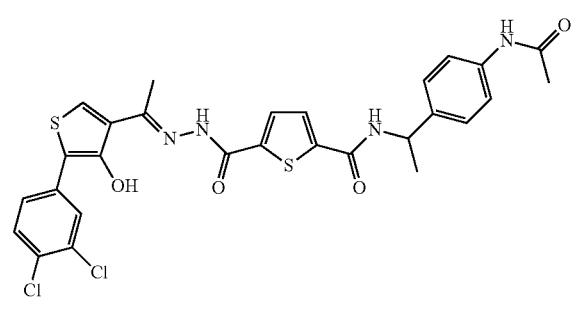
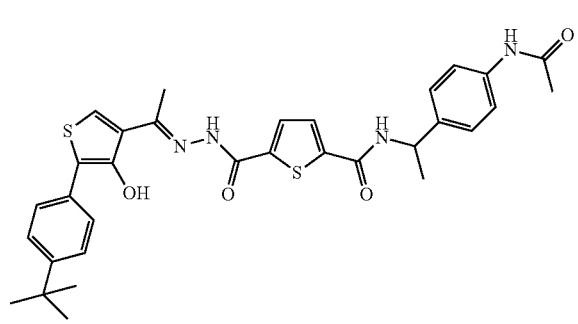
164
-continued
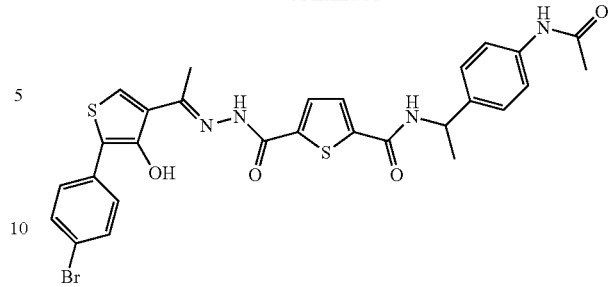
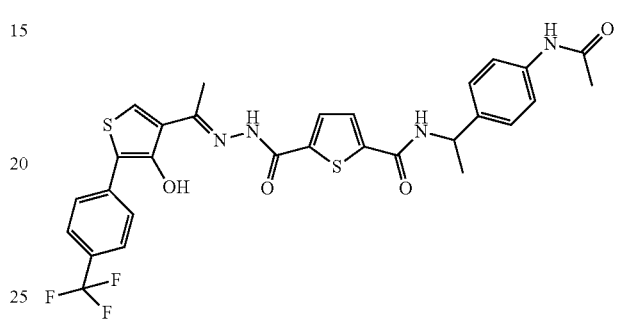
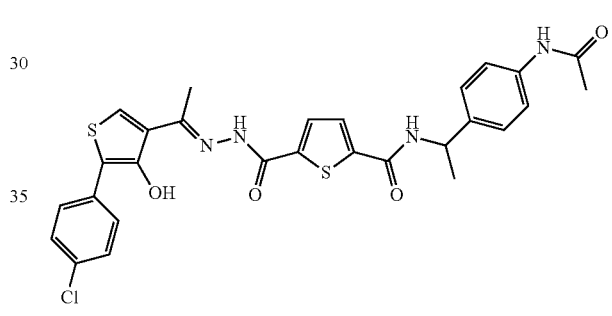
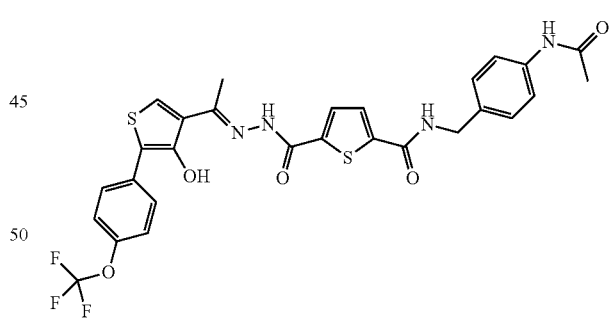
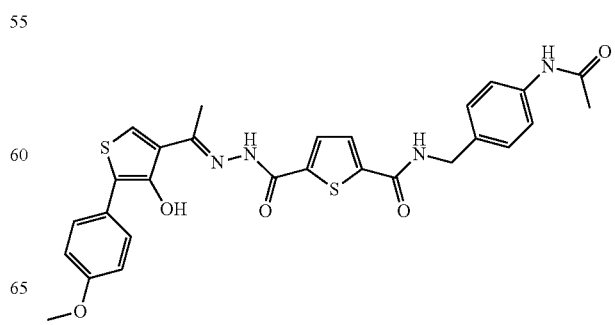

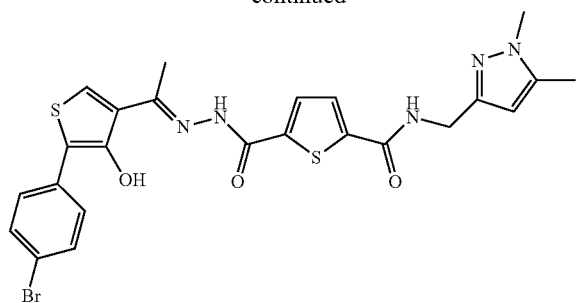

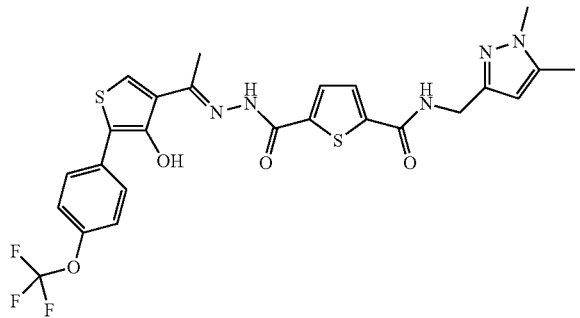

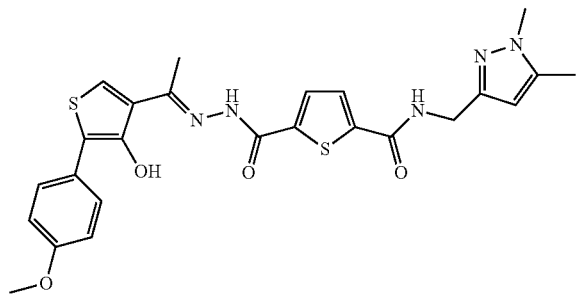

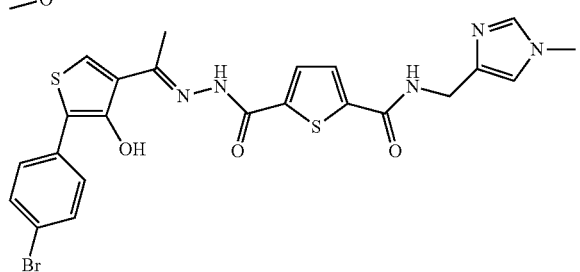

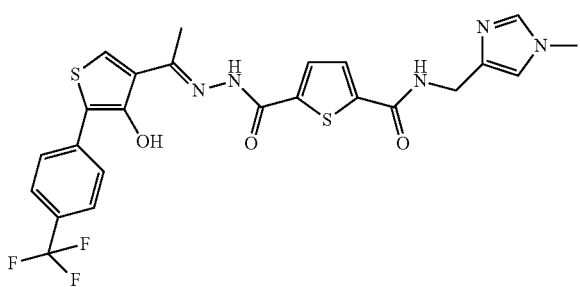

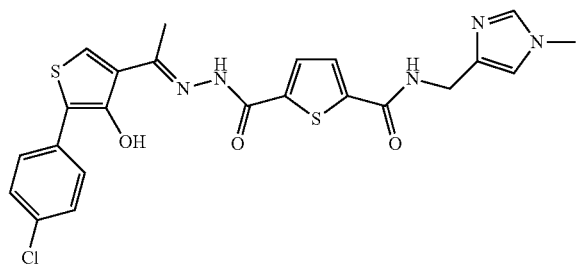

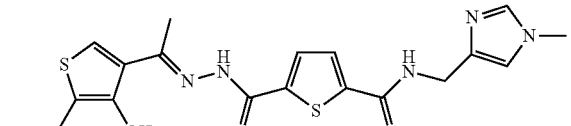

a tautomer or pharmaceutically acceptable salt or a solvate thereof.

12. A method for expanding hematopoietic stem cells and/or hematopoietic progenitor cells, which comprises culturing hematopoietic stem cells and/or hematopoietic progenitor cells ex vivo in a medium containing the following compound

a tautomer or pharmaceutically acceptable salt or a solvate thereof.

13. A method for expanding hematopoietic stem cells and/or hematopoietic progenitor cells, which comprises culturing hematopoietic stem cells and/or hematopoietic progenitor cells ex vivo in a medium containing the following compound

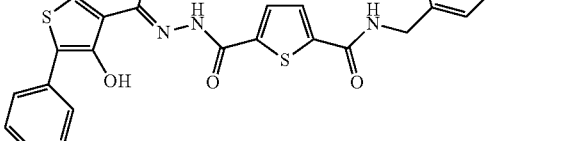

a tautomer or pharmaceutically acceptable salt or a solvate thereof.

14. A method for expanding hematopoietic stem cells and/or hematopoietic progenitor cells, which comprises culturing hematopoietic stem cells and/or hematopoietic progenitor cells ex vivo in a medium containing the following compound

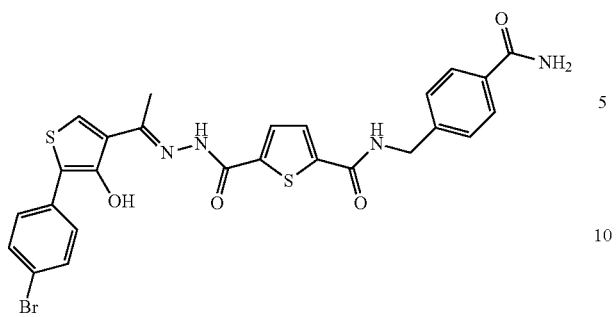
a tautomer or pharmaceutically acceptable salt or a solvate thereof.
* * * * *